(12) United States Patent
Matsuda et al.

(10) Patent No.: US 8,168,666 B2
(45) Date of Patent: May 1, 2012

(54) SUBSTITUTED CARBINOL COMPOUND

(75) Inventors: Takayuki Matsuda, Higashimurayama (JP); Ayumu Okuda, Higashimurayama (JP); Minoru Koura, Higashimurayama (JP); Yuki Yamaguchi, Higashimurayama (JP); Sayaka Kurobuchi, Higashimurayama (JP); Yuuichirou Watanabe, Higashimurayama (JP); Kimiyuki Shibuya, Higashimurayama (JP)

(73) Assignee: Kowa Company, Ltd., Nagoya-shi (JP)

( * ) Notice: Subject to any disclaimer, the term of this patent is extended or adjusted under 35 U.S.C. 154(b) by 216 days.

(21) Appl. No.: 12/516,944

(22) PCT Filed: Nov. 29, 2007

(86) PCT No.: PCT/JP2007/001318
§ 371 (c)(1),
(2), (4) Date: May 29, 2009

(87) PCT Pub. No.: WO2008/065754
PCT Pub. Date: Jun. 5, 2008

(65) Prior Publication Data
US 2010/0063119 A1 Mar. 11, 2010

(30) Foreign Application Priority Data
Nov. 30, 2006 (JP) ................. 2006-322963

(51) Int. Cl.
*A61K 31/4015* (2006.01)
*C07D 233/32* (2006.01)

(52) U.S. Cl. .............. 514/386; 514/389; 548/316.7; 548/323.5

(58) Field of Classification Search .............. None
See application file for complete search history.

(56) References Cited

U.S. PATENT DOCUMENTS

| 6,316,503 B1 | 11/2001 | Li et al. |
| 7,125,865 B2 | 10/2006 | Jones et al. |
| 2006/0074115 A1 | 4/2006 | Dehmlow et al. |

FOREIGN PATENT DOCUMENTS

| WO | 00/54759 A2 | 9/2000 |
| WO | 03/106435 A1 | 12/2003 |
| WO | 2004/011448 A1 | 2/2004 |
| WO | 2005/023782 A1 | 3/2005 |
| WO | 2006/010643 A1 | 2/2006 |

OTHER PUBLICATIONS

Byrn et al., Solid-State Chemistry of Drugs, 2d, Chapter 11 Hydrates and Solvates, 233-247 (1999).*
Morissette et al., Adv. Drug Delivery Rev., 56:275 (2004).*
A.M. Rouhi, Chem. & Eng. News, 81:32 (Feb. 24, 2003).*
Horig et al. Journal of Translational Medicine, 2:44 (2004).*
Schafer et al. Drug Discovery Today, 13:913 (2008).*
International Search Report of PCT/JP2007/001318, Mailing Date of Jan. 15, 2008.
Notification of Transmittal of the International Preliminary Report on Patentability (Forms PCT/IB/338) of International Application No. PCT/JP2007/001318 mailed Jun. 11, 2009 with forms PCT/IB/373 and PCT/ISA/237.
Supplementary European Search Report dated Apr. 11, 2010, issued in corresponding European Patent Application No. 07828095.5.

* cited by examiner

*Primary Examiner* — Yong Chu
*Assistant Examiner* — Michael Barker
(74) *Attorney, Agent, or Firm* — Westerman, Hattori, Daniels & Adrian, LLP

(57) ABSTRACT

There is provided a novel LXRβ agonist useful as a preventative and/or therapeutic agent for arteriosclerosis; arteriosclerosis such as those resulting from diabetes; hyperlipidemia; hypercholesterolemia; lipid-related diseases; inflammatory diseases caused by inflammatory cytokines, skin diseases such as allergic skin diseases, diabetes or Alzheimer's disease. The agonist is a carbinol derivative represented by the following general formula (1) or salt thereof, or their solvate.

6 Claims, No Drawings

SUBSTITUTED CARBINOL COMPOUND

TECHNICAL FIELD

The present invention relates to a substituted carbinol compound which is a novel LXRβ agonist useful as a preventative and/or therapeutic agent for atherosclerosis; arteriosclerosis such as those resulting from diabetes; hyperlipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including 22-(R)-hydroxycholesterol act as a ligand for LXR (non-patent documents 1 to 3). LXR, together with retinoid X receptor (RXR) which is another nuclear receptor, forms a heterodimer, to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines, or adipose tissues, whereas LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXRα- and LXRβ-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXRβ in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholesterol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a hyperlipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXRβs is considered to have an ideal profile that is expected to suppress the activation of LXRα highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazoline-4-one derivative (patent document 4), tetrahydroquinoline derivative (patent document 5), tetrahydrocarbazol derivative (patent document 6), isoquinoline derivative (patent document 7), and naphthalene derivative (patent document 8), GW3965 that is an aromatic aminoalcohol derivative (Example 16 described in patent document 9), and T0901317 that is a benzenesulfonamide derivative (Example 12 described in patent document 10), but no agonist with high LXRβ selectivity has been reported to date and therefore an LXRβ selective compound has been awaited.

[Patent Document 1]: Published Japanese translation of PCT international publication No. 2002-539155
[Patent Document 2]: Published Japanese translation of PCT international publication No. 2004-509161
[Patent Document 3]: WO2003/82192

[Patent Document 4]: WO2004/24161
[Patent Document 5]: WO2004/72046
[Patent Document 6]: U.S. Patent publication No. 2005/215577
[Patent Document 7]: WO2004/58717
[Patent Document 8]: WO2005/23188
[Patent Document 9]: WO2002/24632
[Patent Document 10]: WO2000/54759
[Non-patent Document 1]: Janowski et al., Nature, 383, pp. 728-731, 1996
[Non-patent Document 2]: Lehmann et al., J. Biol. Chem., 272, pp. 3137-3140, 1997
[Non-patent Document 3]: Fu et al., J. Biol. Chem., 276, pp. 38378-38387, 2001
[Non-patent Document 4]: Auboeuf et al., Diabetes, 46, pp. 1319-1327, 1997
[Non-patent Document 5]: Lu et al., J. Biol. Chem., 276, pp. 37735-37738, 2001
[Non-patent Document 6]: Zelcer et al., J. Clin. Invest., 116, pp. 607-614, 2006
[Non-patent Document 7]: Joseph et al., Nat. Med., 9, pp. 213-219, 2003
[Non-patent Document 8]: Geyeregger et al., Cell. Mol. Life. Sci. 63, pp. 524-539, 2006
[Non-patent Document 9]: Peet et al., Cell, 93, pp. 693-704, 1998
[Non-patent Document 10]: Alberti et al., J. Clin. Invest., 107, pp. 565-573, 2001
[Non-patent Document 11]: Tangirala et al., Proc. Natl. Acad. Sci. USA, 99, pp. 11896-11901, 2002
[Non-patent Document 12]: Terasaka et al., FEBS Lett., 536, pp. 6-11, 2003
[Non-patent Document 13]: Cao et al., J. Biol. Chem., 278, pp. 1131-1136, 2003
[Non-patent Document 14]: Laffitte et al., Proc. Natl. Acad. Sci. USA, 100, pp. 5419-5424, 2003
[Non-patent Document 15]: Lala et al., Curr. Opin. Investig. Drugs, 6, pp. 934-943, 2005
[Non-patent Document 16]: Groot et al., J. Lipid Res., 46, pp. 2182-2191, 2005
[Non-patent Document 17]: Schultz et al., Genes Dev., 14, pp. 2831-2838, 2000
[Non-patent Document 18]: Lund et al., Arterioscler. Thromb. Vasc. Biol., 23, pp. 1169-1177, 2003
[Non-patent Document 19]: Bradley et al., Drug Discov. Today Ther. Strateg. 2, pp. 97-103, 2005

DISCLOSURE OF THE INVENTION

Thus, the object of the present invention is to prepare a novel compound that exhibits an agonist activity with high LXRβ selectivity.

The present inventors made a keen study to achieve the above object and consequently, found that a compound having a hexafluorocarbinol skeleton and an imidazolidin-2-one skeleton represented by general formula (1) described hereinbelow has an agonist activity with high LXRβ selectivity, and thus completed the present invention.

More specifically, the present invention relates to [1] A carbinol derivative represented by the following general formula (1) or salt thereof, or their solvate:

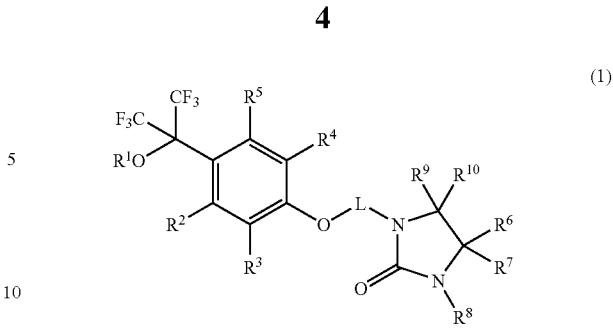

wherein $R^1$ represents a hydrogen atom, $C_{1-8}$ alkyl group, $C_{1-6}$ alkoxy-$C_{1-8}$ alkyl group or $C_{1-8}$ acyl group, $R^2$, $R^3$, $R^4$ and $R^5$ each independently represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl-$C_{1-8}$ alkyl group, $C_{1-6}$ alkoxy group, $C_{6-10}$ aryl group, $C_{6-10}$ aryl-$C_{1-8}$ alkyl group, $C_{6-10}$ aryl-$C_{2-6}$ alkenyl group, $C_{1-6}$ alkylthio group, $C_{1-6}$ alkylsulfinyl group, $C_{1-6}$ alkylsulfonyl group, $C_{6-10}$ arylsulfonyl group, nitro group, amino group, mono-$C_{1-6}$ alkylamino group, di-$C_{1-6}$ alkylamino group, $C_{3-8}$ cycloalkyl-$C_{1-2}$ alkyl group, $C_{3-8}$ cycloalkyl-$C_{2-8}$ alkenyl group, $C_{3-8}$ cycloalkyl-$C_{2-8}$ alkynyl group or halo-$C_{1-6}$ alkyl group (wherein the $C_{6-10}$ aryl may be substituted with the same or different 1 to 3 substituents selected from the following group A), $R^6$ and $R^7$ each independently represents a hydrogen atom, $C_{1-8}$ alkyl group, $C_{3-8}$ cycloalkyl group, $C_{6-10}$ aryl group or 5- to 11-membered heterocyclic group (wherein the $C_{6-10}$ aryl or the 5- to 11-membered heterocycle may be substituted with the same or different 1 to 3 substituents selected from the following group A), or $R^6$ and $R^7$ may together form a 5- to 7-membered carbocycle, $R^8$ represents a hydrogen atom, $C_{1-8}$ alkyl group, halo-$C_{1-6}$ alkyl group or $C_{3-8}$ cycloalkyl group, $R^9$ and $R^{10}$ each independently represents a hydrogen atom, hydroxy group or $C_{1-6}$ alkoxy group, or $R^9$ and $R^{10}$ may together form a carbonyl group, and L represents a $C_{3-15}$ alkyl chain, $C_{3-15}$ alkenyl chain or $C_{3-15}$ alkynyl chain

[Group A: a halogen atom, $C_{1-8}$ alkyl group, halo-$C_{1-6}$ alkyl group, cyano group, nitro group, hydroxy group, amino group, mono-$C_{1-6}$ alkylamino group, di-$C_{1-6}$ alkylamino group, $C_{1-6}$ alkoxy group, halo-$C_{1-6}$ alkoxy group, carboxyl group, $C_{2-8}$ acyloxy group, $C_{1-6}$ alkoxycarbonyl group, $C_{6-10}$ aryl group, $C_{6-10}$ aryl-$C_{1-6}$ alkoxy group (which may be substituted with the same or different 1 to 3 substituents selected from a $C_{1-8}$ alkyl group, halogen atom or $C_{1-6}$ alkoxy group), $C_{1-6}$ alkylthio group, $C_{1-6}$ alkylsulfinyl group, $C_{1-6}$ alkylsulfonyl group or $C_{6-10}$ arylsulfonyl group];

[2] A medicine comprising the carbinol derivative or salt thereof, or their solvate according to [1] as an active ingredient;

[3] The medicine according to [2], which is a preventative and/or therapeutic agent for atherosclerosis, arteriosclerosis resulting from diabetes, hyperlipidemia, hypercholesterolemia, lipid-related diseases, inflammatory diseases caused by inflammatory cytokines, skin diseases, diabetes or Alzheimer's disease;

[4] An LXR regulator comprising the carbinol derivative or salt thereof, or their solvate according to [1] as an active ingredient;

[5] A pharmaceutical composition consisting of the carbinol derivative or salt thereof, or their solvate according to [1] and a pharmaceutically acceptable carrier;

[6] A method for preventing and/or treating atherosclerosis, arteriosclerosis resulting from diabetes, hyperlipidemia, hypercholesterolemia, lipid-related diseases, inflammatory diseases caused by inflammatory cytokines, skin diseases, diabetes or Alzheimer's disease, which method comprises administering an effective amount of the carbinol derivative or salt thereof, or their solvate according to [1] to a patient in need of treatment; and

[7] Use of the carbinol derivative or salt thereof, or their solvate according to [1] for preparing a formulation for preventing and/or treating atherosclerosis, arteriosclerosis resulting from diabetes, hyperlipidemia, hypercholesterolemia, lipid-related diseases, inflammatory diseases caused by inflammatory cytokines, skin diseases, diabetes or Alzheimer's disease.

EFFECT OF THE INVENTION

The carbinol derivative represented by the general formula (1) according to the present invention has an LXRβ agonist effect and is useful as a preventative and/or therapeutic agent for atherosclerosis, arteriosclerosis such as those resulting from diabetes; hyperlipidemia; hypercholesterolemia; lipid-related diseases; inflammatory diseases caused by inflammatory cytokines such as chronic rheumatism, osteoarthritis, allergic disease, asthma, sepsis, psoriasis and osteoporosis; autoimmune diseases such as systemic lupus erythematosus, ulcerative colitis and Crohn's disease; cardiovascular diseases such as ischemic heart disease and heart failure; cerebrovascular diseases; renal diseases; diabetes; diabetic complications such as retinopathy, nephropathy, neurosis and coronary artery disease; skin diseases such as allergic skin diseases; obesity; nephritis; hepatitis; cancer; or Alzheimer's disease, and more preferably a preventative and/or therapeutic agent for atherosclerosis, arteriosclerosis such as those resulting from diabetes, hyperlipidemia, hypercholesterolemia, lipid-related diseases, inflammatory diseases caused by inflammatory cytokines, skin diseases such as allergic skin diseases, diabetes or Alzheimer's disease, for example.

DETAILED DESCRIPTION OF THE INVENTION

The definitions of terms in the present invention are as follows.

In the present invention, the "$C_{1-8}$ alkyl group" refers to a linear or branched alkyl group having 1 to 8 carbon atoms. Examples of the group include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group and n-octyl group.

In the present invention, the "$C_{3-8}$ cycloalkyl group" refers to a cyclic alkyl group having 3 to 8 carbon atoms. Examples of the group include a cyclopropyl group, cyclobutyl group, cyclopentyl group, cyclohexyl group, cycloheptyl group and cyclooctyl group. The group is preferably a "$C_{3-6}$ cycloalkyl group" having 3 to 6 carbon atoms.

In the present invention, the "$C_{3-8}$ cycloalkyl-$C_{1-8}$ alkyl group" refers to a group in which the above $C_{3-8}$ cycloalkyl group and the above $C_{1-8}$ alkyl group are bonded to each other. Examples of the group include a cyclopropylmethyl group, cyclobutylethyl group, cyclohexylmethyl group, cyclohexylethyl group and cyclohexyl-n-butyl group.

In the present invention, the "$C_{1-6}$ alkoxy-$C_{1-8}$ alkyl group" refers to a group in which the following $C_{1-6}$ alkoxy group and the above $C_{1-8}$ alkyl group are bonded to each other. Examples of the group include a methoxymethyl group, ethoxymethyl group, methoxyethyl group and ethoxyethyl group.

In the present invention, the "$C_{6-10}$ aryl-$C_{1-8}$ alkyl group" refers to a group in which the following $C_{6-10}$ aryl group and the above $C_{1-8}$ alkyl group are bonded to each other. Examples of the group include a benzyl group, phenethyl group, 3-phenyl-n-propyl group, 4-phenyl-n-butyl group, 5-phenyl-n-pentyl group, 8-phenyl-n-octyl group and naphthylmethyl group.

In the present invention, the "$C_{2-8}$ alkenyl group" refers to a linear or branched alkenyl group having 2 to 8 carbon atoms which has a carbon-carbon double bond in any one or more locations. Examples of the group include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, kept-1-en-1-yl group, kept-6-en-1-yl group, oct-1-en-1-yl group and oct-7-en-1-yl group.

The "$C_{3-8}$ cycloalkyl-$C_{2-8}$ alkenyl group" of the present invention refers to a group in which the above $C_{3-8}$ cycloalkyl group and the above $C_{2-8}$ alkenyl group are bonded to each other. Examples of the group include a cyclopropylethenyl group, cyclobutylethenyl group, cyclopentylethenyl group, cyclohexylethenyl group, 3-cyclopropyl-prop-1-en-1-yl group, 4-cyclopropyl-but-1-en-1-yl group, 5-cyclopropyl-pent-1-en-1-yl group and 6-cyclopropyl-hex-1-en-1-yl group.

The "$C_{6-10}$ aryl-$C_{2-6}$ alkenyl group" of the present invention refers to a group in which the following $C_{6-10}$ aryl group and alkenyl group having 2 to 6 carbon atoms which is the above $C_{2-8}$ alkenyl group are bonded to each other. Examples of the group include a styryl group, 3-phenylprop-1-en-1-yl group, 3-phenylprop-2-en-1-yl group, 4-phenylbut-1-en-1-yl group, 4-phenylbut-3-en-1-yl group, 5-phenylpent-1-en-1-yl group, 5-phenylpent-4-en-1-yl group, 8-phenyloct-1-en-1-yl group, 8-phenyloct-7-en-1-yl group and naphthylethenyl group.

Specific examples of the "$C_{2-8}$ alkynyl group" in the "$C_{3-8}$ cycloalkyl-$C_{2-8}$ alkynyl group" of the present invention include an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group and hex-5-yn-1-yl group. The group is preferably a linear or branched "$C_{2-6}$ alkynyl group" having 2 to 6 carbon atoms.

The "$C_{3-8}$ cycloalkyl-$C_{2-8}$ alkynyl group" refers to a group in which the above $C_{3-8}$ cycloalkyl group and the above $C_{2-8}$ alkynyl group are bonded to each other. Examples of the group include a 3-cyclopropylprop-1-yn-1-yl group, 3-cyclobutylprop-1-yn-1-yl group, 3-cyclopentylprop-1-yn-1-yl group, 3-cyclohexylprop-1-yn-1-yl group, 4-cyclopropylbut-1-yn-1-yl group, 5-cyclopropylpent-1-yn-1-yl group and 6-cyclopropylhex-1-yn-1-yl group.

In the present invention, the "$C_{3-8}$ cycloalkenyl group" refers to an alkenyl group having 3 to 8 carbon atoms which has a carbon-carbon double bond in any one or more locations and has a cyclic moiety. Examples of the group include a 1-cyclopenten-1-yl group, 2-cyclopenten-1-yl group, 1-cyclohexen-1-yl group, 2-cyclohexen-1-yl group and 3-cyclohexen-1-yl group. The group is preferably a "$C_{3-6}$ cycloalkenyl group" having 3 to 6 carbon atoms.

In the present invention, the "$C_{3-8}$ cycloalkenyl-$C_{1-8}$ alkyl group" refers to a group in which an alkenyl group having 3 to 8 carbon atoms, which has a carbon-carbon double bond in any one or more locations and has a cyclic moiety, and the above $C_{1-8}$ alkyl group are bonded to each other. Examples of the group include a 1-cyclopenten-1-ylmethyl group, 1-cyclopenten-1-ylethyl group, 2-cyclopenten-1-ylmethyl group, 2-cyclopenten-1-ylethyl group, 1-cyclohexen-1-ylmethyl group, 1-cyclohexen-1-ylethyl group, 2-cyclohexen-1-ylmethyl group, 2-cyclohexen-1-ylethyl group, 3-cyclohexen-1-ylmethyl group and 3-cyclohexen-1-ylethyl group.

Specific examples of the "$C_{1-6}$ alkoxy group" of the present invention include a methoxy group, ethoxy group, n-propoxy group, isopropoxy group, n-butoxy group, isobutoxy group, sec-butoxy group, tert-butoxy group, n-pentoxy group, isopentoxy group, neopentoxy group, 4-methylbutoxy group, 1-ethylpropoxy group, n-hexyloxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group and 2-ethylbutoxy group.

The "$C_{6-10}$ aryl-$C_{1-6}$ alkoxy group" of the present invention refers to a group in which the following $C_{6-10}$ aryl group and the $C_{1-6}$ alkoxy group are bonded to each other. Examples of the group include a phenylmethoxy group, 2-phenylethoxy group, 3-phenyl-n-propoxy group, 4-phenyl-n-butoxy group, 5-phenyl-n-pentoxy group, naphthylmethoxy group, 2-naphthylethoxy group and 5-naphthyl-n-pentoxy group.

Specific examples of the "$C_{1-6}$ alkylthio group" of the present invention include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 4-methylbutylthio group, 1-ethylpropylthio group, n-hexylthio group, isohexylthio group, 4-methylpentylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group and 2-ethylbutylthio group.

Specific examples of the "$C_{1-6}$ alkylsulfinyl group" of the present invention include a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-pentylsulfinyl group, isopentylsulfinyl group, neopentylsulfinyl group, 4-methylbutylsulfinyl group, 1-ethylpropylsulfinyl group, n-hexylsulfinyl group, isohexylsulfinyl group, 4-methylpentylsulfinyl group, 3-methylpentylsulfinyl group, 2-methylpentylsulfinyl group, 1-methylpentylsulfinyl group, 3,3-dimethylbutylsulfinyl group, 2,2-dimethylbutylsulfinyl group, 1,1-dimethylbutylsulfinyl group, 1,2-dimethylbutylsulfinyl group, 1,3-dimethylbutylsulfinyl group, 2,3-dimethylbutylsulfinyl group, 1-ethylbutylsulfinyl group and 2-ethylbutylsulfinyl group.

In the present invention, examples of the "$C_{1-8}$ acyl group" include a formyl group, acetyl group, propionyl group, butyryl group, isobutyryl group, valeryl group, isovaleryl group and pivaloyl group.

In the present invention, examples of the "$C_{2-8}$ acyloxy group" include an acetyloxy group, propionyloxy group, butyryloxy group, isobutyryloxy group, valeryloxy group, isovaleryloxy group and pivaloyloxy group.

In the present invention, the "$C_{6-10}$ aryl group" refers to a monocyclic or polycyclic aryl group having 6 to 10 carbon atoms. Here, the polycyclic aryl group encompasses a partially saturated group, in addition to a fully unsaturated group. Accordingly, examples of the $C_{6-10}$ aryl group include a phenyl group, naphthyl group, indenyl group, indanyl group and tetralinyl group.

In the present invention, examples of the "halogen" atom in a halogen atom, halo-$C_{1-6}$ alkyl group or halo-$C_{1-6}$ alkoxy group include a fluorine atom, chlorine atom, bromine atom and iodine atom.

Examples of the "halo-$C_{1-6}$ alkyl group" of the present invention include a trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2-trifluoroethyl group, 3,3,3-trifluoropropyl group, pentafluoroethyl group and 2,2,2-trifluoro-1-trifluoromethylethyl group.

Examples of the "halo-$C_{1-6}$ alkoxy group" of the present invention include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group and 2,2,2-trifluoro-1-(trifluoromethyl)ethoxy group.

Specific examples of the "$C_{1-6}$ alkylsulfonyl group" of the present invention include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 4-methylbutylsulfonyl group, 1-ethylpropylsulfonyl group, n-hexylsulfonyl group, isohexylsulfonyl group, 4-methylpentylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group and 2-ethylbutylsulfonyl group.

Specific examples of "$C_{6-10}$ arylsulfonyl group" of the present invention include a benzenesulfonyl group, p-toluenesulfonyl group, p-chlorobenzenesulfonyl group, naphthalen-1-ylsulfonyl group and naphthalen-2-ylsulfonyl group.

Specific examples of the "$C_{1-6}$ alkoxycarbonyl group" of the present invention include a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 4-methylbutoxycarbonyl group, 1-ethylpropoxycarbonyl group, n-hexyloxycarbonyl group, isohexyloxycarbonyl group, 4-methylpentoxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, a 1-ethylbutoxycarbonyl group and a 2-ethylbutoxycarbonyl group.

Specific examples of the "mono-$C_{1-6}$ alkylamino group" of the present invention include a methylamino group, ethylamino group, n-propylamino group, isopropylamino group, n-butylamino group, sec-butylamino group, tert-butylamino group, n-pentylamino group, isopentylamino group, neopentylamino group, 4-methylbutylamino group, 1-ethylpropylamino group, n-hexylamino group, isohexylamino group, 4-methylpentylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group and 2-ethylbutylamino group.

Specific examples of the "di-$C_{1-6}$ alkylamino group" of the present invention include a dimethylamino group, methylethylamino group, diethylamino group, methyl-n-propylamino group, ethyl-n-propylamino group, di-n-propylamino group, methylisopropylamino group, ethylisopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group and dihexylamino group.

In the present invention, the "5- to 11-membered heterocycle" refers to a 5- to 7-membered aromatic heterocycle, saturated heterocycle or unsaturated heterocycle which contains 1 to 3 heteroatoms selected from a nitrogen atom, oxygen atom and sulfur atom as ring-forming atoms other than carbon atoms, or a fused heterocycle in which the aforementioned heterocycle is fused with a benzene ring. Examples of the heterocycle include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyridazin-3-yl group, pyridazin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-4-yl group, benzofuran-5-yl group, benzofuran-6-yl group, benzofuran-7-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-4-yl group, indol-5-yl group, indol-6-yl group, indol-7-yl group, isoindol-4-yl group, isoindol-5-yl group, isoindol-6-yl group, isoindol-7-yl group, isobenzofuran-4-yl group, isobenzofuran-5-yl group, isobenzofuran-6-yl group, isobenzofuran-7-yl group, chromen-5-yl group, chromen-6-yl group, chromen-7-yl group, chromen-8-yl group, imidazol-1-yl group, imidazol-2-yl group, imidazol-4-yl group, imidazol-5-yl group, pyrazol-1-yl group, pyrazol-3-yl group, pyrazol-4-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrimidin-2-yl group, pyrimidin-4-yl group, pyrimidin-5-yl group, pyridin-2-yl group, pyridin-3-yl group, pyridin-4-yl group, pyrrolidin-2-yl group, pyrrolidin-3-yl group, benzimidazol-1-yl group, benzimidazol-2-yl group, benzothiazol-2-yl group, benzoxazol-2-yl group, quinolin-2-yl group, quinolin-3-yl group, quinolin-4-yl group, isoquinolin-1-yl group, isoquinolin-3-yl group, isoquinolin-4-yl group, 1,3,4-thiadiazol-2-yl group and morpholin-4-yl group.

Examples of the 5- to 7-membered carbocycle in the phrase "$R^6$ and $R^7$ may together form a 5- to 7-membered carbocycle" include a cyclopentane ring, cyclohexane ring and cycloheptane ring.

In the present invention, the "substituent" in the "$C_{6-10}$ aryl group or 5- to 11-membered heterocycle" may be a halogen atom, $C_{1-8}$ alkyl group, halo-$C_{1-6}$ alkyl group, cyano group, nitro group, hydroxy group, amino group, mono-$C_{1-6}$ alkylamino group, di-$C_{1-6}$ alkylamino group, $C_{1-6}$ alkoxy group, halo-$C_{1-6}$ alkoxy group, carboxyl group, $C_{2-8}$ acyloxy group, $C_{1-6}$ alkoxycarbonyl group, $C_{6-10}$ aryl group, $C_{6-10}$ aryl-$C_{1-6}$ alkoxy group (which may be substituted with the same or different 1 to 3 substituents selected from a $C_{1-8}$ alkyl group, halogen atom or $C_{1-6}$ alkoxy group), $C_{1-6}$ alkylthio group, $C_{1-6}$ alkylsulfinyl group, $C_{1-6}$ alkylsulfonyl group or $C_{6-10}$ arylsulfonyl group. The number of substituents is not particularly limited; however, when there are two or more substituents, they may be the same or different.

In the present invention, the "$C_{3-15}$ alkyl chain" refers to a linear or branched divalent hydrocarbon chain having 3 to 15 carbon atoms. Examples thereof include a propylene chain, methylethylene chain, butylene chain, 1,2-dimethylethylene chain, pentylene chain, 1-methylbutylene chain, 2-methylbutylene chain, hexylene chain, heptylene chain, octylene chain, nonylene chain, decalene chain, undecalene chain, dodecalene chain, tridecalene chain, tetradecalene chain and pentadecalene chain.

The "$C_{3-15}$ alkenyl chain" refers to a linear or branched divalent hydrocarbon chain having 3 to 15 carbon atoms, which has a carbon-carbon double bond in any one or more locations in the "$C_{3-15}$ alkyl chain" encompassed in the above $C_{3-15}$ alkyl chain. Examples thereof include a propenylene chain, methylvinylene chain, butenylene chain (such as a 1-butenylene chain or 2-butenylene chain), 1,2-dimethylvinylene chain, pentenylene chain, 1-methylbutenylene chain, 2-methylbutenylene chain, hexenylene chain, heptenylene chain, octenylene chain, nonenylene chain, decenylene chain and isoprenylene chain.

The "$C_{3-15}$ alkynyl chain" refers to a linear or branched divalent hydrocarbon chain having 3 to 15 carbon atoms, which has a carbon-carbon triple bond in any one or more locations in the "$C_{3-15}$ alkyl chain" encompassed in the above $C_{3-15}$ alkyl chain. Examples thereof include a propynylene chain, methylethynylene chain, butynylene chain (such as a 1-butynylene chain or 2-butynylene chain), 1,2-dimethylethynylene chain, pentynylene chain, 1-methylbutynylene chain, 2-methylbutynylene chain, hexynylene chain, heptynylene chain, octynylene chain, nonynylene chain and decynylene chain.

Other groups not defined here are as conventionally defined.

Preferred embodiments of the present invention can be as follows.

In the general formula (1), $R^1$ represents a hydrogen atom, $C_{1-8}$ alkyl group, $C_{1-6}$ alkoxy-$C_{1-8}$ alkyl group or $C_{1-8}$ acyl group. $R^1$ preferably represents a hydrogen atom, methoxymethyl group, methyl group, ethyl group or propyl group, and more preferably hydrogen atom.

In the general formula (1), $R^2$, $R^3$, $R^4$ and $R^5$ each independently represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{1-6}$ alkoxy group, $C_{6-10}$ aryl group, $C_{6-10}$ aryl-$C_{1-8}$ alkyl group, $C_{6-10}$ aryl-$C_{2-6}$ alkenyl group, $C_{1-6}$ alkylthio group, $C_{1-6}$ alkylsulfinyl group, $C_{1-6}$ alkylsulfonyl group, $C_{6-10}$ arylsulfonyl group, nitro group, amino group, mono-$C_{1-6}$ alkylamino group, di-$C_{1-6}$ alkylamino group, $C_{3-8}$ cycloalkyl-$C_{1-8}$ alkyl group, $C_{3-8}$ cycloalkyl-$C_{2-8}$ alkenyl group, $C_{3-8}$ cycloalkyl-$C_{2-8}$ alkynyl group or halo-$C_{1-6}$ alkyl group. Preferable examples among these include a hydrogen atom, halogen atom such as a chlorine atom, $C_{1-8}$ alkyl group, $C_{3-8}$ cycloalkyl group, $C_{2-8}$ alkenyl group, $C_{1-6}$ alkoxy group, $C_{6-10}$ aryl group, $C_{6-10}$ aryl-$C_{1-8}$ alkyl group, $C_{6-10}$ aryl-$C_{2-6}$ alkenyl group, nitro group, $C_{1-10}$ cycloalkyl-$C_{1-8}$ alkyl group and $C_{3-8}$ cycloalkyl-$C_{2-8}$ alkenyl group.

The halogen atom in $R^2$, $R^3$, $R^4$ and $R^5$ is preferably a chlorine atom or iodine atom.

Examples of the $C_{1-8}$ alkyl group in $R^2$, $R^3$, $R^4$ and $R^5$ include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group and n-octyl group. Among these, a methyl group, n-propyl group, isopropyl group, isobutyl group, n-pentyl group and n-octyl group are preferable.

Examples of the $C_{3-8}$ cycloalkyl group in $R^2$, $R^3$, $R^4$ and $R^5$ include a cyclopropyl group, cyclobutyl group, cyclopentyl group, cyclohexyl group, cycloheptyl group and cyclooctyl group. Among these, a cyclohexyl group is preferable.

Examples of the $C_{2-8}$ alkenyl group in $R^2$, $R^3$, $R^4$ and $R^5$ include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, kept-1-en-1-yl group, kept-6-en-1-yl group, oct-1-en-1-yl group and oct-7-en-1-yl group. Among these, prop-1-en-1-yl group, prop-2-en-1-yl group, but-1-en-1-yl group, but-2-en-1-yl group, but-3-en-1-yl group, oct-1-en-1-yl group and oct-7-en-1-yl group are preferable.

Examples of the $C_{1-6}$ alkoxy group in $R^2$, $R^3$, $R^4$ and $R^5$ include a methoxy group, ethoxy group, n-propoxy group, isopropoxy group, n-butoxy group, isobutoxy group, sec-butoxy group, tert-butoxy group, n-pentoxy group, isopentoxy group, neopentoxy group, 4-methylbutoxy group, 1-ethylpropoxy group, n-hexyloxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group and 2-ethylbutoxy group. Among these, a methoxy group is preferable.

Examples of the $C_{6-10}$ aryl group in $R^2$, $R^3$, $R^4$ and $R^5$ include a phenyl group, naphthyl group, indenyl group, indanyl group and tetralinyl group. Among these, a phenyl group is preferable.

The $C_{6-10}$ aryl-$C_{1-8}$ alkyl group in $R^2$, $R^3$, $R^4$ and $R^5$ is preferably a $C_{6-10}$ aryl-$C_{1-4}$ alkyl group such as a benzyl group or phenethyl group.

The $C_{6-10}$ aryl-$C_{2-6}$ alkenyl group in $R^2$, $R^3$, $R^4$ and $R^5$ is preferably a $C_{6-10}$ aryl-$C_{2-4}$ alkenyl group such as a styryl group.

The $C_{3-8}$ cycloalkyl-$C_{1-8}$ alkyl group in $R^2$, $R^3$, $R^4$ and $R^5$ is preferably a $C_{3-6}$ cycloalkyl-$C_{1-4}$ alkyl group such as a cyclohexylethyl group.

The $C_{3-8}$ cycloalkyl-$C_{2-8}$ alkenyl group in $R^2$, $R^3$, $R^4$ and $R^5$ is preferably a $C_{3-6}$ cycloalkyl-$C_{2-4}$ alkenyl group such as a cyclohexylethenyl group.

In the general formula (1), $R^6$ and $R^7$ each independently represents a hydrogen atom, $C_{1-8}$ alkyl group, $C_{3-8}$ cycloalkyl group, $C_{6-10}$ aryl group which may have 1 to 3 substituents or a 5- to 11-membered heterocyclic group which may have 1 to 3 substituents, or $R^6$ and $R^7$ may together form a 5- to 7-membered carbocycle.

$R^6$ and $R^7$ each preferably represents a $C_{1-8}$ alkyl group, $C_{3-8}$ cycloalkyl group, $C_{6-10}$ aryl group which may have 1 to 3 substituents or 5- to 11-membered heterocyclic group which may have 1 to 3 substituents, and particularly preferably a $C_{1-8}$ alkyl group, $C_{6-10}$ aryl group which may have 1 to 3 substituents or 5- to 11-membered heterocycle which may have 1 to 3 substituents.

Examples of the $C_{1-8}$ alkyl group in $R^6$ and $R^7$ include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group and n-octyl group. Among these, alkyl groups having 1 to 4 carbon atoms such as a methyl group, ethyl group, n-propyl group, isopropyl group, n-butyl group and t-butyl group are preferable.

Preferable examples of the $C_{3-8}$ cycloalkyl group in $R^6$ and $R^7$ include cycloalkyl groups having 3 to 6 carbon atoms such as a cyclopropyl group and cyclobutyl group.

The aryl group which may have 1 to 3 substituents in $R^6$ and $R^7$ is preferably a phenyl group which may have 1 to 3 substituents. Examples of the phenyl group include a phenyl group, 4-methylphenyl group, 4-ethylphenyl group, 4-(1-methylethyl)phenyl group, 4-(1,1-dimethylethyl)phenyl group, 4-fluorophenyl group, 3,4-difluorophenyl group, 4-chlorophenyl group, 4-bromophenyl group, 4-trifluoromethylphenyl group, 4-cyanophenyl group, 4-nitrophenyl group, 4-dimethylaminophenyl group, 4-trifluoromethoxyphenyl group, 3-bromo-4-fluorophenyl group, 3,4-dichlorophenyl group, 2,3,4-trichlorophenyl group, 2-methoxyphenyl group, 3-methoxyphenyl group, 4-methoxyphenyl group, 3,4-dimethoxyphenyl group, 3-fluoro-4-methoxyphenyl group, 3,4,5-trimethoxyphenyl group, 4-ethoxyphenyl group, 4-(n-propoxy)phenyl group, 4-(n-butoxy)phenyl group, 4-(2-methylpropoxy)phenyl group, 4-(1-methylethoxy)phenyl group, 4-(1,1-dimethylethoxy)carbonylphenyl group, 3-fluoro-4-(1-methylethoxy)phenyl group, 3-methoxy-4-(1-methylethoxy)phenyl group, 3-methoxy-4-(n-propoxy)phenyl group, 3-hydroxyphenyl group, 4-hydroxyphenyl group, 3-benzyloxyphenyl group, 4-benzyloxyphenyl group, 3-carboxyphenyl group, 4-(4-methylbenzyloxy)phenyl group, 4-(4-chlorobenzyl)phenyl group, 4-(3,5-dimethoxybenzyloxy)phenyl group and 4-methoxybenzylphenyl group.

Preferable examples of the 5- to 11-membered heterocycle which may have 1 to 3 substituents in $R^6$ and $R^7$ include a 2-furyl group, 3-thienyl group, 1,3-benzodioxol-5-yl group, 1,4-benzodioxan-6-yl group, 3,4-dihydro-2H-1,5-benzodioxepin-7-yl group, 2,3-dihydrobenzofuran-6-yl group, benzofuran-4-yl group, benzofuran-5-yl group, benzothiophen-4-yl group, benzothiophen-5-yl group, indol-4-yl group, indol-5-yl group, indol-6-yl group, indol-7-yl group, isoindol-4-yl group, isoindol-5-yl group, isoindol-6-yl group, isoindol-7-yl group, isobenzofuran-4-yl group, isobenzofuran-5-yl group, chromen-4-yl group, chromen-5-yl group, 2-methoxypyridin-3-yl group, 2-(1-methylethoxy)pyridin-3-yl group and quinoxalin-6-yl group.

Preferable examples of the substituent for the $C_{6-10}$ aryl group and the 5- to 11-membered heterocyclic group in $R^6$ and $R^7$ include halogen atoms such as a fluorine atom, chlorine atom and bromine atom, $C_{1-6}$ alkyl groups such as a methyl group, ethyl group, isopropyl group and t-butyl group, cyano group, nitro group, di-$C_{1-6}$ alkylamino groups such as a dimethylamino group, halo-$C_{1-6}$ alkyl groups such as a trifluoromethyl group, $C_{1-6}$ alkoxy groups such as a methoxy group, ethoxy group, n-propoxy group, isopropoxy group, n-butoxy group, isobutoxy group and t-butoxy group, halo-$C_{1-6}$ alkoxy groups such as a trifluoromethyloxy group, $C_{6-10}$ aryl groups such as a phenyl group, and $C_{1-6}$ alkoxycarbonyl groups such as a t-butoxycarbonyl group.

When $R^6$ and $R^7$ together form a 5- to 7-membered carbocycle, the formed carbocycle is preferably a cyclopentane ring, cyclohexane ring or cycloheptane ring.

In the general formula (1), $R^8$ represents a hydrogen atom, $C_{1-8}$ alkyl group, halo-$C_{1-6}$ alkyl group or $C_{3-8}$ cycloalkyl group. $R^8$ preferably represents a hydrogen atom or $C_{1-8}$ alkyl group such as a methyl group.

In the general formula (1), $R^9$ and $R^{10}$ each independently represents a hydrogen atom, hydroxy group or $C_{1-6}$ alkoxy group, or $R^9$ and $R^{10}$ together represent a carbonyl group.

Preferably, $R^9$ and $R^{10}$ each represents a hydrogen atom or hydroxy group, or $R^9$ and $R^{10}$ together form a carbonyl group.

In the general formula (1), L represents a $C_{3-15}$ alkyl chain, $C_{3-15}$ alkenyl chain or $C_{3-15}$ alkynyl chain.

The $C_{3-15}$ alkyl chain in L is preferably a butylene chain, pentylene chain, 1-methylbutylene chain, hexylene chain, heptylene chain, octylene chain, nonylene chain or decalene chain.

The $C_{3-15}$ alkenyl chain in L is preferably a butenylene chain (such as a 1-butenylene chain or 2-butenylene chain).

The $C_{3-15}$ alkynyl chain in L is preferably a butynylene chain (such as a 1-butynylene chain or 2-butynylene chain).

Examples of the addition salt of the carbinol derivative represented by the general formula (1) include alkaline metal salts such as sodium salts and potassium salts, alkaline earth metal salts such as calcium salts and magnesium salts, organic base salts such as ammonium salts and trialkylamine salts, mineral acid salts such as hydrochlorides and sulfates, and organic acid salts such as acetates; however, the addition salt is not particularly limited insofar as it is a pharmaceutically acceptable salt.

Examples of the solvate of the carbinol derivative represented by the general formula (1) include a hydrate.

When the present compound has a geometric isomer or an optical isomer, these isomers are also within the scope of the present invention.

The compound (I) can be prepared by various known methods without particular limitations, and can be prepared according to the following reaction process, for example.

Specifically, a derivative represented by the general formula (IV) is obtained by reacting the hydroxyl group of a 4-hydroxyphenylhexafluoropropyl derivative represented by the general formula (II) with a dihalide (III). The compound (I) can be prepared by reacting the resulting compound represented by the general formula (IV) with a cyclic amide compound represented by the general formula (V). This reaction route is shown in the following chemical reaction formula.

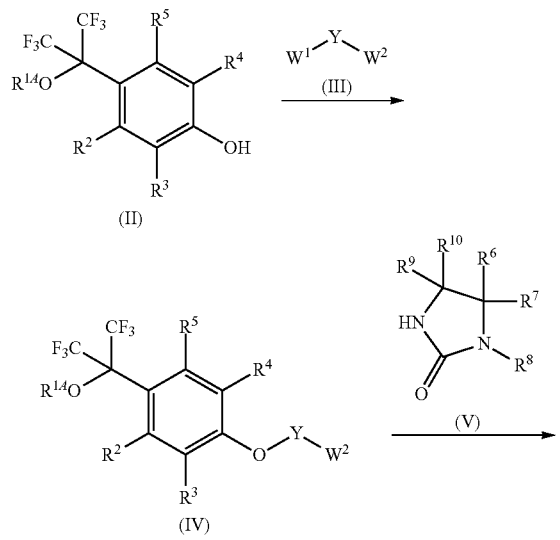

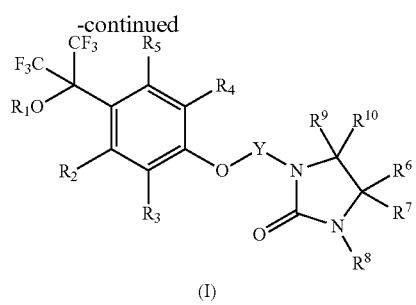

In the formula, $R^{14}$ represents a protecting group or the above $R^1$, $R^2$ to $R^{10}$ and L are as defined above, and $W^1$ and $W^2$ each represents a halogen atom.

The objective derivative of the general formula (IV) is obtained by reacting a 4-hydroxyphenylhexafluoropropyl derivative represented by the general formula (II) with an excess of a dihalide (III) in a solvent in the presence or absence of a base. The solvent is not particularly limited, and tetrahydrofuran, toluene, dioxane, N,N-dimethylformamide, N-methylpyrrolidone, dimethyl sulfoxide, acetonitrile, propionitrile, acetone, methyl ethyl ketone and water can be used singly or in combination, for example. The dihalide (III) may also be used as a solvent. The base is not particularly limited, and it is possible to use alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, metal salts of alcohols such as sodium methoxide, potassium methoxide, sodium ethoxide, potassium ethoxide, t-butoxysodium and t-butoxypotassium, and organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium and t-butyllithium, for example. The objective derivative of the general formula (IV) is obtained by reaction at −80 to 150° C., and preferably 0 to 100° C., for one minute to five days, and preferably one hour to three days.

The objective compound (I) can be prepared by reacting the halogenated derivative (IV) obtained in the above reaction with an imide compound (V) in a solvent in the presence or absence of a base. The solvent is not particularly limited, and tetrahydrofuran, toluene, dioxane, N,N-dimethylformamide, N-methylpyrrolidone, dimethyl sulfoxide, acetonitrile, propionitrile, acetone, methyl ethyl ketone and water can be used singly or in combination, for example. The dihalide (III) may also be used as a solvent. The base is not particularly limited, and it is possible to use alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, metal salts of alcohols such as sodium methoxide, potassium methoxide, sodium ethoxide, potassium ethoxide, t-butoxysodium and t-butoxypotassium, and organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium and t-butyllithium, for example. The objective compound is obtained by reaction at −80 to 150° C., and preferably 0 to 100° C., for one minute to five days, and preferably one hour to three days.

The 4-hydroxyphenylhexafluoropropyl derivative represented by the general formula (II) can be prepared by various methods without particular limitations, and can be prepared according to the following reaction process, for example.

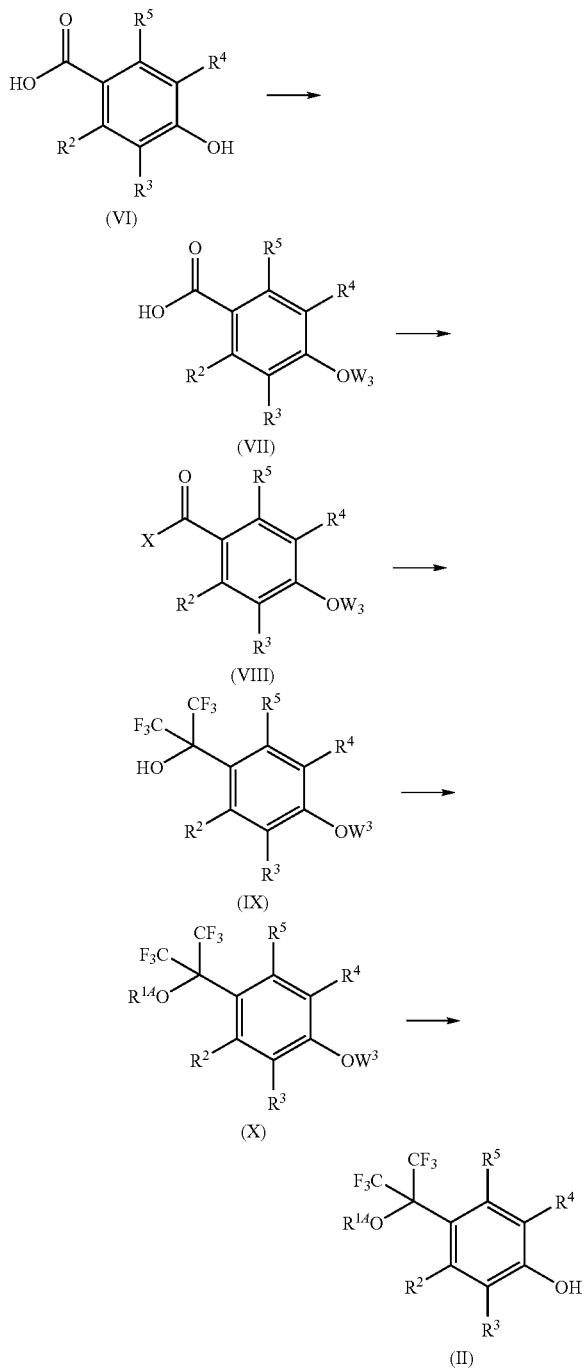

In the formula, $R^{14}$ represents a protecting group or the above $R^1$, $R^2$ to $R^5$ are as defined above, $W^3$ represents a protecting group, and X represents halogen or a leaving residue.

The protecting group $W^3$ can be introduced into a 4-hydroxybenzoic acid derivative (VI) under the protection conditions for the protecting group with reference to a generally used method (Protective Groups in Organic Synthesis Third Edition, John Wiley & Sons, Inc.).

A hexafluorocarbinol compound (IX) can be derived from the carboxylic acid compound (VII) obtained by the above method by conversion with reference to a known document (Tetrahedron 61 (2006) 1813-1819). The hexafluorocarbinol compound (IX) can be derived from the carboxylic acid compound (VII) by conversion to an acid halide, acid anhydride, ester or amide (VIII) with reference to a generally used method (Comprehensive Organic Transformations Second Edition, John Wiley & Sons, Inc.) and subsequent treatment with (trifluoromethyl) trimethylsilane and tetramethylammonium fluoride.

(Trifluoromethyl)trimethylsilane is used as a trifluoromethyl source according to the document; however, the trifluoromethyl source is not limited thereto. Triethyl(trifluoromethyl)silane, triisopropyl(trifluoromethyl)silane, methyldiphenyl(trifluoromethyl)silane, dimethyl(diphenyl)trifluoromethylsilane or the like may also be used. Perfluoroalkylation can also be carried out by use of perfluoroalkylsilanes such as (pentafluoroethyl)trimethylsilane or (heptafluoropropyl)trimethylsilane.

Tetramethylammonium fluoride is used as a fluorine compound; however, the fluorine compound is not limited thereto. It is possible to use tetraalkylammonium salts such as tetraethylammonium fluoride and tetrabutylammonium fluoride, and metal salts such as lithium fluoride, sodium fluoride, potassium fluoride and cesium fluoride. Solvents such as tetrahydrofuran, toluene, dioxane, N,N-dimethylformamide, N-methylpyrrolidone, tetramethylurea, dimethyl sulfoxide, acetonitrile, propionitrile, acetone and methyl ethyl ketone can be used singly or in combination, in addition to dimethoxyethane.

The objective compound (X) can be prepared by reacting the resulting hexafluorocarbinol compound (IX) with a halide of $R^{14}$ in a solvent in the presence or absence of a base. The solvent is not particularly limited, and tetrahydrofuran, toluene, dioxane, N,N-dimethylformamide, N-methylpyrrolidone, tetramethylurea, dimethyl sulfoxide, acetonitrile, propionitrile, acetone, methyl ethyl ketone and water can be used singly or in combination, for example. The halide of $R^{14}$ may also be used as a solvent. The base is not particularly limited, and it is possible to use alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, metal salts of alcohols such as sodium methoxide, potassium methoxide, sodium ethoxide, potassium ethoxide, t-butoxysodium and t-butoxypotassium, and organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium and t-butyllithium, for example.

$R^{14}$ can also be introduced into the hexafluorocarbinol compound (IX) as a protecting group. The introduction can be carried out under the protection conditions for the protecting group with reference to a generally used method (Protective Groups in Organic Synthesis Third Edition, John Wiley & Sons, Inc.).

The deprotection of the protecting group $W^3$ of the compound (X) obtained by the above method is not particularly limited, and can be carried out under the deprotection conditions for the protecting group with reference to a generally used method (Protective Groups in Organic Synthesis Third Edition, John Wiley & Sons, Inc.).

The 4-hydroxyphenylhexafluoropropyl derivative represented by the general formula (II) can also be prepared by the following method.

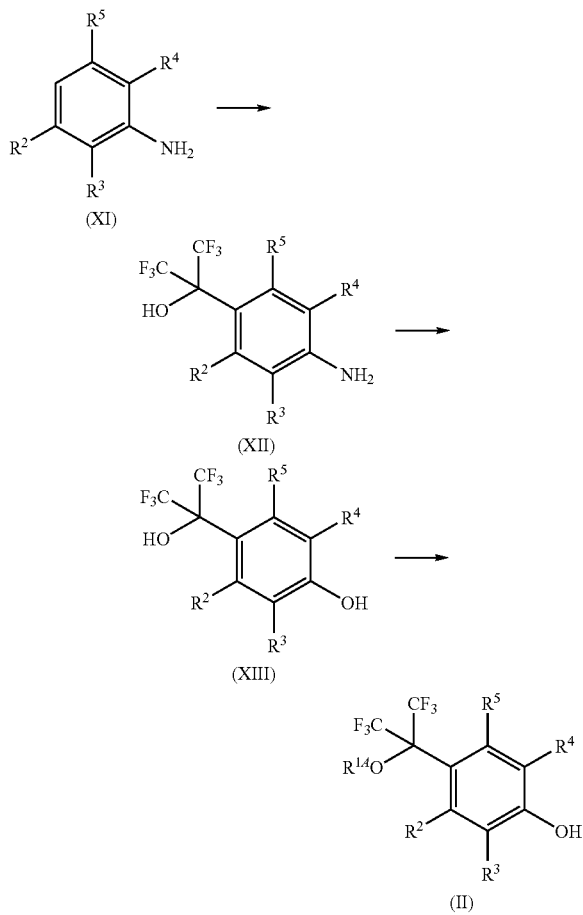

In the formula, $R^{1A}$ represents a protecting group or the above $R^1$, and $R^2$ to $R^5$ are as defined above.

A compound (XII) can be synthesized by reacting an aniline derivative (XI) with hexafluoroacetone in a solvent or without a solvent in the presence or absence of an acid. The solvent is not particularly limited, and tetrahydrofuran, toluene, dioxane, N,N-dimethylformamide, N-methylpyrrolidone, tetramethylurea, dimethyl sulfoxide and water can be used singly or in combination, for example. The acid is not particularly limited, and it is possible to use acids including, but not limited to, p-toluenesulfonic acid, benzenesulfonic acid, methanesulfonic acid, trifluoromethanesulfonic acid, acetic acid, formic acid, sulfuric acid and trifluoroacetic acid. The objective compound is obtained by reaction at 0 to 250° C., and preferably 100 to 200° C., for one minute to five days, and preferably one hour to three days.

The amino group of the compound (XII) can be converted to a hydroxyl group with reference to a generally used method (Comprehensive Organic Transformations Second Edition, John Wiley& Sons, Inc.). Specifically, a phenol derivative (XIII) can be derived from the compound (XII) by diazotizing the compound and thermally decomposing the resulting diazonium salt in an acidic aqueous solution.

$R^{1A}$ can be introduced into the phenol derivative (XII) as a protecting group. The introduction can be carried out under the protection conditions for the protecting group with reference to a generally used method (Protective Groups in Organic Synthesis Third Edition, John Wiley & Sons, Inc.).

The 4-hydroxyphenylhexafluoropropyl derivative represented by the general formula (II) can also be prepared by a known method (WO 2006/037480 or U.S. Patent Publication No. 3396159).

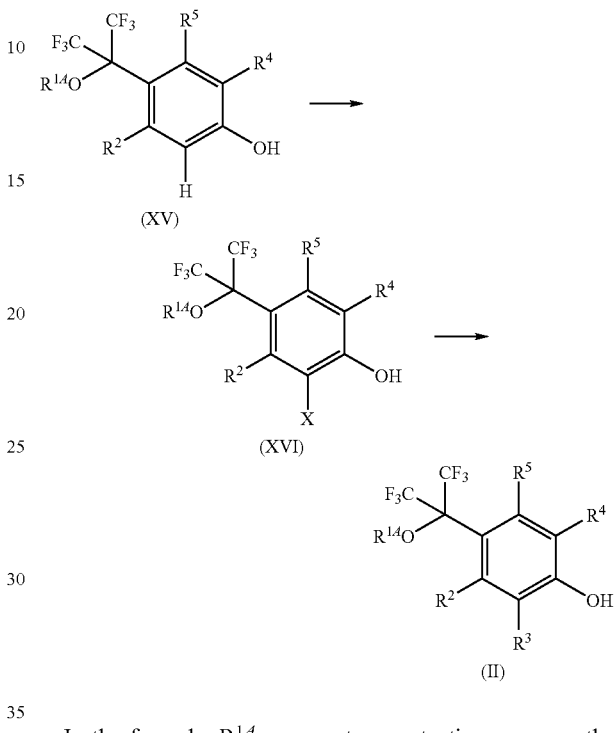

In the formula, $R^{1A}$ represents a protecting group or the above $R^1$, $R^2$ to $R^5$ are as defined above, and X represents halogen.

The objective derivative of the general formula (XVI) is obtained by reacting a 4-hydroxyphenylhexafluoropropyl derivative represented by the general formula (XV) with a halogenating agent in a solvent in the presence or absence of a base. The solvent is not particularly limited, and tetrahydrofuran, toluene, dioxane, N,N-dimethylformamide, N-methylpyrrolidone, dimethyl sulfoxide, acetonitrile, propionitrile, acetone, methyl ethyl ketone, methanol, ethanol, isopropanol and water can be used singly or in combination, for example. The halogenating agent or the base may also be used as a solvent. The base is not particularly limited, and it is possible to use alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, metal salts of alcohols such as sodium methoxide, potassium methoxide, sodium ethoxide, potassium ethoxide, t-butoxysodium and t-butoxypotassium, organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium and t-butyllithium, and organic base compounds such as pyridine and triethylamine, for example. The halogenating agent is not particularly limited, and it is possible to use chlorine, bromine, iodine, tetrabutylammonium chloride, tetrabutylammonium bromide, tetrabutylammonium iodide, N-chlorosuccinimide, N-bromosuccinimide, N-iodosuccinimide and carbon tetrabromide, for example. The halogenating agent can also be generated in the system for the reaction by oxidizing a halide salt such as potassium bromide, potassium iodide, sodium bromide or sodium iodide with an oxidizing agent such as a hydrogen peroxide solution or sodium hypochlorite solution. The objective derivative of the general formula (XVI) is obtained by reaction at −80 to 150° C., and preferably 0 to 100° C., for one minute to five days, and preferably one hour to three days.

The objective derivative of the general formula (II) is obtained by reacting the 4-hydroxyphenylhexafluoropropyl derivative represented by the general formula (XVI) with an organometallic compound in a solvent in the presence or absence of a base and in the presence of a catalyst. The solvent is not particularly limited, and tetrahydrofuran, toluene, dioxane, N,N-dimethylformamide, N-methylpyrrolidone, dimethyl sulfoxide, acetonitrile, propionitrile, acetone, methyl ethyl ketone, methanol, ethanol, isopropanol and water can be used singly or in combination, for example. The base is not particularly limited, and it is possible to use alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, metal salts of alcohols such as sodium methoxide, potassium methoxide, sodium ethoxide, potassium ethoxide, t-butoxysodium and t-butoxypotassium, organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium and t-butyllithium, and fluoride salts such as tetraethylammonium fluoride, tetrabutylammonium fluoride, lithium fluoride, sodium fluoride, potassium fluoride and cesium fluoride, for example. The catalyst is not particularly limited, and it is possible to use palladium reagents such as [1,1'-bis(diphenylphosphino)ferrocene]dichloropalladium (II), bis(triphenylphosphine)palladium (II) diacetate, bis(triphenylphosphine)dichloropalladium (II), palladium (II) diacetate and tetrakis(triphenylphosphine) palladium (0), for example. The organometallic compound is not particularly limited, and it is possible to use an organoboron compound, organozinc compound, organotin compound or the like having $R^3$. The reaction can also be carried out after transmetallation by addition of a metal halide such as copper (I) bromide or copper (I) iodide. The objective derivative of the general formula (II) is obtained by reaction at −80 to 150° C., and preferably 0 to 100° C., for one minute to five days, and preferably one hour to three days.

The carbinol derivative represented by the general formula (1) according to the present invention is obtained by the above method, and can be further purified by a common purification means such as recrystallization or column chromatography, as necessary. The carbinol derivative can also be converted to the aforementioned desired salt or solvate by a conventional method, as necessary.

The carbinol derivative represented by the general formula (1) or salt thereof, or their solvate obtained in this manner (hereinafter sometimes collectively described as "compound represented by the general formula (1)") has an excellent LXRβ agonist effect as shown in the later-described Test Example, and is useful as an active ingredient in a preventative and/or therapeutic agent for diseases caused by abnormality of cholesterol metabolism in animals including humans, for example, atherosclerosis, arteriosclerosis such as those resulting from diabetes, hyperlipidemia, hypercholesterolemia, lipid-related diseases, inflammatory diseases caused by inflammatory cytokine, skin diseases such as allergic dermatitis, diabetes or Alzheimer's disease.

The pharmaceutical composition of the present invention may contain the carbinol derivative represented by the general formula (1) or salt thereof, or their solvate alone; however, the composition also contains a pharmaceutically acceptable carrier or additive or the like, usually. The administration form of the pharmaceutical composition is not particularly limited and can be appropriately selected according to the therapeutic purpose. For example, the administration form may be any of an oral formulation, injection, suppository, ointment, inhalant, eye drop, nasal drop and patch. The pharmaceutical composition suitable for these administration forms can be prepared by a known formulation method.

An oral solid formulation can be prepared as tablets, coated tablets, granules, powder, capsules, or the like by addition of an excipient and, as necessary, a binder, disintegrant, lubricant, coloring agent, taste-masking agent, odor-masking agent or the like to the compound represented by the general formula (1) and subsequent treatment by a conventional method. The additive may be one generally used in this field. Examples of the excipient include lactose, sucrose, sodium chloride, glucose, starch, calcium carbonate, kaolin, microcrystalline cellulose and silicic acid. Examples of the binder include water, ethanol, propanol, simple syrup, glucose solutions, starch solutions, gelatin solutions, carboxymethylcellulose, hydroxypropylcellulose, hydroxypropyl starch, methylcellulose, ethylcellulose, shellac, calcium phosphate and polyvinylpyrrolidone. Examples of the disintegrant include dry starch, sodium alginate, powdered agar, sodium bicarbonate, calcium carbonate, sodium lauryl sulfate, monoglyceride stearate and lactose. Examples of the lubricant include purified talc, stearates, borax and polyethylene glycol. Examples of the taste-masking agent include sucrose, bitter orange peel, citric acid and tartaric acid.

An oral liquid formulation can be prepared as a drink, syrup, elixir or the like by addition of a taste-masking agent, buffer, stabilizer, odor-masking agent or the like to the compound represented by the general formula (1) and treatment by a conventional method. Examples of the taste-masking agent include those described above. Examples of the buffer include sodium citrate. Examples of the stabilizer include tragacanth, gum arabic and gelatin.

An injection can be prepared as a subcutaneous, intramuscular or intravenous injection by addition of a pH adjuster, buffer, stabilizer, tonicity adjusting agent, local anesthetic or the like to the compound represented by the general formula (1) and treatment by a conventional method. Examples of the pH adjuster and the buffer include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the tonicity adjusting agent include sodium chloride and glucose.

A suppository can be prepared by addition of a known suppository carrier, for example, polyethylene glycol, lanolin, cacao butter or fatty acid triglyceride and, as necessary, a surfactant such as Tween® to the compound represented by the general formula (1) and subsequent treatment by a conventional method.

An ointment is prepared by addition of a base, a stabilizer, humectant, preservative or the like commonly used to the compound represented by the general formula (1) as necessary and mixing by a conventional method. Examples of the base include liquid paraffin, white petrolatum, white beeswax, octyldodecyl alcohol and paraffin. Examples of the preservative include methyl p-hydroxybenzoate, ethyl p-hydroxybenzoate and propyl p-hydroxybenzoate.

In addition to the above formulations, an inhalant, eye drop or a nasal drop can be prepared by a conventional method.

The dose of the compound represented by the general formula (1) varies depending on the age, the body weight, the symptom, the administration form, the frequency of administration, or the like; however, it is usually preferable to orally or parenterally administer the carbinol derivative represented by the general formula (1) to an adult at 1 to 1000 mg per day in one or several doses.

EXAMPLES

The present invention will be described in detail below with reference to Examples; however, the present invention is not limited to these Examples.

Preparation Example 1

Preparation of 4-[1,1,1,3,3,3-hexafluoro-2-(methoxymethyl)oxypropan-2-yl]-2-propylphenol a) Preparation of methyl 4-(2-propen-1-yl)oxybenzoate

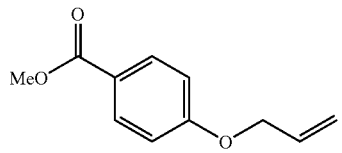

A solution of methyl 4-hydroxybenzoate (15.21 g, 0.10 mol), allyl chloride (11.48 g, 0.15 mol) and potassium carbonate (20.73 g, 0.15 mol) in N,N-dimethylformamide (40 mL) was stirred at 50° C. overnight. Water was added to the reaction solution, followed by extraction with ethyl acetate. Then, the organic layer was washed with saturated saline, dried over anhydrous sodium sulfate and concentrated under reduced pressure. The resulting residue was purified by silica gel column chromatography (hexane:ethyl acetate=10:1) to obtain 19.27 g of the title compound (yield: 100%) as a pale yellow oil.

$^1$H-NMR (CDCl$_3$) δ: 3.86 (3H, s), 4.55 (2H, ddd, J=1.6, 1.6, 5.3 Hz), 5.29 (1H, ddd, J=1.6, 3.0, 10.6 Hz), 5.41 (1H, ddd, J=1.6, 3.0, 17.5 Hz), 6.02 (1H, ddd, J=5.3, 10.6, 17.5 Hz), 6.90 (2H, d, J=8.9 Hz), 7.97 (2H, d, J=8.9 Hz).

b) Preparation of methyl 4-hydroxy-3-(2-propen-1-yl)benzoate

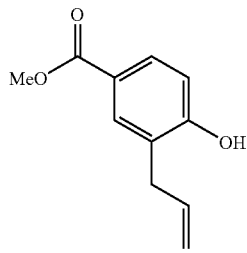

A mixed solution of methyl 4-(2-propen-1-yl)oxybenzoate (19.17 g, 0.10 mol) and N,N-dimethylaniline (40 mL) was heated under reflux at 210° C. for 18 hours. Dilute hydrochloric acid (1 mol/L) was added to the reaction solution, followed by extraction with ethyl acetate. Then, the organic layer was washed with saturated saline, dried over anhydrous sodium sulfate and concentrated under reduced pressure. The resulting residue was purified by silica gel column chromatography (hexane:ethyl acetate=10:1) to obtain 12.26 g of the title compound (yield: 64%) as a colorless powder.

1H-NMR (CDCl3) δ: 3.44 (2H, d, J=6.2 Hz), 3.89 (3H, s), 5.13 (1H, d, J=3.6 Hz), 5.18 (1H, s), 5.93-6.17 (2H, m), 6.85 (1H, d, J=8.9 Hz), 7.78-7.88 (2H, m).

c) Preparation of methyl 4-hydroxy-3-propylbenzoate

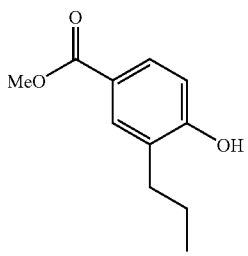

A 10% palladium-carbon catalyst (608 mg) was added to a mixed solution of methyl 4-hydroxy-3-(2-propen-1-yl)benzoate (12.16 g, 0.63 mol) in methanol (50 mL), followed by hydrogenation overnight. The catalyst was separated from the reaction solution by filtration, followed by concentration under reduced pressure. The resulting residue was purified by silica gel column chromatography (hexane:ethyl acetate=5:1) to obtain 10.83 g of the title compound (yield: 88%) as a colorless powder.

1H-NMR (CDCl3) δ: 0.96 (3H, t, J=7.6 Hz), 1.65 (2H, qt, J=7.6, 7.6 Hz), 2.61 (2H, t, J=7.6 Hz), 3.89 (3H, s), 4.16 (1H, brs), 6.82 (1H, d, J=8.6 Hz), 7.78 (1H, dd, J=2.0, 8.6 Hz) 7.83 (1H, d, J=2.0 Hz).

d) Preparation of methyl 4-benzyloxy-3-propylbenzoate

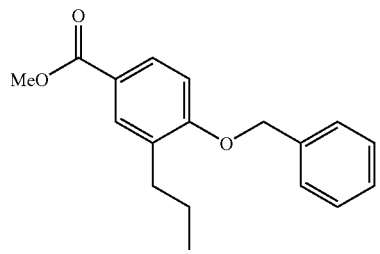

A solution of methyl 4-hydroxy-3-propylbenzoate (7.00 g, 36.0 mmol), benzyl bromide (11.48 g, 0.15 mol) and potassium carbonate (20.73 g, 0.15 mol) in N,N-dimethylformamide (20 mL) was heated with stirring at 80° C. for two hours. Water was added to the reaction solution, followed by extraction with ethyl acetate. Then, the organic layer was washed with saturated saline, dried over anhydrous sodium sulfate and concentrated under reduced pressure. The resulting residue was purified by silica gel column chromatography (hexane:ethyl acetate=10:1) to obtain 10.25 g of the title compound (yield: 100%) as a pale yellow oil.

1H-NMR (CDCl3) δ: 0.95 (3H, t, J=7.6 Hz), 1.66 (2H, qt, J=7.6, 7.6 Hz), 2.67 (2H, t, J=7.6 Hz), 3.86 (3H, s), 5.11 (2H, s), 6.88 (1H, d, J=9.2 Hz), 7.27-7.43 (5H, m) 7.83-7.88 (2H, m).

e) Preparation of 4-benzyloxy-3-propylbenzoic acid

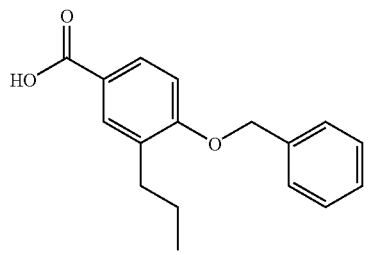

A solution of methyl 4-benzyloxy-3-propylbenzoate (6.84 g, 24.1 mmol) and a sodium hydroxide solution (2 mol/L, 30 ml) in ethanol (100 mL) was heated under reflux for two hours. The reaction solution was concentrated and then made acidic with dilute hydrochloric acid, followed by extraction with ethyl acetate. The organic layer was washed with saturated saline, dried over anhydrous sodium sulfate, and concentrated under reduced pressure. The resulting residue was recrystallized (hexane-ethyl acetate) to obtain 6.35 g of the title compound (yield: 98%) as a white powder.

1H-NMR (CD3OD) δ: 0.94 (3H, t, J=7.6 Hz), 1.65 (2H, qt, J=7.6, 7.6 Hz), 2.68 (2H, t, J=7.6 Hz), 5.09 (2H, s), 6.93 (1H, d, J=9.2 Hz), 7.31-7.49 (7H, m).

f) Preparation of 2-(4-benzyloxy-3-propylphenyl)-1,1,1,3,3,3-hexafluoropropan-2-ol

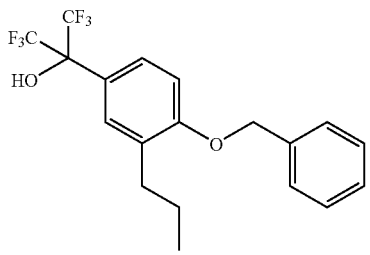

A mixed solution of 4-benzyl-3-propylbenzoic acid (6.34 g, 23.5 mmol) and thionyl chloride (6.3 mL) was heated at 70° C. for two hours. The solvent was evaporated under reduced pressure, and dimethoxyethane (20 mL) and tetramethylammonium fluoride (4.82 g, 51.7 mmol) were added to the resulting residue. (Trifluoromethyl)trimethylsilane (7.35 g, 51.7 mmol) was added dropwise in an argon atmosphere at −78° C., followed by stirring overnight. Dilute hydrochloric acid (1 mol/L) was added to the reaction solution, followed by extraction with ethyl acetate. Then, the organic layer was washed with a saturated sodium bicarbonate solution and saturated saline, dried over anhydrous sodium sulfate and concentrated under reduced pressure. The resulting residue was purified by silica gel column chromatography (hexane:ethyl acetate=10:1) to obtain 6.58 g of the title compound (yield: 72%) as a pale yellow oil.

1H-NMR (CDCl3) δ: 0.94 (3H, t, J=7.6 Hz), 1.65 (2H, qt, J=7.6, 7.6 Hz), 2.68 (2H, t, J=7.6 Hz), 3.39 (1H, s), 5.10 (2H, s), 6.93 (1H, dd, J=2.3, 7.3 Hz), 7.30-7.51 (7H, m).

g) Preparation of 4-[1,1,1,3,3,3-hexafluoro-2-(methoxymethyl)oxypropan-2-yl]-2-propylphenyl benzyl ether

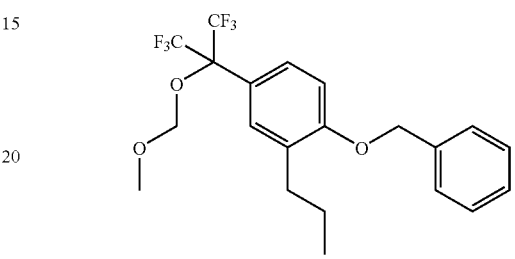

Sodium hydride (purity: 50%) (38.9 mg, 0.81 mmol) was added to a mixed solution of 2-(4-benzyloxy-3-propylphenyl)-1,1,1,3,3,3-hexafluoropropan-2-ol (264.0 mg, 0.67 mmol) in tetrahydrofuran (5 mL) under ice-cooling. Then, chloromethyl methyl ether (65.0 mg, 0.81 mmol) was added, followed by stirring overnight. Water was added to the reaction solution, followed by extraction with ethyl acetate. Then, the organic layer was washed with saturated saline, dried over anhydrous sodium sulfate and concentrated under reduced pressure. The resulting residue was purified by silica gel preparative thin-layer chromatography (hexane:ethyl acetate=10:1) to obtain 264.9 mg of the title compound (yield: 90%) as a pale yellow oil.

1H-NMR (CDCl3) δ: 0.94 (3H, t, J=7.6 Hz), 1.65 (2H, qt, J=7.6, 7.6 Hz), 2.68 (2H, t, J=7.6 Hz), 3.54 (3H, s), 4.83 (2H, s), 5.10 (2H, s), 6.93 (1H, d, J=8.9 Hz), 7.29-7.44 (7H, m).

h) Preparation of 4-[1,1,1,3,3,3-hexafluoro-2-(methoxymethyl)oxypropan-2-yl]-2-propylphenol

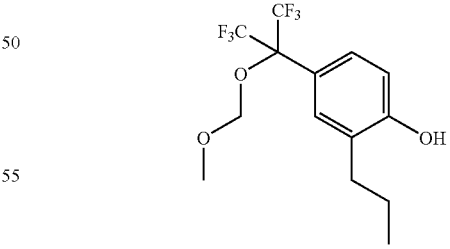

A 10% palladium carbon catalyst (30 mg) was added to a mixed solution of 4-[1,1,1,3,3,3-hexafluoro-2-(methoxymethyl)oxypropan-2-yl]-2-propylphenyl benzyl ether (264.9 mg, 0.61 mmol) in methanol (10 mL), followed by hydrogenation overnight. The catalyst was separated from the reaction solution by filtration, followed by concentration under reduced pressure to obtain 221.1 mg of the title compound (yield: 100%) as a pale yellow oil.

1H-NMR (CDCl3) δ: 0.94 (3H, t, J=7.6 Hz), 1.62 (2H, qt, J=7.6, 7.6 Hz), 2.60 (2H, t, J=7.6 Hz), 3.56 (3H, s), 4.84 (2H, s), 5.77 (1H, brs), 6.81 (1H, d, J=8.6 Hz), 7.30 (1H, d, J=8.6 Hz) 7.33 (1H, s).

Preparation Example 2

Preparation of 2,6-dipropyl-4-[1,1,1,3,3,3-hexafluoro-2-(methoxymethyl)oxypropan-2-yl]phenol

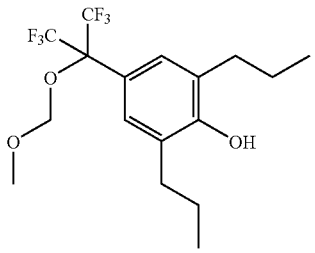

Methyl 4-hydroxy-3-propylbenzoate was propylated according to Preparation Example 1-a) to c) to obtain methyl 3,5-dipropyl-4-hydroxybenzoate, which was then treated by the method of Preparation Example 1-d) to h) to obtain the title compound as a white powder.

1H-NMR (CDCl3) δ: 0.97 (6H, t, J=7.6 Hz), 1.64 (4H, qt, J=7.6, 7.6 Hz), 2.59 (4H, t, J=7.6 Hz), 3.54 (3H, s), 4.83 (2H, s), 4.88 (1H, s), 7.19 (2H, s).

Preparation Example 3

Preparation of 4-[1,1,1,3,3,3-hexafluoro-2-(methoxymethyl)oxypropan-2-yl]-2-propylphenol a) Preparation of 2-(4-amino-3-propylphenyl)-1,1,1,3,3,3-hexafluoro-2-propanol

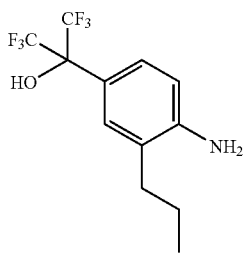

A mixture of 2-propylaniline (3.00 g, 21.2 mmol), trifluoroacetone hydrate (4.5 mL) and p-toluenesulfonic acid monohydrate (422 mg, 2.12 mmol) was reacted in a microwave reactor (manufactured by Biotage AB; Initiator) at 170° C. for 1.5 hours to perform seven batch reactions, followed by reaction with 2-propylaniline (20.86 g, 0.15 mol). The resulting reaction solutions were combined and water was added, followed by extraction with ethyl acetate. The organic layer was washed with saturated saline, dried over anhydrous sodium sulfate, and concentrated under reduced pressure. The resulting residue was purified by silica gel column chromatography (hexane:ethyl acetate=3:1) to obtain 34.70 g of the title compound (yield: 75%) as a yellow brown crystalline powder.

1H-NMR (CDCl3) δ: 0.94 (3H, t, J=7.6 Hz), 1.65 (2H, qt, J=7.6, 7.6 Hz), 2.68 (2H, t, J=7.6 Hz), 3.39 (1H, s), 5.10 (2H, s), 6.93 (1H, dd, J=2.3, 7.3 Hz), 7.30-7.51 (7H, m).

b) Preparation of 2-(4-hydroxy-3-propylphenyl)-1,1,1,3,3,3-hexafluoro-2-propanol

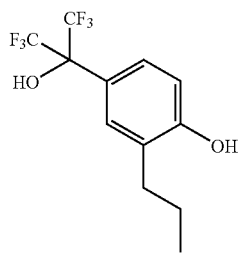

The title compound was obtained as a colorless oil from 2-(4-amino-3-propylphenyl)-1,1,1,3,3,3-hexafluoro-2-propanol with reference to the method of U.S. Pat. No. 3,396,159.

1H-NMR (CDCl3) δ: 0.97 (3H, t, J=7.3 Hz), 1.57-1.72 (2H, m), 2.61 (2H, t, J=7.5 Hz), 3.39 (1H, s), 4.97 (1H, s), 6.82 (1H, d, J=8.4 Hz), 7.39-7.44 (2H, m).

c) Preparation of 2-propyl-4-[1,1,1,3,3,3-hexafluoro-2-hydroxypropan-2-yl]phenyl acetate

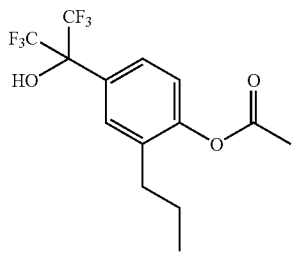

Pyridine (14.7 mL) was added to 2-(4-hydroxy-3-propylphenyl)-1,1,1,3,3,3-hexafluoro-2-propanol (13.76 g, 45.5 mmol) in dichloromethane (200 mL) at room temperature, and then acetic anhydride (17.3 mL) was added. After stirring overnight, methanol (300 mL) was added. After stirring at room temperature for one hour, the reaction solution was concentrated under reduced pressure. Water was added to the resulting residue, followed by extraction with ethyl acetate. The organic layer was washed with saturated saline, dried over anhydrous sodium sulfate, and concentrated under reduced pressure. The resulting residue was purified by silica gel column chromatography (hexane:ethyl acetate=10:1) to obtain 13.67 g of the title compound (yield: 87%) as a red brown oil.

d) Preparation of 4-[1,1,1,3,3,3-hexafluoro-2-(methoxymethyl)oxypropan-2-yl]-2-propylphenol

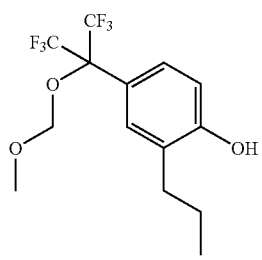

N,N-Diisopropylethylamine (27.6 mL) was added to 2-propyl-4-[1,1,1,3,3,3-hexafluoro-2-hydroxypropan-2-yl] phenyl acetate (13.67 g, 39.7 mmol) in dichloromethane (160 mL), and then chloromethyl methyl ether (6.0 mL) was added. After stirring at 40° C. for 18 hours, methanol (20 mL) was added at room temperature. After stirring for 1.5 hours, potassium carbonate (11 g, 39.7 mmol) was added, followed by stirring overnight. Water was added to the reaction solution, followed by extraction with ethyl acetate. The organic layer was washed with saturated saline, dried over anhydrous sodium sulfate, and concentrated under reduced pressure. The resulting residue was purified by silica gel column chromatography (hexane:ethyl acetate=5:1) to obtain 10.87 g of the title compound (yield: 79%) as a pale yellow oil.

Preparation Example 4

Preparation of 4-[1,1,1,3,3,3-hexafluoro-2-(methoxymethyl)oxypropan-2-yl]-2-propylphenyl 4-bromobutyl ether

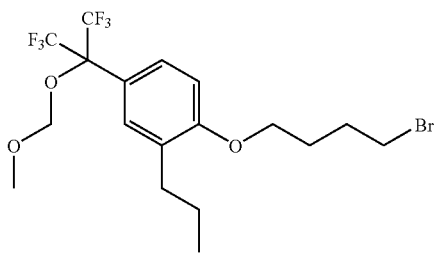

Potassium carbonate (132.4 mg, 0.96 mmol) was added to a mixed solution of 4-[1,1,1,3,3,3-hexafluoro-2-(methoxymethyl)oxypropan-2-yl]-2-propylphenol (221.1 mg, 0.64 mmol) and 1,4-dibromobutane (1.38 g, 6.39 mmol) in N,N-dimethylformamide (20 mL), followed by stirring overnight. Water was added to the reaction solution, followed by extraction with ethyl acetate. Then, the organic layer was washed with saturated saline, dried over anhydrous sodium sulfate and concentrated under reduced pressure. The resulting residue was purified by silica gel preparative thin-layer chromatography (hexane:ethyl acetate=10:1) to obtain 219.5 mg of the title compound (yield: 71%) as a colorless oil.

1H-NMR (CDCl3) δ: 0.93 (3H, t, J=7.6 Hz), 1.59 (2H, qt, J=7.6 Hz), 1.92-2.13 (4H, m), 2.61 (2H, t, J=7.6 Hz), 3.51 (2H, t, J=6.3 Hz), 3.55 (3H, s), 4.02 (2H, t, J=5.9 Hz), 4.83 (2H, s), 6.85 (1H, d, J=8.8 Hz), 7.34 (1H, s), 7.39 (1H, d, J=8.8 Hz).

Preparation Example 5

Preparation of 2,6-dipropyl-4-[1,1,1,3,3,3-hexafluoro-2-(methoxymethyl)oxypropan-2-yl]phenol a) Preparation of 4-[1,1,1,3,3,3-hexafluoro-2-(methoxymethyl)oxypropan-2-yl]-2-iodo-6-propylphenol Iodine (13.3 g) was added to a mixed solution of 4-[1,1,1,3,3,3-hexafluoro-2-(methoxymethyl)oxypropan-2-yl]-2-propylphenol (3.63 g, 10.5 mmol) in pyridine (50 mL) at room temperature, followed by heating in an oil bath at an external temperature of 60° C. overnight. A 1 mol/L sodium thiosulfate aqueous solution was added to the reaction solution at room temperature, followed by extraction with ethyl acetate-water. The organic layer was concentrated under reduced pressure. The residue was purified by silica gel column chromatography (hexane:ethyl acetate=10:1) to obtain 4.20 g of the title compound (yield: 85%) as a brown solid.

$^1$H-NMR (CDCl$_3$) δ: 0.94 (3H, t, J=7.6 Hz), 1.56-1.70 (2H, m), 2.67 (2H, t, J=7.6 Hz), 3.56 (3H, s), 4.84 (2H, s), 5.52 (1H, brs), 7.31 (1H, s), 7.70 (1H, s).

b) Preparation of 4-[1,1,1,3,3,3-hexafluoro-2-(methoxymethyl)oxypropan-2-yl]-2-[(1Z)-1-propenyl]-6-propylphenol

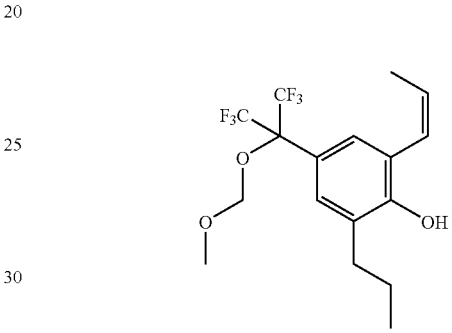

Cesium fluoride (1.24 g), cis-propenylboronic acid (1.54 g) and [1,1'-bis(diphenylphosphino)ferrocene]dichloropalladium (II) (0.49 g) were added to a mixed solution of 4-[1,1,1,3,3,3-hexafluoro-2-(methoxymethyl)oxypropan-2-yl]-2-iodo-6-propylphenol (2.83 g, 5.99 mmol) in toluene (60 mL) in an argon atmosphere at room temperature, followed by stirring overnight. After completion of the reaction, the reaction solution was extracted with ethyl acetate-water, and the organic layer was concentrated under reduced pressure. The residue was purified by silica gel column chromatography (hexane:ethyl acetate=10:1) to obtain 4.20 g of the title compound (yield: 85%) as a brown solid.

$^1$H-NMR (CDCl$_3$) δ: 0.96 (3H, t, J=7.6 Hz), 1.58-1.71 (5H, m), 2.63 (2H, t, J=7.6 Hz), 3.54 (3H, s), 4.84 (2H, s), 5.23 (1H, brs), 6.09 (1H, dq, J=6.9, 11.1 Hz), 7.18 (1H, s), 7.26 (1H, s).

c) Preparation of 2,6-dipropyl-4-[1,1,1,3,3,3-hexafluoro-2-(methoxymethyl)oxypropan-2-yl]phenol

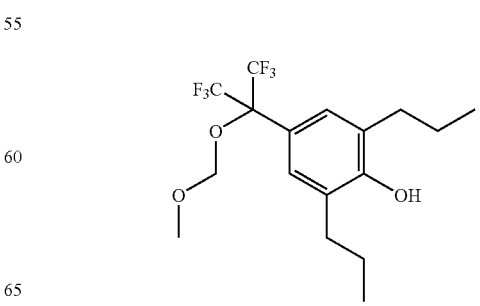

Methanol (30 mL) was added to 4-[1,1,1,3,3,3-hexafluoro-2-(methoxymethyl)oxypropan-2-yl]-2-[(1Z)-1-propenyl]-6-propylphenol (1.29 g, 3.34 mmol). A 10% palladium-carbon catalyst (130 mg) was added to the mixed solution, followed by hydrogenation for 20 hours. The catalyst was separated from the reaction solution by filtration, followed by concentration under reduced pressure to obtain 929 mg of 2,6-dipropyl-4-[1,1,1,3,3,3-hexafluoro-2-(methoxymethyl)oxypropan-2-yl]phenol (yield: 72%) as white crystals.

Preparation Example 6

Preparation of 2,6-diiodo-4-[1,1,1,3,3,3-hexafluoro-2-(methoxymethyl)oxypropan-2-yl]phenol

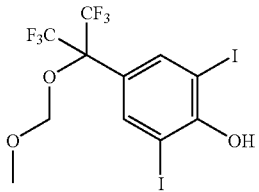

Potassium iodide (1.24 g) and potassium hydroxide (0.46 g) were added to a mixed solution of 4-[1,1,1,3,3,3-hexafluoro-2-(methoxymethyl)oxypropan-2-yl]phenol (2.50 g, 8.21 mmol) in methanol (63 mL) at room temperature. Then, a 4% sodium hypochlorite solution (15.4 mL) was added in an ice bath over three hours. The mixture was returned to room temperature and stirred overnight. A 1 mol/l sodium thiosulfate aqueous solution was added to the reaction solution at room temperature, and then the pH was adjusted to 7 with 2 mol/L hydrochloric acid. After extraction with diethyl ether-water, the organic layer was concentrated under reduced pressure. The residue was purified by silica gel column chromatography (hexane:ethyl acetate=10:1) to obtain the title compound (yield: 6%) as a colorless solid.
$^1$H-NMR (CDCl$_3$) δ: 3.51 (2H, t, J=6.3 Hz), 3.55 (3H, s), 4.02 (2H, t, J=5.9 Hz), 4.83 (2H, s), 6.85 (1H, d, J=8.8 Hz), 7.34 (1H, s), 7.39 (1H, d, J=8.8 Hz).

Preparation Example 7

Preparation of 4-[1,1,1,3,3,3-hexafluoro-2-(methoxymethyl)oxypropan-2-yl]-2-iodophenol

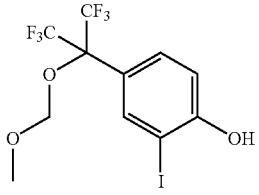

Potassium iodide (1.24 g) and potassium hydroxide (0.46 g) were added to a mixed solution of 4-[1,1,1,3,3,3,-hexafluoro-2-(methoxymethyl)oxypropan-2-yl]phenol (2.50 g, 8.21 mmol) in methanol (63 mL) at room temperature. Then, a 4% sodium hypochlorite solution (15.4 mL) was added in an ice bath over three hours. The mixture was returned to room temperature and stirred overnight. A 1 mol/L sodium thiosulfate aqueous solution was added to the reaction solution at room temperature, and then the pH was adjusted to 7 with 2 mol/L hydrochloric acid. After extraction with diethyl ether-water, the organic layer was concentrated under reduced pressure. The residue was purified by silica gel column chromatography (hexane:ethyl acetate=10:1) to obtain 2.44 g of the title compound (yield: 69%) as a colorless solid.
$^1$H-NMR (CDCl$_3$) δ: 3.55 (3H, s), 4.85 (2H, s), 5.61 (1H, brs), 7.05 (1H, d, J=8.6 Hz), 7.51 (1H, dd, J=1.6, 8.6 Hz).

Preparation Example 8

Preparation of 4-[1,1,1,3,3,3-hexafluoro-2-(methoxymethyl)oxypropan-2-yl]-2-(2-methylpropyl)-6-propylphenol

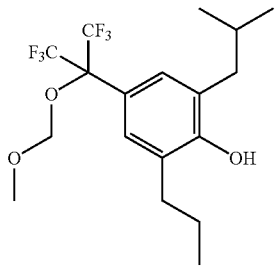

[1,1'-Bis(diphenylphosphino)ferrocene]dichloropalladium (II) (0.49 g), copper (I) iodide (3.9 mg) and a solution of diisobutylzinc bromide in tetrahydrofuran (0.5 mol/L, 1.3 mL) were added to a solution of 4-[1,1,1,3,3,3-hexafluoro-2-(methoxymethyl)oxypropan-2-yl]-2-iodo-6-propylphenol (123 mg, 260 μmol) in tetrahydrofuran (2 mL) in an argon atmosphere at room temperature, followed by stirring overnight. After completion of the reaction, 2 mol/L hydrochloric acid was added. Then, the reaction solution was extracted with ethyl acetate-water, and the organic layer was concentrated under reduced pressure. The residue was purified by silica gel column chromatography (hexane:ethyl acetate=10:1) to obtain 66 mg of the title compound (yield: 63%) as a colorless oil.
$^1$H-NMR (CDCl$_3$) δ: 0.88-1.00 (9H, m), 1.58-1.68 (2H, m), 1.87-2.05 (1H, m), 2.49 (2H, d, J=7.3 Hz), 2.59 (2H, t, J=7.6 Hz), 3.54 (3H, s), 4.83 (2H, s), 4.87 (1H, br), 7.14 (1H, s), 7.18 (1H, s).

Preparation Example 9

Preparation of 3-(4-bromo-2-butynyl)-5-methyl-5-[4-(1-methylethoxy)phenyl]imidazolidine-2,4-dione a) Preparation of t-butyl-diphenylsilyloxy-2-butyn-1-ol

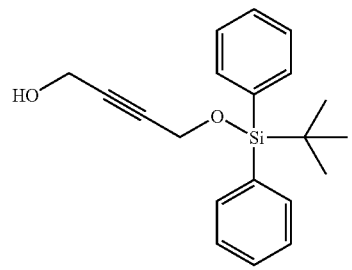

Imidazole (474 mg) and t-butyldiphenylsilyl chloride (905 µL) were added to a mixed solution of 2-butyne-1,2-diol (300 mg, 3.47 mmol) in N,N-dimethylformamide (10 mL) at room temperature. After completion of the reaction, methanol (0.35 mL) was added, followed by extraction with ethyl acetate-water. The organic layer was washed with a saturation sodium chloride solution and then dried over sodium sulfate. The solvent of the filtrate was evaporated, and the residue was purified by silica gel column chromatography (hexane:ethyl acetate=2:1) to obtain 326 mg of the title compound (yield: 29%) as a colorless oil.

$^1$H-NMR (CDCl$_3$) δ: 1.06 (9H, s), 1.31 (3H, t, J=6.3 Hz), 4.20 (2H, td, J=2.0, 6.3 Hz), 4.36 (2H, d, J=2.0 Hz), 7.35-7.46 (6H, m), 7.71 (4H, dd, J=2.0, 7.6 Hz).

b) Preparation of 3-[4-(t-butyl-diphenylsilyloxy)-2-butynyl]-5-methyl-5-[4-(1-methylethoxy)phenyl]imidazolidine-2,4-dione

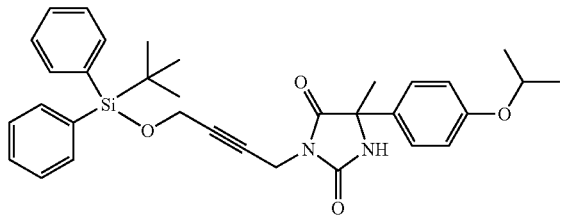

5-Methyl-5-[4-(1-methylethoxy)phenyl]imidazolidine-2,4-dione (248 mg), triphenylphosphine (655 mg) and a solution of ethyl azodicarboxylate in toluene (2.2 mol/L, 1.00 mL) were added to a mixed solution of t-butyl-diphenylsilyloxy-2-butyn-1-ol (326 mg, 1.00 mmol) in tetrahydrofuran (10 mL) at room temperature. After completion of the reaction, the solvent was evaporated, and the residue was purified by silica gel column chromatography (hexane:ethyl acetate=2:1) to obtain 303 mg of the title compound (yield: 55%) as a colorless oil.

$^1$H-NMR (CDCl$_3$) δ: 1.03 (9H, s), 1.30 (6H, d, J=5.9 Hz), 1.79 (3H, s), 4.26 (4H, s), 6.32 (1H, s), 6.61 (2H, d, J=8.9 Hz), 7.32-7.44 (8H, m), 7.67 (4H, dd, J=2.0, 7.6 Hz).

c) Preparation of 3-(4-hydroxy-2-butynyl)-5-methyl-5-[4-(1-methylethoxy)phenyl]imidazolidine-2,4-dione

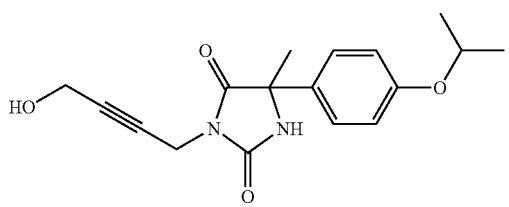

A solution of tetrabutylammonium fluoride in tetrafuran (602 µL) was added to a mixed solution of 3-[4-(t-butyl-diphenylsilyloxy)-2-butynyl]-5-methyl-5-[4-(1-methylethoxy)phenyl]imidazolidine-2,4-dione (300 mg, 547 µmol) in tetrahydrofuran (5 mL) at room temperature. After completion of the reaction, 1 mol/L hydrochloric acid (0.5 mL) was added, followed by extraction with ethyl acetate-water. The organic layer was washed with a saturation sodium chloride solution and then dried over sodium sulfate. The solvent of the filtrate was evaporated, and the residue was purified by silica gel column chromatography (chloroform:methanol=20:1) to obtain 115 mg of the title compound (yield: 90%) as a colorless oil.

$^1$H-NMR (CDCl$_3$) δ: 1.33 (6H, d, J=6.3 Hz), 1.71 (1H, t, J=6.3 Hz), 1.82 (3H, s), 4.23 (2H, td, J=2.0, 6.3 Hz), 4.31 (2H, t, J=2.0 Hz), 4.53 (1H, q, J=6.3 Hz), 5.74 (1H, s), 6.88 (2H, d, J=8.9 Hz), 7.36 (2H, d, J=8.9 Hz).

d) Preparation of 3-(4-bromo-2-butynyl)-5-methyl-5-[4-(1-methylethoxy)phenyl]imidazolidine-2,4-dione

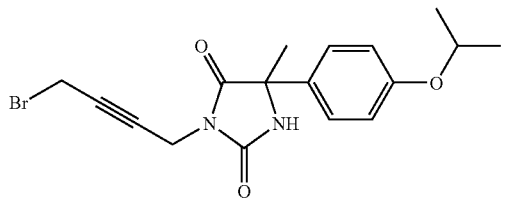

Triphenylphosphine (196 mg) and carbon tetrabromide (247 mg) were added to a mixed solution of 3-(4-hydroxy-2-butynyl)-5-methyl-5-[4-(1-methylethoxy)phenyl]imidazolidine-2,4-dione (157 mg, 498 µmol) in dichloromethane (10 mL) at room temperature. After completion of the reaction, the solvent was evaporated, and the residue was purified by silica gel column chromatography (hexane:ethyl acetate=1:1) to obtain 165 mg of the title compound (yield: 87%) as a colorless oil.

Example 1

Preparation of 3-[4-[4-[1,1,1,3,3,3-hexafluoro-2-(methoxymethyl)oxypropan-2-yl]-2-propylphenyloxy]butyl]-1,5,5-trimethylimidazolidine-2,4-dione 4-[1,1,1,3,3,3-Hexafluoro-2-(methoxymethyl)oxypropan-2-yl]-2-propylphenyl 4-bromobutyl ether (70 mg, 0.15 mmol), 1,5,5-trimethylimidazolidine-2,4-dione (24.8 mg, 0.17 mmol) and potassium carbonate (31.1 mg, 0.23 mmol) were added, followed by stirring overnight at room temperature. The reaction solution was extracted with ethyl acetate-water, and the organic layer was dried over anhydrous sodium sulfate and concentrated under reduced pressure. The resulting residue was purified by silica gel preparative thin-layer chromatography (hexane:ethyl acetate=3:1) to obtain 78.8 mg of the title compound (yield: 100%) as a colorless oil.

Example 2

Preparation of 3-[4-[4-(1,1,1,3,3,3-hexafluoro-2-hydroxypropan-2-yl)-2-propylphenyloxy]butyl]-1,5,5-trimethylimidazolidine-2,4-dione Hydrochloric acid-ethanol (2 mol/L, 2 mL) was added to 3-[4-[4-[1,1,1,3,3,3-hexafluoro-2-(methoxymethyl)oxypropan-2-yl]-2-propylphenyloxy]butyl]-1,5,5-trimethylimidazolidine-2,4-dione (55.7 mg, 0.11 mmol), followed by stirring at room temperature for one hour. The reaction solution was concentrated under reduced pressure, and the resulting residue was purified by silica gel preparative thin-layer chromatography (hexane:ethyl acetate=2:1) to obtain 41.8 mg of the title compound (yield: 82%) as a colorless crystalline powder.

Example 3

Preparation of 5-(1,3-benzodioxol-5-yl)-3-[4-[4-[1,1,1,3,3,3-hexafluoro-2-(methoxymethyl)oxypropan-2-yl]-2-propylphenyloxy]butyl]-5-methylimidazolidine-2,4-dione The title compound was obtained as a colorless oil by the same reaction and treatment as in Example 1 using 5-(1,3-benzodioxol-5-yl)-5-methylimidazolidine-2,4-dione instead of 1,5,5-trimethylimidazolidine-2,4-dione.

Example 4

Preparation of 5-(1,3-benzodioxol-5-yl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by subjecting the compound of Example 3 to the same reaction and treatment as in Example 2.

Example 5

Preparation of 3-[4-[4-(1,1,1,3,3,3-hexafluoro-2-hydroxypropan-2-yl)-2-propyl-phenyloxy]butyl]-5-methyl-5-(4-methylphenyl)imidazolidine-2,4-dione The title compound was obtained as a colorless oil by the same reaction and treatment as in Example 1 and Example 2 using 5-methyl-5-(4-methylphenyl)imidazolidine-2,4-dione instead of 1,5,5-trimethylimidazolidine-2,4-dione.

Example 6

Preparation of 5-(4-ethylphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-ethylphenyl)-5-methylimidazolidine-2,4-dione instead of 1,5,5-trimethylimidazolidine-2,4-dione.

Example 7

Preparation of 3-[4-[4-(1,1,1,3,3,3-hexafluoro-2-hydroxypropan-2-yl)-2-propylphenyloxy]butyl]-5-methyl-5-[4-(1-methylethyl)phenyl]imidazolidine-2,4-dione The title compound was obtained as a colorless oil by the same reaction and treatment as in Example 1 and Example 2 using 5-methyl-5-[4-(1-methylethyl)phenyl]imidazolidine-2,4-dione instead of 1,5,5-trimethylimidazolidine-2,4-dione.

Example 8

Preparation of 5-[4-(1,1-dimethylethyl)phenyl]-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-[4-(1,1-dimethylethyl)phenyl]-5-methylimidazolidine-2,4-dione instead of 1,5,5-trimethylimidazolidine-2,4-dione.

Example 9

Preparation of 5-(4-fluorophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-fluorophenyl)-5-methylimidazolidine-2,4-dione instead of 1,5,5-trimethylimidazolidine-2,4-dione.

Example 10

Preparation of 5-(4-chlorophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-chlorophenyl)-5-methylimidazolidine-2,4-dione instead of 1,5,5-trimethylimidazolidine-2,4-dione.

Example 11

Preparation of 5-(4-bromophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-bromophenyl)-5-methylimidazolidine-2,4-dione instead of 1,5,5-trimethylimidazolidine-2,4-dione.

Example 12

Preparation of 3-[4-[4-(1,1,1,3,3,3-hexafluoro-2-hydroxypropan-2-yl)-2-propylphenyloxy]butyl]-5-methyl-5-(4-trifluoromethylphenyl)imidazolidine-2,4-dione The title compound was obtained as a colorless oil by the same reaction and treatment as in Example 1 and Example 2 using 5-methyl-5-(4-trifluoromethylphenyl)imidazolidine-2,4-dione instead of 1,5,5-trimethylimidazolidine-2,4-dione.

Example 13

Preparation of 5-(4-cyanophenyl)-3-[4-[4-(1,1,1,3,3,3-hexafluoro-2-hydroxypropan-2-yl)-2-propylphenyloxy]butyl]-5-methyl-imidazolidine-2,4-dione The title compound was obtained as a colorless oil by the same reaction and treatment as in Example 1 and Example 2 using 5-(4-cyanophenyl)-5-methylimidazolidine-2,4-dione instead of 1,5,5-trimethylimidazolidine-2,4-dione.

Example 14

Preparation of 3-[4-[4-(1,1,1,3,3,3-hexafluoro-2-hydroxypropan-2-yl)-2-propylphenyloxy]butyl]-5-(4-nitrophenyl)-5-methylimidazolidine-2,4-dione The title compound was obtained as a colorless oil by the same reaction and treatment as in Example 1 and Example 2 using 5-(4-nitrophenyl)-5-methylimidazolidine-2,4-dione instead of 1,5,5-trimethylimidazolidine-2,4-dione.

Example 15

Preparation of 5-(4-dimethylaminophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-dimethylaminophenyl)-5-methylimidazolidine-2,4-dione instead of 1,5,5-trimethylimidazolidine-2,4-dione.

Example 16

Preparation of 3-[4-[4-(1,1,1,3,3,3-hexafluoro-2-hydroxypropan-2-yl)-2-propylphenyloxy]butyl]-5-(4-methoxyphenyl)-5-methylimidazolidine-2,4-dione The title compound was obtained as a colorless oil by the same reaction and treatment as in Example 1 and Example 2 using 5-(4-methoxyphenyl)-5-methyl-imidazolidine-2,4-dione instead of 1,5,5-trimethylimidazolidine-2,4-dione.

Example 17

Preparation of 3-[4-[4-(1,1,1,3,3,3-hexafluoro-2-hydroxypropan-2-yl)-2-propylphenyloxy]butyl]-5-(2-methoxyphenyl)-5-methylimidazolidine-2,4-dione The title compound was obtained as a colorless oil by the same reaction and treatment as in Example 1 and Example 2 using 5-(2-methoxyphenyl)-5-methyl-imidazolidine-2,4-dione instead of 1,5,5-trimethylimidazolidine-2,4-dione.

Example 18

Preparation of 5-(4-ethoxyphenyl)-3-[4-[4-(1,1,1,3,3,3-hexafluoro-2-hydroxypropan-2-yl)-2-propyl-phenyloxy]butyl]-5-methyl-imidazolidine-2,4-dione The title compound was obtained as a colorless oil by the same reaction and treatment as in Example 1 and Example 2 using 5-(4-ethoxyphenyl)-5-methylimidazolidine-2,4-dione instead of 1,5,5-trimethylimidazolidine-2,4-dione.

Example 19

Preparation of 3-[4-[4-(1,1,1,3,3,3-hexafluoro-2-hydroxypropan-2-yl)-2-propylphenyloxy]butyl]-5-methyl-5-(4-propoxyphenyl)imidazolidine-2,4-dione The title compound was obtained as a colorless oil by the same reaction and treatment as in Example 1 and Example 2 using 5-methyl-5-(4-propoxyphenyl)imidazolidine-2,4-dione instead of 1,5,5-trimethylimidazolidine-2,4-dione.

Example 20

Preparation of 3-[4-[4-(1,1,1,3,3,3-hexafluoro-2-hydroxypropan-2-yl)-2-propylphenyloxy]butyl]-5-methyl-5-[4-(1-methylethoxy)phenyl]imidazolidine-2,4-dione The title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 21

Preparation of 5-(4-butoxyphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-butoxyphenyl)-5-methylimidazolidine-2,4-dione instead of 1,5,5-trimethylimidazolidine-2,4-dione.

Example 22

Preparation of 3-[4-[4-(1,1,1,3,3,3-hexafluoro-2-hydroxypropan-2-yl)-2-propylphenyloxy]butyl]-5-methyl-5-[4-(2-methylpropoxy)phenyl]imidazolidine-2,4-dione The title compound was obtained as a colorless oil by the same reaction and treatment as in Example 1 and Example 2 using 5-methyl-5-[4-(2-methylpropoxy)phenyl]imidazolidine-2,4-dione instead of 1,5,5-trimethylimidazolidine-2,4-dione.

Example 23

Preparation of 3-[4-[4-(1,1,1,3,3,3-hexafluoro-2-hydroxypropan-2-yl)-2-propylphenyloxy]butyl]-5-methyl-5-(4-trifluoromethoxyphenyl)imidazolidine-2,4-dione The title compound was obtained as a colorless oil by the same reaction and treatment as in Example 1 and Example 2 using 5-methyl-5-(4-trifluoromethoxyphenyl)imidazolidine-2,4-dione instead of 1,5,5-trimethylimidazolidine-2,4-dione.

Example 24

Preparation of 5-[4-(1,1-dimethylethoxy)carbonylphenyl]-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-[4-(1,1-dimethylethoxy)carbonylphenyl]-5-methylimidazolidine-2,4-dione instead of 1,5,5-trimethylimidazolidine-2,4-dione.

Example 25

Preparation of 5-(4-biphenyl)-1)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-biphenyl)-1)-5-methylimidazolidine-2,4-dione instead of 1,5,5-trimethylimidazolidine-2,4-dione.

Example 26

Preparation of 5-(3,4-difluorophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3,4-difluorophenyl)-5-methyl-imidazolidine-2,4-dione instead of 1,5,5-trimethylimidazolidine-2,4-dione.

Example 27

Preparation of 5-(3-bromo-4-fluorophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3-bromo-4-fluorophenyl)-5-methylimidazolidine-2,4-dione instead of 1,5,5-trimethylimidazolidine-2,4-dione.

Example 28

Preparation of 5-(3,4-dichlorophenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3,4-dichlorophenyl)-5-methylimidazolidine-2,4-dione instead of 1,5,5-trimethylimidazolidine-2,4-dione.

Example 29

Preparation of 3-[4-[4-(1,1,1,3,3,3-hexafluoro-2-hydroxypropan-2-yl)-2-propylphenyloxy]butyl]-5-methyl-5-(2,3,4-trichlorophenyl)imidazolidine-2,4-dione The title compound was obtained as a colorless oil by the same reaction and treatment as in Example 1 and Example 2 using 5-methyl-5-(2,3,4-trichlorophenyl)imidazolidine-2,4-dione instead of 1,5,5-trimethylimidazolidine-2,4-dione.

Example 30

Preparation of 5-(3-fluoro-4-methoxyphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3-fluoro-4-methoxyphenyl)-5-methylimidazolidine-2,4-dione instead of 1,5,5-trimethylimidazolidine-2,4-dione.

Example 31

Preparation of 5-(3,4-dimethoxyphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3,4-dimethoxyphenyl)-5-methylimidazolidine-2,4-dione instead of 1,5,5-trimethylimidazolidine-2,4-dione.

Example 32

Preparation of 3-[4-[4-(1,1,1,3,3,3-hexafluoro-2-hydroxypropan-2-yl)-2-propylphenyloxy]butyl]-5-methyl-5-(3,4,5-trimethoxyphenyl)imidazolidine-2,4-dione The title compound was obtained as a colorless oil by the same reaction and treatment as in Example 1 and Example 2 using 5-methyl-5-(3,4,5-trimethoxyphenyl)imidazolidine-2,4-dione instead of 1,5,5-trimethylimidazolidine-2,4-dione.

Example 33

Preparation of 5-(2,3-dihydro-1,4-benzodioxan-6-yl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(2,3-dihydro-1,4-benzodioxan-6-yl)-5-methylimidazolidine-2,4-dione instead of 1,5,5-trimethylimidazolidine-2,4-dione.

Example 34

Preparation of 3-[4-[4-(1,1,1,3,3,3-hexafluoro-2-hydroxypropan-2-yl)-2-propylphenyloxy]butyl]-5-methyl-5-(naphthalen-1-yl)imidazolidine-2,4-dione The title compound was obtained as a colorless oil by the same reaction and treatment as in Example 1 and Example 2 using 5-methyl-5-(naphthalen-1-yl)imidazolidine-2,4-dione instead of 1,5,5-trimethylimidazolidine-2,4-dione.

Example 35

Preparation of 3-[4-[4-(1,1,1,3,3,3-hexafluoro-2-hydroxypropan-2-yl)-2-propylphenyloxy]butyl]-5-methyl-5-(naphthalen-2-yl)imidazolidine-2,4-dione The title compound was obtained as a colorless oil by the same reaction and treatment as in Example 1 and Example 2 using 5-methyl-5-(naphthalen-2-yl)imidazolidine-2,4-dione instead of 1,5,5-trimethylimidazolidine-2,4-dione.

Example 36

Preparation of 5-(furan-2-yl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(furan-2-yl)-5-methylimidazolidine-2,4-dione instead of 1,5,5-trimethylimidazolidine-2,4-dione.

Example 37

Preparation of 3-[4-[4-(1,1,1,3,3,3-hexafluoro-2-hydroxypropan-2-yl)-2-propylphenyloxy]butyl]-5-methyl-5-(thien-3-yl)imidazolidine-2,4-dione The title compound was obtained as a colorless oil by the same reaction and treatment as in Example 1 and Example 2 using 5-methyl-5-(thien-3-yl)imidazolidine-2,4-dione instead of 1,5,5-trimethylimidazolidine-2,4-dione.

Example 38

Preparation of 5-cyclopropyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-cyclopropyl-5-methylimidazolidine-2,4-dione instead of 1,5,5-trimethylimidazolidine-2,4-dione.

Example 39

Preparation of 5-cyclobutyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-cyclobutyl-5-methylimidazolidine-2,4-dione instead of 1,5,5-trimethylimidazolidine-2,4-dione.

Example 40

Preparation of 5-ethyl-3-[4-[4-(1,1,1,3,3,3-hexafluoro-2-hydroxypropan-2-yl)-2-propylphenyloxy]butyl]-5-(4-methoxyphenyl)imidazolidine-2,4-dione The title compound was obtained as a colorless oil by the same reaction and treatment as in Example 1 and Example 2 using 5-ethyl-5-(4-methoxyphenyl)imidazolidine-2,4-dione instead of 1,5,5-trimethylimidazolidine-2,4-dione.

Example 41

Preparation of 5-(1,3-benzodioxol-5-yl)-5-ethyl-3-[4-[4-(1,1,1,3,3,3-hexafluoro-2-hydroxypropan-2-yl)-2-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 1,5,5-trimethylimidazolidine-2,4-dione.

Example 42

Preparation of 5-(1,1-dimethylethyl)-3-[4-[4-(1,1,1,3,3,3-hexafluoro-2-hydroxypropan-2-yl)-2-propylphenyloxy]butyl]-5-phenylimidazolidine-2,4-dione The title compound was obtained as a colorless oil by the same reaction and treatment as in Example 1 and Example 2 using 5-(1,1-dimethylethyl)-5-phenylimidazolidine-2,4-dione instead of 1,5,5-trimethylimidazolidine-2,4-dione.

Example 43

Preparation of 3-[4-[4-(1,1,1,3,3,3-hexafluoro-2-hydroxypropan-2-yl)-2-propylphenyloxy]butyl]-1,3-diazaspiro[4,4]nonane-2,4-dione The title compound was obtained as a colorless oil by the same reaction and treatment as in Example 1 and Example 2 using 1,3-diazaspiro[4.4]nonane-2,4-dione instead of 1,5,5-trimethylimidazolidine-2,4-dione.

Example 44

Preparation of 3-[3-[2,6-dichloro-4-(1,1,1,3,3,3-hexafluoro-2-hydroxypropan-2-yl)phenyloxy]propyl]-1,5,5-trimethylimidazolidine-2,4-dione 2-(3,5-Dichloro-4-hydroxyphenyl)-1,1,1,3,3,3-hexafluoro-2-propanol was obtained by reaction and treatment with 2,6-dichloroaniline instead of 2-propylaniline in Preparation Example 3. The reaction and treatment were carried out using 1,3-dibromopropane instead of 1,4-dibromobutane in Preparation Example 4, and then the same reaction and treatment as in Example 1 were carried out to obtain the title compound as a colorless oil.

Example 45

Preparation of 3-[4-[2,6-dichloro-4-(1,1,1,3,3,3-hexafluoro-2-hydroxypropan-2-yl)phenyloxy]butyl]-1,5,5-trimethylimidazolidine-2,4-dione The title compound was obtained as a colorless oil by the same reaction and treatment as in Preparation Example 4 and Example 1 using 2-(3,5-dichloro-4-hydroxyphenyl)-1,1,1,3,3-hexafluoro-2-propanol obtained in Example 44.

Example 46

Preparation of 3-[5-[2,6-dichloro-4-(1,1,1,3,3,3-hexafluoro-2-hydroxypropan-2-yl)phenyloxy]pentyl]-1,5,5-trimethylimidazolidine-2,4-dione 2-(3,5-Dichloro-4-hydroxyphenyl)-1,1,1,3,3,3-hexafluoro-2-propanol obtained in Example 44 was reacted and treated with 1,5-dibromopentane instead of 1,4-dibromobutane in Preparation Example 4, and then the same reaction and treatment as in Example 1 were carried out to obtain the title compound as a colorless oil.

Example 47

Preparation of 3-[3-[2,6-dipropyl-4-(1,1,1,3,3,3-hexafluoro-2-hydroxypropan-2-yl)phenyloxy]propyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,3-dibromopropane instead of 1,4-dibromobutane in Preparation Example 4, and then the same reaction and treatment as in Example 1 and Example 2 were carried out to obtain the title compound as a colorless oil.

Example 48

Preparation of 3-[4-[2,6-dipropyl-4-(1,1,1,3,3,3-hexafluoro-2-hydroxypropan-2-yl)phenyloxy]butyl]-1,5,5-trimethylimidazolidine-2,4-dione The title compound was obtained as a colorless oil by the same reaction and treatment as in Preparation Example 4, Example 1 and Example 2 using 2,6-dipropyl-4-[1,1,1,3,3,3-hexafluoro-2-(methoxymethyl)oxypropan-2-yl]phenol obtained in Preparation Example 2.

Example 49

Preparation of 3-[5-[2,6-dipropyl-4-(1,1,1,3,3,3-hexafluoro-2-hydroxypropan-2-yl)phenyloxy]pentyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,5-dibromopentane instead of 1,4-dibromobutane in Preparation Example 4, and then the same reaction and treatment as in Example 1 and Example 2 were carried out to obtain the title compound as a colorless oil.

Example 50

Preparation of 3-[6-[2,6-dipropyl-4-(1,1,1,3,3,3-hexafluoro-2-hydroxypropan-2-yl)phenyloxy]hexyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,6-dibromohexane instead of 1,4-dibromobutane in Preparation Example 4, and then the same reaction and treatment as in Example 1 and Example 2 were carried out to obtain the title compound as a colorless oil.

Example 51

Preparation of 3-[7-[2,6-dipropyl-4-(1,1,1,3,3,3-hexafluoro-2-hydroxypropan-2-yl)phenyloxy]heptyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,7-dibromoheptane instead of 1,4-dibromobutane in Preparation Example 4, and then the same reaction and treatment as in Example 1 and Example 2 were carried out to obtain the title compound as a colorless oil.

Example 52

Preparation of 3-[3-[2-chloro-4-(1,1,1,3,3,3-hexafluoro-2-hydroxypropan-2-yl)phenyloxy]propyl]-1,5,5-trimethylimidazolidine-2,4-dione 2-(3-Chloro-4-hydroxyphenyl)-1,1,1,3,3,3-hexafluoro-2-propanol was obtained by reaction and treatment with 2-chloroaniline instead of 2-propylaniline in Preparation Example 3. The reaction and treatment were carried out using 1,3-dibromopropane instead of 1,4-dibromobutane in Preparation Example 4, and then the same reaction and treatment as in Example 1 were carried out to obtain the title compound as a colorless oil.

Example 53

Preparation of 3-[4-[2-chloro-4-(1,1,1,3,3,3-hexafluoro-2-hydroxypropan-2-yl)phenyloxy]butyl]-1,5,5-trimethylimidazolidine-2,4-dione The title compound was obtained as a colorless oil by the same reaction and treatment as in Preparation Example 4 and Example 1 using 2-(3-chloro-4-hydroxyphenyl)-1,1,1,3,3,3-hexafluoro-2-propanol obtained in Example 52.

Example 54

Preparation of 3-[5-[2-chloro-4-(1,1,1,3,3,3-hexafluoro-2-hydroxypropan-2-yl)phenyloxy]pentyl]-1,5,5-trimethylimidazolidine-2,4-dione 2-(3-Chloro-4-hydroxyphenyl)-1,1,1,3,3,3-hexafluoro-2-propanol obtained in Example 52 was reacted and treated with 1,5-dibromopentane instead of 1,4-dibromobutane in Preparation Example 4, and then the same reaction and treatment as in Example 1 were carried out to obtain the title compound as a colorless oil.

Example 55

Preparation of 3-[3-[4-(1,1,1,3,3,3-hexafluoro-2-hydroxypropan-2-yl)-3-(1-methylethyl)phenyloxy]propyl]-1,5,5-trimethylimidazolidine-2,4-dione 2-[4-Hydroxy-2-(1-methylethyl)phenyl]-1,1,1,3,3,3-hexafluoro-2-propanol was obtained by reaction and treatment with 3-isopropylaniline instead of 2-propylaniline in Preparation Example 3. The reaction and treatment were carried out using 1,3-dibromopropane instead of 1,4-dibromobutane in Preparation Example 4, and then the same reaction and treatment as in Example 1 were carried out to obtain the title compound as a colorless oil.

Example 56

Preparation of 3-[4-[4-(1,1,1,3,3,3-hexafluoro-2-hydroxypropan-2-yl)-3-(1-methylethyl)phenyloxy]butyl]-1,5,5-trimethylimidazolidine-2,4-dione The title compound was obtained as a colorless oil by the same reaction and treatment as in Preparation Example 4 and Example 1 using 2-[4-hydroxy-2-(1-methylethyl)phenyl]-1,1,1,3,3,3-hexafluoro-2-propanol obtained in Example 55.

Example 57

Preparation of 3-[5-[4-(1,1,1,3,3,3-hexafluoro-2-hydroxypropan-2-yl)-3-(1-methylethyl)phenyloxy]pentyl]-1,5,5-trimethylimidazolidine-2,4-dione 2-[4-Hydroxy-2-(1-methylethyl)phenyl]-1,1,1,3,3,3-hexafluoro-2-propanol obtained in Example 55 was reacted and treated with 1,5-dibromopentane instead of 1,4-dibromobutane in Preparation Example 4, and then the same reaction and treatment as in Example 1 were carried out to obtain the title compound as a colorless oil.

Example 58

Preparation of 3-[3-[2-benzyl-4-(1,1,1,3,3,3-hexafluoro-2-hydroxypropan-2-yl)phenyloxy]propyl]-1,5,5-trimethylimidazolidine-2,4-dione 2-(3-Benzyl-4-hydroxyphenyl)-1,1,1,3,3,3-hexafluoro-2-propanol was obtained by reaction and treatment with 2-benzylaniline instead of 2-propylaniline in Preparation Example 3. The reaction and treatment were carried out using 1,3-dibromopropane instead of 1,4-dibromobutane in Preparation Example 4, and then the same reaction and treatment as in Example 1 were carried out to obtain the title compound as a colorless oil.

Example 59

Preparation of 3-[4-[2-benzyl-4-(1,1,1,3,3,3-hexafluoro-2-hydroxypropan-2-yl)phenyloxy]butyl]-1,5,5-trimethylimidazolidine-2,4-dione The title compound was obtained as a colorless oil by the same reaction and treatment as in Preparation Example 4 and Example 1 using 2-(3-benzyl-4-hydroxyphenyl)-1,1,1,3,3,3-hexafluoro-2-propanol obtained in Example 58.

Example 60

Preparation of 3-[5-[2-benzyl-4-(1,1,1,3,3,3-hexafluoro-2-hydroxypropan-2-yl)phenyloxy]pentyl]-1,5,5-trimethylimidazolidine-2,4-dione 2-(3-Benzyl-4-hydroxyphenyl)-1,1,1,3,3,3-hexafluoro-2-propanol obtained in Example 58 was reacted and treated with 1,5-dibromopentane instead of 1,4-dibromobutane in Preparation Example 4, and then the same reaction and treatment as in Example 1 were carried out to obtain the title compound as a colorless oil.

Example 61

Preparation of 3-[4-[4-(1,1,1,3,3,3-hexafluoro-2-hydroxypropan-2-yl)-2-propylphenyloxy]butyl]-1-methylimidazolidine-2,4-dione The title compound was obtained as a colorless oil by the same reaction and treatment as in Example 1 and Example 2 using 1-methylimidazolidine-2,4-dione instead of 1,5,5-trimethylimidazolidine-2,4-dione.

Example 62

Preparation of 5,5-dimethyl-3-[4-[4-(1,1,1,3,3,3-hexafluoro-2-hydroxypropan-2-yl)-2-propylphenyloxy]butyl]imidazolidine-2,4-dione The title compound was obtained as a colorless oil by the same reaction and treatment as in Example 1 and Example 2 using 5,5-dimethylimidazolidine-2,4-dione instead of 1,5,5-trimethylimidazolidine-2,4-dione.

Example 63

Preparation of 5-ethyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-ethyl-5-methylimidazolidine-2,4-dione instead of 1,5,5-trimethylimidazolidine-2,4-dione.

Example 64

Preparation of 3-[4-[4-(1,1,1,3,3,3-hexafluoro-2-hydroxypropan-2-yl)-2-propylphenyloxy]butyl]-5-methyl-5-phenylimidazolidine-2,4-dione The title compound was obtained as a colorless oil by the same reaction and treatment as in Example 1 and Example 2 using 5-methyl-5-phenylimidazolidine-2,4-dione instead of 1,5,5-trimethylimidazolidine-2,4-dione.

Example 65

Preparation of 3-[8-[2,6-dipropyl-4-(1,1,1,3,3,3-hexafluoro-2-hydroxypropan-2-yl)phenyloxy]octyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,8-dibromooctane instead of 1,4-dibromobutane in Preparation Example 4, and then the same reaction and treatment as in Example 1 and Example 2 were carried out to obtain the title compound as a colorless oil.

Example 66

Preparation of 3-[9-[2,6-dipropyl-4-(1,1,1,3,3,3-hexafluoro-2-hydroxypropan-2-yl)phenyloxy]nonyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,9-dibromononane instead of 1,4-dibromobutane in Preparation Example 4, and then the same reaction and treatment as in Example 1 and Example 2 were carried out to obtain the title compound as a colorless oil.

Example 67

Preparation of 3-[10-[2,6-dipropyl-4-(1,1,1,3,3,3-hexafluoro-2-hydroxypropan-2-yl)phenyloxy]decanyl]-1,5,5-trimethylimidazolidine-2,4-dione 2,6-Dipropyl-4-[1,1,1,3,3,3-hexafluoro-2-(methoxymethyl)oxypropan-2-yl]phenol obtained in Preparation Example 2 was reacted and treated with 1,10-dibromodecane instead of 1,4-dibromobutane in Preparation Example 4, and then the same reaction and treatment as in Example 1 and Example 2 were carried out to obtain the title compound as a colorless oil.

Example 68

Preparation of 5-(1,3-benzodioxol-5-yl)-3-[8-[2,6-dipropyl-4-(1,1,1,3,3,3-hexafluoro-2-hydroxypropan-2-yl)phenyloxy]octyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 65.

Example 69

Preparation of 5-(1,3-benzodioxol-5-yl)-3-[9-[2,6-dipropyl-4-(1,1,1,3,3,3-hexafluoro-2-hydroxypropan-2-yl)phenyloxy]nonyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 66.

Example 70

Preparation of 5-(1,3-benzodioxol-5-yl)-3-[10-[2,6-dipropyl-4-(1,1,1,3,3,3-hexafluoro-2-hydroxypropan-2-yl)phenyloxy]decanyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 67.

Example 71

Preparation of 5-(1,3-benzodioxol-5-yl)-3-[4-[4-(1,1,1,3,3,3-hexafluoro-2-propoxypropan-2-yl)-2-propylphenyloxy]butyl]-5-methylimidazolidine-2,4-dione

[4-(1,1,1,3,3,3-Hexafluoro-2-propoxypropan-2-yl)-2-propylphenyl]benzyl ether was obtained by reaction and treatment with propyl iodide instead of chloromethyl methyl ether in Preparation Example 1-g). The title compound was obtained as a colorless oil by the same reaction and treatment as in Preparation Example 1-h), Preparation Example 4 and Example 3 using this.

Example 72

Preparation of 5-(1,3-benzodioxol-5-yl)-3-[4-[4-(2-ethoxy-1,1,1,3,3,3-hexafluoropropan-2-yl)-2-propylphenyloxy]butyl]-5-methylimidazolidine-2,4-dione

[4-(2-Ethoxy-1,1,1,3,3,3-hexafluoropropan-2-yl)-2-propylphenyl]benzyl ether was obtained by reaction and treatment with ethyl iodide instead of chloromethyl methyl ether in Preparation Example 1-g). The title compound was obtained as a colorless oil by the same reaction and treatment as in Preparation Example 1-h), Preparation Example 4 and Example 3 using this.

Example 73

Preparation of 5-(1,3-benzodioxol-5-yl)-3-[4-[4-(1,1,1,3,3,3-hexafluoro-2-methoxypropan-2-yl)-2-propylphenyloxy]butyl]-5-methylimidazolidine-2,4-dione

[4-(1,1,1,3,3,3-Hexafluoro-2-methoxypropan-2-yl)-2-propylphenyl]benzyl ether was obtained by reaction and treatment with methyl iodide instead of chloromethyl methyl ether in Preparation Example 1-g). The title compound was obtained as a colorless oil by the same reaction and treatment as in Preparation Example 1-h), Preparation Example 4 and Example 3 using this.

Example 74

Preparation of 3-[3-[4-(1,1,1,3,3,3-hexafluoro-2-hydroxypropan-2-yl)-2-propylphenyloxy]propyl]-1,5,5-trimethylimidazolidine-2,4-dione The reaction and treatment were carried out using 1,3-dibromopropane instead of 1,4-dibromobutane in Preparation Example 4, and then the same reaction and treatment as in Example 1 and Example 2 were carried out to obtain the title compound as a colorless oil.

Example 75

Preparation of 3-[5-[4-(1,1,1,3,3,3-hexafluoro-2-hydroxypropan-2-yl)-2-propylphenyloxy]pentyl]-1,5,5-trimethylimidazolidine-2,4-dione The reaction and treatment were carried out using 1,5-dibromopentane instead of 1,4-dibromobutane in Preparation Example 4, and then the same reaction and treatment as in Example 1 and Example 2 were carried out to obtain the title compound as a colorless oil.

Example 76

Preparation of 3-[6-[4-(1,1,1,3,3,3-hexafluoro-2-hydroxypropan-2-yl)-2-propylphenyloxy]hexyl]-1,5,5-trimethylimidazolidine-2,4-dione The reaction and treatment were carried out using 1,6-dibromohexane instead of 1,4-dibromobutane in Preparation Example 4, and then the same reaction and treatment as in Example 1 and Example 2 were carried out to obtain the title compound as a colorless oil.

Example 77

Preparation of 3-[7-[4-(1,1,1,3,3,3-hexafluoro-2-hydroxypropan-2-yl)-2-propylphenyloxy]heptyl]-1,5,5-trimethylimidazolidine-2,4-dione The reaction and treatment were carried out using 1,7-dibromoheptane instead of 1,4-dibromobutane in Preparation Example 4, and then the same reaction and treatment as in Example 1 and Example 2 were carried out to obtain the title compound as a colorless oil.

Example 78

Preparation of 3-[8-[4-(1,1,1,3,3,3-hexafluoro-2-hydroxypropan-2-yl)-2-propylphenyloxy]octyl]-1,5,5-trimethylimidazolidine-2,4-dione The reaction and treatment were carried out using 1,8-dibromooctane instead of 1,4-dibromobutane in Preparation Example 4, and then the same reaction and treatment as in Example 1 and Example 2 were carried out to obtain the title compound as a colorless oil.

Example 79

Preparation of 3-[9-[4-(1,1,1,3,3,3-hexafluoro-2-hydroxypropan-2-yl)-2-propylphenyloxy]nonyl]-1,5,5-trimethylimidazolidine-2,4-dione The reaction and treatment were carried out using 1,9-dibromononane instead of 1,4-dibromobutane in Preparation Example 4, and then the same reaction and treatment as in Example 1 and Example 2 were carried out to obtain the title compound as a colorless oil.

Example 80

Preparation of 3-[10-[4-(1,1,1,3,3,3-hexafluoro-2-hydroxypropan-2-yl)-2-propylphenyloxy]decanyl]-1,5,5-trimethylimidazolidine-2,4-dione The reaction and treatment were carried out using 1,10-dibromodecane instead of 1,4-dibromobutane in Preparation Example 4, and then the same reaction and treatment as in Example 1 and Example 2 were carried out to obtain the title compound as a colorless oil.

Example 81

Preparation of 3-[4-[2,6-dipropyl-4-(1,1,1,3,3,3-hexafluoro-2-hydroxypropan-2-yl)phenyloxy]butyl]-5-methyl-5-(4-methylphenyl)imidazolidine-2,4-dione The title compound was obtained as a colorless oil by the same reaction and treatment as in Example 1 and Example 2 using 5-methyl-5-(4-methylphenyl)imidazolidine-2,4-dione instead of 1,5,5-trimethylimidazolidine-2,4-dione in Example 48.

Example 82

Preparation of 5-(4-ethylphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-ethylphenyl)-5-methylimidazolidine-2,4-dione instead of 1,5,5-trimethylimidazolidine-2,4-dione in Example 48.

Example 83

Preparation of 3-[4-[2,6-dipropyl-4-(1,1,1,3,3,3-hexafluoro-2-hydroxypropan-2-yl)phenyloxy]butyl]-5-methyl-5-[4-(1-methylethyl)phenyl]imidazolidine-2,4-dione The title compound was obtained as a colorless oil by the same reaction and treatment as in Example 1 and Example 2 using 5-methyl-5-[4-(1-methylethyl)phenyl]imidazolidine-2,4-dione instead of 1,5,5-trimethylimidazolidine-2,4-dione in Example 48.

Example 84

Preparation of 5-[4-(1,1-dimethylethyl)phenyl]-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-[4-(1,1-dimethylethyl)phenyl]-5-methylimidazolidine-2,4-dione instead of 1,5,5-trimethylimidazolidine-2,4-dione in Example 48.

Example 85

Preparation of 5-(4-fluorophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-fluorophenyl)-5-methylimidazolidine-2,4-dione instead of 1,5,5-trimethylimidazolidine-2,4-dione in Example 48.

Example 86

Preparation of 5-(4-chlorophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-chlorophenyl)-5-methylimidazolidine-2,4-dione instead of 1,5,5-trimethylimidazolidine-2,4-dione in Example 48.

Example 87

Preparation of 5-(4-bromophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-bromophenyl)-5-methylimidazolidine-2,4-dione instead of 1,5,5-trimethylimidazolidine-2,4-dione in Example 48.

Example 88

Preparation of 3-[4-[2,6-dipropyl-4-(1,1,1,3,3,3-hexafluoro-2-hydroxypropan-2-yl)phenyloxy]butyl]-5-methyl-5-(4-trifluoromethylphenyl)imidazolidine-2,4-dione The title compound was obtained as a colorless oil by the same reaction and treatment as in Example 1 and Example 2 using 5-methyl-5-(4-trifluoromethylphenyl)imidazolidine-2,4-dione instead of 1,5,5-trimethylimidazolidine-2,4-dione in Example 48.

Example 89

Preparation of 5-(4-cyanophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-cyanophenyl)-5-methylimidazolidine-2,4-dione instead of 1,5,5-trimethylimidazolidine-2,4-dione in Example 48.

Example 90

Preparation of 3-[4-[2,6-dipropyl-4-(1,1,1,3,3,3-hexafluoro-2-hydroxypropan-2-yl)phenyloxy]butyl]-5-methyl-5-(4-nitrophenyl)imidazolidine-2,4-dione The title compound was obtained as a colorless oil by the same reaction and treatment as in Example 1 and Example 2 using 5-methyl-5-(4-nitrophenyl)imidazolidine-2,4-dione instead of 1,5,5-trimethylimidazolidine-2,4-dione in Example 48.

Example 91

Preparation of 5-(4-dimethylaminophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-dimethylaminophenyl)-5-methylimidazolidine-2,4-dione instead of 1,5,5-trimethylimidazolidine-2,4-dione in Example 48.

Example 92

Preparation of 3-[4-[2,6-dipropyl-4-(1,1,1,3,3,3-hexafluoro-2-hydroxypropan-2-yl)phenyloxy]butyl]-5-(4-methoxyphenyl)-5-methylimidazolidine-2,4-dione The title compound was obtained as a colorless oil by the same reaction and treatment as in Example 1 and Example 2 using 5-(4-methoxyphenyl)-5-methylimidazolidine-2,4-dione instead of 1,5,5-trimethylimidazolidine-2,4-dione in Example 48.

Example 93

Preparation of 3-[4-[2,6-dipropyl-4-(1,1,1,3,3,3-hexafluoro-2-hydroxypropan-2-yl)phenyloxy]butyl]-5-(2-methoxyphenyl)-5-methylimidazolidine-2,4-dione The title compound was obtained as a colorless oil by the same reaction and treatment as in Example 1 and Example 2 using 5-(2-methoxyphenyl)-5-methylimidazolidine-2,4-dione instead of 1,5,5-trimethylimidazolidine-2,4-dione in Example 48.

Example 94

Preparation of 5-(4-ethoxyphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-ethoxyphenyl)-5-methylimidazolidine-2,4-dione instead of 1,5,5-trimethylimidazolidine-2,4-dione in Example 48.

Example 95

Preparation of 3-[4-[2,6-dipropyl-4-(1,1,1,3,3,3-hexafluoro-2-hydroxypropan-2-yl)phenyloxy]butyl]-5-methyl-5-(4-propoxyphenyl)imidazolidine-2,4-dione The title compound was obtained as a colorless oil by the same reaction and treatment as in Example 1 and Example 2 using 5-methyl-5-(4-propoxyphenyl)imidazolidine-2,4-dione instead of 1,5,5-trimethylimidazolidine-2,4-dione in Example 48.

Example 96

Preparation of 3-[4-[2,6-dipropyl-4-(1,1,1,3,3,3-hexafluoro-2-hydroxypropan-2-yl)phenyloxy]butyl]-5-methyl-5-[4-(1-methylethoxy)phenyl]imidazolidine-2,4-dione The title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione in Example 48.

Example 97

Preparation of 5-(4-butoxyphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-butoxyphenyl)-5-methylimidazolidine-2,4-dione instead of 1,5,5-trimethylimidazolidine-2,4-dione in Example 48.

Example 98

Preparation of 3-[4-[2,6-dipropyl-4-(1,1,1,3,3,3-hexafluoro-2-hydroxypropan-2-yl)phenyloxy]butyl]-5-methyl-5-[4-(1-methylpropoxy)phenyl]imidazolidine-2,4-dione The title compound was obtained as a colorless oil by the same reaction and treatment as in Example 1 and Example 2 using 5-methyl-5-[4-(1-methylpropoxy)phenyl]imidazolidine-2,4-dione instead of 1,5,5-trimethylimidazolidine-2,4-dione in Example 48.

Example 99

Preparation of 3-[4-[2,6-dipropyl-4-(1,1,1,3,3,3-hexafluoro-2-hydroxypropan-2-yl)phenyloxy]butyl]-5-methyl-5-(4-trifluoromethoxyphenyl)imidazolidine-2,4-dione The title compound was obtained as a colorless oil by the same reaction and treatment as in Example 1 and Example 2 using 5-methyl-5-(4-trifluoromethoxyphenyl)imidazolidine-2,4-dione instead of 1,5,5-trimethylimidazolidine-2,4-dione in Example 48.

Example 100

Preparation of 3-[4-[4-(1,1,1,3,3,3-hexafluoro-2-hydroxypropan-2-yl)-2-propylphenyloxy]butyl]-imidazolidine-2,4-dione The title compound was obtained as a colorless oil by the same reaction and treatment as in Example 1 and Example 2 using imidazolidine-2,4-dione instead of 1,5,5-trimethylimidazolidine-2,4-dione.

Example 101

Preparation of 5-(4-biphenylyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-biphenylyl)-5-methylimidazolidine-2,4-dione instead of 1,5,5-trimethylimidazolidine-2,4-dione in Example 48.

Example 102

Preparation of 5-(3,4-difluorophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(3,4-difluorophenyl)-5-methylimidazolidine-2,4-dione instead of 1,5,5-trimethylimidazolidine-2,4-dione in Example 48.

Example 103

Preparation of 5-(3-bromo-4-fluorophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(3-bromo-4-fluorophenyl)-5-methylimidazolidine-2,4-dione instead of 1,5,5-trimethylimidazolidine-2,4-dione in Example 48.

Example 104

Preparation of 5-(3,4-dichlorophenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(3,4-dichlorophenyl)-5-methylimidazolidine-2,4-dione instead of 1,5,5-trimethylimidazolidine-2,4-dione in Example 48.

Example 105

Preparation of 3-[4-[4-(1,1,1,3,3,3-hexafluoro-2-hydroxypropan-2-yl)-2,6-dipropylphenyloxy]butyl]-5-methyl-5-(2,3,4-trichlorophenyl)imidazolidine-2,4-dione The title compound was obtained as a colorless oil by the same reaction and treatment as in Example 1 and Example 2 using 5-methyl-5-(2,3,4-trichlorophenyl)imidazolidine-2,4-dione instead of 1,5,5-trimethylimidazolidine-2,4-dione in Example 48.

Example 106

Preparation of 3-[4-[2,6-dipropyl-4-(1,1,1,3,3,3-hexafluoro-2-hydroxypropan-2-yl)phenyloxy]butyl]-5-(3-fluoro-4-methoxyphenyl)-5-methylimidazolidine-2,4-dione The title compound was obtained as a colorless oil by the same reaction and treatment as in Example 1 and Example 2 using 5-(3-fluoro-4-methoxyphenyl)-5-methylimidazolidine-2,4-dione instead of 1,5,5-trimethylimidazolidine-2,4-dione in Example 48.

Example 107

Preparation of 5-(3,4-dimethoxyphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(3,4-dimethoxyphenyl)-5-methylimidazolidine-2,4-dione instead of 1,5,5-trimethylimidazolidine-2,4-dione in Example 48.

Example 108

Preparation of 5-(1,3-benzodioxol-5-yl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 48.

Example 109

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(2,3-dihydro-1,4-benzodioxan-6-yl)-5-methylimidazolidine-2,4-dione instead of 1,5,5-trimethylimidazolidine-2,4-dione in Example 48.

Example 110

Preparation of 3-[4-[2,6-dipropyl-4-(1,1,1,3,3,3-hexafluoro-2-hydroxypropan-2-yl)phenyloxy]butyl]-5-methyl-5-(naphthalen-1-yl)imidazolidine-2,4-dione The title compound was obtained as a colorless oil by the same reaction and treatment as in Example 1 and Example 2 using 5-methyl-5-(naphthalen-1-yl)imidazolidine-2,4-dione instead of 1,5,5-trimethylimidazolidine-2,4-dione in Example 48.

Example 111

Preparation of 3-[4-[2,6-dipropyl-4-(1,1,1,3,3,3-hexafluoro-2-hydroxypropan-2-yl)phenyloxy]butyl]-5-methyl-5-(naphthalen-2-yl)imidazolidine-2,4-dione The title compound was obtained as a colorless oil by the same reaction and treatment as in Example 1 and Example 2 using 5-methyl-5-(naphthalen-2-yl)imidazolidine-2,4-dione instead of 1,5,5-trimethylimidazolidine-2,4-dione in Example 48.

Example 112

Preparation of 3-[2,6-dipropyl-4-[4-(1,1,1,3,3,3-hexafluoro-2-hydroxypropan-2-yl)phenyloxy]butyl]-5-(furan-2-yl)-5-methylimidazolidine-2,4-dione The title compound was obtained as a colorless oil by the same reaction and treatment as in Example 1 and Example 2 using 5-(furan-2-yl)-5-methylimidazolidine-2,4-dione instead of 1,5,5-trimethylimidazolidine-2,4-dione in Example 48.

Example 113

Preparation of 3-[4-[2,6-dipropyl-4-(1,1,1,3,3,3-hexafluoro-2-hydroxypropan-2-yl)phenyloxy]butyl]-5-methyl-5-(thien-3-yl)imidazolidine-2,4-dione The title compound was obtained as a colorless oil by the same reaction and treatment as in Example 1 and Example 2 using 5-(thien-3-yl)-5-methylimidazolidine-2,4-dione instead of 1,5,5-trimethylimidazolidine-2,4-dione in Example 48.

Example 114

Preparation of 5-cyclopropyl-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-cyclopropyl-5-methylimidazolidine-2,4-dione instead of 1,5,5-trimethylimidazolidine-2,4-dione in Example 48.

Example 115

Preparation of 5-cyclobutyl-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-cyclobutyl-5-methylimidazolidine-2,4-dione instead of 1,5,5-trimethylimidazolidine-2,4-dione in Example 48.

Example 116

Preparation of 5-ethyl-3-[4-[2,6-dipropyl-4-(1,1,1,3,3,3-hexafluoro-2-hydroxypropan-2-yl)phenyloxy]butyl]-5-(4-methoxyphenyl)imidazolidine-2,4-dione The title compound was obtained as a colorless oil by the same reaction and treatment as in Example 1 and Example 2 using 5-ethyl-5-(4-methoxyphenyl)imidazolidine-2,4-dione instead of 1,5,5-trimethylimidazolidine-2,4-dione in Example 48.

Example 117

Preparation of 5-(1,3-benzodioxol-5-yl)-5-ethyl-3-[4-[2,6-dipropyl-4-(1,1,1,3,3,3-hexafluoro-2-hydroxypropan-2-yl)phenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 1,5,5-trimethylimidazolidine-2,4-dione in Example 48.

Example 118

Preparation of 5-(1,1-dimethylethyl)-3-[4-[2,6-dipropyl-4-(1,1,1,3,3,3-hexafluoro-2-hydroxypropan-2-yl)phenyloxy]butyl]-5-phenylimidazolidine-2,4-dione The title compound was obtained as a colorless oil by the same reaction and treatment as in Example 1 and Example 2 using 5-(1,1-dimethylethyl)-5-phenylimidazolidine-2,4-dione instead of 1,5,5-trimethylimidazolidine-2,4-dione in Example 48.

Example 119

Preparation of 3-[4-[2,6-dipropyl-4-(1,1,1,3,3,3-hexafluoro-2-hydroxypropan-2-yl)phenyloxy]butyl]-1,3-diazaspiro[4,4]nonane-2,4-dione The title compound was obtained as a colorless oil by the same reaction and treatment as in Example 1 and Example 2 using 1,3-diazaspiro[4,4]nonane-2,4-dione instead of 1,5,5-trimethylimidazolidine-2,4-dione in Example 48.

Example 120

Preparation of 5-(2,3-dihydrobenzofuran-5-yl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(2,3-dihydrobenzofuran-5-yl)-5-methylimidazolidine-2,4-dione instead of 1,5,5-trimethylimidazolidine-2,4-dione.

Example 121

Preparation of 5-ethyl-1,5-dimethyl-3-[4-[4-(1,1,1,3,3,3-hexafluoro-2-methoxypropan-2-yl)-2-propylphenyloxy]butyl]imidazolidine-2,4-dione The title compound was obtained as a colorless oil by the same reaction and treatment as in Example 73 using 5-ethyl-1,5-dimethylimidazolidine-2,4-dione instead of 5-(1,3-benzodioxol-5-yl)-5-methylimidazolidine-2,4-dione of Example 3 used in the process of Example 73.

Example 122

Preparation of 3-[4-[2-benzyl-4-(1,1,1,3,3,3-hexafluoro-2-hydroxypropan-2-yl)phenyloxy]butyl]-5-methyl-5-[4-(1-methylethoxy)phenyl]imidazolidine-2,4-dione The title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione in Example 59.

Example 123

Preparation of 5-ethyl-1,5-dimethyl-3-[4-[4-(1,1,1,3,3,3-hexafluoro-2-hydroxypropan-2-yl)-2-propylphenyloxy]butyl]-imidazolidine-2,4-dione The title compound was obtained as a colorless oil by the same reaction and treatment as in Example 1 and Example 2 using 5-ethyl-1,5-dimethyl-imidazolidine-2,4-dione instead of 1,5,5-trimethylimidazolidine-2,4-dione.

Example 124

Preparation of 5-(1,3-benzodioxol-5-yl)-5-propyl-3-[4-[4-(1,1,1,3,3,3-hexafluoro-2-hydroxypropan-2-yl)-2-propylphenyloxy]butyl]imidazolidine-2,4-dione The title compound was obtained as a colorless oil by the same reaction and treatment as in Example 1 and Example 2 using 5-(1,3-benzodioxol-5-yl)-5-propylimidazolidine-2,4-dione instead of 1,5,5-trimethylimidazolidine-2,4-dione.

Example 125

Preparation of 5-(1,3-benzodioxol-5-yl)-5-butyl-3-[4-[4-(1,1,1,3,3,3-hexafluoro-2-hydroxypropan-2-yl)-2-propylphenyloxy]butyl]imidazolidine-2,4-dione The title compound was obtained as a colorless oil by the same reaction and treatment as in Example 1 and Example 2 using 5-(1,3-benzodioxol-5-yl)-5-butylimidazolidine-2,4-dione instead of 1,5,5-trimethylimidazolidine-2,4-dione.

Example 126

Preparation of 5-(3,4-dihydro-2H-1,5-benzodioxepin-7-yl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3,4-dihydro-2H-1,5-benzodioxepin-7-yl)-5-methylimidazolidine-2,4-dione instead of 1,5,5-trimethylimidazolidine-2,4-dione.

Example 127

Preparation of 5-(1,3-benzodioxol-5-yl)-3-[4-[2-benzyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 59.

Example 128

Preparation of 5-(2,3-dihydro-1,4-benzodioxan-6-yl)-3-[4-[2-benzyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(2,3-dihydro-1,4-benzodioxan-6-yl)-5-methylimidazolidine-2,4-dione instead of 1,5,5-trimethylimidazolidine-2,4-dione in Example 59.

Example 129

Preparation of 5-(2,3-dihydro-1,4-benzodioxan-6-yl)-5-ethyl-3-[4-[4-(1,1,1,3,3,3-hexafluoro-2-hydroxypropan-2-yl)-2-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione.

Example 130

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]butyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 48.

Example 131

Preparation of 3-[4-[4-(1,1,1,3,3,3-hexafluoro-2-hydroxypropan-2-yl)phenyloxy]butyl]-1,5,5-trimethylimidazolidine-2,4-dione 4-[1,1,1,3,3,3-Hexafluoro-2-(methoxymethyl)oxypropan-2-yl]phenol was obtained by reaction and treatment with aniline instead of 2-propylaniline in Preparation Example 3. The title compound was obtained as a colorless oil by the same reaction and treatment as in Preparation Example 4, Example 1 and Example 2.

Example 132

Preparation of 5-(1,3-benzodioxol-5-yl)-3-[4-[4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 131.

Example 133

Preparation of 3-[4-[4-(1,1,1,3,3,3-hexafluoro-2-hydroxypropan-2-yl)-3-methylphenyloxy]butyl]-1,5,5-trimethylimidazolidine-2,4-dione 4-[1,1,1,3,3,3-hexafluoro-2-(methoxymethyl)oxypropan-2-yl]-3-methylphenol was obtained by reaction and treatment with 3-methylaniline instead of 2-propylaniline in Preparation Example 3. The title compound was obtained as a colorless oil by the same reaction and treatment as in Preparation Example 4, Example 1 and Example 2.

Example 134

Preparation of 5-(1,3-benzodioxol-5-yl)-3-[4-[4-(1,1,1,3,3,3-hexafluoro-2-hydroxypropan-2-yl)-3-methylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 133.

Example 135

Preparation of 3-[4-[4-(1,1,1,3,3,3-hexafluoro-2-hydroxypropan-2-yl)-3-methoxyphenyloxy]butyl]-1,5,5-trimethylimidazolidine-2,4-dione 4-[1,1,1,3,3,3-Hexafluoro-2-(methoxymethyl)oxypropan-2-yl]-3-methoxyphenol was obtained by reaction and treatment with 3-methoxyaniline instead of 2-propylaniline in Preparation Example 3. The title compound was obtained as a colorless oil by the same reaction and treatment as in Preparation Example 4, Example 1 and Example 2.

Example 136

Preparation of 5-(1,3-benzodioxol-5-yl)-3-[4-[4-(1,1,1,3,3,3-hexafluoro-2-hydroxypropan-2-yl)-3-methoxyphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 135.

Example 137

Preparation of 3-[4-[[2,3-dihydro-7-(1,1,1,3,3,3-hexafluoro-2-hydroxypropan-2-yl)-1H-inden-4-yl]oxy]butyl]-1,5,5-trimethylimidazolidine-2,4-dione 2,3-Dihydro-7-[1,1,1,3,3,3-hexafluoro-2-(methoxymethyl)oxypropan-2-yl]-1H-inden-4-ol was obtained by reaction and treatment with 2,3-dihydro-1H-inden-4-ylamine instead of 2-propylaniline in Preparation Example 3. The title compound was obtained as a colorless oil by the same reaction and treatment as in Preparation Example 4, Example 1 and Example 2.

Example 138

Preparation of 5-(1,3-benzodioxol-5-yl)-3-[4-[[2,3-dihydro-7-(1,1,1,3,3,3-hexafluoro-2-hydroxypropan-2-yl)-1H-inden-4-yl]oxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 137.

Example 139

Preparation of 5-(2,3-dihydro-1,4-benzodioxan-6-yl)-3-[4-[[2,3-dihydro-7-(1,1,1,3,3,3-hexafluoro-2-hydroxypropan-2-yl)-1H-inden-4-yl]oxy]butyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 137.

Example 140

Preparation of 3-[4-[2-benzyl-4-(1,1,1,3,3,3-hexafluoro-2-hydroxypropan-2-yl)phenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 59.

Example 141

Preparation of 5-(1,3-benzodioxol-5-yl)-3-[4-[2-benzyl-4-(1,1,1,3,3,3-hexafluoro-2-hydroxypropan-2-yl)phenyloxy]butyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 1,5,5-trimethylimidazolidine-2,4-dione in Example 59.

Example 142

Preparation of 3-[4-[2,6-bis(1-methylethyl)-4-(1,1,1,3,3,3-hexafluoro-2-hydroxypropan-2-yl)phenyloxy]butyl]-1,5,5-trimethylimidazolidine-2,4-dione 2,6-Bis(1-methylethyl)-4-[1,1,1,3,3,3-hexafluoro-2-(methoxymethyl)oxypropan-2-yl]phenol was obtained by reaction and treatment with 2,6-diisopropylaniline instead of 2-propylaniline in Preparation Example 3. The title compound was obtained as a colorless oil by the same reaction and treatment as in Preparation Example 4, Example 1 and Example 2.

Example 143

Preparation of 5-(1,3-benzodioxol-5-yl)-3-[4-[2,6-bis(1-methylethyl)-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 142.

Example 144

Preparation of 3-[4-[2,6-bis(1-methylethyl)-4-(1,1,1,3,3,3-hexafluoro-2-hydroxypropan-2-yl)phenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 142.

Example 145

Preparation of 5-(2,3-dihydro-1,4-benzodioxan-6-yl)-3-[4-[4-(1,1,1,3,3,3-hexafluoro-2-hydroxypropan-2-yl)-2-propylphenyloxy]butyl]-5-(1-methylethyl)imidazolidine-2,4-dione The title compound was obtained as a colorless oil by the same reaction and treatment as in Example 1 and Example 2 using 5-(2,3-dihydro-1,4-benzodioxan-6-yl)-5-(1-methylethyl)imidazolidine-2,4-dione instead of 1,5,5-trimethylimidazolidine-2,4-dione.

Example 146

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]butyl]-5-(1-methylethyl)imidazolidine-2,4-dione The title compound was obtained as a colorless oil by the same reaction and treatment as in Example 1 and Example 2 using 5-(2,3-dihydro-1,4-benzodioxan-6-yl)-5-(1-methylethyl)imidazolidine-2,4-dione instead of 1,5,5-trimethylimidazolidine-2,4-dione in Example 48.

Example 147

Preparation of 5-(2,3-dihydro-1,4-benzodioxan-6-yl)-5-(1,1-dimethylethyl)-3-[4-[4-(1,1,1,3,3,3-hexafluoro-2-hydroxypropan-2-yl)-2-propylphenyloxy]butyl]imidazolidine-2,4-one The title compound was obtained as a colorless oil by the same reaction and treatment as in Example 1 and Example 2 using 5-(2,3-dihydro-1,4-benzodioxan-6-yl)-5-(1,1-dimethylethyl)imidazolidine-2,4-dione instead of 1,5,5-trimethylimidazolidine-2,4-dione.

Example 148

Preparation of 5-(2,3-dihydro-1,4-benzodioxan-6-yl)-5-(1,1-dimethylethyl)-3-[4-[2,6-dipropyl-4-(1,1,1,3,3,3-hexafluoro-2-hydroxypropan-2-yl)phenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-(1,1-dimethylethyl)imidazolidine-2,4-dione instead of 1,5,5-trimethylimidazolidine-2,4-dione in Example 48.

Example 149

Preparation of 5-(2,3-dihydro-1,4-benzodioxan-6-yl)-3-[4-[4-(1,1,1,3,3,3-hexafluoro-2-hydroxypropan-2-yl)-2-propylphenyloxy]butyl]-5-propylimidazolidine-2,4-dione The title compound was obtained as a colorless oil by the same reaction and treatment as in Example 1 and Example 2 using 5-(2,3-dihydro-1,4-benzodioxan-6-yl)-5-propylimidazolidine-2,4-dione instead of 1,5,5-trimethylimidazolidine-2,4-dione.

Example 150

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]butyl]-5-propylimidazolidine-2,4-dione The title compound was obtained as a colorless oil by the same reaction and treatment as in Example 1 and Example 2 using 5-(2,3-dihydro-1,4-benzodioxan-6-yl)-5-propylimidazolidine-2,4-dione instead of 1,5,5-trimethylimidazolidine-2,4-dione in Example 48.

Example 151

Preparation of 5-(4-benzyloxyphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(4-benzyloxyphenyl)-5-methylimidazolidine-2,4-dione instead of 1,5,5-trimethylimidazolidine-2,4-dione.

Example 152

Preparation of 5-(4-benzyloxyphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(4-benzyloxyphenyl)-5-methylimidazolidine-2,4-dione instead of 1,5,5-trimethylimidazolidine-2,4-dione in Example 48.

Example 153

Preparation of 3-[4-[4-(1,1,1,3,3,3-hexafluoro-2-hydroxypropan-2-yl)-2-propylphenyloxy]butyl]-5-(4-methoxybenzyl)-5-methylimidazolidine-2,4-dione The title compound was obtained as a colorless oil by the same reaction and treatment as in Example 1 and Example 2 using 5-(4-methoxybenzyl)-5-methylimidazolidine-2,4-dione instead of 1,5,5-trimethylimidazolidine-2,4-dione.

Example 154

Preparation of 3-[4-[2,6-dipropyl-4-(1,1,1,3,3,3-hexafluoro-2-hydroxypropan-2-yl)phenyloxy]butyl]-5-(4-methoxybenzyl)-5-methylimidazolidine-2,4-dione The title compound was obtained as a colorless oil by the same reaction and treatment as in Example 1 and Example 2 using 5-(4-methoxybenzyl)-5-methylimidazolidine-2,4-dione instead of 1,5,5-trimethylimidazolidine-2,4-dione in Example 48.

Example 155

Preparation of 3-[4-[4-(1,1,1,3,3,3-hexafluoro-2-hydroxypropan-2-yl)-2-propylphenyloxy]butyl]-5-methyl-5-[4-(4-methylbenzyloxy)]phenylimidazolidine-2,4-dione The title compound was obtained as a colorless oil by the same reaction and treatment as in Example 1 and Example 2 using 5-methyl-5-[4-(4-methylbenzyloxy)]phenylimidazolidine-2,4-dione instead of 1,5,5-trimethylimidazolidine-2,4-dione Example 156

Preparation of 3-[4-[2,6-dipropyl-4-(1,1,1,3,3,3-hexafluoro-2-hydroxypropan-2-yl)phenyloxy]butyl]-5-methyl-5-[4-(4-methylbenzyloxy)]phenylimidazolidine-2,4-dione The title compound was obtained as a colorless oil by the same reaction and treatment as in Example 1 and Example 2 using 5-methyl-5-[4-(4-methylbenzyloxy)]phenylimidazolidine-2,4-dione instead of 1,5,5-trimethylimidazolidine-2,4-dione in Example 48.

Example 157

Preparation of 5-[4-(4-chlorobenzyloxy)]phenyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-[4-(4-chlorobenzyloxy)]phenyl-5-methylimidazolidine-2,4-dione instead of 1,5,5-trimethylimidazolidine-2,4-dione.

Example 158

Preparation of 5-[4-(4-chlorobenzyloxy)]phenyl-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-[4-(4-chlorobenzyloxy)]phenyl-5-methylimidazolidine-2,4-dione instead of 1,5,5-trimethylimidazolidine-2,4-dione in Example 48.

Example 159

Preparation of 5-[4-(3,5-dimethoxybenzyloxy)]phenyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-[4-(3,5-dimethoxybenzyloxy)]phenyl-5-methylimidazolidine-2,4-dione instead of 1,5,5-trimethylimidazolidine-2,4-dione.

Example 160

Preparation of 5-[4-(3,5-dimethoxybenzyloxy)]phenyl-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-[4-(3,5-dimethoxybenzyloxy)]phenyl-5-methylimidazolidine-2,4-dione instead of 1,5,5-trimethylimidazolidine-2,4-dione in Example 48.

Example 161

Preparation of 3-[4-[4-(1,1,1,3,3,3-hexafluoro-2-hydroxypropan-2-yl)-2-[(1Z)-1-propenyl]-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-[(1Z)-1-propenyl]-6-propylphenol obtained in Preparation Example 5 was subjected to the same reaction and treatment as in Preparation Example 4. Then, the title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 162

Preparation of 5-(1,3-benzodioxol-5-yl)-3-[4-[4-(1,1,1,3,3,3-hexafluoro-2-hydroxypropan-2-yl)-2-[(1Z)-1-propenyl]-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 161.

Example 163

Preparation of 5-(1,3-benzodioxol-5-yl)-5-ethyl-3-[4-[4-(1,1,1,3,3,3-hexafluoro-2-hydroxypropan-2-yl)-2-[(1Z)-1-propenyl]-6-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 161.

Example 164

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[(1Z)-1-propenyl]-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 161.

Example 165

Preparation of 3-[4-[4-(1,1,1,3,3,3-hexafluoro-2-hydroxypropan-2-yl)-2-[(1E)-1-propenyl]-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-[(1E)-1-propenyl]-6-propylphenol was obtained using trans-propenylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 166

Preparation of 5-(1,3-benzodioxol-5-yl)-3-[4-[4-(1,1,1,3,3,3-hexafluoro-2-hydroxypropan-2-yl)-2-[(1E)-1-propenyl]-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 165.

Example 167

Preparation of 5-(1,3-benzodioxol-5-yl)-5-ethyl-3-[4-[4-(1,1,1,3,3,3-hexafluoro-2-hydroxypropan-2-yl)-2-[(1E)-1-propenyl]-6-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 165.

Example 168

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[(1E)-1-propenyl]-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 165.

Example 169

Preparation of 3-[4-[4-(1,1,1,3,3,3-hexafluoro-2-hydroxypropan-2-yl)-2-[(1E)-1-octenyl]-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-[(1E)-1-octenyl]-6-propylphenol was obtained using trans-1-octen-1-ylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 170

Preparation of 5-(1,3-benzodioxol-5-yl)-3-[4-[4-(1,1,1,3,3,3-hexafluoro-2-hydroxypropan-2-yl)-2-[(1E)-1-octenyl]-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 169.

Example 171

Preparation of 5-(1,3-benzodioxol-5-yl)-5-ethyl-3-[4-[4-(1,1,1,3,3,3-hexafluoro-2-hydroxypropan-2-yl)-2-[(1E)-1-octenyl]-6-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 169.

Example 172

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[(1E)-1-octenyl]-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 169.

Example 173

Preparation of 3-[4-[2-[(1E)-2-cyclohexylethenyl]-4-(1,1,1,3,3,3-hexafluoro-2-hydroxypropan-2-yl)-6-propylphenyloxy]butyl]-5-methyl-5-[4-(1-methylethoxy)phenyl]imidazolidine-2,4-dione 2-[(1E)-2-Cyclohexylethenyl]-4-[1,1,1,3,3,3-hexafluoro-2-(methoxymethyl)oxypropan-2-yl]-6-propylphenol was obtained using (E)-2-cyclohexylethenylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 174

Preparation of 5-(1,3-benzodioxol-5-yl)-3-[4-[2-[(1E)-2-cyclohexylethenyl]-4-(1,1,1,3,3,3-hexafluoro-2-hydroxypropan-2-yl)-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 173.

Example 175

Preparation of 5-(1,3-benzodioxol-5-yl)-3-[4-[2-[(1E)-2-cyclohexylethenyl]-4-(1,1,1,3,3,3-hexafluoro-2-hydroxypropan-2-yl)-6-propylphenyloxy]butyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 173.

Example 176

Preparation of 3-[4-[2-[(1E)-2-cyclohexylethenyl]-4-(1,1,1,3,3,3-hexafluoro-2-hydroxypropan-2-yl)-6-propylphenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 173.

Example 177

Preparation of 3-[4-[4-(1,1,1,3,3,3-hexafluoro-2-hydroxypropan-2-yl)-6-propyl-2-[(E)-styryl]phenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-6-propyl-2-[(E)-styryl]phenol was obtained using (E)-styrylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 178

Preparation of 5-(1,3-benzodioxol-5-yl)-3-[4-[4-(1,1,1,3,3,3-hexafluoro-2-hydroxypropan-2-yl)-6-propyl-2-[(E)-styryl]phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-

Example 179

Preparation of 5-(1,3-benzodioxol-5-yl)-5-ethyl-3-[4-[4-(1,1,1,3,3,3-hexafluoro-2-hydroxypropan-2-yl)-6-propyl-2-[(E)-styryl]phenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 177.

Example 180

Preparation of 5-(2,3-dihydro-1,4-benzodioxan-6-yl)-5-ethyl-3-[4-[4-(1,1,1,3,3,3-hexafluoro-2-hydroxypropan-2-yl)-6-propyl-2-[(E)-styryl]phenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 177.

Example 181

Preparation of 3-[4-[4-(1,1,1,3,3,3-hexafluoro-2-hydroxypropan-2-yl)-2-octyl-6-propylphenyloxy]butyl]-5-methyl-5-[4-(1-methylethoxy)phenyl]imidazolidine-2,4-dione The title compound was obtained as a colorless oil by subjecting the compound of Example 169 to the same reaction and treatment as in Preparation Example 5c).

Example 182

Preparation of 5-(1,3-benzodioxol-5-yl)-3-[4-[4-(1,1,1,3,3,3-hexafluoro-2-hydroxypropan-2-yl)-2-octyl-6-propylphenyloxy]butyl]-5-methylimidazolidine-2,4-dione The title compound was obtained as a colorless oil by subjecting the compound of Example 170 to the same reaction and treatment as in Preparation Example 5c).

Example 183

Preparation of 5-(1,3-benzodioxol-5-yl)-3-[4-[4-(1,1,1,3,3,3-hexafluoro-2-hydroxypropan-2-yl)-2-octyl-6-propylphenyloxy]butyl]-5-ethylimidazolidine-2,4-dione The title compound was obtained as a colorless oil by subjecting the compound of Example 171 to the same reaction and treatment as in Preparation Example 5c).

Example 184

Preparation of 5-(2,3-dihydro-1,4-benzodioxan-6-yl)-3-[4-[4-(1,1,1,3,3,3-hexafluoro-2-hydroxypropan-2-yl)-2-octyl-6-propylphenyloxy]butyl]-5-ethylimidazolidine-2,4-dione The title compound was obtained as a colorless oil by subjecting the compound of Example 172 to the same reaction and treatment as in Preparation Example 5c).

Example 185

Preparation of 3-[4-[2-(2-cyclohexylethyl)-4-(1,1,1,3,3,3-hexafluoro-2-hydroxypropan-2-yl)-6-propylphenyloxy]butyl]-5-methyl-5-[4-(1-methylethoxy)phenyl]imidazolidine-2,4-dione The title compound was obtained as a colorless oil by subjecting the compound of Example 173 to the same reaction and treatment as in Preparation Example 5c).

Example 186

Preparation of 5-(1,3-benzodioxol-5-yl)-3-[4-[2-(2-cyclohexylethyl)-4-(1,1,1,3,3,3-hexafluoro-2-hydroxypropan-2-yl)-6-propylphenyloxy]butyl]-5-methylimidazolidine-2,4-dione The title compound was obtained as a colorless oil by subjecting the compound of Example 174 to the same reaction and treatment as in Preparation Example 5c).

Example 187

Preparation of 5-(1,3-benzodioxol-5-yl)-3-[4-[2-(2-cyclohexylethyl)-4-(1,1,1,3,3,3-hexafluoro-2-hydroxypropan-2-yl)-6-propylphenyloxy]butyl]-5-ethylimidazolidine-2,4-dione The title compound was obtained as a colorless oil by subjecting the compound of Example 175 to the same reaction and treatment as in Preparation Example 5c).

Example 188

Preparation of 3-[4-[2-(2-cyclohexylethyl)-4-(1,1,1,3,3,3-hexafluoro-2-hydroxypropan-2-yl)-6-propylphenyloxy]butyl]-5-(2,3-dihydro-1,4-benzodioxan-6-yl)-5-ethylimidazolidine-2,4-dione The title compound was obtained as a colorless oil by subjecting the compound of Example 176 to the same reaction and treatment as in Preparation Example 5c).

Example 189

Preparation of 3-[4-[4-(1,1,1,3,3,3-hexafluoro-2-hydroxypropan-2-yl)-2-phenethyl-6-propylphenyloxy]butyl]-5-methyl-5-[4-(1-methylethoxy)phenyl]imidazolidine-2,4-dione The title compound was obtained as a colorless oil by subjecting the compound of Example 177 to the same reaction and treatment as in Preparation Example 5c).

Example 190

Preparation of 5-(1,3-benzodioxol-5-yl)-3-[4-[4-(1,1,1,3,3,3-hexafluoro-2-hydroxypropan-2-yl)-2-phenethyl-6-propylphenyloxy]butyl]-5-methylimidazolidine-2,4-dione The title compound was obtained as a colorless oil by subjecting the compound of Example 178 to the same reaction and treatment as in Preparation Example 5c).

Example 191

Preparation of 5-(1,3-benzodioxol-5-yl)-5-ethyl-3-[4-[4-(1,1,1,3,3,3-hexafluoro-2-hydroxypropan-2-yl)-2-phenethyl-6-propylphenyloxy]butyl]imidazolidine-2,4-dione The title compound was obtained as a colorless oil by subjecting the compound of Example 179 to the same reaction and treatment as in Preparation Example 5c).

Example 192

Preparation of 5-(2,3-dihydro-1,4-benzodioxan-6-yl)-5-ethyl-3-[4-[4-(1,1,1,3,3,3-hexafluoro-2-hydroxypropan-2-yl)-2-phenethyl-6-propylphenyloxy]butyl]imidazolidine-2,4-dione The title compound was obtained as a colorless oil by subjecting the compound of Example 180 to the same reaction and treatment as in Preparation Example 5c).

Example 193

Preparation of 3-[4-[2-cyclohexyl-4-(1,1,1,3,3,3-hexafluoro-2-hydroxypropan-2-yl)-6-propylphenyloxy]butyl]-5-methyl-5-[4-(1-methylethoxy)phenyl]imidazolidine-2,4-dione 2-cyclohexyl-4-[1,1,1,3,3,3-hexafluoro-2-(methoxymethyl)oxypropan-2-yl]-6-propylphenol was obtained using cyclohexylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 194

Preparation of 5-(1,3-benzodioxol-5-yl)-3-[4-[2-cyclohexyl-4-(1,1,1,3,3,3-hexafluoro-2-hydroxypropan-2-yl)-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 193.

Example 195

Preparation of 5-(1,3-benzodioxol-5-yl)-3-[4-[2-cyclohexyl-4-(1,1,1,3,3,3-hexafluoro-2-hydroxypropan-2-yl)-6-propylphenyloxy]butyl]-5-ethylimidazolidine-2,4-dione:

The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 193.

Example 196

Preparation of 3-[4-[2-cyclohexyl-4-(1,1,1,3,3,3-hexafluoro-2-hydroxypropan-2-yl)-6-propylphenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 193.

Example 197

Preparation of 3-[4-[4-(1,1,1,3,3,3-hexafluoro-2-hydroxypropan-2-yl)-2-iodo-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-iodo-6-propylphenol obtained in Preparation Example 5a) was subjected to the same reaction and treatment as in Preparation Example 4. Then, the title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 198

Preparation of 5-(1,3-benzodioxol-5-yl)-3-[4-[4-(1,1,1,3,3,3-hexafluoro-2-hydroxypropan-2-yl)-2-iodo-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 197.

Example 199

Preparation of 5-(1,3-benzodioxol-5-yl)-3-[4-[4-(1,1,1,3,3,3-hexafluoro-2-hydroxypropan-2-yl)-2-iodo-6-propylphenyloxy]butyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 197.

Example 200

Preparation of 3-[4-[4-(1,1,1,3,3,3-hexafluoro-2-hydroxypropan-2-yl)-2-iodo-6-propylphenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 197.

Example 201

Preparation of 3-[4-[4-(1,1,1,3,3,3-hexafluoro-2-hydroxypropan-2-yl)-2-phenyl-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-phenyl-6-propylphenol was obtained using phenylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 202

Preparation of 5-(2,3-dihydro-1,4-benzodioxan-6-yl)-5-ethyl-3-[4-[4-(1,1,1,3,3,3-hexafluoro-2-hydroxypropan-2-yl)-2-phenyl-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 201.

Example 203

Preparation of 3-[4-[4-(1,1,1,3,3,3-hexafluoro-2-hydroxypropan-2-yl)-2-[(1E)-1-pentenyl]-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-[(1E)-1-pentenyl]-6-propylphenol was obtained using (1E)-1-pentenylboronic acid instead of cis-propenylboronic acid in Preparation Example 5b). The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 204

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[(1E)-1-pentenyl]-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 203.

Example 205

Preparation of 3-[4-[4-(1,1,1,3,3,3-hexafluoro-2-hydroxypropan-2-yl)-2-pentyl-6-propylphenyloxy]butyl]-5-methyl-5-[4-(1-methylethoxy)phenyl]imidazolidine-2,4-dione The title compound was obtained as a colorless oil by subjecting the compound of Example 203 to the same reaction and treatment as in Preparation Example 5c).

Example 206

Preparation of 5-(2,3-dihydro-1,4-benzodioxan-6-yl)-5-ethyl-3-[4-[4-(1,1,1,3,3,3-hexafluoro-2-hydroxypropan-2-yl)-2-pentyl-6-propylphenyloxy]butyl]imidazolidine-2,4-dione The title compound was obtained as a colorless oil by subjecting the compound of Example 204 to the same reaction and treatment as in Preparation Example 5c).

Example 207

Preparation of 5-(4-hydroxyphenyl)-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by subjecting the compound of Example 151 to the same reaction and treatment as in Preparation Example 5c).

Example 208

Preparation of 5-(4-hydroxyphenyl)-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by subjecting the compound of Example 152 to the same reaction and treatment as in Preparation Example 5c).

Example 209

Preparation of 5-ethyl-3-[4-[4-(1,1,1,3,3,3-hexafluoro-2-hydroxypropan-2-yl)-2-propylphenyloxy]butyl]-5-[4-(1-methylethoxy)phenyl]imidazolidine-2,4-dione The title compound was obtained as a colorless oil by the same reaction and treatment as in Example 1 and Example 2 using 5-ethyl-5-[4-(1-methylethoxy)phenyl]imidazolidine-2,4-dione instead of 1,5,5-trimethylimidazolidine-2,4-dione.

Example 210

Preparation of 3-[4-[2,6-dipropyl-4-(1,1,1,3,3,3-hexafluoro-2-hydroxypropan-2-yl)phenyloxy]butyl]-5-ethyl-5-[4-(1-methylethoxy)phenyl]imidazolidine-2,4-dione The title compound was obtained as a colorless oil by the same reaction and treatment as in Example 1 and Example 2 using 5-ethyl-5-[4-(1-methylethoxy)phenyl]imidazolidine-2,4-dione instead of 1,5,5-trimethylimidazolidine-2,4-dione in Example 48.

Example 211

Preparation of 5-ethyl-3-[4-[4-(1,1,1,3,3,3-hexafluoro-2-hydroxypropan-2-yl)-2-propylphenyloxy]butyl]-5-(4-propoxyphenyl)imidazolidine-2,4-dione The title compound was obtained as a colorless oil by the same reaction and treatment as in Example 1 and Example 2 using 5-ethyl-5-(4-propoxyphenyl)imidazolidine-2,4-dione instead of 1,5,5-trimethylimidazolidine-2,4-dione.

Example 212

Preparation of 3-[4-[2,6-dipropyl-4-(1,1,1,3,3,3-hexafluoro-2-hydroxypropan-2-yl)phenyloxy]butyl]-5-ethyl-5-(4-propoxyphenyl)imidazolidine-2,4-dione The title compound was obtained as a colorless oil by the same reaction and treatment as in Example 1 and Example 2 using 5-ethyl-5-(4-propoxyphenyl)imidazolidine-2,4-dione instead of 1,5,5-trimethylimidazolidine-2,4-dione in Example 48.

Example 213

Preparation of 3-[4-[4-(1,1,1,3,3,3-hexafluoro-2-hydroxypropan-2-yl)-2-propylphenyloxy]butyl]-5-(indan-5-yl)-5-methylimidazolidine-2,4-dione The title compound was obtained as a colorless oil by the same reaction and treatment as in Example 1 and Example 2 using 5-(indan-5-yl)-5-methylimidazolidine-2,4-dione instead of 1,5,5-trimethylimidazolidine-2,4-dione.

Example 214

Preparation of 3-[4-[2,6-dipropyl-4-(1,1,1,3,3,3-hexafluoro-2-hydroxypropan-2-yl)phenyloxy]butyl]-5-(indan-5-yl)-5-methylimidazolidine-2,4-dione The title compound was obtained as a colorless oil by the same reaction and treatment as in Example 1 and Example 2 using 5-(indan-5-yl)-5-methylimidazolidine-2,4-dione instead of 1,5,5-trimethylimidazolidine-2,4-dione in Example 48.

Example 215

Preparation of 3-[4-[4-(1,1,1,3,3,3-hexafluoro-2-hydroxypropan-2-yl)-2-propylphenyloxy]butyl]-5-methyl-5-[3-methoxy-4-(1-methylethoxy)phenyl]imidazolidine-2,4-dione The title compound was obtained as a colorless oil by the same reaction and treatment as in Example 1 and Example 2 using 5-methyl-5-[3-methoxy-4-(1-methylethoxy)phenyl]imidazolidine-2,4-dione instead of 1,5,5-trimethylimidazolidine-2,4-dione.

Example 216

Preparation of 3-[4-[2,6-dipropyl-4-(1,1,1,3,3,3-hexafluoro-2-hydroxypropan-2-yl)phenyloxy]butyl]-5-methyl-5-[3-methoxy-4-(1-methylethoxy)phenyl]imidazolidine-2,4-dione The title compound was obtained as a colorless oil by the same reaction and treatment as in Example 1 and Example 2 using 5-methyl-5-[3-methoxy-4-(1-methylethoxy)phenyl]imidazolidine-2,4-dione instead of 1,5,5-trimethylimidazolidine-2,4-dione in Example 48.

Example 217

Preparation of 3-[4-[4-(1,1,1,3,3,3-hexafluoro-2-hydroxypropan-2-yl)-2-propylphenyloxy]butyl]-5-(4-propoxy-3-methoxy)phenyl-5-methylimidazolidine-2,4-dione The title compound was obtained as a colorless oil by the same reaction and treatment as in Example 1 and Example 2 using 5-(4-propoxy-3-methoxy)phenyl-5-methylimidazolidine-2,4-dione instead of 1,5,5-trimethylimidazolidine-2,4-dione.

Example 218

Preparation of 3-[4-[2,6-dipropyl-4-(1,1,1,3,3,3-hexafluoro-2-hydroxypropan-2-yl)phenyloxy]butyl]-5-(4-propoxy-3-methoxy)phenyl-5-methylimidazolidine-2,4-dione The title compound was obtained as a colorless oil by the same reaction and treatment as in Example 1 and Example 2 using 5-(4-propoxy-3-methoxy)phenyl-5-methylimidazolidine-2,4-dione instead of 1,5,5-trimethylimidazolidine-2,4-dione in Example 48.

Example 219

Preparation of 3-[3-[4-[4-(1,1,1,3,3,3-hexafluoro-2-hydroxypropan-2-yl)-2-propylphenyloxy]butyl]-5-methylimidazolidine-2,4-dion-5-yl]benzoic acid The same reaction and treatment as in Example 1 and Example 2 were carried out using 5-[3-(1,1-dimethylethoxy)carbonyl]phenyl-5-methylimidazolidine-2,4-dione instead of 1,5,5-trimethylimidazolidine-2,4-dione, followed by treatment with trifluoroacetic acid to obtain the title compound as a colorless oil.

Example 220

Preparation of 3-[3-[4-[2,6-dipropyl-4-(1,1,1,3,3,3-hexafluoro-2-hydroxypropan-2-yl)phenyloxy]butyl]-5-methylimidazolidine-2,4-dion-5-yl]benzoic acid The same reaction and treatment as in Example 1 and Example 2 were carried out using 5-[3-(1,1-dimethylethoxy)carbonyl]phenyl-5-methylimidazolidine-2,4-dione instead of 1,5,5-trimethylimidazolidine-2,4-dione in Example 48, followed by treatment with trifluoroacetic acid to obtain the title compound as a colorless oil.

Example 221

Preparation of 5-(3-benzyloxy)phenyl-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-(3-benzyloxy)phenyl-5-methylimidazolidine-2,4-dione instead of 1,5,5-trimethylimidazolidine-2,4-dione.

Example 222

Preparation of 5-(3-benzyloxy)phenyl-3-[4-[2,6-dipropyl-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(3-benzyloxy)phenyl-5-methylimidazolidine-2,4-dione instead of 1,5,5-trimethylimidazolidine-2,4-dione in Example 48.

Example 223

Preparation of 3-[4-[4-(1,1,1,3,3,3-hexafluoro-2-hydroxypropan-2-yl)-2-propylphenyloxy]butyl]-5-(3-hydroxyphenyl)-5-methylimidazolidine-2,4-dione The title compound was obtained as a colorless oil by subjecting the compound of Example 221 to the same reaction and treatment as in Preparation Example 5c).

Example 224

Preparation of 3-[4-[2,6-dipropyl-4-(1,1,1,3,3,3-hexafluoro-2-hydroxypropan-2-yl)phenyloxy]butyl]-5-(3-hydroxyphenyl)-5-methylimidazolidine-2,4-dione The title compound was obtained as a colorless oil by subjecting the compound of Example 222 to the same reaction and treatment as in Preparation Example 5c).

Example 225

Preparation of 3-[4-[4-(1,1,1,3,3,3-hexafluoro-2-hydroxypropan-2-yl)-2-methylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-methylphenol was obtained by reaction and treatment with 2-methylaniline instead of 2-propylaniline in Preparation Example 3. This was subjected to the reaction and treatment in Preparation Example 4. Then, the title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 226

Preparation of 5-(1,3-benzodioxol-5-yl)-3-[4-[4-(1,1,1,3,3,3-hexafluoro-2-hydroxypropan-2-yl)-2-methylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 225.

Example 227

Preparation of 5-(1,3-benzodioxol-5-yl)-5-ethyl-3-[4-[4-(1,1,1,3,3,3-hexafluoro-2-hydroxypropan-2-yl)-2-methylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 225.

Example 228

Preparation of 5-(2,3-dihydro-1,4-benzodioxan-6-yl)-5-ethyl-3-[4-[4-(1,1,1,3,3,3-hexafluoro-2-hydroxypropan-2-yl)-2-methylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 225.

Example 229

Preparation of 3-[4-[4-(1,1,1,3,3,3-hexafluoro-2-hydroxypropan-2-yl)-2-methyl-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-methyl-6-propylphenol was obtained by the same reaction and treatment as in Preparation Example 5a) to c) for 4-[1,1,1,3,3,3-hexafluoro-2-(methoxymethyl)oxypropan-2-yl]-2-methylphenol obtained in Example 225. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 230

Preparation of 5-(1,3-benzodioxol-5-yl)-3-[4-[4-(1,1,1,3,3,3-hexafluoro-2-hydroxypropan-2-yl)-2-methyl-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 229.

Example 231

Preparation of 5-(1,3-benzodioxol-5-yl)-5-ethyl-3-[4-[4-(1,1,1,3,3,3-hexafluoro-2-hydroxypropan-2-yl)-2-methyl-6-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 229.

Example 232

Preparation of 5-(2,3-dihydro-1,4-benzodioxan-6-yl)-5-ethyl-3-[4-[4-(1,1,1,3,3,3-hexafluoro-2-hydroxypropan-2-yl)-2-methyl-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 229.

Example 233

Preparation of 3-[4-[2-benzyl-4-(1,1,1,3,3,3-hexafluoro-2-hydroxypropan-2-yl)-6-[(1E)-1-propenyl]phenyloxy]butyl]-5-methyl-5-[4-(1-methylethoxy)phenyl]imidazolidine-2,4-dione 2-Benzyl-4-[1,1,1,3,3,3-hexafluoro-2-(methoxymethyl)oxypropan-2-yl]phenol was obtained by reaction and treatment with 2-benzylaniline instead of 2-propylaniline in Preparation Example 3. 2-Benzyl-4-[1,1,1,3,3,3-hexafluoro-2-(methoxymethyl)oxypropan-2-yl]-6-[(1E)-1-propenyl]phenol was obtained by the same reaction and treatment as in Preparation Example 5a) and in Preparation Example 5b) in which trans-propenylboronic acid was used instead of cis-propenylboronic acid. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 234

Preparation of 3-[4-[2-benzyl-4-(1,1,1,3,3,3-hexafluoro-2-hydroxypropan-2-yl)-6-[(1E)-1-propenyl]phenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 233.

Example 235

Preparation of 3-[4-[2-benzyl-4-(1,1,1,3,3,3-hexafluoro-2-hydroxypropan-2-yl)-6-[(1E)-1-propenyl]phenyloxy]butyl]-5-methyl-5-(4-butoxyphenyl)imidazolidine-2,4-dione The title compound was obtained as a colorless oil by the same reaction and treatment as in Example 1 and Example 2 using 5-methyl-5-(4-butoxyphenyl)imidazolidine-2,4-dione instead of 5-methyl-5-[4-(1-methylethoxy)phenyl]imidazolidine-2,4-dione in Example 233.

Example 236

Preparation of 3-[4-[2-benzyl-4-(1,1,1,3,3,3-hexafluoro-2-hydroxypropan-2-yl)-6-[(1E)-1-propenyl]phenyloxy]butyl]-5-ethyl-5-(4-methoxyphenyl)imidazolidine-2,4-dione The title compound was obtained as a colorless oil by the same reaction and treatment as in Example 1 and Example 2 using 5-ethyl-5-(4-methoxyphenyl)imidazolidine-2,4-dione instead of 5-methyl-5-[4-(1-methylethoxy)phenyl]imidazolidine-2,4-dione in Example 233.

Example 237

Preparation of 3-[4-[2-benzyl-4-(1,1,1,3,3,3-hexafluoro-2-hydroxypropan-2-yl)-6-propylphenyloxy]butyl]-5-methyl-5-[4-(1-methylethoxy)phenyl]imidazolidine-2,4-dione The title compound was obtained as a colorless oil by subjecting the compound of Example 233 to the same reaction and treatment as in Preparation Example 5c).

Example 238

Preparation of 3-[4-[2-benzyl-4-(1,1,1,3,3,3-hexafluoro-2-hydroxypropan-2-yl)-6-propylphenyloxy]butyl]-5-(2,3-dihydro-1,4-benzodioxan-6-yl)-5-ethylimidazolidine-2,4-dione The title compound was obtained as a colorless oil by subjecting the compound of Example 234 to the same reaction and treatment as in Preparation Example 5c).

Example 239

Preparation of 3-[4-[2-benzyl-4-(1,1,1,3,3,3-hexafluoro-2-hydroxypropan-2-yl)-6-propylphenyloxy]butyl]-5-methyl-5-(4-butoxyphenyl)imidazolidine-2,4-dione The title compound was obtained as a colorless oil by subjecting the compound of Example 235 to the same reaction and treatment as in Preparation Example 5c).

Example 240

Preparation of 3-[4-[2-benzyl-4-(1,1,1,3,3,3-hexafluoro-2-hydroxypropan-2-yl)-6-propylphenyloxy]butyl]-5-ethyl-5-(4-methoxyphenyl)imidazolidine-2,4-dione The title compound was obtained as a colorless oil by subjecting the compound of Example 236 to the same reaction and treatment as in Preparation Example 5c).

Example 241

Preparation of 3-[4-[[2,3-dihydro-7-(1,1,1,3,3,3-hexafluoro-2-hydroxypropan-2-yl)-5-[(1Z)-1-propenyl]-1H-inden-4-yl]oxy]butyl]-5-methyl-5-[4-(1-methylethoxy)phenyl]imidazolidine-2,4-dione 2,3-Dihydro-7-[1,1,1,3,3,3-hexafluoro-2-(methoxymethyl)oxypropan-2-yl]-5-[(1Z)-1-propenyl]-1H-inden-4-ol was obtained by the same reaction and treatment as in Preparation Example 5a) and Preparation Example 5b) for 2,3-dihydro-7-[1,1,1,3,3,3-hexafluoro-2-(methoxymethyl)oxypropan-2-yl]-1H-inden-4-ol obtained in Example 137. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 242

Preparation of 5-(2,3-dihydro-1,4-benzodioxan-6-yl)-3-[4-[[2,3-dihydro-7-(1,1,1,3,3,3-hexafluoro-2-hydroxypropan-2-yl)-5-[(1Z)-1-propenyl]-1H-inden-4-yl]oxy]butyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 241.

Example 243

Preparation of 3-[4-[[2,3-dihydro-7-(1,1,1,3,3,3-hexafluoro-2-hydroxypropan-2-yl)-5-propyl-1H-inden-4-yl]oxy]butyl]-5-methyl-5-[4-(1-methylethoxyphenyl)]imidazolidine-2,4-dione The title compound was obtained as a colorless oil by subjecting the compound of Example 241 to the same reaction and treatment as in Preparation Example 5c).

Example 244

Preparation of 5-(2,3-dihydro-1,4-benzodioxan-6-yl)-3-[4-[[2,3-dihydro-7-(1,1,1,3,3,3-hexafluoro-2-hydroxypropan-2-yl)-5-propyl-1H-inden-4-yl]oxy]butyl]-5-ethylimidazolidine-2,4-dione The title compound was obtained as a colorless oil by subjecting the compound of Example 242 to the same reaction and treatment as in Preparation Example 5c).

Example 245

Preparation of 3-[4-[2,6-bis[(E)-styryl]-4-(1,1,1,3,3,3-hexafluoro-2-hydroxypropan-2-yl)phenyloxy]butyl]-5-methyl-5-[4-(1-methylethoxy)phenyl]imidazolidine-2,4-dione 2,6-Bis[(E)-styryl]-4-[1,1,1,3,3,3-hexafluoro-2-(methoxymethyl)oxypropan-2-yl]phenol was obtained the same reaction and treatment as in Preparation Example 5b) using (E)-2-phenylethenylboronic acid instead of cis-propenylboronic acid for 2,6-diiodo-4-[1,1,1,3,3,3-hexafluoro-2-(methoxymethyl)oxypropan-2-yl]phenol obtained in Preparation Example 6. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 246

Preparation of 5-(1,3-benzodioxol-5-yl)-3-[4-[2,6-bis[(E)-styryl]-4-(1,1,1,3,3,3-hexafluoro-2-hydroxypropan-2-yl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 245.

Example 247

Preparation of 5-(1,3-benzodioxol-5-yl)-3-[4-[2,6-bis[(E)-styryl]-4-(1,1,1,3,3,3-hexafluoro-2-hydroxypropan-2-yl)phenyloxy]butyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 245.

Example 248

Preparation of 3-[4-[2,6-bis[(E)-styryl]-4-(1,1,1,3,3,3-hexafluoro-2-hydroxypropan-2-yl)phenyloxy]butyl]-5-(2,3-dihydro-1,4-benzodioxan-6-yl)-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 245.

Example 249

Preparation of 3-[4-[2,6-bis(2-phenylethyl)-4-(1,1,1,3,3,3-hexafluoro-2-hydroxypropan-2-yl)phenyloxy]butyl]-5-methyl-5-[4-(1-methylethoxy)phenyl]imidazolidine-2,4-dione The title compound was obtained as a colorless oil by subjecting the compound of Example 245 to the same reaction and treatment as in Preparation Example 5c).

Example 250

Preparation of 5-(1,3-benzodioxol-5-yl)-3-[4-[2,6-bis(2-phenylethyl)-4-(1,1,1,3,3,3-hexafluoro-2-hydroxypropan-2-yl)phenyloxy]butyl]-5-methylimidazolidine-2,4-dione The title compound was obtained as a colorless oil by subjecting the compound of Example 246 to the same reaction and treatment as in Preparation Example 5c).

Example 251

Preparation of 5-(1,3-benzodioxol-5-yl)-3-[4-[2,6-bis(2-phenylethyl)-4-(1,1,1,3,3,3-hexafluoro-2-hydroxypropan-2-yl)phenyloxy]butyl]-5-ethylimidazolidine-2,4-dione The title compound was obtained as a colorless oil by subjecting the compound of Example 247 to the same reaction and treatment as in Preparation Example 5c).

Example 252

Preparation of 3-[4-[2,6-bis(2-phenylethyl)-4-(1,1,1,3,3,3-hexafluoro-2-hydroxypropan-2-yl)phenyloxy]butyl]-5-(2,3-dihydro-1,4-benzodioxan-6-yl)-5-ethylimidazolidine-2,4-dione The title compound was obtained as a colorless oil by subjecting the compound of Example 248 to the same reaction and treatment as in Preparation Example 5c).

Example 253

Preparation of 3-[4-[4-(1,1,1,3,3,3-hexafluoro-2-hydroxypropan-2-yl)-2-(2-methylpropyl)-6-propylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-(2-methylpropyl)-6-propylphenol obtained in Preparation Example 8 was subjected to the same reaction and treatment as in Preparation Example 4. Then, the title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 254

Preparation of 5-(1,3-benzodioxol-5-yl)-3-[4-[4-(1,1,1,3,3,3-hexafluoro-2-hydroxypropan-2-yl)-2-(2-methylpropyl)-6-propylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 253.

Example 255

Preparation of 5-(1,3-benzodioxol-5-yl)-5-ethyl-3-[4-[4-(1,1,1,3,3,3-hexafluoro-2-hydroxypropan-2-yl)-2-(2-methylpropyl)-6-propylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 253.

Example 256

Preparation of 5-(2,3-dihydro-1,4-benzodioxan-6-yl)-5-ethyl-3-[4-[4-(1,1,1,3,3,3-hexafluoro-2-hydroxypropan-2-yl)-2-(2-methylpropyl)-6-propylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 253.

Example 257

Preparation of 3-[4-[4-(1,1,1,3,3,3-hexafluoro-2-hydroxypropan-2-yl)-2-(2-methylpropyl)phenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-(2-methylpropyl)phenol was obtained by the same reaction and treatment as in Preparation Example 8 for 4-[1,1,1,3,3,3-hexafluoro-2-(methoxymethyl)oxypropan-2-yl]-2-iodophenol obtained in Preparation Example 7. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 258

Preparation of 5-(1,3-benzodioxol-5-yl)-3-[4-[4-(1,1,1,3,3,3-hexafluoro-2-hydroxypropan-2-yl)-2-(2-methylpropyl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 257.

Example 259

Preparation of 5-(1,3-benzodioxol-5-yl)-5-ethyl-3-[4-[4-(1,1,1,3,3,3-hexafluoro-2-hydroxypropan-2-yl)-2-(2-methylpropyl)phenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 257.

Example 260

Preparation of 5-(2,3-dihydro-1,4-benzodioxan-6-yl)-5-ethyl-3-[4-[4-(1,1,1,3,3,3-hexafluoro-2-hydroxypropan-2-yl)-2-(2-methylpropyl)phenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 257.

Example 261

Preparation of 3-[4-[4-(1,1,1,3,3,3-hexafluoro-2-hydroxypropan-2-yl)-2-phenethylphenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-phenethylphenol was obtained by the same reaction and treatment as in Preparation Example 5b) to 5c) using (E)-2-phenylethenylboronic acid instead of cis-propenylboronic acid for 4-[1,1,1,3,3,3-hexafluoro-2-(methoxymethyl)oxypropan-2-yl]-2-iodophenol obtained in Preparation Example 7. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 262

Preparation of 5-(1,3-benzodioxol-5-yl)-3-[4-[4-(1,1,1,3,3,3-hexafluoro-2-hydroxypropan-2-yl)-2-phenethylphenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 261.

Example 263

Preparation of 5-(1,3-benzodioxol-5-yl)-5-ethyl-3-[4-[4-(1,1,1,3,3,3-hexafluoro-2-hydroxypropan-2-yl)-2-phenethylphenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 261.

Example 264

Preparation of 5-(2,3-dihydro-1,4-benzodioxan-6-yl)-5-ethyl-3-[4-[4-(1,1,1,3,3,3-hexafluoro-2-hydroxypropan-2-yl)-2-phenethylphenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 261.

Example 265

Preparation of 3-[4-[4-(1,1,1,3,3,3-hexafluoro-2-hydroxypropan-2-yl)-2-[2-(4-methoxyphenethyl)phenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-(4-methoxyphenethyl)phenol was obtained by the same reaction and treatment as in Preparation Example 5b) to 5c) using (E)-2-(4-methoxyphenyl)ethenylboronic acid instead of cis-propenylboronic acid for 4-[1,1,1,3,3,3-hexafluoro-2-(methoxymethyl)oxypropan-2-yl]-2-iodophenol obtained in Preparation Example 7. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 266

Preparation of 5-(1,3-benzodioxol-5-yl)-3-[4-[4-(1,1,1,3,3,3-hexafluoro-2-hydroxypropan-2-yl)-2-[2-(4-methoxyphenethyl)phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 265.

Example 267

Preparation of 5-(1,3-benzodioxol-5-yl)-5-ethyl-3-[4-[4-(1,1,1,3,3,3-hexafluoro-2-hydroxypropan-2-yl)-2-[2-(4-methoxyphenethyl)phenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 265.

Example 268

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[2-(4-methoxyphenethyl)phenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 265.

Example 269

Preparation of 3-[4-[4-(1,1,1,3,3,3-hexafluoro-2-hydroxypropan-2-yl)-2-[2-[4-(trifluoromethyl)phenethyl]phenyloxy]butyl]-5-methyl-5-[4-(1-methylethoxy)phenyl]imidazolidine-2,4-dione 4-[1,1,1,3,3,3-Hexafluoro-2-(methoxymethyl)oxypropan-2-yl]-2-[4-(trifluoromethyl)phenethyl]phenol was obtained by the same reaction and treatment as in Preparation Example 5b) to 5c) using (E)-2-[4-(trifluoromethyl)phenyl]ethenylboronic acid instead of cis-propenylboronic acid for 4-[1,1,1,3,3,3-hexafluoro-2-(methoxymethyl)oxypropan-2-yl]-2-iodophenol obtained in Preparation Example 7. The title compound was obtained as a colorless oil by subjecting this to the same reaction and treatment as in Preparation Example 4 and then carrying out the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione.

Example 270

Preparation of 5-(1,3-benzodioxol-5-yl)-3-[4-[4-(1,1,1,3,3,3-hexafluoro-2-hydroxypropan-2-yl)-2-[2-[4-(trifluoromethyl)phenethyl]phenyloxy]butyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 269.

Example 271

Preparation of 5-(1,3-benzodioxol-5-yl)-5-ethyl-3-[4-[4-(1,1,1,3,3,3-hexafluoro-2-hydroxypropan-2-yl)-2-[4-(trifluoromethyl)phenethyl]phenyloxy]butyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 269.

Example 272

Preparation of 5-(2,3-dihydro-1,4-benzodioxan-6-yl)-5-ethyl-3-[4-[4-(1,1,1,3,3,3-hexafluoro-2-hydroxypropan-2-yl)-2-[4-(trifluoromethyl)phenethyl]phenyloxy]butyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 269.

Example 273

Preparation of 3-[3-[4-(1,1,1,3,3,3-hexafluoro-2-hydroxypropan-2-yl)-2-propylphenyloxy]propyl]-5-methyl-5-[4-(1-methylethoxy)phenyl]imidazolidine-2,4-dione The title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione in Example 74.

Example 274

Preparation of 5-(1,3-benzodioxol-5-yl)-3-[3-[4-(1,1,1,3,3,3-hexafluoro-2-hydroxypropan-2-yl)-2-propylphenyloxy]propyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 74.

Example 275

Preparation of 5-(1,3-benzodioxol-5-yl)-5-ethyl-3-[3-[4-(1,1,1,3,3,3-hexafluoro-2-hydroxypropan-2-yl)-2-propylphenyloxy]propyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 1,5,5-trimethylimidazolidine-2,4-dione in Example 74.

Example 276

Preparation of 5-(2,3-dihydro-1,4-benzodioxan-6-yl)-5-ethyl-3-[3-[4-(1,1,1,3,3,3-hexafluoro-2-hydroxypropan-2-yl)-2-propylphenyloxy]propyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 74.

Example 277

Preparation of 3-[3-[4-(1,1,1,3,3,3-hexafluoro-2-hydroxypropan-2-yl)-2-propylphenyloxy]propyl]-5-(4-methoxyphenyl)methyl-5-methylimidazolidine-2,4-dione The title compound was obtained as a colorless oil by the same reaction and treatment as in Example 1 and Example 2 using 5-(4-methoxyphenyl)methyl-5-methylimidazolidine-2,4-dione instead of 1,5,5-trimethylimidazolidine-2,4-dione in Example 74.

Example 278

Preparation of 3-[3-[2,6-dipropyl-4-(1,1,1,3,3,3-hexafluoro-2-hydroxypropan-2-yl)phenyloxy]propyl]-5-methyl-5-[4-(1-methylethoxy)phenyl]imidazolidine-2,4-dione The title compound was obtained as a colorless oil by the same reaction and treatment as in Example 1 and Example 2 using 5-methyl-5-[4-(1-methylethoxy)phenyl]imidazolidine-2,4-dione instead of 1,5,5-trimethylimidazolidine-2,4-dione in Example 47.

Example 279

Preparation of 5-(1,3-benzodioxol-5-yl)-3-[3-[2,6-dipropyl-4-(1,1,1,3,3,3-hexafluoro-2-hydroxypropan-2-yl)phenyloxy]propyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 1,5,5-trimethylimidazolidine-2,4-dione in Example 47.

Example 280

Preparation of 5-(1,3-benzodioxol-5-yl)-3-[3-[2,6-dipropyl-4-(1,1,1,3,3,3-hexafluoro-2-hydroxypropan-2-yl)phenyloxy]propyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 1,5,5-trimethylimidazolidine-2,4-dione in Example 47.

Example 281

Preparation of 5-(2,3-dihydro-1,4-benzodioxan-6-yl)-3-[3-[2,6-dipropyl-4-(1,1,1,3,3,3-hexafluoro-2-hydroxypropan-2-yl)phenyloxy]propyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 1,5,5-trimethylimidazolidine-2,4-dione in Example 47.

Example 282

Preparation of 3-[3-[2,6-dipropyl-4-(1,1,1,3,3,3-hexafluoro-2-hydroxypropan-2-yl)phenyloxy]propyl]-5-(4-methoxyphenyl)methyl-5-methylimidazolidine-2,4-dione The title compound was obtained as a colorless oil by the same reaction and treatment as in Example 1 and Example 2 using 5-(4-methoxyphenyl)methyl-5-methylimidazolidine-2,4-dione instead of 1,5,5-trimethylimidazolidine-2,4-dione in Example 47.

Example 283

Preparation of 3-[4-[4-(1,1,1,3,3,3-hexafluoro-2-hydroxypropan-2-yl)-2-propylphenyloxy]-(2E)-2-butenyl]-5-methyl-5-[4-(1-methylethoxy)phenyl]imidazolidine-2,4-dione The reaction and treatment were carried out using (2E)-1,4-dichloro-2-butene instead of 1,4-dibromobutane in Preparation Example 4, and then the same reaction and treatment as in Example 1 and Example 2 were carried using 5-methyl-5-[4-(1-methylethoxy)phenyl]imidazolidine-2,4-dione instead of 1,5,5-trimethylimidazolidine-2,4-dione to obtain the title compound as a colorless oil.

Example 284

Preparation of 5-(1,3-benzodioxol-5-yl)-3-[4-[4-(1,1,1,3,3,3-hexafluoro-2-hydroxypropan-2-yl)-2-propylphenyloxy]-(2E)-2-butenyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 283.

Example 285

Preparation of 5-(2,3-dihydro-1,4-benzodioxan-6-yl)-5-ethyl-3-[4-[4-(1,1,1,3,3,3-hexafluoro-2-hydroxypropan-2-yl)-2-propylphenyloxy]-(2E)-2-butenyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 283.

Example 286

Preparation of 3-[4-[2,6-dipropyl-4-(1,1,1,3,3,3-hexafluoro-2-hydroxypropan-2-yl)phenyloxy]-(2E)-2-butenyl]-5-methyl-5-[4-(1-methylethoxy)phenyl]imidazolidine-2,4-dione The reaction and treatment were carried out using (2E)-1,4-dichloro-2-butene instead of 1,4-dibromobutane in the preparation process of Example 48, and then the same reaction and treatment as in Example 1 and Example 2 were carried using 5-methyl-5-[4-(1-methylethoxy)phenyl]imidazolidine-2,4-dione instead of 1,5,5-trimethylimidazolidine-2,4-dione to obtain the title compound as a colorless oil.

Example 287

Preparation of 5-(1,3-benzodioxol-5-yl)-3-[4-[2,6-dipropyl-4-(1,1,1,3,3,3-hexafluoro-2-hydroxypropan-2-yl)phenyloxy]-(2E)-2-butenyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 286.

Example 288

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]-(2E)-2-butenyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 286.

Example 289

Preparation of 3-[4-[4-(1,1,1,3,3,3-hexafluoro-2-hydroxypropan-2-yl)-2-propylphenyloxy]-(2Z)-2-butenyl]-5-methyl-5-[4-(1-methylethoxy)phenyl]imidazolidine-2,4-dione The reaction and treatment were carried out using (2Z)-1,4-dichloro-2-butene instead of 1,4-dibromobutane in Preparation Example 4, and then the same reaction and treatment as in Example 1 and Example 2 were carried using 5-methyl-5-[4-(1-methylethoxy)phenyl]imidazolidine-2,4-dione instead of 1,5,5-trimethylimidazolidine-2,4-dione to obtain the title compound as a colorless oil.

Example 290

Preparation of 5-(1,3-benzodioxol-5-yl)-3-[4-[4-(1,1,1,3,3,3-hexafluoro-2-hydroxypropan-2-yl)-2-propylphenyloxy]-(2Z)-2-butenyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 289.

Example 291

Preparation of 5-(1,3-benzodioxol-5-yl)-5-ethyl-3-[4-[4-(1,1,1,3,3,3-hexafluoro-2-hydroxypropan-2-yl)-2-propylphenyloxy]-(2Z)-2-butenyl]imidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 289.

Example 292

Preparation of 5-(2,3-dihydro-1,4-benzodioxan-6-yl)-5-ethyl-3-[4-[4-(1,1,1,3,3,3-hexafluoro-2-hydroxypropan-2-yl)-2-propylphenyloxy]-(2Z)-2-butenyl]imidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 289.

Example 293

Preparation of 3-[4-[2,6-dipropyl-4-(1,1,1,3,3,3-hexafluoro-2-hydroxypropan-2-yl)phenyloxy]-(2Z)-2-butenyl]-5-methyl-5-[4-(1-methylethoxy)phenyl]imidazolidine-2,4-dione The reaction and treatment were carried out using (2Z)-1,4-dichloro-2-butene instead of 1,4-dibromobutane in the preparation process of Example 48, and then the same reaction and treatment as in Example 1 and Example 2 were carried using 5-methyl-5-[4-(1-methylethoxy)phenyl]imidazolidine-2,4-dione instead of 1,5,5-trimethylimidazolidine-2,4-dione to obtain the title compound as a colorless oil.

Example 294

Preparation of 5-(1,3-benzodioxol-5-yl)-3-[4-[2,6-dipropyl-4-(1,1,1,3,3,3-hexafluoro-2-hydroxypropan-2-yl)phenyloxy]-(2Z)-2-butenyl]-5-methylimidazolidine-2,4-dione The title compound was obtained as a colorless oil by the same reaction and treatment as in Example 1 and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 293.

Example 295

Preparation of 5-(1,3-benzodioxol-5-yl)-3-[4-[2,6-dipropyl-4-(1,1,1,3,3,3-hexafluoro-2-hydroxypropan-2-yl)phenyloxy]-(2Z)-2-butenyl]-5-ethylimidazolidine-2,4-dione The title compound was obtained as a colorless oil by the same reaction and treatment as in Example 1 and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 293.

Example 296

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]-(2Z)-2-butenyl]-5-ethylimidazolidine-2,4-dione The title compound was obtained as a colorless oil by the same reaction and treatment as in Example 1 and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 293.

Example 297

Preparation of 3-[4-[4-(1,1,1,3,3,3-hexafluoro-2-hydroxypropan-2-yl)-2-propylphenyloxy]-2-butynyl]-5-methyl-5-[4-(1-methylethoxy)phenyl]imidazolidine-2,4-dione The reaction and treatment were carried out using 3-(4-bromo-2-butynyl)-5-methyl-5-[4-(1-methylethoxy)phenyl]imidazolidine-2,4-dione obtained in Preparation Example 9 instead of 1,4-dibromobutane in Preparation Example 4, and then the same reaction and treatment as in Example 2 were carried out to obtain the title compound as a colorless oil.

Example 298

Preparation of 5-(1,3-benzodioxol-5-yl)-3-[4-[4-(1,1,1,3,3,3-hexafluoro-2-hydroxypropan-2-yl)-2-propylphenyloxy]-2-butynyl]-5-methylimidazolidine-2,4-dione 5-(1,3-Benzodioxol-5-yl)-3-(4-bromo-2-butynyl)-5-methylimidazolidine-2,4-dione was obtained by reaction and treatment using 5-(1,3-benzodioxol-5-yl)-5-methylimidazolidine-2,4-dione instead of 5-methyl-5-[4-(1-methylethoxy)

phenyl]imidazolidine-2,4-dione in Preparation Example 9b). The title compound was obtained as a colorless oil by the same reaction and treatment as in Preparation Example 4 and Example 2 using this.

Example 299

Preparation of 5-(1,3-benzodioxol-5-yl)-5-ethyl-3-[4-[4-(1,1,1,3,3,3-hexafluoro-2-hydroxypropan-2-yl)-2-propylphenyloxy]-2-butynyl]imidazolidine-2,4-dione 5-(1,3-Benzodioxol-5-yl)-3-(4-bromo-2-butynyl)-5-ethylimidazolidine-2,4-dione was obtained by reaction and treatment using 5-(1,3-benzodioxol-5-yl)-5-ethylimidazolidine-2,4-dione instead of 5-methyl-5-[4-(1-methylethoxy)phenyl]imidazolidine-2,4-dione in Preparation Example 9b). The title compound was obtained as a colorless oil by the same reaction and treatment as in Preparation Example 4 and Example 2 using this.

Example 300

Preparation of 5-(2,3-dihydro-1,4-benzodioxan-6-yl)-5-ethyl-3-[4-[4-(1,1,1,3,3,3-hexafluoro-2-hydroxypropan-2-yl)-2-propylphenyloxy]-2-butynyl]imidazolidine-2,4-dione 3-(4-Bromo-2-butynyl)-5-(2,3-dihydro-1,4-benzodioxan-6-yl)-5-ethylimidazolidine-2,4-dione was obtained by reaction and treatment using 5-(1,3-benzodioxol-5-yl)-5-ethylimidazolidine-2,4-dione instead of 5-methyl-5-[4-(1-methylethoxy)phenyl]imidazolidine-2,4-dione in Preparation Example 9b). The title compound was obtained as a colorless oil by the same reaction and treatment as in Preparation Example 4 and Example 2 using this.

Example 301

Preparation of 3-[4-[2,6-dipropyl-4-(1,1,1,3,3,3-hexafluoro-2-hydroxypropan-2-yl)phenyloxy]-2-butynyl]-5-methyl-5-[4-(1-methylethoxy)phenyl]imidazolidine-2,4-dione The title compound was obtained as a colorless oil by the same reaction and treatment as in Preparation Example 4 and Example 2 using 2,6-dipropyl-4-[1,1,1,3,3,3-hexafluoro-2-(methoxymethyl)oxypropan-2-yl]phenol obtained in Preparation Example 2 and 3-(4-bromo-2-butynyl)-5-methyl-5-[4-(1-methylethoxy)phenyl]imidazolidine-2,4-dione obtained in Preparation Example 9.

Example 302

Preparation of 5-(1,3-benzodioxol-5-yl)-3-[4-[2,6-dipropyl-4-(1,1,1,3,3,3-hexafluoro-2-hydroxypropan-2-yl)phenyloxy]-2-butynyl]-5-methylimidazolidine-2,4-dione The title compound was obtained as a colorless oil by the same reaction and treatment as in Preparation Example 4 and Example 2 using 2,6-dipropyl-4-[1,1,1,3,3,3-hexafluoro-2-(methoxymethyl)oxypropan-2-yl]phenol obtained in Preparation Example 2 and 5-(1,3-benzodioxol-5-yl)-3-(4-bromo-2-butynyl)-5-methylimidazolidine-2,4-dione obtained in Example 298.

Example 303

Preparation of 5-(1,3-benzodioxol-5-yl)-3-[4-[2,6-dipropyl-4-(1,1,1,3,3,3-hexafluoro-2-hydroxypropan-2-yl)phenyloxy]-2-butynyl]-5-ethylimidazolidine-2,4-dione The title compound was obtained as a colorless oil by the same reaction and treatment as in Preparation Example 4 and Example 2 using 2,6-dipropyl-4-[1,1,1,3,3,3-hexafluoro-2-(methoxymethyl)oxypropan-2-yl]phenol obtained in Preparation Example 2 and 5-(1,3-benzodioxol-5-yl)-3-(4-bromo-2-butynyl)-5-ethylimidazolidine-2,4-dione obtained in Example 299.

Example 304

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]-2-butynyl]-5-ethylimidazolidine-2,4-dione The title compound was obtained as a colorless oil by the same reaction and treatment as in Preparation Example 4 and Example 2 using 2,6-dipropyl-4-[1,1,1,3,3,3-hexafluoro-2-(methoxymethyl)oxypropan-2-yl]phenol obtained in Preparation Example 2 and 3-(4-bromo-2-butynyl)-5-(2,3-dihydro-1,4-benzodioxan-6-yl)-5-ethylimidazolidine-2,4-dione obtained in Example 300.

Example 305

Preparation of 3-[4-[4-(1,1,1,3,3,3-hexafluoro-2-hydroxypropan-2-yl)-2-propylphenyloxy]butyl]-5-methyl-5-(2-methoxypyridin-5-yl)imidazolidine-2,4-dione The title compound was obtained as a colorless oil by the same reaction and treatment as in Example 1 and Example 2 using 5-methyl-5-(2-methoxypyridin-5-yl)imidazolidine-2,4-dione instead of 1,5,5-trimethylimidazolidine-2,4-dione.

Example 306

Preparation of 3-[4-[2,6-dipropyl-4-(1,1,1,3,3,3-hexafluoro-2-hydroxypropan-2-yl)phenyloxy]butyl]-5-methyl-5-(2-methoxypyridin-5-yl)imidazolidine-2,4-dione The title compound was obtained as a colorless oil by the same reaction and treatment as in Example 1 and Example 2 using 5-methyl-5-(2-methoxypyridin-5-yl)imidazolidine-2,4-dione instead of 1,5,5-trimethylimidazolidine-2,4-dione in Example 48.

Example 307

Preparation of 3-[4-[4-(1,1,1,3,3,3-hexafluoro-2-hydroxypropan-2-yl)-2-propylphenyloxy]butyl]-5-methyl-5-[2-(1-methylethoxy)pyridin-5-yl]imidazolidine-2,4-dione The title compound was obtained as a colorless oil by the same reaction and treatment as in Example 1 and Example 2 using 5-methyl-5-[2-(1-methylethoxy)pyridin-5-yl]imidazolidine-2,4-dione instead of 1,5,5-trimethylimidazolidine-2,4-dione.

Example 308

Preparation of 3-[4-[2,6-dipropyl-4-(1,1,1,3,3,3-hexafluoro-2-hydroxypropan-2-yl)phenyloxy]butyl]-5-methyl-5-[2-(1-methylethoxy)pyridin-5-yl]imidazolidine-2,4-dione The title compound was obtained as a colorless oil by the same reaction and treatment as in Example 1 and Example 2 using 5-methyl-5-[2-(1-methylethoxy)pyridin-5-yl]imidazolidine-2,4-dione instead of 1,5,5-trimethylimidazolidine-2,4-dione in Example 48.

Example 309

Preparation of 5-[3-fluoro-4-(1-methylethoxy)phenyl]-3-[4-[4-(1,1,1,3,3,3-hexafluoro-2-hydroxypropan-2-yl)-2-propylphenyloxy]butyl]-5-methylimidazolidine-2,4-dione The title compound was obtained as a colorless oil by the same reaction and treatment as in Example 1 and Example 2 using 5-[3-fluoro-4-(1-methylethoxy)phenyl]-5-methylimidazolidine-2,4-dione instead of 1,5,5-trimethylimidazolidine-2,4-dione.

Example 310

Preparation of 3-[4-[2,6-dipropyl-4-(1,1,1,3,3,3-hexafluoro-2-hydroxypropan-2-yl)phenyloxy]butyl]-5-[3-fluoro-4-(1-methylethoxy)phenyl]-5-methylimidazolidine-2,4-dione The title compound was obtained as a colorless oil by the same reaction and treatment as in Example 1 and Example 2 using 5-[3-fluoro-4-(1-methylethoxy)phenyl]-5-methylimidazolidine-2,4-dione instead of 1,5,5-trimethylimidazolidine-2,4-dione in Example 48.

Example 311

Preparation of 5-[3-fluoro-4-(1-methylethoxy)phenyl]-3-[4-[4-(1,1,1,3,3,3-hexafluoro-2-hydroxypropan-2-yl)-2-propylphenyloxy]butyl]-5-ethylimidazolidine-2,4-dione The title compound was obtained as a colorless oil by the same reaction and treatment as in Example 1 and Example 2 using 5-[3-fluoro-4-(1-methylethoxy)phenyl]-5-ethylimidazolidine-2,4-dione instead of 1,5,5-trimethylimidazolidine-2,4-dione.

Example 312

Preparation of 3-[4-[2,6-dipropyl-4-(1,1,1,3,3,3-hexafluoro-2-hydroxypropan-2-yl)phenyloxy]butyl]-5-[3-fluoro-4-(1-methylethoxy)phenyl]-5-ethylimidazolidine-2,4-dione The title compound was obtained as a colorless oil by the same reaction and treatment as in Example 1 and Example 2 using 5-[3-fluoro-4-(1-methylethoxy)phenyl]-5-ethylimidazolidine-2,4-dione instead of 1,5,5-trimethylimidazolidine-2,4-dione in Example 48.

Example 313

Preparation of 3-[4-[4-(1,1,1,3,3,3-hexafluoro-2-hydroxypropan-2-yl)-2-propylphenyloxy]butyl]-5-methyl-5-(quinoxalin-6-yl)imidazolidine-2,4-dione The title compound was obtained as a colorless oil by the same reaction and treatment as in Example 1 and Example 2 using 5-methyl-5-(quinoxalin-6-yl)imidazolidine-2,4-dione instead of 1,5,5-trimethylimidazolidine-2,4-dione.

Example 314

Preparation of 3-[4-[2,6-dipropyl-4-(1,1,1,3,3,3-hexafluoro-2-hydroxypropan-2-yl)phenyloxy]butyl]-5-methyl-5-(quinoxalin-6-yl)imidazolidine-2,4-dione The title compound was obtained as a colorless oil by the same reaction and treatment as in Example 1 and Example 2 using 5-methyl-5-(quinoxalin-6-yl)imidazolidine-2,4-dione instead of 1,5,5-trimethylimidazolidine-2,4-dione in Example 48.

Example 315

Preparation of 3-[4-[4-(1,1,1,3,3,3-hexafluoro-2-hydroxypropan-2-yl)-2-propylphenyloxy]-1-methylbutyl]-5-methyl-5-[4-(1-methylethoxy)phenyl]imidazolidine-2,4-dione a) Preparation of 5-benzyloxy-2-pentanone

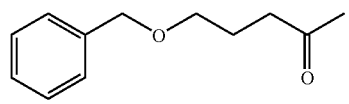

Benzyl trichloroacetimidate (1.85 g) was added to a mixed solution of 5-hydroxy-2-pentanone (500 mg, 4.89 mmol) in dichloromethane (20 mL) in an argon atmosphere at room temperature, and then trifluoromethanesulfonic acid (87 µL) was added in an ice bath. The mixture was returned to room temperature and stirred overnight. After completion of the reaction, a saturated sodium bicarbonate solution was added to the reaction solution in an ace bath, and the pH was adjusted to 8. After extraction with chloroform-water, the organic layer was concentrated under reduced pressure. The residue was purified by silica gel column chromatography (hexane:ethyl acetate=4:1) to obtain 610 mg of the title compound (yield: 65%) as a pale yellow oil.

b) Preparation of 5-benzyloxypentan-2-ol

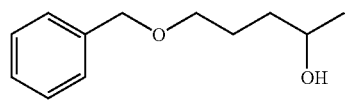

Sodium borohydride (236 mg) was added to a mixed solution of 5-benzyloxy-2-pentanone (1.09 g, 5.67 mmol) in methanol (50 mL) in an ice bath, followed by stirring. After completion of the reaction, water was added to the reaction solution in an ice bath, and methanol was evaporated. The pH was adjusted to 4 with 2 mol/L hydrochloric acid. After extraction with chloroform-water, the organic layer was washed with a saturated sodium chloride solution and concentrated under reduced pressure. The residue was purified by silica gel column chromatography (hexane:ethyl acetate=3:1) to obtain 957 mg of the title compound (yield: 87%) as a colorless solid.

c) Preparation of 5-benzyloxypent-2-yl acetate

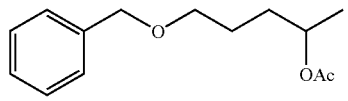

Acetic anhydride (1.86 mL) was added to a mixed solution of 5-benzyloxypentan-2-ol (957 mg, 4.93 mmol) in pyridine (1.8 mL) in an ice bath. After completion of the reaction, methanol (1.6 mL) was added to the reaction solution in an ice bath, and the solvent was evaporated. The pH was adjusted to 4 with 2 mol/L hydrochloric acid. After extraction with chloroform-water, the organic layer was washed with a saturated sodium chloride solution and concentrated under reduced pressure. The residue was purified by silica gel column chromatography (hexane:ethyl acetate=3:1) to obtain 420 mg of the title compound (yield: 36%) as a colorless oil.

d) Preparation of 5-hydroxypent-2-yl acetate

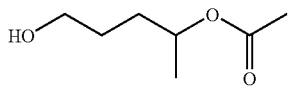

10% palladium-active carbon (48 mg) was added to a mixed solution of 5-benzyloxypent-2-yl acetate (419 mg, 1.78 mmol) in methanol (1.86 mL) in an ice bath in an argon atmosphere, followed by stirring at room temperature in a hydrogen atmosphere. After completion of the reaction, filtration was carried out and the filtrate was concentrated under reduced pressure. 257 mg of the title compound (yield: 87%) was obtained as a colorless oil.

e) Preparation of 5-[4-[1,1,1,3,3,3-hexafluoro-2-(methoxymethyl)oxypropan-2-yl]-2-propylphenyloxy]pent-2-yl acetate

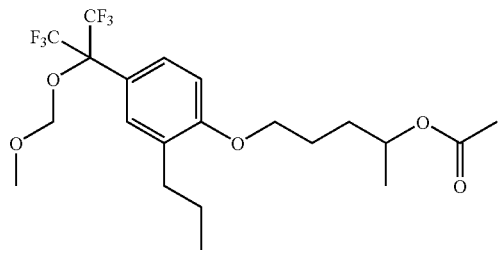

5-Hydroxypent-2-yl acetate (58.5 mg), triphenylphosphine (131 mg) and ethyl azodicarboxylate (2.2 mol/L, 200 μL) were added to a mixed solution of 4-[1,1,1,3,3,3-hexafluoro-2-(methoxymethyl)oxypropan-2-yl]-2-propylphenol (69.3 mg, 200 μmol) in tetrahydrofuran (2 mL) at room temperature. After completion of the reaction, the solvent was evaporated, and the residue was purified by silica gel preparative thin-layer chromatography (hexane:ethyl acetate=5:1) to obtain 80.4 mg of the title compound (yield: 85%) as a colorless oil.

f) Preparation of 5-[4-[1,1,1,3,3,3-hexafluoro-2-(methoxymethyl)oxypropan-2-yl]-2-propylphenyloxy]pentan-2-ol

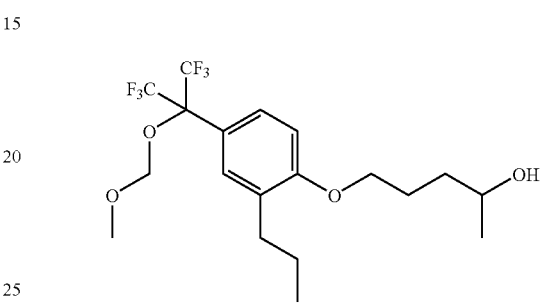

A 2 mol/L Lithium hydroxide solution (2 mL) was added to a mixed solution of 5-[4-[1,1,1,3,3,3-hexafluoro-2-(methoxymethyl)oxypropan-2-yl]-2-propylphenyloxy]pent-2-yl acetate (80.4 mg, 169 μmol) in methanol (1.5 mL) at room temperature, followed by heating at an external temperature of 60° C. in an oil bath overnight. After completion of the reaction, methanol was evaporated under reduced pressure. The pH was adjusted to 7 by adding 4 mol/L hydrochloric acid (2 mL) to the residue. After extraction with chloroform-water, the organic layer was washed with a saturated sodium chloride solution and dried over sodium sulfate. After filtration, the filtrate was concentrated under reduced pressure. 68.1 mg of the title compound (yield: 93%) was obtained as a colorless oil.

g) Preparation of 3-[4-[1,1,1,3,3,3-hexafluoro-2-(methoxymethyl)oxypropan-2-yl]-2-propylphenyloxy]-1-methylbutyl]-5-methyl-5-[4-(1-methylethoxy)phenyl]imidazolidine-2,4-dione

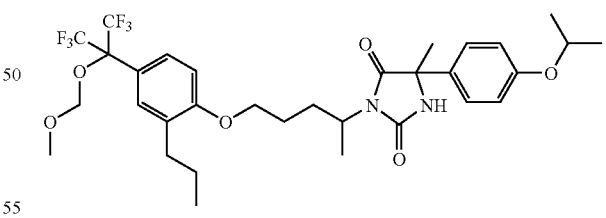

5-Methyl-5-[4-(1-methylethoxy)phenyl]imidazolidine-2,4-dione (25.8 mg), triphenylphosphine (22.8 mg) and a solution of ethyl azodicarboxylate in toluene (2.2 mol/L, 34.7 μL) were added to a mixed solution of 5-[4-[1,1,1,3,3,3-hexafluoro-2-(methoxymethyl)oxypropan-2-yl]-2-propylphenyloxy]pentan-2-ol (15.0 mg, 34.7 μmol) in tetrahydrofuran (1 mL) at room temperature. After completion of the reaction, the solvent was evaporated, and the residue was purified by silica gel column chromatography (hexane:ethyl acetate=2:1) to obtain 19.0 mg of the title compound (yield: 89%) as a colorless oil.

h) Preparation of 3-[4-[4-(1,1,1,3,3,3-hexafluoro-2-hydroxypropan-2-yl)-2-propylphenyloxy]-1-methylbutyl]-5-methyl-5-[4-(1-methylethoxy)phenyl]imidazolidine-2,4-dione The title compound was obtained as a colorless oil by the same reaction and treatment as in Example 2 for 3-[4-[1,1,1,3,3,3-hexafluoro-2-(methoxymethyl)oxypropan-2-yl]-2-propylphenyloxy]-1-methylbutyl]-5-methyl-5-[4-(1-methylethoxy)phenyl]imidazolidine-2,4-dione.

Example 316

Preparation of 5-(1,3-benzodioxol-5-yl)-3-[4-[4-(1,1,1,3,3,3-hexafluoro-2-hydroxypropan-2-yl)-2-propylphenyloxy]-1-methylbutyl]-5-methylimidazolidine-2,4-dione The title compound was obtained as a colorless oil by carrying out reaction and treatment using 5-(1,3-benzodioxol-5-yl)-5-methylimidazolidine-2,4-dione instead of 5-methyl-5-[4-(1-methylethoxy)phenyl]imidazolidine-2,4-dione in Example 315g) and then carrying out the same reaction and treatment as in Example 2.

Example 317

Preparation of 5-(1,3-benzodioxol-5-yl)-5-ethyl-3-[4-[4-(1,1,1,3,3,3-hexafluoro-2-hydroxypropan-2-yl)-2-propylphenyloxy]-1-methylbutyl]imidazolidine-2,4-dione The title compound was obtained as a colorless oil by carrying out reaction and treatment using 5-(1,3-benzodioxol-5-yl)-5-ethylimidazolidine-2,4-dione instead of 5-methyl-5-[4-(1-methylethoxy)phenyl]imidazolidine-2,4-dione in Example 315g) and then carrying out the same reaction and treatment as in Example 2.

Example 318

Preparation of 5-(2,3-dihydro-1,4-benzodioxan-6-yl)-5-ethyl-3-[4-[4-(1,1,1,3,3,3-hexafluoro-2-hydroxypropan-2-yl)-2-propylphenyloxy]-1-methylbutyl]imidazolidine-2,4-dione The title compound was obtained as a colorless oil by carrying out reaction and treatment using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 315g) and then carrying out the same reaction and treatment as in Example 2.

Example 319

Preparation of 3-[4-[2,6-dipropyl-4-(1,1,1,3,3,3-hexafluoro-2-hydroxypropan-2-yl)phenyloxy]-1-methylbutyl]-5-methyl-5-[4-(1-methylethoxy)phenyl]imidazolidine-2,4-dione The title compound was obtained as a colorless oil by subjecting 2,6-dipropyl-4-[1,1,1,3,3,3-hexafluoro-2-(methoxymethyl)oxypropan-2-yl]phenol obtained in Preparation Example 2 to the reaction and treatment in Example 315e) to g) and then carrying out the same reaction and treatment as in Example 2.

Example 320

Preparation of 5-(1,3-benzodioxol-5-yl)-3-[4-[2,6-dipropyl-4-(1,1,1,3,3,3-hexafluoro-2-hydroxypropan-2-yl)phenyloxy]-1-methylbutyl]-5-methylimidazolidine-2,4-dione The title compound was obtained as a colorless oil by the same reaction and treatment as in Example 315g) and Example 2 using 5-(1,3-benzodioxol-5-yl)-5-methylimidazolidine-2,4-dione instead of 5-methyl-5-[4-(1-methylethoxy)phenyl]imidazolidine-2,4-dione in Example 319.

Example 321

Preparation of 5-(1,3-benzodioxol-5-yl)-3-[4-[2,6-dipropyl-4-(1,1,1,3,3,3-hexafluoro-2-hydroxypropan-2-yl)phenyloxy]-1-methylbutyl]-5-ethylimidazolidine-2,4-dione The title compound was obtained as a colorless oil by the same reaction and treatment as in Example 315g) and Example 2 using 5-(1,3-benzodioxol-5-yl)-5-ethylimidazolidine-2,4-dione instead of 5-methyl-5-[4-(1-methylethoxy)phenyl]imidazolidine-2,4-dione in Example 319.

Example 322

Preparation of 5-(2,3-dihydro-1,4-benzodioxan-6-yl)-3-[4-[2,6-dipropyl-4-(1,1,1,3,3,3-hexafluoro-2-hydroxypropan-2-yl)phenyloxy]-1-methylbutyl]-5-ethylimidazolidine-2,4-dione The title compound was obtained as a colorless oil by the same reaction and treatment as in Example 315g) and Example 2 using 5-(2,3-dihydro-1,4-benzodioxan-6-yl)-5-ethylimidazolidine-2,4-dione instead of 5-methyl-5-[4-(1-methylethoxy)phenyl]imidazolidine-2,4-dione in Example 319.

Example 323

Preparation of 5-(1,3-benzodioxol-5-yl)-3-[4-[4-(1,1,1,3,3,3-hexafluoro-2-hydroxypropan-2-yl)-2-propylphenyloxy]butyl]-4-hydroxy-5-methylimidazolidin-2-one a) Preparation of 5-(1,3-benzodioxol-5-yl)-3-[4-[4-[1,1,1,3,3,3-hexafluoro-2-(methoxymethyl)oxypropan-2-yl]-2-propylphenyloxy]butyl]-4-hydroxy-5-methylimidazolidin-2-one Lithium aluminum hydride (2.3 mg, 0.06 mmol) was added to a solution of the compound of Example 3 (25 mg, 0.04 mmol) in THF (3 mL) under ice-cooling, followed by stirring at room temperature for three hours. Water was added to the reaction solution under ice-cooling, followed by extraction with ethyl acetate. The organic layer was dried over anhydrous sodium sulfate and concentrated under reduced pressure. The resulting residue was purified by silica gel preparative thin-layer chromatography (hexane:ethyl acetate=1:1) to obtain 22.5 mg of the title compound (yield: 90%) as a colorless oil.

b) Preparation of 5-(1,3-benzodioxol-5-yl)-3-[4-[4-(1,1,1,3,3,3-hexafluoro-2-hydroxypropan-2-yl)-2-propylphenyloxy]butyl]-4-hydroxy-5-methylimidazolidin-2-one The title compound was obtained as a colorless oil by the same reaction and treatment as in Example 2 for 5-(1,3-benzodioxol-5-yl)-3-[4-[4-[1,1,1,3,3,3-hexafluoro-2-(methoxymethyl)oxypropan-2-yl]-2-propylphenyloxy]butyl]-4-hydroxy-5-methylimidazolidin-2-one.

Example 324

Preparation of 3-[4-[2,6-dipropyl-4-(1,1,1,3,3,3-hexafluoro-2-hydroxypropan-2-yl)phenyloxy]butyl]-4-hydroxy-5-methyl-5-[4-(1-methylethoxy)phenyl]imidazolidin-2-one The title compound was obtained as a colorless oil by the same reaction and treatment as in Example 323 for 3-[4-[2,6-dipropyl-4-[1,1,1,3,3,3-hexafluoro-2-(methoxymethyl)oxypropan-2-yl]phenyloxy]butyl]-5-methyl-5-[4-(1-methylethoxy)phenyl]imidazolidine-2,4-dione obtained in the preparation process of Example 96.

Example 325

Preparation of 5-(1,3-benzodioxol-5-yl)-3-[4-[4-(1,1,1,3,3,3-hexafluoro-2-hydroxypropan-2-yl)-2-propylphenyloxy]butyl]-5-methylimidazolidin-2-one a) Preparation of 5-(1,3-benzodioxol-5-yl)-3-[4-[4-[1,1,1,3,3,3-hexafluoro-2-(methoxymethyl)oxypropan-2-yl]-2-propylphenyloxy]butyl]-5-methylimidazolidin-2-one Aluminum chloride (597 mg, 4.48 mmol) was added to a solution of the compound of Example 3 (710 mg, 1.12 mmol) in THF (20 mL) under ice-cooling. Then, lithium aluminum hydride (127.5 mg, 3.36 mmol) was added, followed by stirring at room temperature for three hours. Water was added to the reaction solution under ice-cooling, followed by extraction with ethyl acetate. The organic layer was dried over anhydrous sodium sulfate and concentrated under reduced pressure. The resulting residue was purified by silica gel column chromatography (hexane:ethyl acetate=1:1) to obtain 481 mg of the title compound (yield: 69%) as a colorless oil.

b) Preparation of 5-(1,3-benzodioxol-5-yl)-3-[4-[4-(1,1,1,3,3,3-hexafluoro-2-hydroxypropan-2-yl)-2-propylphenyloxy]butyl]-5-methylimidazolidin-2-one The title compound was obtained as a colorless oil by the same reaction and treatment as in Example 2 for 5-(1,3-benzodioxol-5-yl)-3-[4-[4-[1,1,1,3,3,3-hexafluoro-2-(methoxymethyl)oxypropan-2-yl]-2-propylphenyloxy]butyl]-5-methylimidazolidin-2-one.

Example 326

Preparation of 5-(1,3-benzodioxol-5-yl)-3-[4-[2-benzyl-4-(1,1,1,3,3,3-hexafluoro-2-hydroxypropan-2-yl)phenyloxy]butyl]-4,4-dihydro-5-ethylimidazolidine-2-one The title compound was obtained as a colorless oil by subjecting the compound of Example 141 to the same reaction and treatment as in Example 325a).

Example 327

Preparation of 5-(1,3-benzodioxol-5-yl)-5-ethyl-3-[4-[4-(1,1,1,3,3,3-hexafluoro-2-hydroxypropan-2-yl)-2-nitro-6-propylphenyloxy]butyl]imidazolidine-2,4-dione a) Preparation of 2-(4-hydroxy-3-nitro-5-propylphenyl)-1,1,1,3,3,3-hexafluoro-2-propanol

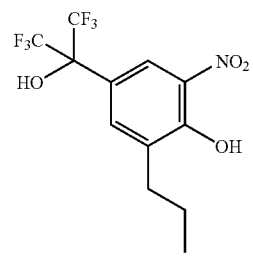

Concentrated sulfuric acid (1.2 mL) was added to 2-(4-hydroxy-3-propylphenyl)-1,1,1,3,3,3-hexafluoro-2-propanol (500 mg, 1.65 mmol) under ice-cooling. Then, a mixed solution of nitric acid (109 μL) and concentrated sulfuric acid (219 μL) was added dropwise at 30 to 35° C., followed by stirring at 40° C. for three hours. The reaction solution was cooled and then added dropwise to ice water. After neutralization to pH 7 with a sodium hydroxide solution (1 mol/L), the neutralized solution was concentrated under reduced pressure. The resulting residue was purified by silica gel column chromatography (hexane:ethyl acetate=3:1) to obtain 94.3 mg of the title compound (yield: 16%) as a red orange oil.

b) Preparation of 5-(1,3-benzodioxol-5-yl)-5-ethyl-3-[4-[4-(1,1,1,3,3,3-hexafluoro-2-hydroxypropan-2-yl)-2-nitro-6-propylphenyloxy]butyl]imidazolidine-2,4-dione 4-[1,1,1,3,3,3-Hexafluoro-2-(methoxymethyl)oxypropan-2-yl]-2-nitro-6-propylphenol was obtained by subjecting 2-(4-hydroxy-3-nitro 5-propylphenyl)-1,1,1,3,3,3-hexafluoro-2-propanol to the reaction of Preparation Example 3c) and Preparation Example 3d). The title compound was obtained as a colorless oil by subjecting this to the reaction of Preparation Example 4 and then carrying out the same reaction and treatment as in Example 1 and Example 2 using 5-(1,3-benzodioxol-5-yl)-5-ethylimidazolidine-2,4-dione instead of 1,5,5-trimethylimidazolidine-2,4-dione.

Example 328

Preparation of 3-[4-[2-benzyl-4-(1,1,1,3,3,3-hexafluoro-2-hydroxypropan-2-yl)-6-propylphenyloxy]butyl]-1,5,5-trimethylimidazolidine-2,4-dione The title compound was obtained as a colorless oil by subjecting 2-benzyl-4-[1,1,1,3,3,3-hexafluoro-2-(methoxymethyl)oxypropan-2-yl]-6-[(1E)-1-propenyl]phenol obtained in Example 233 to the reaction and treatment of Preparation Example 4 and then carrying out the same reaction and treatment as in Example 1, Example 2 and Preparation Example 5c).

Tables 1-1 to 1-110 show the structural formulas and property values of the compounds of Examples.

TABLE 1-1

| Example | Structural formula | Property values |
|---|---|---|
| 1 | | $^1$H-NMR (CDCl$_3$) δ: 0.92 (3H, t, J = 7.3 Hz), 1.37 (6H, s), 1.59 (2H, qt, J = 7.3, 7.3 Hz), 1.77-1.88 (4H, m), 2.60 (2H, t, J = 7.3 Hz), 2.89 (3H, s), 3.54 (3H, s), 3.60 (2H, t, J = 6.3 Hz), 4.02 (2H, t, J = 5.9 Hz), 4.82 (2H, s), 6.85 (1H, d, J = 8.8 Hz), 7.33 (1H, s), 7.37 (1H, d, J = 8.8 Hz). |
| 2 | | $^1$H-NMR (CDCl$_3$) δ: 0.92 (3H, t, J = 7.6 Hz), 1.33 (6H, s), 1.58 (2H, qt, J = 7.6, 7.6 Hz), 1.76-1.85 (4H, m), 2.59 (2H, t, J = 7.6 Hz), 2.88 (3H, s), 3.58 (2H, t, J = 6.3 Hz), 3.93 (1H, brs), 3.99 (2H, t, J = 5.6 Hz), 6.83 (1H, d, J = 8.9 Hz), 7.42 (1H, s), 7.46 (1H, d, J = 8.9 Hz). |
| 3 | | $^1$H-NMR (CDCl$_3$) δ: 0.89 (3H, t, J = 7.3 Hz), 1.56 (2H, qt, J = 7.3, 7.3 Hz), 1.71-1.88 (7H, m), 2.57 (2H, t, J = 7.3 Hz), 3.54 (3H, s), 3.59 (2H, t, J = 6.3 Hz), 3.98 (2H, t, J = 5.3 Hz), 4.82 (2H, s), 5.93 (2H, s), 6.77 (1H, d, J = 7.9 Hz), 6.81 (1H, d, J = 8.9 Hz), 6.97 (1H, dd, J = 2.0, 7.9 Hz), 7.01 (1H, d, J = 2.0 Hz), 7.14 (1H, brs), 7.32 (1H, s), 7.36 (1H, d, J = 8.9 Hz). |
| 4 | | $^1$H-NMR (CDCl$_3$) δ: 0.88 (3H, t, J = 7.6 Hz), 1.55 (2H, qt, J = 7.6, 7.6 Hz), 1.68-1.77 (7H, m), 2.56 (2H, t, J =7.6 Hz), 3.57 (2H, t, J = 6.3 Hz), 3.93 (2H, t, J = 5.3 Hz), 4.65 (1H, s), 5.92 (2H, s), 6.61-6.81 (3H, m), 6.93 (1H, dd, J = 2.0, 8.2 Hz), 6.97 (1H, d, J = 2.0 Hz), 7.40-7.49 (2H, m). |

TABLE 1-2

| Example | Structural formula | Property values |
|---|---|---|
| 5 | | $^1$H-NMR (CDCl$_3$) δ: 0.90 (3H, t, J = 7.6 Hz), 1.52-1.61 (2H, m), 1.75-1.85 (7H, m), 2.33 (3H, s), 2.57 (2H, t, J = 7.6 Hz), 3.59 (2H, t, J = 6.5 Hz), 3.67 (1H, s), 3.96 (2H, t, J = 5.7 Hz), 5.79 (1H, s), 6.81 (1H, d, J = 8.6 Hz), 7.18 (2H, d, J = 8.3 Hz), 7.35 (2H, d, J = 8.3 Hz), 7.42-7.47 (2H, m). |

TABLE 1-2-continued

| Example | Structural formula | Property values |
|---|---|---|
| 6 | | $^1$H-NMR (CDCl$_3$) δ: 0.90 (3H, t, J = 7.4 Hz), 1.22 (3H, t, J = 7.6 Hz), 1.50-1.67 (2H, m), 1.75-1.87 (7H, m), 2.55-2.68 (4H, m), 3.60 (2H, t, J = 7.0 Hz), 3.65 (1H ,s), 3.97 (2H, t, J = 5.7 Hz), 5.79 (1H, s), 6.81 (1H, d, J = 8.6 Hz), 7.21 (2H, d, J = 8.4 Hz), 7.38 (2H, d, J = 8.4 Hz), 7.42-7.47 (2H, m). |
| 7 | | $^1$H-NMR (CDCl$_3$) δ: 0.90 (3H, t, J = 7.3 Hz), 1.23 (6H, d, J = 6.9 Hz), 1.53-1.64 (2H, m), 1.77-1.87 (7H, m), 2.58 (2H, t, J = 7.3 Hz), 2.90 (1H, q, J = 6.9 Hz), 3.57-3.61 (3H, m), 3.98 (2H, t, J = 5.7 Hz), 5.75 (1H, s), 6.82 (1H, d, J = 8.9 Hz), 7.24 (2H, d, J = 8.4 Hz), 7.38 (2H, d, J = 8.4 Hz), 7.42-7.47 (2H, m). |

TABLE 1-3

| Example | Structural formula | Property values |
|---|---|---|
| 8 | | $^1$H-NMR (CDCl$_3$) δ: 0.90 (3H, t, J = 7.6 Hz), 1.30 (9H, s), 1.53-1.65 (2H, m), 1.78-1.92 (7H, m), 2.58 (2H, t, J = 7.4 Hz), 3.57-3.62 (3H, m), 3.98 (2H, t, J = 5.7 Hz), 5.73 (1H, s), 6.82 (1H, d, J = 8.6 Hz), 7.40-7.47 (6H, m). |
| 9 | | $^1$H-NMR (CDCl$_3$) δ: 0.90 (3H, t, J = 7.5 Hz), 1.50-1.65 (2H, m), 1.75-1.86 (7H, m), 2.57 (2H, t, J = 7.4 Hz), 3.58-3.60 (3H, m), 3.97 (2H, t, J = 5.9 Hz), 5.80 (1H, s), 6.81 (1H, d, J = 8.6 Hz), 7.07 (2H, dd, J = 8.4, 8.6 Hz), 7.42-7.49 (4H, m). |

TABLE 1-3-continued

| Example | Structural formula | Property values |
|---|---|---|
| 10 | (4-Cl phenyl hydantoin structure) | ¹H-NMR (CDCl₃) δ: 0.90 (3H, t, J = 7.3 Hz), 1.52-1.66 (2H, m), 1.73-1.86 (7H, m), 2.57 (2H, t, J = 7.6 Hz), 3.59 (2H, t, J = 6.4 Hz), 3.64 (1H, s), 3.97 (2H, t, J = 5.9 Hz), 5.92 (1H, s), 6.81 (1H, d, J = 8.6 Hz), 7.34-7.47 (6H, m). |
| 11 | (4-Br phenyl hydantoin structure) | ¹H-NMR (CDCl₃) δ: 0.90 (3H, t, J = 7.3 Hz), 1.49-1.67 (2H, m), 1.74-1.86 (7H, m), 2.57 (2H, t, J = 7.2 Hz), 3.59 (2H, t, J = 6.2 Hz), 3.68 (1H, s), 3.97 (2H, t, J = 5.9 Hz), 5.98 (1H, s), 6.81 (1H, d, J = 8.6 Hz), 7.37 (2H, d, J = 8.1 Hz), 7.51 (2H, d, J = 8.1 Hz), 7.42-7.47 (2H, m). |

TABLE 1-4

| Example | Structural formula | Property values |
|---|---|---|
| 12 | (4-CF₃ phenyl hydantoin structure) | ¹H-NMR (CDCl₃) δ: 0.89 (3H, t, J = 7.3 Hz), 1.49-1.63 (2H, m), 1.73-1.90 (7H, m), 2.57 (2H, t, J = 7.7 Hz), 3.60 (2H, t, J = 6.3 Hz), 3.69 (1H, s), 3.97 (2H, t, J = 5.5 Hz), 6.16 (1H, s), 6.81 (1H, d, J = 8.6 Hz), 7.42 (1H, s), 7.45 (1H, d, J = 8.6 Hz), 7.63-7.68 (4H, m). |
| 13 | (4-CN phenyl hydantoin structure) | ¹H-NMR (CDCl₃) δ: 0.89 (3H, t, J = 7.5 Hz), 1.49-1.63 (2H, m), 1.73-1.90 (7H, m), 2.56 (2H, t, J = 7.6 Hz), 3.60 (2H, t, J = 6.9 Hz), 3.74 (1H, s), 3.97 (2H, t, J = 5.5 Hz), 6.19 (1H, s), 6.80 (1H, d, J = 8.6 Hz), 7.42-7.47 (2H, m), 7.65-7.70 (4H, m) |
| 14 | (4-NO₂ phenyl hydantoin structure) | ¹H-NMR (CDCl₃) δ: 0.89 (3H, t, J = 7.4 Hz), 1.49-1.63 (2H, m), 1.74-1.90 (7H, m), 2.56 (2H, t, J = 7.6 Hz), 3.61 (2H, t, J = 6.5 Hz), 3.74 (1H, s), 3.97 (2H, t, J = 5.5 Hz), 6.34 (1H, s), 6.80 (1H, d, J = 8.6 Hz), 7.42-7.47 (2H, m), 7.73 (2H, d, J = 8.9 Hz), 8.24 (2H, d, J = 8.9 Hz). |

TABLE 1-4-continued

| Example | Structural formula | Property values |
|---|---|---|
| 15 | | ¹H-NMR (CDCl₃) δ: 0.90 (3H, t, J = 7.3 Hz), 1.50-1.65 (2H, m), 1.75-1.85 (7H, m), 2.57 (2H, t, J = 7.4 Hz), 2.93 (6H, s), 3.59 (2H, t, J = 5.7 Hz), 3.75 (1H, s), 3.97 (2H, t, J = 6.9 Hz), 5.67 (1H, s), 6.69 (2H, d, J = 8.9 Hz), 6.79 (1H, d, J = 8.4 Hz), 7.29 (2H, d, J = 8.9 Hz), 7.41-7.44 (2H, m). |

TABLE 1-5

| Example | Structural formula | Property values |
|---|---|---|
| 16 | | ¹H-NMR (CDCl₃) δ: 0.90 (3H, t, J = 7.3 Hz), 1.50-1.63 (2H, m), 1.76-1.87 (7H, m), 2.57 (2H, t, J = 7.6 Hz), 3.59 (2H, t, J = 6.2 Hz), 3.77-3.82 (4H, m), 3.96 (2H, t, J = 5.7 Hz), 6.00 (1H, s), 6.80 (1H, d, J = 8.4 Hz), 6.84-6.88 (1H, m), 7.03-7.06 (2H, m), 7.27-7.32 (1H, m), 7.42-7.46 (2H, m). |
| 17 | | ¹H-NMR (CDCl₃) δ: 0.92 (3H, t, J = 7.3 Hz), 1.52-1.66 (2H, m), 1.76 (3H, s), 1.85-1.87 (4H, m), 2.60 (2H, t, J = 7.4 Hz), 3.64-3.69 (3H, m), 3.86 (3H, s), 4.01 (2H, t, J = 5.4 Hz), 6.25 (1H, s), 6.83 (1H, d, J = 8.6 Hz), 6.92-6.97 (2H, m), 7.29-7.52 (4H, m). |
| 18 | | ¹H-NMR (CDCl₃) δ: 0.90 (3H, t, J = 7.3 Hz), 1.40 (3H, t, J = 7.3 Hz), 1.50-1.63 (2H, m), 1.73-1.90 (7H, m), 2.57 (2H, t, J = 7.6 Hz), 3.59 (2H, t, J = 6.6 Hz), 3.74 (1H, s), 3.94-4.02 (4H, m), 5.84 (1H, s), 6.80 (1H, d, J = 8.6 Hz), 6.87 (2H, d, J = 8.9 Hz), 7.36 (2H, d, J = 8.9 Hz), 7.42-7.46 (2H, m). |

TABLE 1-5-continued

| Example | Structural formula | Property values |
| --- | --- | --- |
| 19 | | $^1$H-NMR (CDCl$_3$) δ: 0.90 (3H, t, J = 7.3 Hz), 1.02 (3H, t, J = 7.4 Hz), 1.50-1.63 (2H, m), 1.75-1.85 (9H, m), 2.57 (2H, t, J = 7.6 Hz), 3.59 (2H, t, J = 6.3 Hz), 3.85 (1H, s), 3.90 (2H, t, J = 6.3 Hz), 3.96 (2H, t, J = 5.4 Hz), 5.92 (1H, s), 6.80 (1H, d, J = 8.9 Hz), 6.88 (2H, d, J = 8.9 Hz), 7.36 (2H, d, J = 8.9 Hz), 7.42-7.46 (2H, m). |

TABLE 1-6

| Example | Structural formula | Property values |
| --- | --- | --- |
| 20 | | $^1$H-NMR (CDCl$_3$) δ: 0.90 (3H, t, J = 7.3 Hz), 1.31 (6H, d, J = 6.8 Hz), 1.50-1.63 (2H, m), 1.71-1.88 (7H, m), 2.57 (2H, t, J = 7.6 Hz), 3.59 (2H, t, J = 6.2 Hz), 3.70 (1H, s), 3.97 (2H, t, J = 5.5 Hz), 4.52 (1H, q, J = 6.8 Hz), 5.80 (1H, s), 6.80 (1H, d, J = 8.6 Hz), 6.86 (2H, d, J = 8.9 Hz), 7.34 (2H, d, J = 8.9 Hz), 7.42-7.46 (2H, m). |
| 21 | | $^1$H-NMR (CDCl$_3$) δ: 0.90 (3H, t, J = 7.3 Hz), 0.96 (3H, t, J = 7.3 Hz), 1.40-1.64 (4H, m), 1.70-1.86 (9H, m), 2.57 (2H, t, J = 7.6 Hz), 3.59 (2H, t, J = 6.5 Hz), 3.75 (1H, s), 3.92-3.99 (4H, m), 5.86 (1H, s), 6.80 (1H, d, J = 8.6 Hz), 6.88 (2H, d, J = 8.9 Hz), 7.36 (2H, d, J = 8.9 Hz), 7.42-7.46 (2H, m). |
| 22 | | $^1$H-NMR (CDCl$_3$) δ: 0.90 (3H, t, J = 7.3 Hz), 1.00 (6H, d, J = 7.0 Hz), 1.50-1.64 (2H, m), 1.73-1.90 (7H, m), 2.06 (1H, tq, J = 6.5, 7.0 Hz), 2.57 (2H, t, J = 7.3 Hz), 3.59 (2H, d, J = 6.2 Hz), 3.69 (2H, d, J = 6.5 Hz), 3.77 (1H, s), 3.96 (2H, t, J = 5.4 Hz), 5.87 (1H, s), 6.80 (1H, d, J = 8.6 Hz), 6.88 (2H, d, J = 8.9 Hz), 7.35 (2H, d, J = 8.9 Hz), 7.42 -7.46 (2H, m). |

TABLE 1-7

| Example | Structural formula | Property values |
|---|---|---|
| 23 | | ¹H-NMR (CDCl₃) δ: 0.89 (3H, t, J = 7.3 Hz), 1.49-1.67 (2H, m), 1.75-1.92 (7H, m), 2.57 (2H, t, J = 7.6 Hz), 3.55 (1H, s), 3.61 (2H, t, J = 6.5 Hz), 3.97 (2H, t, J = 5.4 Hz), 5.99 (1H, s), 6.81 (1H, d, J = 8.6 Hz), 7.20-7.47 (6H, m) |
| 24 | | ¹H-NMR (CDCl₃) δ: 0.88 (3H, t, J = 7.3 Hz), 1.50-1.68 (11H, m), 1.72-1.95 (7H, m), 2.55 (2H, t, J = 7.6 Hz), 3.61 (2H, t, J = 6.7 Hz), 3.94-3.99 (3H, m), 6.11 (1H, s), 6.79 (1H, d, J = 8.6 Hz), 7.42-7.47 (2H, m), 7.53 (2H, d, J = 8.9 Hz), 7.94 (2H, d, J = 8.9 Hz). |
| 25 | | ¹H-NMR (CDCl₃) δ: 0.89 (3H, t, J = 7.2 Hz), 1.50-1.66 (2H, m), 1.75-1.93 (7H, m), 2.57 (2H, t, J = 7.6 Hz), 3.60-3.64 (3H, m), 3.97 (2H, t, J = 5.4 Hz), 5.95 (1H, s), 6.81 (1H, d, J = 8.6 Hz), 7.36-7.63 (11H, m). |
| 26 | | ¹H-NMR (CDCl₃) δ: 0.90 (3H, t, J = 7.3 Hz), 1.49-1.63 (2H, m), 1.72-1.90 (7H, m), 2.57 (2H, t, J = 7.6 Hz), 3.58-3.63 (3H, m), 3.97 (2H, t, J = 5.5 Hz), 6.09 (1H, s), 6.81 (1H, d, J = 8.6 Hz), 7.16-7.47 (5H, m). |

TABLE 1-8

| Example | Structural formula | Property values |
|---|---|---|
| 27 | 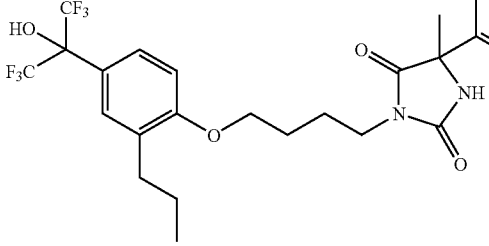 | ¹H-NMR (CDCl₃) δ: 0.89 (3H, t, J = 7.3 Hz), 1.50-1.64 (2H, m), 1.72-1.85 (7H, m), 2.58 (2H, t, J = 7.3 Hz), 3.57-3.64 (2H, m), 3.68 (1H, s), 3.93-4.10 (2H, m), 6.10 (1H, s), 6.81 (1H, d, J = 8.5 Hz), 7.12 (1H, dd, J = 8.4, 8.5 Hz), 7.42-7.47 (3H, m), 7.71 (1H, d, J = 6.2 Hz). |
| 28 | 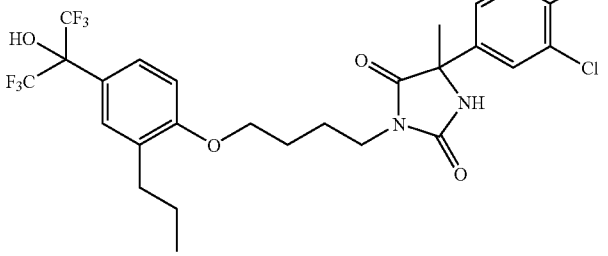 | ¹H-NMR (CDCl₃) δ: 0.89 (3H, t, J = 7.4 Hz), 1.56 (2H, qt, J = 7.4, 7.4 Hz), 1.73-1.88 (7H, m), 2.57 (2H, t, J = 7.4 Hz), 3.60 (2H, t, J = 6.2 Hz), 3.69 (1H, s), 3.97 (2H, t, J = 5.7 Hz), 6.22 (1H, s), 6.81 (1H, d, J = 8.6 Hz), 7.34-7.62 (5H, m). |
| 29 | 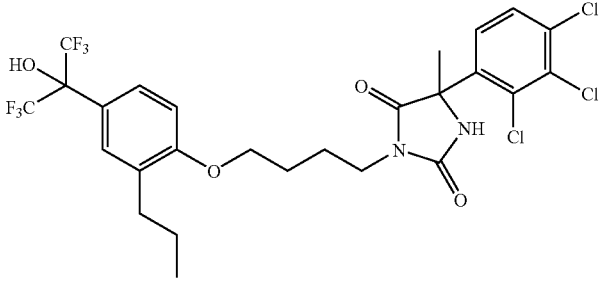 | ¹H-NMR (CDCl₃) δ: 0.92 (3H, t, J = 7.3 Hz), 1.53-1.69 (2H, m), 1.80-1.95 (7H, m), 2.61 (2H, t, J = 7.7 Hz), 3.66-3.70 (3H, m), 4.02 (2H, t, J = 5.4 Hz), 6.23 (1H, s), 6.85 (1H, d, J = 8.9 Hz), 7.39-7.52 (4H, m). |
| 30 | 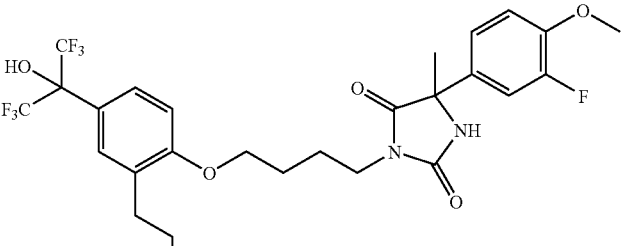 | ¹H-NMR (CDCl₃) δ: 0.90 (3H, t, J = 7.3 Hz), 1.50-1.64 (2H, m), 1.75-1.88 (7H, m), 2.57 (2H, t, J = 7.6 Hz), 3.60 (2H, t, J = 6.5 Hz), 3.71 (1H, s), 3.88 (3H, s), 3.97 (2H, t, J = 5.7 Hz), 6.03 (1H, s), 6.81 (1H, d, J = 8.9 Hz), 6.92-6.98 (1H, m), 7.18-7.47 (4H, m). |

TABLE 1-9

| Example | Structural formula | Property values |
|---|---|---|
| 31 | 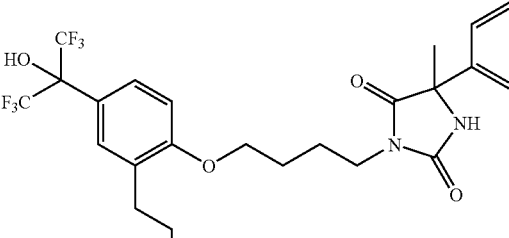 | ¹H-NMR (CDCl₃) δ: 0.90 (3H, t, J = 7.8 Hz), 1.50-1.63 (2H, m), 1.72-1.88 (7H, m), 2.57 (2H, t, J = 7.6 Hz), 3.60 (2H, t, J = 6.5 Hz), 3.75 (1H, s), 3.86 (3H, s), 3.87 (3H, s), 3.97 (2H, t, J = 5.7 Hz), 5.90 (1H, s), 6.80 (1H, d, J = 8.6 Hz), 6.85 (1H, d, J = 8.6 Hz), 7.00-7.03 (2H, m), 7.42-7.46 (2H, m). |

TABLE 1-9-continued

| Example | Structural formula | Property values |
|---|---|---|
| 32 | | ¹H-NMR (CDCl₃) δ: 0.90 (3H, t, J = 7.3 Hz), 1.52-1.63 (2H, m), 1.75-1.90 (7H, m), 2.57 (2H, t, J = 7.3 Hz), 3.59-3.63 (3H, m), 3.83 (3H, s), 3.85 (3H, s), 3.87 (3H, s), 3.98 (2H, t, J = 5.7 Hz), 5.97 (1H, s), 6.70-6.72 (2H, m), 7.29 (1H, s), 7.42-7.50 (2H, m). |
| 33 | | ¹H-NMR (CDCl₃) δ: 0.90 (3H, t, J = 7.4 Hz), 1.50-1.64 (2H, m), 1.74-1.86 (7H, m), 2.58 (2H, t, J = 7.4 Hz), 3.59 (2H, t, J = 6.6 Hz), 3.72 (1H, s), 3.97 (2H, t, J = 5.7 Hz), 4.22-4.26 (4H, m), 5.85 (1H, s), 6.79-6.99 (4H, m), 7.42-7.47 (2H, m). |
| 34 | | ¹H-NMR (CDCl₃) δ: 0.90 (3H, t, J = 7.3 Hz), 1.52-1.65 (2H, m), 1.82-2.00 (4H, m), 2.08 (3H, s), 2.60 (2H, t, J =7.7 Hz), 3.72-3.77 (3H, m), 4.02 (2H, t, J = 5.7 Hz), 6.07 (1H, s), 6.83 (1H, d, J = 8.6 Hz), 7.43-7.54 (5H, m), 7.67 (1H, d, J = 6.2 Hz), 7.84-7.93 (3H, m). |

TABLE 1-10

| Example | Structural formula | Property values |
|---|---|---|
| 35 | | ¹H-NMR (CDCl₃) δ: 0.87 (3H, t, J = 7.3 Hz), 1.48-1.61 (2H, m), 1.73-1.89 (4H, m), 1.93 (3H, s), 2.55 (2H, t, J = 7.6 Hz), 3.62 (2H, t, J = 6.5 Hz), 3.74 (1H, s), 3.94 (2H, t, J = 5.5 Hz), 6.05 (1H, s), 6.78 (1H, d, J = 8.6 Hz), 7.41-7.61 (5H, m), 7.61-7.94 (4H, m). |
| 36 | | ¹H-NMR (CDCl₃) δ: 0.91 (3H, t, J = 7.4 Hz), 1.52-1.66 (2H, m), 1.79-1.85 (7H, m), 2.60 (2H, t, J = 7.6 Hz), 3.62-3.67 (3H, m), 4.01 (2H, t, J = 5.4 Hz), 5.63 (1H, s), 6.34-6.38 (2H, m), 6.84 (1H, d, J = 8.4 Hz), 7.36-7.48 (3H, m). |

TABLE 1-10-continued

| Example | Structural formula | Property values |
|---|---|---|
| 37 | | $^1$H-NMR (CDCl$_3$) δ: 0.91 (3H, t, J = 7.3 Hz), 1.51-1.64 (2H, m), 1.76-1.87 (7H, m), 2.58 (2H, t, J = 7.6 Hz), 3.60 (2H, t, J = 6.6 Hz), 3.80 (1H, s), 3.98 (2H, t, J = 5.4 Hz), 6.00 (1H, s), 6.82 (1H, d, J = 8.6 Hz), 7.11 (1H, dd, J = 1.6, 5.0 Hz), 7.29-7.48 (4H, m). |
| 38 | | $^1$H-NMR (CDCl$_3$) δ: 0.19-0.60 (4H, m), 0.92 (3H, t, J = 7.0 Hz), 1.17-1.25 (1H, m), 1.52-1.64 (5H, m), 1.78-1.87 (4H, m), 2.60 (2H, t, J = 7.6 Hz), 3.55-3.60 (2H, m), 3.81 (1H, s), 3.96-4.06 (2H, m), 5.26 (1H, s), 6.84 (1H, d, J = 8.4 Hz), 7.43-7.48 (2H, m). |

TABLE 1-11

| Example | Structural formula | Property values |
|---|---|---|
| 39 | | $^1$H-NMR (CDCl$_3$) δ: 0.92 (3H, t, J = 7.4 Hz), 1.30 (3H, s,), 1.54-1.90 (13H, m), 2.59 (2H, t, J = 7.7 Hz), 3.54-3.61 (2H, m), 3.70 (1H, s), 3.92-4.05 (2H, m), 5.50 (1H, s), 6.84 (1H, d, J = 8.9 Hz), 7.43-7.48 (2H, m). |
| 40 | | $^1$H-NMR (CDCl$_3$) δ: 0.87-0.93 (6H, m), 1.49-1.63 (2H, m), 1.76-1.84 (4H, m), 1.98-2.28 (2H, m), 2.57 (2H, t, J = 7.6 Hz), 3.58 (2H, t, J = 6.8 Hz), 3.71 (1H, s), 3.79 (3H, s), 3.96 (2H, t, J = 5.7 Hz), 5.97 (1H, s), 6.80 (1H, d, J = 8.4 Hz), 6.90 (2H, d, J = 6.5 Hz), 7.40-7.46 (4H, m). |
| 41 | | $^1$H-NMR (CDCl$_3$) δ: 0.89 (3H, t, J = 7.0 Hz), 0.90 (3H, t, J = 7.3 Hz), 1.50-1.66 (2H, m), 1.79-1.81 (4H, m), 2.00-2.25 (2H, m), 2.57 (2H, t, J = 7.6 Hz), 3.58 (2H, t, J = 6.2 Hz), 3.61 (1H, s), 3.97 (2H, t, J = 5.9 Hz), 5.94-5.98 (3H, m), 6.77-6.82 (2H, m), 6.93-7.03 (2H, m), 7.42-7.47 (2H, m). |

TABLE 1-11-continued

| Example | Structural formula | Property values |
|---|---|---|
| 42 | | ¹H-NMR (CDCl₃) δ: 0.91 (3H, t, J = 7.2 Hz), 1.01 (9H, s), 1.51-1.64 (2H, m), 1.76-1.87 (4H, m), 2.58 (2H, t, J = 7.4 Hz), 3.53-3.62 (3H, m), 3.94-4.02 (2H, m), 6.81 (1H, d, J = 8.6 Hz), 7.16 (1H, s), 7.26-7.46 (5H, m), 7.60-7.63 (2H, m). |

TABLE 1-12

| Example | Structural formula | Property values |
|---|---|---|
| 43 | | ¹H-NMR (CDCl₃) δ: 0.92 (3H, t, J = 7.3 Hz), 1.52-1.66 (2H, m), 1.76-1.91 (10H, m), 2.12-2.25 (2H, m), 2.60 (2H, t, J = 7.7 Hz), 3.59 (2H, t, J = 6.2 Hz), 3.78 (1H, s), 4.00 (2H, t, J = 5.4 Hz), 5.68 (1H, s), 6.84 (1H, d, J = 8.6 Hz), 7.43-7.48 (2H, m). |
| 44 | | ¹H-NMR (CDCl₃) δ: 1.38 (6H, s), 2.13-2.25 (2H, m), 2.90 (3H, s), 3.79 (2H, t, J = 7.3 Hz), 4.08 (2H, t, J = 6.3 Hz), 5.05 1H, s), 7.66 (2H, s). |
| 45 | | ¹H-NMR (CDCl₃) δ: 1.38 (6H, s), 1.76-1.92 (4H, m), 2.89 (3H, s), 3.61 (2H, t, J = 6.8 Hz), 4.07 (2H, t, J = 5.8 Hz), 5.16 (1H, s) , 7.66 (2H, s). |
| 46 | | ¹H-NMR (CDCl₃) δ: 1.37 (6H, s), 1.52-1.75 (4H, m), 1.87 (2H, tt, J = 6.8, 7.3 Hz), 2.88 (3H, s), 3.53 (2H, t, J = 7.0 Hz), 4.05 (2H, t, J = 6.3 Hz), 4.62 (1H, s), 7.65 (2H, s). |

TABLE 1-12-continued

| Example | Structural formula | Property values |
|---|---|---|
| 47 | 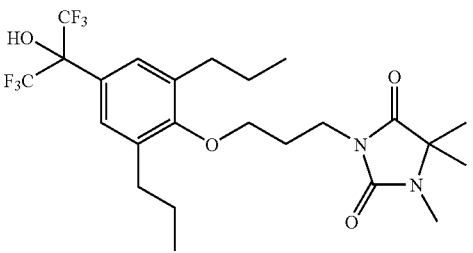 | $^1$H-NMR (CDCl$_3$) δ: 0.95 (6H, t, J = 7.2 Hz), 1.37 (6H, s), 1.62 (4H, qt, J = 7.2, 7.6 Hz), 2.14 (2H, tt, J = 6.5, 7.3 Hz), 2.58 (4H, t, J = 7.6 Hz), 2.89 (3H, s), 3.75 (2H, t, J = 7.3 Hz), 3.81 (2H, t, J = 6.5 Hz), 3.84 (1H, s), 7.32 (2H, s). |
| 48 | 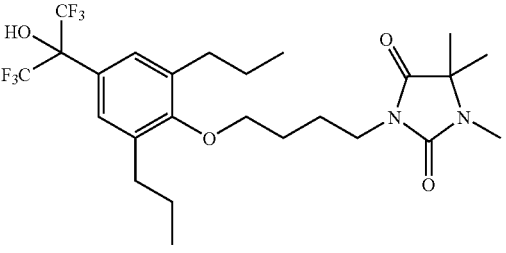 | $^1$H-NMR (CDCl$_3$) δ: 0.94 (6H, t, J = 7.4 Hz), 1.38 (6H, s), 1.62 (4H, qt, J = 7.4, 7.6 Hz), 1.76-1.92 (4H, m), 2.58 (4H, t, J = 7.6 Hz), 2.90 (3H, s), 3.55-3.64 (3H, m), 3.77 (2H, t, J = 5.7 Hz), 7.32 (2H, s). |

TABLE 1-13

| Example | Structural formula | Property values |
|---|---|---|
| 49 | 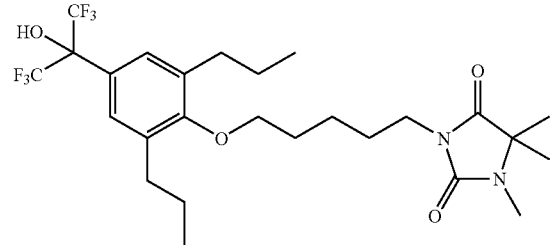 | $^1$H-NMR (CDCl$_3$) δ: 0.95 (6H, t, J = 7.3 Hz), 1.37 (6H, s), 1.49-1.89 10H, m), 2.59 (4H, t, J = 7.8 Hz), 2.88 (3H, s), 3.54 (2H, t, J = 7.2 Hz), 3.63 (1H, s), 3.75 (2H, t, J = 6.5 Hz), 7.32 (2H, s). |
| 50 | 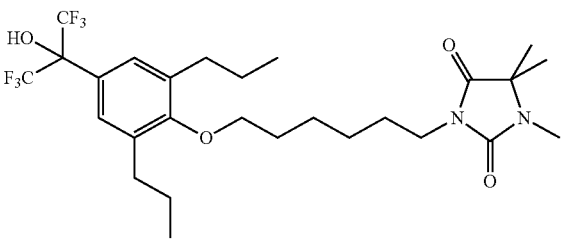 | $^1$H-NMR (CDCl$_3$) δ: 0.95 (6H, t, J = 7.3 Hz), 1.37 (6H, s), 1.51-1.88 (12H, m), 2.59 (4H, t, J = 7.7 Hz), 2.88 (3H, s), 3.51 (2H, t, J = 7.3Hz), 3.60 (1H, s), 3.75 (2H, t, J = 6.3 Hz), 7.32 (2H, s). |
| 51 | 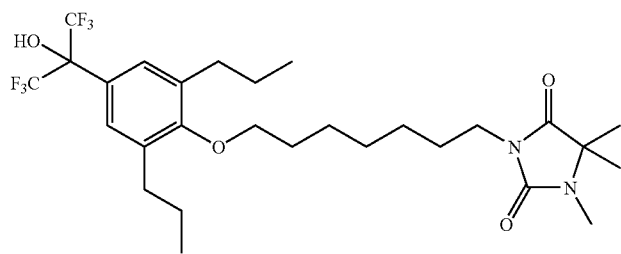 | $^1$H-NMR (CDCl$_3$) δ: 0.95 (6H, t, J = 7.3 Hz), 1.37 (6H, s), 1.56-1.86 (14H, m), 2.60 (4H, t, J = 7.7 Hz), 2.88 (3H, s), 3.50 (2H, t, J = 7.3 Hz), 3.70 (1H, s), 3.75 (2H, t, J = 6.5 Hz), 7.32 (2H, s). |

TABLE 1-13-continued

| Example | Structural formula | Property values |
|---|---|---|
| 52 | | $^1$H-NMR (CDCl$_3$) δ: 1.25 (6H, s), 2.18 (2H, tt, J = 6.3, 7.0 Hz), 2.88 (3H, s), 3.75 (2H, t, J = 7.0 Hz), 3.95 (1H, s), 4.08 (2H, t, J = 6.3 Hz), 6.94 (1H, d, J = 8.9 Hz), 7.53 (1H, d, J = 8.9 Hz), 7.72 (1H, s). |
| 53 | | $^1$H-NMR (CDCl$_3$) δ: 1.25 (6H, s), 1.80-1.89 (4H, m), 2.89 (3H, s), 3.60 (2H, t, J = 7.0 Hz), 3.84 (1H, s), 4.08 (2H, t, J = 6.3 Hz), 6.96 (1H, d, J = 8.4 Hz), 7.53 (1H, d, J = 8.4 Hz), 7.72 (1H, s). |

TABLE 1-14

| Example | Structural formula | Property values |
|---|---|---|
| 54 | | $^1$H-NMR (CDCl$_3$) δ: 1.37 (6H, s), 1.47-1.73 (4H, m), 1.88 (2H, tt, J = 6.8, 7.3 Hz), 2.88 (3H, s), 3.53 (2H, t, J = 7.2 Hz), 4.04 (2H, t, J = 6.2 Hz), 4.07 (1H, s), 6.93 (1H, d, J = 8.6 Hz), 7.53 (1H, d, J = 8.6 Hz), 7.72 (1H, s). |
| 55 | | $^1$H-NMR (CDCl$_3$) δ: 1.26 (6H, d, J = 7.0 Hz), 1.37 (6H, s), 2.17 (2H, tt, J = 6.5, 6.6 Hz), 2.85-2.96 (4H, m), 3.71 (2H, t, J = 6.5 Hz), 4.17 (2H, t, J = 6.6 Hz), 6.88 (1H, s), 6.93 (1H, d, J = 8.4 Hz), 7.43-7.47 (2H, m). |
| 56 | | $^1$H-NMR (CDCl$_3$) δ: 1.26 (6H, d, J = 7.0 Hz), 1.38 (6H, s), 1.80-1.82 (4H, m), 2.84-2.95 (4H, m), 3.59 (2H, t, J = 6.3 Hz), 4.18 (2H, t, J = 5.9 Hz), 6.88 (1H, s), 6.93 (1H, d, J = 8.4 Hz), 7.44 (1H, d, J = 8.1 Hz), 7.59 (1H, s). |
| 57 | | $^1$H-NMR (CDCl$_3$) δ: 1.26 (6H, d, J = 7.0 Hz), 1.37 (6H, s), 1.42-1.53 (2H, m), 1.71 (2H, tt, J = 7.0, 7.3 Hz), 1.90 (2H, tt, J = 6.2, 7.0 Hz), 2.83-2.95 (4H, m), 3.55 (2H, t, J = 7.0 Hz), 4.14 (2H, t, J = 6.2 Hz), 6.86 (1H, s), 6.93 (1H, d, J = 8.4 Hz), 7.44 (1H, d, J = 8.4 Hz), 7.63 (1H, s). |

TABLE 1-15

| Example | Structural formula | Property values |
|---|---|---|
| 58 | | $^1$H-NMR (CDCl$_3$) δ: 1.36 (6H, s), 2.02-2.12 (2H, m), 2.89 (3H, s), 3.58 (1H, s), 3.63 (2H, t, J = 7.3 Hz), 3.95 (2H, t, J = 6.3 Hz), 4.00 (2H, s), 6.84 (1H, d, J = 8.4 Hz), 7.15-7.28 (5H, m), 7.47-7.51 (2H, m). |
| 59 | | $^1$H-NMR (CDCl$_3$) δ: 1.36 (6H, s), 1.70-1.73 (4H, m), 2.88 (3H, s), 3.50 (2H, t, J = 7.3 Hz), 3.59 (1H, s), 3.40-4.08 (4H, m), 6.85 (1H, d, J = 8.6 Hz), 7.14-7.26 (5H, m), 7.45 (1H, s), 7.50 (1H, d, J = 8.9 Hz). |
| 60 | | $^1$H-NMR (CDCl$_3$) δ: 1.35 (6H, s), 1.60-1.70 (4H, m), 1.77 (2H, tt, J = 6.2, 7.6 Hz), 2.87 (3H, s), 3.47 (2H, t, J = 7.2 Hz), 3.61 (1H, s), 3.93 (2H, t, J = 6.2 Hz), 3.96 (2H, s), 6.85 (1H, d, J = 8.6 Hz), 7.15-7.26 (5H, m), 7.45 (1H, s), 7.50 1H, d, J = 8.9 Hz.) |
| 61 | | $^1$H-NMR (CDCl$_3$) δ: 0.92 (3H, t, J = 7.3 Hz), 1.52-1.65 (2H, m), 1.80-1.85 (4H, m), 2.60 (2H, t, J = 7.6 Hz), 2.99 (3H, s), 3.59 (2H, t, J = 7.0 Hz), 3.79 (1H, s), 3.83 (2H, s), 3.99 (2H, t, J = 6.3 Hz), 6.83 (1H, d, J = 8.6 Hz), 7.43 (1H, m), 7.46 (1H, d, J = 8.6 Hz). |

TABLE 1-16

| Example | Structural formula | Property values |
|---|---|---|
| 62 | 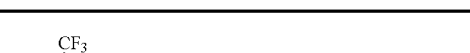 | $^1$H-NMR (CDCl$_3$) δ: 0.92 (3H, t, J = 7.4 Hz), 1.42 (6H, s), 1.59 (2H, qt, J = 7.4, 7.5 Hz), 1.81-1.83 (4H, m), 2.60 (2H, t, J = 7.6 Hz), 3.58 (2H, t, J = 6.3 Hz), 3.70-4.02 (3H, m), 5.64 (1H, s), 6.83 (1H, d, J = 8.6 Hz), 7.43 (1H, s), 7.46 (1H, d, J = 8.6 Hz). |

TABLE 1-16-continued

| Example | Structural formula | Property values |
|---|---|---|
| 63 | | $^1$H-NMR (CDCl$_3$) δ: 0.85 (3H, t, J = 7.4 Hz), 0.92 (3H, t, J = 7.3 Hz), 1.40 (3H, s), 1.52-1.71 (4H, m), 1.78-1.90 (4H, m), 2.59 (2H, t, J = 7.6 Hz), 3.55-3.62 2H, m), 3.96-4.05 (2H, m), 4.28 (1H, s), 5.71 (1H, s), 6.83 (1H, d, J = 8.9 Hz), 7.44 (1H, s), 7.47 (1H, d, J = 8.9 Hz). |
| 64 | | $^1$H-NMR (CDCl$_3$) δ: 0.89 (3H, t, J = 7.3 Hz), 1.49-1.63 (2H, m), 1.72-1.92 (7H, m), 2.57 (2H, t, J = 7.6 Hz), 3.59 (2H, t, J = 6.5 Hz), 3.78 (1H, s), 3.96 (2H, t, J = 5.8 Hz), 6.05 (1H, s), 6.80 (1H, d, J = 8.4 Hz), 7.30-7.50 (7H, m). |
| 65 | | $^1$H-NMR (CDCl$_3$) δ: 0.95 (6H, t, J = 7.3 Hz), 1.26-1.82 (22H, m), 2.60 (4H, t, J = 7.8 Hz), 2.88 (3H, s), 3.49 (2H, t, J = 7.3 Hz), 3.75 (2H, t, J = 6.5 Hz), 3.82 (1H, s), 7.33 (2H, s). |

TABLE 1-17

| Example | Structural formula | Property values |
|---|---|---|
| 66 | | $^1$H-NMR (CDCl$_3$) δ: 0.96 (6H, t, J = 7.3 Hz), 1.26-1.82 (24H, m), 2.60 (4H, t, J = 7.8 Hz), 2.88 (3H, s), 3.48 (2H, t, J = 7.3 Hz), 3.75 (2H, t, J = 6.5 Hz), 3.85 (1H, s), 7.33 (2H, s). |
| 67 | | $^1$H-NMR (CDCl$_3$) δ: 0.96 (6H, t, J = 7.3 Hz), 1.26-1.85 (26H, m), 2.61 (4H, t, J = 7.8 Hz), 2.88 (3H, s), 3.48 (2H, t, J = 7.3 Hz), 3.76 (2H, t, J = 6.8 Hz), 3.80 (1H, s), 7.33 (2H, s). |

TABLE 1-17-continued

| Example | Structural formula | Property values |
|---|---|---|
| 68 | | ¹H-NMR (CDCl₃) δ: 0.95 (6H, t, J = 7.3 Hz), 1.26-1.82 (19H, m), 2.60 (4H, t, J = 7.8 Hz), 3.50 (2H, t, J = 7.6 Hz), 3.64 (1H, s), 3.74 (2H, t, J = 6.8 Hz), 5.81 (1H, s), 5.95 (2H, s), 6.79 (1H, d, J = 8.1 Hz), 6.92 (1H, dd, J = 1.9, 8.1 Hz), 6.97 (1H, d, J = 1.9 Hz), 7.32 (2H, s). |
| 69 | | ¹H-NMR (CDCl₃) δ: 0.95 (6H, t, J = 7.3 Hz), 1.26-1.82 (21H, m), 2.60 (4H, t, J = 7.8 Hz), 3.49 (2H, t, J = 7.5 Hz), 3.72 (1H, s), 3.74 (2H, t, J = 6.8 Hz), 5.89 (1H, s), 5.96 (2H, s), 6.79 (1H, d, J = 8.1 Hz), 6.92 (1H, dd, J = 1.9, 8.1 Hz), 6.97 (1H, d, J = 1.9 Hz), 7.32 (2H, s). |

TABLE 1-18

| Example | Structural formula | Property values |
|---|---|---|
| 70 | | ¹H-NMR (CDCl₃) δ: 0.96 (6H, t, J = 7.3 Hz), 1.26-1.84 (23H, m), 2.60 (4H, t, J = 7.8 Hz), 3.49 (2H, t, J = 7.5 Hz), 3.69 (1H, s), 3.75 (2H, t, J = 6.5 Hz), 5.85 (1H, s), 5.96 (2H, s), 6.79 (1H, d, J = 8.1 Hz), 6.92 (1H, dd, J = 1.9, 8.1 Hz), 6.97 (1H, d, J = 1.9 Hz), 7.33 (2H, s). |
| 71 | | ¹H-NMR (CDCl₃) δ: 0.90 (3H, t, J = 7.3 Hz), 0.97 (3H, t, J = 7.3 Hz), 1.50-1.81 (11H, m), 2.58 (2H, t, J = 7.4 Hz), 3.49 (2H, t, J = 6.8 Hz), 3.60 (2H, t, J = 6.8 Hz), 3.98 (2H, t, J = 5.4 Hz), 5.96 (2H, s), 6.12 (1H, s), 6.78 (1H, d, J = 8.1 Hz), 6.81 (1H, d, J = 8.1 Hz), 6.94 (1H, dd, J = 1.9, 8.1 Hz), 6.98 (1H, d, J = 1.9 Hz), 7.28-7.32 (2H, m). |
| 72 | | ¹H-NMR (CDCl₃) δ: 0.90 (3H, t, J = 7.3 Hz), 1.31 (3H, t, J = 7.3 Hz), 1.51-1.60 (2H, m), 1.78-1.90 (7H, m), 2.58 (2H, t, J = 7.4 Hz), 3.57-3.65 (4H, m), 3.98 (2H, t, J = 5.4 Hz), 5.95-5.97 (3H, m), 6.78 (1H, d, J = 8.1 Hz), 6.82 (1H, d, J = 8.1 Hz), 6.93 (1H, dd, J = 1.9, 8.1 Hz), 6.98 (1H, d, J = 1.9 Hz), 7.28-7.32 (2H, m). |

TABLE 1-19

| Example | Structural formula | Property values |
|---|---|---|
| 73 | | ¹H-NMR (CDCl₃) δ: 0.91 (3H, t, J = 7.3 Hz), 1.53-1.92 (9H, m), 2.59 (2H, t, J = 7.4 Hz), 3.45 (3H, s), 3.60 (2H, t, J = 6.8 Hz), 3.99 (2H, t, J = 5.4 Hz), 5.94 (1H, s), 5.96 (2H, s), 6.78 (1H, d, J = 8.1 Hz), 6.83 (1H, d, J = 8.1 Hz), 6.94 (1H, dd, J = 1.9, 8.1 Hz), 6.98 (1H, d, J = 1.9 Hz), 7.27-7.33 (2H, m). |
| 74 | | ¹H-NMR (CDCl₃) δ: 0.95 (3H, t, J = 7.4 Hz), 1.36 (6H, s), 1.58-1.70 (2H, m), 2.10-2.20 (2H, m), 2.63 (2H, t, J = 7.4 Hz), 2.89 (3H, s), 3.72 (2H, t, J = 7.3 Hz), 3.83 (1H, s), 4.00 (2H, t, J = 6.2 Hz), 6.83 (1H, d, J = 8.6 Hz), 7.44-7.48 (2H, m). |
| 75 | | ¹H-NMR (CDCl₃) δ: 0.93 (3H, t, J = 7.4 Hz), 1.36 (6H, s), 1.41-1.89 (8H, m), 2.60 (2H, t, J = 7.4 Hz), 2.88 (3H, s), 3.53 (2H, t, J = 7.3 Hz), 3.71 (1H, s), 3.96 (2H, t, J = 6.2 Hz), 6.83 (1H, d, J = 8.9 Hz), 7.42-7.48 (2H, m). |
| 76 | | ¹H-NMR (CDCl₃) δ: 0.93 (3H, t, J = 7.4 Hz), 1.36 (6H, s), 1.48-1.82 (10H, m), 2.60 (2H, t, J = 7.4 Hz), 3.22 (3H, s), 3.50 (2H, t, J = 7.4 Hz), 3.63 (1H, s), 3.96 (2H, t, J = 6.2 Hz), 6.83 (1H, d, J = 8.6 Hz), 7.42-7.48 (2H, m). |

TABLE 1-20

| Example | Structural formula | Property values |
|---|---|---|
| 77 | | ¹H-NMR (CDCl₃) δ: 0.93 (3H, t, J = 7.4 Hz), 1.25-1.81 (18H, m), 2.60 (2H, t, J = 7.4 Hz), 2.87 (3H, s), 3.49 (2H, t, J = 7.4 Hz), 3.74 (1H, s), 3.96 (2H, t, J = 6.2 Hz), 6.84 (1H, d, J = 8.6 Hz), 7.42-7.48 (2H, m). |

TABLE 1-20-continued

| Example | Structural formula | Property values |
|---|---|---|
| 78 | | $^1$H-NMR (CDCl$_3$) δ: 0.93 (3H, t, J = 7.4 Hz), 1.26-1.81 (20H, m), 2.61 (2H, t, J = 7.4 Hz), 2.88 (3H, s), 3.46 (2H, t, J = 7.3 Hz), 3.71 (1H, s), 3.97 (2H, t, J = 6.2 Hz), 6.84 (1H, d, J = 8.4 Hz), 7.43-7.48 (2H, m). |
| 79 | | $^1$H-NMR (CDCl$_3$) δ: 0.93 (3H, t, J = 7.4 Hz), 1.23-1.81 (22H, m), 2.61 (2H, t, J = 7.3 Hz), 2.87 (3H, s), 3.46 (2H, t, J = 7.3 Hz), 3.83 (1H, s), 3.97 (2H, t, J = 6.2 Hz), 6.84 (1H, d, J = 8.4 Hz), 7.43-7.48 (2H, m). |
| 80 | | $^1$H-NMR (CDCl$_3$) δ: 0.93 (3H, t, J = 7.4 Hz), 1.28-1.81 (24H, m), 2.61 (2H, t, J = 7.4 Hz), 2.87 (3H, s), 3.46 (2H, t, J = 6.8 Hz), 3.94 (1H, s), 3.97 (2H, t, J = 5.4 Hz), 6.85 (1H, d, J = 8.6 Hz), 7.43-7.48 (2H, m). |
| 81 | | $^1$H-NMR (CDCl$_3$) δ: 0.90 (6H, t, J = 7.3 Hz), 1.53-1.92 (11H, m), 2.33 (3H, s), 2.57 (4H, t, J = 7.6 Hz), 3.54 (1H, s), 3.61 (2H, t, J = 6.5 Hz), 3.74 (2H, t, J = 5.5 Hz), 5.79 (1H, s), 7.19 (2H, d, J = 8.4 Hz), 7.31 (2H, s), 7.36 (2H, d, J = 8.4 Hz). |

TABLE 1-21

| Example | Structural formula | Property values |
|---|---|---|
| 82 | | $^1$H-NMR (CDCl$_3$) δ: 0.92 (6H, t, J = 7.3 Hz), 1.22 (3H, t, J = 7.6 Hz), 1.53-1.95 (11H, m), 2.53-2.68 (6H, m), 3.54 (1H, s), 3.61 (2H, t, J = 7.0 Hz), 3.75 (2H, t, J = 5.7 Hz), 5.80 (1H, s), 7.21 (2H, d, J = 8.3 Hz), 7.31 (2H, s), 7.39 (2H, d, J = 8.3 Hz). |

TABLE 1-21-continued

| Example | Structural formula | Property values |
| --- | --- | --- |
| 83 | | $^1$H-NMR (CDCl$_3$) δ: 0.92 (6H, t, J = 7.3 Hz), 1.22 (6H, d, J = 7.0 Hz), 1.53-1.90 (11H, m), 2.66 (4H, t, J = 7.8 Hz), 2.85-2.93 (1H, m), 3.50 (1H, s), 3.61 (2H, t, J = 6.8 Hz), 3.75 (2H, t, J = 5.8 Hz), 5.76 (1H, s), 7.24 (2H, d, J = 8.1 Hz), 7.31 (2H, s), 7.39 (2H, d, J = 8.1 Hz). |
| 84 | | $^1$H-NMR (CDCl$_3$) δ: 0.92 (6H, t, J = 7.3 Hz), 1.30 (9H, s), 1.53-1.92 (11H, m), 2.56 (4H, t, J = 7.6 Hz), 3.56 (1H, s), 3.61 (2H, t, J = 6.8 Hz), 3.75 (2H, t, J = 5.7 Hz), 5.81 (1H, s), 7.31 (2H, s), 7.38-7.41 (4H, m). |
| 85 | | $^1$H-NMR (CDCl$_3$) δ: 0.90 (6H, t, J = 7.5 Hz), 1.53-1.90 (11H, m) 2.56 (4H, t, J = 7.8 Hz), 3.60-3.64 (3H, m), 3.75 (2H, t, J = 5.9 Hz), 6.00 (1H, s), 7.07 (2H, dd, J = 8.6, 8.6 Hz), 7.32 (2H, s), 7.48 (2H, dd, J = 5.0, 8.6 Hz). |

TABLE 1-22

| Example | Structural formula | Property values |
| --- | --- | --- |
| 86 | | $^1$H-NMR (CDCl$_3$) δ: 0.92 (6H, t, J = 7.3 Hz), 1.53-1.90 (11H, m), 2.56 (4H, t, J = 7.6 Hz), 3.56 (1H, s), 3.61 (2H, t, J = 6.8 Hz), 3.75 (2H, t, J = 5.8 Hz), 5.98 (1H, s), 7.31 (2H, s), 7.36 (2H, d, J = 8.9 Hz), 7.44 (2H, d, J = 8.9 Hz). |

TABLE 1-22-continued

| Example | Structural formula | Property values |
|---|---|---|
| 87 | | $^1$H-NMR (CDCl$_3$) δ: 0.92 (6H, t, J = 7.3 Hz), 1.53-1.90 (11H, m), 2.56 (4H, t, J = 7.6 Hz), 3.53 (1H, s), 3.61 (2H, t, J = 6.8 Hz), 3.75 (2H, t, J = 5.9 Hz), 5.94 (1H, s), 7.31 (2H, s), 7.38 (2H, d, J = 8.6 Hz), 7.51 (2H, d, J = 8.6 Hz). |
| 88 | | $^1$H-NMR (CDCl$_3$) δ: 0.92 (6H, t, J = 7.3 Hz), 1.53-1.90 (11H, m), 2.56 (4H, t, J = 7.6 Hz), 3.56 (1H, s), 3.61 (2H, t, J = 6.8 Hz), 3.75 (2H, t, J = 5.8 Hz), 5.98 (1H, s), 7.31 (2H, s), 7.64-7.68 (4H, m). |
| 89 | | $^1$H-NMR (CDCl$_3$) δ: 0.92 (6H, t, J = 7.3 Hz), 1.53-1.92 (11H, m), 2.56 (4H, t, J = 7.6 Hz), 3.62 (2H, t, J = 7.1 Hz), 3.68 (1H, s), 3.75 (2H, t, J = 5.9 Hz), 5.98 (1H, s), 7.32 (2H, s), 7.66-7.68 (4H, m). |

TABLE 1-23

| Example | Structural formula | Property values |
|---|---|---|
| 90 | | $^1$H-NMR (CDCl$_3$) δ: 0.92 (6H, t, J = 7.4 Hz), 1.53-1.90 (11H, m), 2.56 (4H, t, J = 7.8 Hz), 3.48 (1H, s), 3.64 (2H, t, J = 6.8 Hz), 3.75 (2H, t, J = 5.9 Hz), 6.04 (1H, s), 7.31 (2H, s), 7.74 (2H, d, J = 8.9 Hz), 8.25 (2H, d, J = 8.9 Hz). |
| 91 | | $^1$H-NMR (CDCl$_3$) δ: 0.93 (6H, t, J = 7.4 Hz), 1.55-1.90 (11H, m), 2.56 (4H, t, J = 7.6 Hz), 2.93 (6H, s), 3.54 (1H, s), 3.61 (2H, t, J = 6.8 Hz), 3.75 (2H, t, J = 5.9 Hz), 5.58 (1H, s), 6.69 (2H, d, J = 8.9 Hz), 7.28-7.31 (4H, m) |

TABLE 1-23-continued

| Example | Structural formula | Property values |
|---|---|---|
| 92 | | $^1$H-NMR (CDCl$_3$) δ: 0.92 (6H, t, J = 7.3 Hz), 1.53-1.92 (11H, m), 2.56 (4H, t, J = 7.6 Hz), 3.55 (1H, s), 3.62 (2H, t, J = 6.8 Hz), 3.75 (2H, t, J = 5.9 Hz), 3.80 (3H, s), 5.84 (1H, s), 6.86-6.89 (1H, m), 7.03-7.07 (2H, m), 7.27-7.33 (3H, m) |
| 93 | | $^1$H-NMR (CDCl$_3$) δ: 0.94 (6H, t, J = 7.3 Hz), 1.55-1.95 (11H, m), 2.58 (4H, t, J = 7.8 Hz), 3.65-3.70 (3H, in), 3.79 (2H, t, J = 5.9 Hz), 3.87 (3H, s), 6.26 (1H, s), 6.92-6.97 (2H, m), 7.29-7.35 (3H, m), 7.51 (1H, dd, J = 1.6, 7.8 Hz). |

TABLE 1-24

| Example | Structural formula | Property values |
|---|---|---|
| 94 | | $^1$H-NMR (CDCl$_3$) δ: 0.92 (6H, t, J = 7.3 Hz), 1.40 (3H, t, J =7.0 Hz), 1.53-1.90 (11H, m), 2.56 (4H, t, J = 7.6 Hz), 3.58-3.64 (3H, m), 3.75 (2H, t, J = 5.9 Hz), 4.01 (2H, q, J = 7.0 Hz), 5.77 (1H, s), 6.87 (2H, d, J = 8.9 Hz), 7.31 (2H, s), 7.37 (2H, d, J = 8.9 Hz). |
| 95 | | $^1$H-NMR (CDCl$_3$) δ: 0.92 (6H, t, J = 7.3 Hz), 1.02 (3H, t, J =7.3 Hz), 1.53-1.90 (13H, m), 2.56 (4H, t, J = 7.6 Hz), 3.56 (1H, s), 3.61 (2H, d, J =6.8 Hz), 3.75 (2H, d, J = 6.2 Hz), 3.90 (2H, d, J = 6.5 Hz), 5.74 (1H, s), 6.87 (2H, d, J = 8.9 Hz), 7.31 (2H, s), 7.37 (2H, d, J = 8.9 Hz). |

TABLE 1-24-continued

| Example | Structural formula | Property values |
| --- | --- | --- |
| 96 | | $^1$H-NMR (CDCl$_3$) δ: 0.92 (6H, t, J = 7.3 Hz), 1.31 (6H, d, J = 5.9 Hz), 1.53-1.90 (11H, m), 2.56 (4H, t, J = 7.6 Hz), 3.61 (2H, t, J = 7.0 Hz), 3.72-3.77 (3H, m), 4.52 (1H, q, J = 5.9 Hz), 5.90 (1H, s), 6.86 (2H, d, J = 8.9 Hz), 7.34 (2H, s), 7.37 (2H, d, J = 8.9 Hz). |
| 97 | | $^1$H-NMR (CDCl$_3$) δ: 0.90-0.99 (9H, m), 1.43-1.90 (15H, m), 2.56 (4H, t, J = 7.6 Hz), 3.59-3.63 (3H, m), 3.75 (2H, t, J = 5.9 Hz), 3.94 (2H, t, J = 6.5 Hz), 5.80 (1H, s), 6.89 (2H, d, J = 8.6 Hz), 7.34 (2H, s), 7.37 (2H, d, J = 8.6 Hz). |

TABLE 1-25

| Example | Structural formula | Property values |
| --- | --- | --- |
| 98 | | $^1$H-NMR (CDCl$_3$) δ: 0.92 (6H, t, J = 7.5 Hz), 1.00 (6H, d, J = 6.8 Hz), 1.53-1.95 (11H, m), 2.01-2.11 (1H, m), 2.56 (4H, t, J = 7.6 Hz), 3.60 (2H, t, J = 6.8 Hz), 3.68-3.76 (5H, m), 5.91 (1H, s), 6.88 (2H, d, J = 8.6 Hz), 7.35 (2H, s), 7.37 (2H, d, J = 8.6 Hz). |
| 99 | | $^{11}$H-NMR (CDCl$_3$) δ: 0.91 (6H, t, J = 7.3 Hz), 1.52-1.90 (11H, m), 2.55 (4H, t, J = 7.6 Hz), 3.62 (2H, t, J = 6.8 Hz), 3.72-3.77 (3H, m), 6.37 (1H, s), 7.17-7.22 (1H, m), 7.31 (2H, s), 7.37-7.48 (3H, m). |
| 100 | | $^1$H-NMR (CDCl$_3$) δ: 0.92 (3H, t, J = 7.4 Hz), 1.52-1.65 (2H, m), 1.81-1.85 (4H, m), 2.60 (2H, t, J = 7.4 Hz), 3.60 (2H, t, J = 7.2 Hz), 3.95-4.05 (5H, m), 5.76 (1H, s), 6.84 (1H, d, J = 8.6 Hz), 7.43 (1H, s), 7.46 (1H, d, J = 8.6 Hz). |

TABLE 1-25-continued

| Example | Structural formula | Property values |
| --- | --- | --- |
| 101 | | $^1$H-NMR (CDCl$_3$) δ: 0.90 (6H, t, J = 7.3 Hz), 1.52-1.90 (11H, m), 2.55 (4H, t, J = 7.6 Hz), 3.63 (2H, t, J = 6.8 Hz), 3.74 (2H, t, J = 5.9 Hz), 3.89 (1H, s), 6.37 (1H, s), 7.21-7.62 (11H, m). |
| 102 | | $^1$H-NMR (CDCl$_3$) δ: 0.89-0.95 (6H, m), 1.53-1.91 (11H, m), 2.56 (4H, t, J = 7.6 Hz), 3.61 (2H, t, J = 6.8 Hz), 3.75 (2H, t, J = 5.7 Hz), 3.91 (1H, s), 6.56 (1H, s), 7.15-7.41 (5H, m) |

TABLE 1-26

| Example | Structural formula | Property values |
| --- | --- | --- |
| 103 | | $^1$H-NMR (CDCl$_3$) δ: 0.92 (6H, t, J = 7.3 Hz), 1.53-1.91 (11H, m), 2.55 (4H, t, J = 7.6 Hz), 3.62 (2H, t, J = 6.8 Hz), 3.75 (2H, t, J = 5.9 Hz), 3.87 (1H, s), 6.48 (1H, s), 7.12 (1H, dd, J = 8.6, 8.6 Hz), 7.32 (2H, s), 7.46 (1H, ddd, J = 2.4, 4.5, 8.6 Hz), 7.72 (1H, dd, J = 2.4, 6.4 Hz). |
| 104 | | $^1$H-NMR (CDCl$_3$) δ: 0.92 (6H, t, J = 7.3 Hz), 1.53-1.90 (11H, m), 2.56 (4H, t, J = 7.6 Hz), 3.62 (2H, t, J = 6.8 Hz), 3.71 (1H, s), 3.75 (2H, t, J = 5.9 Hz), 6.32 (1H, s), 7.32 (2H, s), 7.37 (1H, dd, J = 2.2, 8.6 Hz), 7.46 (1H, d, J = 8.6 Hz), 7.62 (1H, d, J = 2.2 Hz). |

TABLE 1-26-continued

| Example | Structural formula | Property values |
|---|---|---|
| 105 | 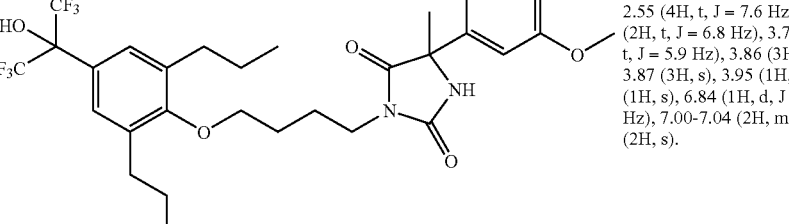 | $^1$H-NMR (CDCl$_3$) δ: 0.94 (6H, t, J = 7.3 Hz), 1.55-1.95 (11H, m) 2.58 (4H, t, J = 7.6 Hz), 3.69 (2H, t, J = 6.8 Hz), 3.78 (2H, t, J = 5.9 Hz), 4.01 (1H, s), 6.36 (1H, s), 7.33 (2H, s), 7.40 (1H, d, J = 8.6 Hz), 7.50 (1H, d, J = 8.6 Hz). |
| 106 | 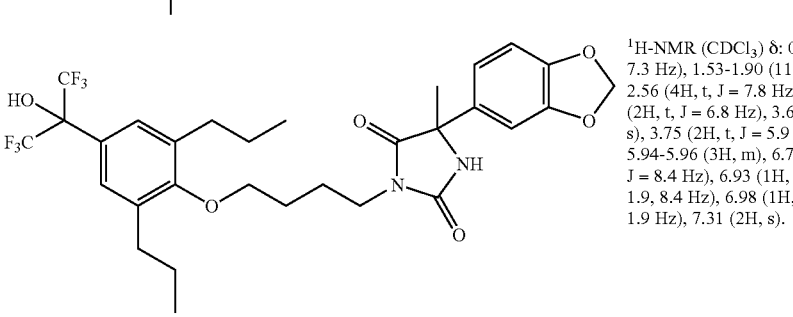 | $^1$H-NMR (CDCl$_3$) δ: 0.91 (6H, t, J = 7.3 Hz), 1.55-1.92 (11H, m), 2.55 (4H, t, J = 7.6 Hz), 3.61 (2H, t, J = 6.8 Hz), 3.75 (2H, t, J = 5.9 Hz), 3.86 (3H, s), 4.04 (1H, s), 6.39 (1H, s), 6.94 (1H, dd, J = 8.4, 8.4 Hz), 7.19-7.27 (2H, m), 7.32 (2H, s). |

TABLE 1-27

| Example | Structural formula | Property values |
|---|---|---|
| 107 | 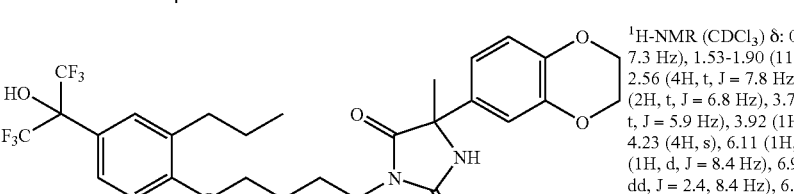 | $^1$H-NMR (CDCl$_3$) δ: 0.92 (6H, t, J = 7.3 Hz), 1.52-1.92 (11H, m), 2.55 (4H, t, J = 7.6 Hz), 3.62 (2H, t, J = 6.8 Hz), 3.75 (2H, t, J = 5.9 Hz), 3.86 (3H, s), 3.87 (3H, s), 3.95 (1H, s), 6.11 (1H, s), 6.84 (1H, d, J = 7.8 Hz), 7.00-7.04 (2H, m), 7.32 (2H, s). |
| 108 | | $^1$H-NMR (CDCl$_3$) δ: 0.92 (6H, t, J = 7.3 Hz), 1.53-1.90 (11H, m), 2.56 (4H, t, J = 7.8 Hz), 3.61 (2H, t, J = 6.8 Hz), 3.67 (1H, s), 3.75 (2H, t, J = 5.9 Hz), 5.94-5.96 (3H, m), 6.78 (1H, d, J = 8.4 Hz), 6.93 (1H, dd, J = 1.9, 8.4 Hz), 6.98 (1H, d, J = 1.9 Hz), 7.31 (2H, s). |
| 109 | | $^1$H-NMR (CDCl$_3$) δ: 0.92 (6H, t, J = 7.3 Hz), 1.53-1.90 (11H, m), 2.56 (4H, t, J = 7.8 Hz), 3.60 (2H, t, J = 6.8 Hz), 3.74 (2H, t, J = 5.9 Hz), 3.92 (1H, s), 4.23 (4H, s), 6.11 (1H, s), 6.84 (1H, d, J = 8.4 Hz), 6.92 (1H, dd, J = 2.4, 8.4 Hz), 6.99 (1H, d, J = 2.4 Hz), 7.32 (2H, s). |

TABLE 1-27-continued

| Example | Structural formula | Property values |
|---|---|---|
| 110 |  | (CDCl₃) δ: 0.93 (6H, t, J = 7.3 Hz), 1.54-2.05 (8H, m), 2.09 (3H, s), 2.59 (4H, t, J = 7.6 Hz), 3.64 (1H, s), 3.74-3.82 (4H, m), 6.07 (1H, s), 7.34 (2H, s), 7.42 (1H, dd, J = 7.6, 7.6 Hz), 7.50-7.55 (2H, m), 7.68 (1H, dd, J = 0.8, 7.6 Hz), 7.84-7.93 (3H, m). |

TABLE 1-28

| Example | Structural formula | Property values |
|---|---|---|
| 111 |  | (CDCl₃) δ: 0.88 (6H, t, J = 7.3 Hz), 1.50-2.00 (11H, m), 2.53 (4H, t, J = 7.6 Hz), 3.64 (2H, t, J = 6.8 Hz), 3.72 (2H, t, J = 5.9 Hz), 3.85 (1H, s), 6.23 (1H, s), 7.16-7.31 (3H, m) 7.47-7.51 (1H, m), 7.59 (1H, dd, J = 1.9, 8.1 Hz), 7.77-7.87 (3H, m), 7.94 (1H, d, J = 1.6 Hz). |
| 112 |  | ¹H-NMR (CDCl₃) δ: 0.94 (6H, t, J = 7.3 Hz), 1.55-1.95 (11H, m), 2.58 (4H, t, J = 7.6 Hz), 3.66 (2H, t, J = 6.8 Hz), 3.73 (1H, s), 3.78 (2H, t, J = 5.9 Hz), 5.74 (1H, s), 6.32-6.38 (2H, m), 7.36 (2H, s), 7.34-7.36 (1H, m). |
| 113 |  | ¹H-NMR (CDCl₃) δ: 0.92 (6H, t, J = 7.3 Hz), 1.53-1.92 (11H, m), 2.56 (4H, t, J = 7.6 Hz), 3.62 (2H, t, J = 6.8 Hz), 3.75 (2H, t, J = 5.9 Hz), 3.95 (1H, s), 6.33 (1H, s), 7.12 (1H, dd, J = 1.6, 4.9 Hz), 7.26-7.36 (4H, m). |
| 114 |  | ¹H-NMR (CDCl₃) δ: 0.19-0.60 (4H, m), 0.94 (6H, t, J = 7.3 Hz), 1.20-1.26 (1H, m), 1.49 (3H, s), 1.53-1.92 (8H, m), 2.58 (4H, t, J = 7.3 Hz), 3.59 (2H, t, J = 6.5 Hz), 3.77 (2H, t, J = 5.9 Hz), 3.93 (1H, s), 5.54 (1H, s), 7.33 (2H, s). |

TABLE 1-29

| Example | Structural formula | Property values |
|---|---|---|
| 115 | | $^1$H-NMR (CDCl$_3$) δ: 0.93 (6H, t, J = 7.3 Hz), 1.32 (3H, s), 1.54-2.10 (15H, m), 2.57 (4H, t, J = 7.6 Hz), 3.59 (2H, t, J = 6.8 Hz), 3.75 (2H, t, J = 5.9 Hz), 4.16 (1H, s), 6.00 (1H, s), 7.33 (2H, s). |
| 116 | | $^1$H-NMR (CDCl$_3$) δ: 0.89-0.94 (9H, m), 1.52-1.95 (8H, m), 2.02-2.29 (2H, m), 2.55 (4H, t, J = 7.6 Hz), 3.60 (2H, t, J = 6.8 Hz), 3.74 (2H, t, J = 5.9 Hz), 3.77-3.79 (4H, m), 6.15 (1H, s), 6.89 (2H, d, J = 8.6 Hz), 7.31 (2H, s), 7.42 (2H, d, J = 8.6 Hz). |
| 117 | | $^1$H-NMR (CDCl$_3$) δ: 0.86-0.94 (9H, m), 1.52-1.92 (8H, m), 2.00-2.25 (2H, m), 2.55 (4H, t, J = 7.6 Hz), 3.59 (2H, t, J = 6.8 Hz), 3.74 (2H, t, J = 5.9 Hz), 3.87 (1H, s), 5.95 (2H, s), 6.39 (1H, s), 6.78 (1H, d, J = 8.1 Hz), 6.95 (1H, dd, J = 1.9, 8.1 Hz), 7.04 (1H, d, J = 1.9 Hz), 7.31 (2H, s). |
| 118 | | $^1$H-NMR (CDCl$_3$) δ: 0.92 (6H, t, J = 7.3 Hz), 1.02 (9H, s), 1.50-1.95 (8H, m), 2.56 (4H, t, J = 7.6 Hz), 3.54-3.62 (3H, m), 3.76 (2H, t, J = 5.4 Hz), 7.12 (1H, s), 7.30-7.35 (5H, m), 7.62 (2H, dd, J = 1.4, 8.1 Hz). |

TABLE 1-30

| Example | Structural formula | Property values |
|---|---|---|
| 119 | | $^1$H-NMR (CDCl$_3$) δ: 0.94 (6H, t, J = 7.3 Hz), 1.57-2.25 (16H, m), 2.58 (4H, t, J = 7.6 Hz), 3.60 (2H, t, J = 6.8 Hz), 3.77 (2H, t, J = 5.9 Hz), 4.10 (1H, s), 6.01 (1H, s), 7.33 (2H, s). |

TABLE 1-30-continued

| Example | Structural formula | Property values |
| --- | --- | --- |
| 120 | | $^1$H-NMR (CDCl$_3$) δ: 0.90 (3H, t, J = 7.3 Hz), 1.45-1.90 (9H, m), 2.57 (2H, t, J = 7.6 Hz), 3.19 (2H, t, J = 8.6 Hz), 3.59 (2H, t, J = 7.0 Hz), 3.96 (2H, t, J = 5.1 Hz), 4.03 (1H, s), 4.57 (2H, t, J = 8.6 Hz), 6.05 (1H, s), 6.74 (1H, d, J = 8.6 Hz), 6.77 (1H, d, J = 8.6 Hz), 7.18 (1H, dd, J = 1.9, 8.6 Hz), 7.26 (1H, d, J = 1.9 Hz), 7.40-7.49 (2H, m). |
| 121 | | $^1$H-NMR (CDCl$_3$) δ: 0.72 (3H, t, J = 7.3 Hz), 0.92 (3H, t, J = 7.3 Hz), 1.35 (3H, s), 1.52-1.72 (4H, m), 1.81-1.97 (4H, m), 2.60 (2H, t, J = 7.4 Hz), 2.86 (3H, s), 3.45 (3H, s), 3.60 (2H, t, J = 7.3 Hz), 4.02 (2H, t, J = 6.5 Hz), 6.85 (1H, d, J = 8.6 Hz), 7.28 (1H, s), 7.32 (1H, d, J = 8.6 Hz). |

TABLE 1-31

| Example | Structural formula | Property values |
| --- | --- | --- |
| 122 | | $^1$H-NMR (CDCl$_3$) δ: 1.31 (6H, d, J = 6.1 Hz), 1.57-1.85 (7H, m), 2.89 (2H, s), 3.50 (1H, s), 3.60 (2H, t, J = 6.8 Hz), 3.72 (2H, t, J = 6.1 Hz), 4.48-4.54 (1H, m), 5.73 (1H, s), 6.84 (2H, d, J = 8.8 Hz), 7.10-7.36 (10H, m). |
| 123 | | $^1$H-NMR (CDCl$_3$) δ: 0.71 (3H, dd, J = 7.3 Hz), 0.92 (3H, t, J = 7.3 Hz), 1.35 (3H, s), 1.58 (1H, dd, J = 7.3, 14.5 Hz), 1.65 (1H, dd, J = 7.3, 14.5 Hz), 1.78-1.95 (6H, m), 2.59 (2H, t, J = 7.3 Hz), 2.85 (3H, s), 3.59 (2H, t, J = 6.5 Hz), 3.95-4.01 (3H, m), 6.83 (1H, d, J = 8.6 Hz), 7.43 (1H, s), 7.46 (1H, d, J = 8.6 Hz) |
| 124 | | $^1$H-NMR (CDCl$_3$) δ: 0.90 (3H, t, J = 7.6 Hz), 0.93 (3H, t, J = 7.6 Hz), 1.17-1.29 (2H, m), 1.52-1.63 (2H, m), 1.74-1.82 (4H, m), 1.97-2.10 (2H, m), 2.57 (2H, t, J = 7.3 Hz), 3.57 (2H, t, J = 6.3 Hz), 3.66 (1H, s), 3.96 (2H, t, = 5.7 Hz), 5.95 (2H, s), 6.08 (1H, s), 6.77 (1H, d, J = 8.2 Hz), 6.80 (1H, d, J = 8.2 Hz), 6.94 (1H, d, J = 8.2 Hz), 7.03 (1H, s), 7.40-7.47 (2H, m). |

TABLE 1-32

| Example | Structural formula | Property values |
|---------|-------------------|-----------------|
| 125 | | ¹H-NMR (CDCl₃) δ: 0.84-0.95 (6H, m), 1.22-1.32 (4H, m), 1.52-1.61 (2H, m), 1.78-1.82 (4H, m), 2.02-2.12 (2H, m), 2.57 (2H, t, J = 7.3 Hz), 3.57 (2H, J = 5.9 Hz), 3.74 (1H, s), 3.96 (2H, t, J = 5.7 Hz), 5.95 (2H, s), 6.13 (1H, s), 6.77 (1H, d, J = 7.3 Hz), 6.80 (1H, d, J = 8.2 Hz), 6.94 (1H, dd, J = 2.0, 8.2 Hz), 7.03 (1H, d, J = 2.0 Hz), 7.40-7.47 (2H, m). |
| 126 | | ¹H-NMR (CDCl₃) δ: 0.90 (3H, t, J = 7.3 Hz), 1.52-1.62 (2H, m), 1.75 (3H, s), 1.77-1.82 (4H, m), 2.18 (2H, quint, J = 5.6 Hz), 2.57 (2H, t, J = 5.6 Hz), 3.59 (2H, t, J = 6.6 Hz), 3.71 (1H, s), 3.97 (2H, t, J = 5.9 Hz), 4.20 (4H, t, J = 5.6 Hz), 5.85 (1H, s), 6.80 (1H, d, J = 8.6 Hz), 6.94 (1H, d, J = 8.2 Hz), 6.99 (1H, dd, J = 2.3, 8.2 Hz), 7.08 (1H, d, J = 2.3 Hz), 7.40-7.46 (2H, m). |

TABLE 1-33

| Example | Structural formula | Property values |
|---------|-------------------|-----------------|
| 127 | | ¹H-NMR (CDCl₃) δ: 1.61-1.72 (4H, m), 1.76 (3H, s), 3.49 (2H, t, J = 6.5 Hz), 3.68 (1H, s), 3.90-3.95 (4H, m), 5.93 (2H, s), 6.06 (1H, s), 6.77 (1H, d, J = 8.2 Hz), 6.81 (1H, d, J = 8.6 Hz), 6.91 (1H, dd, J = 2.0, 7.9 Hz), 6.97 (1H, d, J = 2.0 Hz), 7.10-7.24 (5H, m), 7.45-7.51 (2H, m). |
| 128 | | ¹H-NMR (CDCl₃) δ: 1.62-1.73 (4H, m), 1.75 (3H, s), 3.48 (2H, t, J = 6.5 Hz), 3.88-3.94 (5H, m), 4.20 (4H, s), 6.02 (1H, s), 6.79-6.85 (2H, m), 6.90 (1H, dd, J = 2.3, 8.2 Hz), 6.98 (1H, d, J = 2.3 Hz), 7.09-7.23 (5H, m), 7.46 (1H, s), 7.49 (1H, d, J = 8.9 Hz). |

TABLE 1-33-continued

| Example | Structural formula | Property values |
|---|---|---|
| 129 | | $^1$H-NMR (CDCl$_3$) δ: 0.84-0.96 (6H, m), 1.52-1.61 (2H, m), 1.77-1.82 (4H, m), 2.04 (1H, dd, J = 6.9 Hz, 14.1 Hz), 2.20 (1H, dd, J = 7.3, 14.1 Hz), 2.54-2.70 (2H, m), 3.52-3.58 (3H, m), 3.96 (2H, t, J = 5.7 Hz), 4.23 (4H, s), 5.98 (1H, s), 6.80 (1H, dd, J = 3.6, 8.5 Hz), 6.85 (1H, d, J = 8.5 Hz), 6.93 (1H, dd, J = 2.3, 8.5 Hz), 7.01 (1H, dd, J = 2.3, 5.3 Hz), 7.41-7.47 (2H, m). |

TABLE 1-34

| Example | Structural formula | Property values |
|---|---|---|
| 130 | | $^1$H-NMR (CDCl$_3$) δ: 0.87-0.95 (9H, m), 1.55-1.67 (4H, m), 1.75-1.86 (4H, m), 2.05 (1H, dd, J = 7.3, 14.2 Hz), 2.22 (1H, dd, J = 7.3, 14.2 Hz), 2.55 (4H, t, J = 7.6 Hz), 3.59 (2H, t, J = 6.6 Hz), 3.71-3.77 (3H, m), 4.24 (4H, s), 6.11 (1H, s), 6.85 (1H, d, J = 8.6 Hz), 6.96 (1H, dd, J = 2.3, 8.6 Hz), 7.03 (1H, d, J = 2.3 Hz), 7.31 (2H, s). |
| 131 | | $^1$H-NMR (CDCl$_3$) δ: 1.36 (6H, s), 1.77-1.82 (4H, m), 2.88 (3H, s), 3.75 (2H, t, J = 6.6 Hz), 3.99 (2H, t, J = 5.6 Hz), 4.06 (1H, s), 6.92 (2H, d, J = 8.9 Hz), 7.60 (2H, d, J = 8.9 Hz). |
| 132 | | $^1$H-NMR (CDCl$_3$) δ: 1.72-1.85 (7H, m), 3.58 (2H, t, J = 6.3 Hz), 3.69 (1H, s), 3.97 (2H, t, J = 5.2 Hz), 5.84 (1H, s), 5.96 (2H, s), 6.79 (1H, d, J = 7.9 Hz), 6.88-6.96 (4H, m), 7.59 (2H, d, J = 8.6 Hz). |
| 133 | | $^1$H-NMR (CDCl$_3$) δ: 1.36 (6H, s), 1.75-1.82 (4H, m), 2.54 (3H, s), 2.88 (3H, s), 3.56 (2H, t, J = 6.6 Hz), 3.69 (1H, s), 3.97 (2H, t, J = 5.6 Hz), 6.69-6.74 (2H, m), 7.43 (1H, d, J = 8.2 Hz). |

TABLE 1-35

| Example | Structural formula | Property values |
|---|---|---|
| 134 | 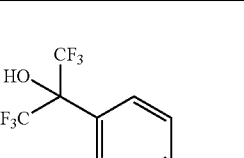 | $^1$H-NMR (CDCl$_3$) δ: 1.69-1.79 (7H, m), 2.56 (3H, s), 3.57 (2H, t, J = 6.6 Hz), 3.60 (1H, s), 3.95 (2H, t, J = 5.6 Hz), 5.90 (1H, s), 5.96 (2H, s), 6.68-6.72 (2H, m), 6.79 (1H, d, J = 8.2 Hz), 6.93 (1H, dd, J = 1.6, 8.2 Hz), 6.97 (1H, d, J = 1.6 Hz), 7.42 (1H, d, J = 8.6 Hz). |
| 135 | | $^1$H-NMR (CDCl$_3$) δ: 1.37 (6H, s), 1.78-1.83 (4H, m), 2.89 (3H, s), 3.58 (2H, t, J = 6.6 Hz), 3.95 (3H, s), 4.01 (2H, t, J = 5.9 Hz), 6.54-6.59 (2H, m), 7.32 (1H, s), 7.43 (1H, d, J = 8.9 Hz). |
| 136 | | $^1$H-NMR (CDCl$_3$) δ: 1.70-1.87 (7H, m), 3.59 (2H, t, J = 6.6 Hz), 3.94 (3H, s), 3.98 (2H, t, J = 5.6 Hz), 5.87 (1H, s), 5.97 (2H, s), 6.52-6.56 (2H, m), 6.80 (1H, d, J = 7.9 Hz), 6.91-6.98 (2H, m), 7.32 (1H, s), 7.42 (1H, d, J = 8.2 Hz). |
| 137 | | $^1$H-NMR (CDCl$_3$) δ: 1.36 (6H, s), 1.76-1.84 (4H, m), 2.02 (2H, quint, J = 7.3 Hz), 2.82 (2H, t, J = 7.3 Hz), 2.88 (3H, s), 3.22 (2H, t, J = 7.3 Hz), 3.43 (1H, s), 3.59 (2H, t, J = 6.6 Hz), 4.01 (2H, t, J = 5.3 Hz), 6.67 (1H, d, J = 8.6 Hz), 7.33 (1H, d, J = 8.6 Hz). |

TABLE 1-36

| Example | Structural formula | Property values |
|---|---|---|
| 138 | 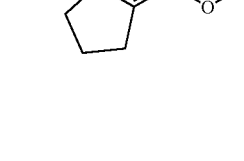 | $^1$H-NMR (CDCl$_3$) δ: 1.75-1.83 (7H, m), 2.01 (2H, quint, J = 7.6 Hz), 2.79 (2H, t, J = 7.6 Hz), 3.22 (2H, t, J = 7.6 Hz), 3.48 (1H, s), 3.58 (2H, t, J = 6.6 Hz), 3.98 (2H, t, J = 5.3 Hz), 5.83 (1H, s), 5.96 (2H, s), 6.64 (1H, d, J = 8.9 Hz), 6.79 (1H, d, J = 7.9 Hz), 6.92 (1H, dd, J = 2.0, 7.9 Hz), 6.97 (1H, d, J = 2.0 Hz), 7.33 (1H, d, J = 8.9 Hz). |
| 139 | | $^1$H-NMR (CDCl$_3$) δ: 0.89 (3H, t, J = 7.3 Hz), 1.77-1.80 (4H, m), 1.94-2.07 (2H, m), 2.16-2.25 (2H, m), 2.79 (2H, t, J = 7.3 Hz), 3.21 (2H, t, J = 7.3 Hz), 3.56 (2H, t, J = 6.6 Hz), 3.60 (1H, s), 3.98 (2H, t, J = 5.9 Hz), 4.23 (4H, s), 5.90 (1H, s), 6.64 (1H, d, J = 8.9 Hz), 6.85 (1H, d, J = 8.6 Hz), 6.94 (1H, dd, J = 2.3, 8.6 Hz), 7.01 (1H, d, J = 2.3 Hz), 7.32 (1H, d, J = 8.9 Hz). |

TABLE 1-37

| Example | Structural formula | Property values |
|---|---|---|
| 140 | | ¹H-NMR (CDCl₃) δ: 0.88 (3H, dd, J = 7.3, 7.3 Hz), 1.66-1.71 (4H, m), 2.03 (1H, dd, J = 7.3, 14.2 Hz), 2.19 (1H, dd, J = 7.3, 14.2 Hz), 3.48 (2H, t, J = 6.3 Hz), 3.67 (1H, s), 3.89-3.95 (4H, m), 4.22 (4H, s), 5.94 (1H, s), 6.81 (1H, d, J = 8.2 Hz), 6.85 (1H, d, J = 8.2 Hz), 6.94 (1H, dd, J = 2.0, 8.6 Hz), 7.02 (1H, d, J = 2.0 Hz), 7.11-7.23 (5H, m), 7.45 (1H, s), 7.49 (1H, d, J = 8.6 Hz). |
| 141 | | ¹H-NMR (CDCl₃) δ: 0.88 (3H, dd, J = 7.3, 7.3 Hz), 1.66-1.71 (4H, m), 2.06 (1H, dd, J = 7.3, 14.2 Hz), 2.18 (1H, dd, J = 7.3, 14.2 Hz), 3.49 (2H, t, J = 6.6 Hz), 3.59 (1H, s), 3.89-3.95 (4H, m), 5.91-5.97 (3H, m), 6.78 (1H, d, J = 8.2 Hz), 6.82 (1H, d, J = 8.6 Hz), 6.94 (1H, dd, J = 2.0, 8.2 Hz), 7.03 (1H, d, J = 2.0 Hz), 7.10-7.23 (5H, m), 7.45 (1H, s), 7.49 (1H, d, J = 8.2 Hz). |
| 142 | | ¹H-NMR (CDCl₃) δ: 1.15-1.26 (12H, m), 1.39 (6H, s), 1.81-1.87 (4H, m), 2.90 (3H, s), 3.22-3.31 (2H, m), 3.57-3.62 (3H, m), 3.74 (2H, t, J = 5.9 Hz), 7.37 (2H, m). |

TABLE 1-38

| Example | Structural formula | Property values |
|---|---|---|
| 143 | | ¹H-NMR (CDCl₃) δ: 1.17-1.26 (12H, m), 1.78-1.86 (7H, m), 3.20-3.27 (2H, m), 3.57-3.62 (3H, m), 3.72 (2H, t, J = 5.9 Hz), 5.87 (1H, s), 5.97 (2H, s), 6.79 (1H, d, J = 8.2 Hz), 6.94 (1H, dd, J = 2.0, 8.2 Hz), 6.98 (1H, d, J = 2.0 Hz), 7.37 (2H, s). |
| 144 | | ¹H-NMR (CDCl₃) δ: 0.91 (3H, dd, J = 7.3, 7.3 Hz), 1.19 (12H, d, J = 6.9 Hz), 1.79-1.86 (4H, m), 2.04 (1H, dd, J = 7.3, 14.2 Hz), 2.23 (1H, dd, J = 7.3, 14.2 Hz), 3.25 (2H, septet, J = 6.9 Hz), 3.51 (1H, s), 3.60 (2H, t, J = 6.6 Hz), 3.72 (2H, t, J = 5.6 Hz), 4.24 (4H, s), 5.77 (1H, s), 6.85 (1H, d, J = 8.6 Hz), 6.95 (1H, d, J = 2.3, 8.6 Hz), 7.02 (1H, d, J = 2.3 Hz), 7.37 (2H, s). |

TABLE 1-38-continued

| Example | Structural formula | Property values |
| --- | --- | --- |
| 145 | | $^1$H-NMR (CDCl$_3$) δ: 0.74 (3H, d, J = 6.9 Hz), 1.23-1.29 (6H, m), 1.49-1.60 (2H, m), 1.76-1.81 (4H, m), 2.56-2.59 (3H, m), 3.54 (2H, t, J = 6.6 Hz), 3.57 (1H, s), 3.95 (2H, t, J = 5.6 Hz), 4.24 (4H, s), 6.02 (1H, s), 6.80 (1H, d, J = 8.6 Hz), 6.85 (1H, d, J = 8.6 Hz), 6.98 (1H, dd, J = 2.3, 8.6 Hz), 7.06 (1H, d, J = 2.3 Hz), 7.41 (1H, s), 7.44 (1H, d, J = 8.6 Hz). |

TABLE 1-39

| Example | Structural formula | Property values |
| --- | --- | --- |
| 146 | | $^1$H-NMR (CDCl$_3$) δ: 0.75 (6H, d, J = 6.9 Hz), 0.91 (3H, t, J = 7.3 Hz), 0.94 (3H, t, J = 7.3 Hz), 1.52-1.67 (4H, m), 1.74-1.85 (4H, m), 2.52-2.66 (5H, m), 3.56 (2H, t, J = 6.3 Hz), 3.62 (1H, s), 3.73 (2H, t, J = 5.9 Hz), 4.23 (4H, s), 6.14 (1H, s), 6.85 (1H, d, J = 8.6 Hz), 6.99 (1H, dd, J = 2.0, 8.6 Hz), 7.07 (1H, d, J = 2.0 Hz), 7.31 (2H, s). |
| 147 | | $^1$H-NMR (CDCl$_3$) δ: 0.91 (3H, t, J = 7.3, 7.3 Hz), 1.00 (9H, s), 1.58 (2H, qt, J = 7.3, 7.3 Hz), 1.78-1.83 (4H, m), 2.58 (2H, t, J = 7.3 Hz), 3.57-3.59 (2H, m), 3.73 (1H, s), 3.98 (2H, t, J = 5.6 Hz), 4.23 (4H, s), 6.14 (1H, s), 6.80 (2H, dd, J = 2.3, 8.2 Hz), 7.06 (1H, dd, J = 2.3, 8.2 Hz), 7.16 (1H, d, J = 2.3 Hz), 7.41-7.47 (2H, m). |
| 148 | | $^1$H-NMR (CDCl$_3$) δ: 0.88-0.96 (6H, m), 1.01 (9H, s), 1.58-1.64 (4H, m), 1.76-1.84 (4H, m), 2.56 (4H, t, J = 7.6 Hz), 3.49 (1H, s), 3.58 (2H, t, J = 6.6 Hz), 3.75 (2H, t, J = 5.6 Hz), 4.23 (4H, s), 6.60 (1H, s), 6.80 (1H, d, J = 8.6 Hz), 7.04 (1H, d, J = 8.6 Hz), 7.14 (1H, s), 7.30 (2H, s). |

TABLE 1-40

| Example | Structural formula | Property values |
|---|---|---|
| 149 | | $^1$H-NMR (CDCl$_3$) δ: 0.87-0.96 (6H, m), 1.16-1.24 (2H, m), 1.52-1.61 (2H, m), 1.77-1.81 (4H, m), 1.93-2.17 (2H, m), 2.57 (2H, t, J = 7.3 Hz), 3.54 (2H, t, J = 6.3 Hz), 3.77 (1H, s), 3.96 (2H, d, J = 5.3 Hz), 4.23 (4H, s), 6.14 (1H, s), 6.80 (1H, d, J = 8.6 Hz), 6.84 (1H, d, J = 8.6 Hz), 6.95 (1H, dd, J = 2.3, 8.6 Hz), 7.02 (1H, d, J = 2.3 Hz), 7.42 (1H, s), 7.45 (1H, d, J = 8.6 Hz). |
| 150 | | $^1$H-NMR (CDCl$_3$) δ: 0.89-0.95 (9H, m), 1.19-1.26 (2H, m), 1.53-1.67 (4H, m), 1.75-1.86 (4H, m), 1.95-2.17 (2H, m), 2.56 (4H, t, J = 7.6 Hz), 3.58 (2H, t, J = 6.6 Hz), 3.65 (1H, s), 3.74 (2H, t, J = 5.6 Hz), 4.23 (4H, s), 5.95 (1H, s), 6.84 (1H, d, J = 8.2 Hz), 6.95 (1H, dd, J = 2.0, 8.2 Hz), 7.02 (1H, d, J = 2.0 Hz), 7.31 (2H, s). |
| 151 | | $^1$H-NMR (CDCl$_3$) δ: 0.90 (3H, t, J = 7.3 Hz), 1.57 (2H, qt, J = 7.3, 7.6 Hz), 1.75-1.86 (7H, m), 2.57 (2H, t, J = 7.6 Hz), 3.59 (2H, t, J = 6.6 Hz), 3.68 (1H, s), 3.97 (2H, t, J = 5.6 Hz), 5.05 (2H, s), 5.81 (1H, s), 6.81 (1H, d, J = 8.9 Hz), 6.97 (2H, d, J = 8.9 Hz), 7.34-7.45 (9H, m). |

TABLE 1-41

| Example | Structural formula | Property values |
|---|---|---|
| 152 | | $^1$H-NMR (CDCl$_3$) δ: 0.92 (6H, t, J = 7.3 Hz), 1.59 (4H, qt, J = 7.3, 7.6 Hz), 1.75-1.85 (7H, m), 2.56 (4H, t, J = 7.6 Hz), 3.61 (2H, t, J = 6.6 Hz), 3.71 (1H, s), 3.74 (2H, t, J = 5.9 Hz), 5.05 (2H, s), 5.87 (1H, s), 6.97 (2H, d, J = 8.9 Hz), 7.30-7.41 (9H, m). |

TABLE 1-41-continued

| Example | Structural formula | Property values |
|---|---|---|
| 153 | | $^1$H-NMR (CDCl$_3$) δ: 0.92 (3H, t, J = 7.3 Hz), 1.47-1.66 (9H, m), 2.59 (2H, t, J = 7.3 Hz), 2.82 (1H, d, J = 13.5 Hz), 3.02 (1H, d, J = 13.5 Hz), 3.40 (2H, t, J = 6.3 Hz), 3.66 (1H, s), 3.78 (3H, s), 3.85 (2H, t, J = 5.3 Hz), 6.14 (1H, s), 6.76-6.84 (3H, m), 7.07 (2H, d, J = 8.6 Hz), 7.43 (1H, s), 7.46 (1H, d, J = 8.6 Hz). |
| 154 | | $^1$H-NMR (CDCl$_3$) δ: 0.95 (6H, t, J = 7.3 Hz), 1.47 (3H, s), 1.54-1.67 (8H, m), 2.57 (4H, t, J = 7.6 Hz), 2.83 (1H, d, J = 13.5 Hz), 3.01 (1H, d, J = 13.5 Hz), 3.45 (2H, t, J = 6.3 Hz), 3.64-3.76 (3H, m), 3.78 (3H, s), 5.42 (1H, s), 6.79 (2H, d, J = 8.2 Hz), 7.07 (2H, d, J = 8.2 Hz), 7.47 (2H, s). |

TABLE 1-42

| Example | Structural formula | Property values |
|---|---|---|
| 155 | | $^1$H-NMR (CDCl$_3$) δ: 0.90 (3H, d, J = 7.3 Hz), 1.57 (2H, qt, J = 7.3, 7.6 Hz), 1.76-1.85 (7H, m), 2.35 (3H, s), 2.57 (2H, t, J = 7.6 Hz), 3.59 (2H, t, J = 6.3 Hz), 3.72 (1H, s), 3.96 (2H, t, J = 5.6 Hz), 5.00 (2H, s), 5.86 (1H, s), 6.81 (1H, d, J = 8.6 Hz), 6.96 (2H, d, J = 8.9 Hz), 7.18 (2H, d, J = 7.9 Hz), 7.29 (2H, d, J = 7.9 Hz), 7.36 (2H, d, J = 8.9 Hz), 7.42 (1H, s), 7.44 (1H, d, J = 8.6 Hz). |

TABLE 1-42-continued
| Example | Structural formula | Property values |
|---|---|---|
| 156 | 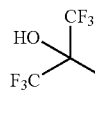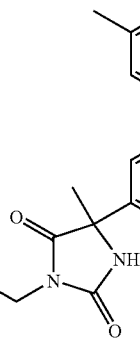 | ¹H-NMR (CDCl₃) δ: 0.92 (6H, t, J = 7.3 Hz), 1.61 (4H, qt, J = 7.3, 7.6 Hz), 1.76-1.86 (7H, m), 2.35 (3H, s), 2.56 (4H, t, J = 7.6 Hz), 3.56 (1H, s), 3.61 (2H, t, J = 6.9 Hz), 3.75 (2H, t, J = 5.9 Hz), 5.00 (2H, s), 5.73 (1H, s), 6.96 (2H, d, J = 8.9 Hz), 7.19 (2H, d, J = 7.9 Hz), 7.27-7.32 (4H, m), 7.37 (2H, d, J = 8.9 Hz). |
| 157 | 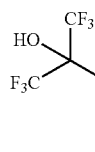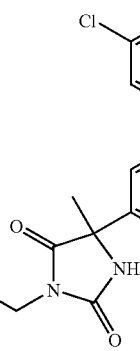 | ¹H-NMR (CDCl₃) δ: 0.90 (3H, t, J = 7.3 Hz), 1.58 (2H, qt, J = 7.3, 7.6 Hz), 1.75-1.86 (7H, m), 2.57 (2H, t, J = 7.6 Hz), 3.59 (2H, t, J = 6.6 Hz), 3.68 (1H, s), 3.97 (2H, t, J = 5.6 Hz), 5.01 (2H, s), 5.81 (1H, s), 6.81 (1H, d, J = 8.6 Hz), 6.94 (2H, d, J = 8.6 Hz), 7.34-7.47 (8H, m). |
TABLE 1-43
| Example | Structural formula | Property values |
|---|---|---|
| 158 | 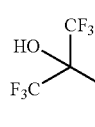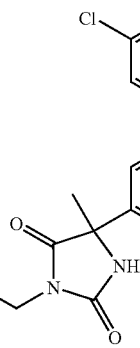 | ¹H-NMR (CDCl₃) δ: 0.92 (6H, t, J = 7.3 Hz), 1.59 (4H, qt, J = 7.3, 7.6 Hz), 1.76-1.86 (7H, m), 2.56 (4H, t, J = 7.6 Hz), 3.61 (2H, t, J = 7.2 Hz), 3.64 (1H, s), 3.75 (2H, t, J = 5.6 Hz), 5.01 (2H, s), 5.83 (1H, s), 6.94 (2H, d, J = 8.9 Hz), 7.30-7.35 (6H, m), 7.38 (2H, d, J = 8.9 Hz). |

TABLE 1-43-continued

| Example | Structural formula | Property values |
|---|---|---|
| 159 | | ¹H-NMR (CDCl₃) δ: 0.90 (3H, t, J = 7.3 Hz), 1.56 (2H, qt, J = 7.3, 7.6 Hz), 1.73-1.85 (7H, m), 2.56 (2H, t, J = 7.6 Hz), 3.67 (2H, t, J = 6.6 Hz), 3.71 (6H, s), 3.78-3.79 (2H, m), 3.96 (2H, t, J = 5.6 Hz), 4.99 (2H, s), 6.08 (1H, s), 6.56 (2H, d, J = 2.0 Hz), 6.80 (1H, 8.6 Hz), 6.96 (2H, d, J = 8.6 Hz), 7.37 (2H, d, J = 8.6 Hz), 7.41-7.47 (2H, m). |
| 160 | | ¹H-NMR (CDCl₃) δ: 0.91 (6H, t, J = 7.3 Hz), 1.61 (4H, qt, J = 7.3, 7.6 Hz), 1.75-1.84 (7H, m), 2.55 (2H, t, J = 7.6 Hz), 2.65 (2H, t, J = 7.6 Hz), 3.58 (2H, t, J = 6.6 Hz), 3.71 (6H, s), 3.75-3.79 (3H, m), 4.99 (2H, s), 6.21 (1H, s), 6.41 (1H, s), 6.55 (2H, d, J = 2.0 Hz), 6.95 (2H, d, J = 8.6 Hz), 7.32 (2H, s), 7.38 (2H, d, J = 8.6 Hz). |

TABLE 1-44

| Example | Structural formula | Property values |
|---|---|---|
| 161 | | ¹H-NMR (CDCl₃) δ: 0.93 (3H, t, J = 7.3 Hz), 1.32 (6H, d, J = 5.9 Hz), 1.60 (2H, qt, J = 7.3, 7.6 Hz), 1.68-1.85 (10H, m), 2.56 (2H, t, J = 7.6 Hz), 3.59 (2H, t, J = 6.6 Hz), 3.71 (1H, s), 3.75 (2H, t, J = 5.9 Hz), 4.53 (1H, q, J = 5.9 Hz), 5.84 (1H, qd, J = 7.3, 11.5 Hz), 5.92 (1H, s), 6.48 (1H, d, J = 11.5 Hz), 6.87 (2H, d, J = 8.6 Hz), 7.34-7.41 (4H, m). |

TABLE 1-44-continued

| Example | Structural formula | Property values |
|---|---|---|
| 162 | 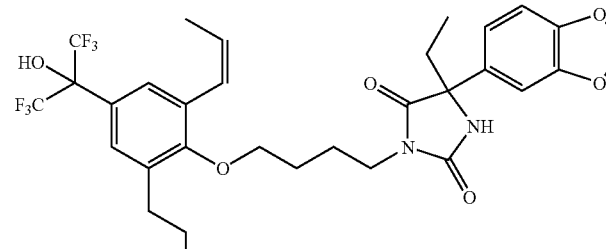 | $^1$H-NMR (CDCl$_3$) δ: 0.93 (3H, t, J = 7.3 Hz), 1.60 (2H, qt, J = 7.3, 7.6 Hz), 1.74-1.85 (10H, m), 2.57 (2H, t, J = 7.6 Hz), 3.59 (2H, d, J = 6.6 Hz), 3.75 (2H, t, J = 5.9 Hz), 3.95 (1H, s), 5.85 (1H, qd, J = 7.3, 11.5 Hz), 5.97 (2H, s), 6.04 (1H, s), 6.49 (1H, d, J = 11.5 Hz), 6.79 (1H, d, J = 7.9 Hz), 6.93 (1H, d, J = 7.9 Hz), 6.98 (1H, s), 7.38 (1H, s), 7.41 (1H, s). |

TABLE 1-45

| Example | Structural formula | Property values |
|---|---|---|
| 163 | 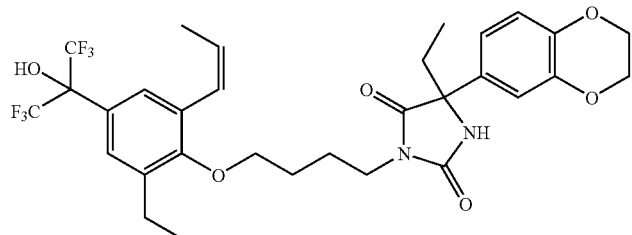 | $^1$H-NMR (CDCl$_3$) δ: 0.87-0.96 (6H, m), 1.59 (2H, qt, J = 7.3, 7.6 Hz), 1.70-1.85 (7H, m), 2.05 (1H, qd, J = 7.3, 14.2 Hz), 2.20 (1H, qd, J = 7.3, 14.2 Hz), 2.56 (2H, t, J = 7.6 Hz), 3.57 (2H, t, J = 6.6 Hz), 3.75 (2H, t, J = 5.9 Hz), 3.85 (1H, s), 5.84 (1H, qd, J = 7.3, 11.5 Hz), 5.96 (2H, s), 6.26 (1H, s), 6.48 (1H, d, J = 11.5 Hz), 6.79 (1H, d, J = 8.2 Hz), 6.95 (1H, dd, J = 1.3, 8.2 Hz), 7.04 (1H, d, J = 1.3 Hz), 7.39 (1H, s), 7.40 (1H, s). |
| 164 | 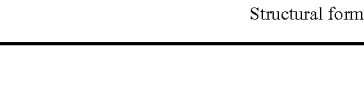 | $^1$H-NMR (CDCl$_3$) δ: 0.89-0.96 (6H, m), 1.53-1.82 (9H, m), 1.98-2.23 (2H, m), 2.56 (2H, t, J = 7.6 Hz), 3.57 (2H, t, J = 6.6 Hz), 3.75 (2H, t, J = 5.6 Hz), 3.84 (1H, s), 4.24 (4H, s), 5.85 (1H, qd, J = 7.3, 10.9 Hz), 6.05 (1H, s), 6.48 (1H, d, J = 10.9 Hz), 6.86 (1H, d, J = 8.2 Hz), 6.94 (1H, d, J = 8.2 Hz), 7.03 (1H, s), 7.39 (1H, s), 7.40 (1H, s). |

TABLE 1-46

| Example | Structural formula | Property values |
|---|---|---|
| 165 | | $^1$H-NMR (CDCl$_3$) δ: 0.91 (3H, t, J = 7.3 Hz), 1.31 (6H, d, J = 5.9 Hz), 1.54-1.90 (12H, m), 2.55 (2H, t, J = 7.3 Hz), 3.62 (2H, t, J = 6.2 Hz), 3.70-3.78 (3H, m), 4.53 (1H, q, J = 5.9 Hz), 5.81 (1H, s), 6.22 (1H, qd, J = 6.2, 15.9 Hz), 6.57 (1H, d, J = 15.9 Hz), 6.86 (2H, d, J = 8.4 Hz), 7.32-7.40 (3H, m), 7.58 (1H, s). |

TABLE 1-46-continued

| Example | Structural formula | Property values |
| --- | --- | --- |
| 166 | | $^1$H-NMR (CDCl$_3$) δ: 0.91 (3H, t, J = 7.3 Hz), 1.59 (2H, qt, J = 7.3, 7.6 Hz), 1.75-1.90 (10H, m), 2.55 (2H, t, J = 7.6 Hz), 3.61 (2H, t, J = 6.2 Hz), 3.74 (2H, t, J = 5.7 Hz), 3.78 (1H, s), 5.96 (2H, s), 6.01 (1H, s), 6.22 (1H, qd, J = 6.8, 15.9 Hz), 6.57 (1H, d, J = 15.9 Hz), 6.78 (1H, d, J = 8.1 Hz), 6.93 (1H, dd, J = 1.9, 8.1 Hz), 6.98 (1H, d, J = 1.9 Hz), 7.31 (1H, s), 7.58 (1H, s). |

TABLE 1-47

| Example | Structural formula | Property values |
| --- | --- | --- |
| 167 | | $^1$H-NMR (CDCl$_3$) δ: 0.88-0.95 (6H, m), 1.58 (2H, tq, J = 7.3, 7.8 Hz), 1.73-1.90 (7H, m), 1.98-2.28 (2H, m), 2.55 (2H, t, J = 7.3 Hz), 3.60 (2H, t, J = 6.5 Hz), 3.72-3.75 (3H, m), 5.96 (2H, s), 6.16 (1H, s), 6.22 (1H, qd, J = 6.5, 15.9 Hz), 6.57 (1H, d, J = 15.9 Hz), 6.78 (1H, d, J = 7.8 Hz), 6.95 (1H, dd, J = 2.2, 7.8 Hz), 7.04 (1H, d, J = 2.2 Hz), 7.32 (1H, s), 7.57 (1H, s). |
| 168 | | $^1$H-NMR (CDCl$_3$) δ: 0.87-0.95 (6H, m), 1.58 (2H, tq, J = 7.3, 7.8 Hz), 1.68-1.90 (7H, m), 2.00-2.26 (2H, m), 2.55 (2H, t, J = 7.3 Hz), 3.59 (2H, t, J = 6.2 Hz), 3.47 (2H, t, J = 5.7 Hz), 3.86 (1H, s), 4.23 (4H, s), 6.13 (1H, s), 6.22 (1H, qd, J = 6.5, 15.4 Hz), 6.57 (1H, d, J = 15.4 Hz), 6.84 (1H, d, J = 8.6 Hz), 6.96 (1H, dd, J = 2.2, 8.6 Hz), 7.03 (1H, d, J = 2.2 Hz), 7.32 (1H, s), 7.57 (1H, s). |

TABLE 1-48

| Example | Structural formula | Property values |
| --- | --- | --- |
| 169 | | $^1$H-NMR (CDCl$_3$) δ: 0.86-0.94 (6H, m), 1.26-1.60 (16H, m), 1.72-1.90 (7H, m), 2.22 (2H, dt, 6.8, 6.8 Hz), 2.55 (2H, t, J = 7.6 Hz), 3.60 (1H, s), 3.61 (2H, t, J = 6.8 Hz), 3.75 (2H, t, J = 5.9 Hz), 4.52 (1H, q, J = 5.9 Hz), 5.73 (1H, s), 6.20 (1H, td, J = 6.8, 15.9 Hz), 6.56 (1H, td, J = 6.8, 15.9 Hz), 6.86 (2H, d, J = 8.9 Hz), 7.31 (1H, s), 7.35 (2H, d, J = 8.9 Hz), 7.59 (1H, s). |

TABLE 1-48-continued

| Example | Structural formula | Property values |
|---|---|---|
| 170 |  | ¹H-NMR (CDCl₃) δ: 0.86-0.95 (6H, m), 1.25-1.63 (10H, m), 1.73-1.90 (7H, m), 2.22 (2H, dt, J = 7.3, 7.3 Hz), 2.56 (2H, t, J = 7.6 Hz), 3.46 (1H, s), 3.46 (2H, d, J = 6.5 Hz), 3.76 (2H, t, J = 5.4 Hz), 5.65 (1H, s), 5.96 (2H, s), 6.14 (1H, s), 6.21 (1H, dt, J = 6.8, 15.9 Hz), 6.56 (1H, d, J = 15.9 Hz), 6.78 (1H, d, J = 8.4 Hz), 6.93 (1H, dd, J = 1.9, 8.4 Hz), 6.97 (1H, d, J = 1.9 Hz), 7.32 (1H, s), 7.58 (1H, s). |

TABLE 1-49

| Example | Structural formula | Property values |
|---|---|---|
| 171 |  | ¹H-NMR (CDCl₃) δ: 0.85-0.94 (9H, m), 1.25-1.63 (10H, m), 1.70-1.90 (4H, m), 2.00-2.25 (4H, m), 2.55 (2H, t, J = 7.6 Hz), 3.56 (1H, s), 3.59 (2H, t, J = 6.5 Hz), 3.75 (2H, t, J = 5.7 Hz), 5.88 (1H, s), 5.95-5.97 (2H, m), 6.20 (1H, td, J = 6.8, 15.9 Hz), 6.55 (1H, d, J = 15.9 Hz), 6.78 (1H, d, J = 7.8 Hz), 6.94 (1H, dd, J = 1.9, 7.8 Hz), 7.03 (1H, d, J = 1.9 Hz), 7.31 (1H, s), 7.58 (1H, s). |
| 172 |  | ¹H-NMR (CDCl₃) δ: 0.85-0.94 (9H, m), 1.25-1.63 (10H, m), 1.70-1.86 (4H, m), 2.00-2.26 (4H, m), 2.55 (2H, t, J = 7.6 Hz), 3.52 (1H, s), 3.59 (2H, t, J = 6.5 Hz), 3.75 (2H, t, J = 5.7 Hz), 4.24 (4H, s), 5.71 (1H, s), 6.14 (1H, s), 6.20 (1H, td, J = 6.8, 15.9 Hz), 6.56 (1H, d, J = 15.9 Hz), 6.84 (1H, dd, J = 2.4, 8.1 Hz), 6.94 (1H, d, J = 2.4 Hz), 7.31 (1H, s), 7.58 (1H, s). |

TABLE 1-50

| Example | Structural formula | Property values |
|---|---|---|
| 173 |  | ¹H-NMR (CDCl₃) δ: 0.91 (3H, t, J = 7.3 Hz), 1.32 (6H, d, J = 5.9 Hz), 1.53-1.66 (20H, m), 2.54 (2H, t, J = 7.6 Hz), 3.61 (2H, t, J = 5.4 Hz), 3.74-3.79 (3H, m), 4.53 (1H, q, J = 5.9 Hz), 5.88 (1H, s), 6.16 (1H, 7.0, 15.9 Hz), 6.53 (1H, d, J = 15.9 Hz), 6.86 (2H, d, J = 8.6 Hz), 7.31 (1H, s), 7.36 (2H, d, J = 8.6 Hz), 7.59 (2H, s). |

TABLE 1-50-continued

| Example | Structural formula | Property values |
|---|---|---|
| 174 | | $^1$H-NMR (CDCl$_3$) δ: 0.91 (3H, t, J = 7.3 Hz), 1.10-1.90 (20H, m), 2.55 (2H, t, J = 7.0 Hz), 3.72-3.79 (3H, m), 5.90-5.97 (5H, m), 6.16 (1H, dd, J = 7.0, 16.2 Hz), 6.53 (1H, d, J = 16.2 Hz), 6.78 (1H, d, J = 8.1 Hz), 6.93 (1H, dd, J = 1.9, 8.1 Hz), 6.98 (1H, d, J = 1.9 Hz), 7.31 (1H, s), 7.58 (1H, s). |
| 175 | | $^1$H-NMR (CDCl$_3$) δ: 0.88-0.95 (6H, m), 1.11-1.83 (17H, m), 2.01-2.25 (2H, m), 2.55 (2H, t, J = 7.0 Hz), 3.55-3.79 (5H, m), 5.96 (2H, s), 6.07 (1H, s), 6.16 (1H, dd, J = 6.8, 15.4 Hz), 6.52 (1H, d, J = 15.4 Hz), 6.78 (1H, d, J = 8.1 Hz), 6.95 (1H, dd, J = 1.9, 8.1 Hz), 7.04 (1H, d, J = 1.9 Hz), 7.31 (1H, s), 7.58 (1H, s). |

TABLE 1-51

| Example | Structural formula | Property values |
|---|---|---|
| 176 | | $^1$H-NMR (CDCl$_3$) δ: 0.88-0.95 (6H, m), 1.12-1.88 (17H, m), 2.00-2.26 (2H, m), 2.55 (2H, t, J = 7.0 Hz), 3.59 (2H, t, 6.2 Hz), 3.73 (2H, t, J = 5.7 Hz), 3.79 (1H, s), 4.20-4.25 (4H, m), 6.07 (1H, s), 6.15 (1H, dd, J = 6.8, 16.2 Hz), 6.15 (1H, d, J = 16.2 Hz), 6.84 (1H, d, J = 8.4 Hz), 6.96 (1H, d, J = 2.2 Hz), 7.03 (1H, d, J = 2.2 Hz), 7.31 (1H, s), 7.59 (1H, s). |
| 177 | | $^1$H-NMR (CDCl$_3$) δ: 0.93 (3H, t, J = 7.3 Hz), 1.30 (6H, d, J = 5.9 Hz), 1.61 (2H, qt, J = 7.3, 7.6 Hz), 1.75-1.94 (7H, m), 2.58 (2H, t, J = 7.6 Hz), 3.60 (2H, t, J = 6.5 Hz), 3.79 (2H, t, J = 5.7 Hz), 3.98 (1H, s), 4.50 (1H, q, J = 5.9 Hz), 5.94 (1H, s), 6.84 (2H, d, J = 8.9 Hz), 7.05-7.53 (10H, m), 7.78 (1H, s). |

TABLE 1-51-continued

| Example | Structural formula | Property values |
|---|---|---|
| 178 | | $^1$H-NMR (CDCl$_3$) δ: 0.93 (3H, t, J = 7.3 Hz), 1.61 (2H, qt, J = 7.3, 7.6 Hz), 1.76-1.93 (7H, m), 2.58 (2H, t, J = 7.6 Hz), 3.60 (2H, d, J = 6.5 Hz), 3.79 (2H, t, J = 5.7 Hz), 3.97 (1H, s), 5.93 (2H, s), 6.09 (1H, s), 6.75 (1H, d, J = 8.4 Hz), 6.91 (1H, dd, J = 1.9, 8.4 Hz), 6.96 (1H, d, J = 1.9 Hz), 7.05-7.52 (8H, m), 7.78 (1H, s). |

TABLE 1-52

| Example | Structural formula | Property values |
|---|---|---|
| 179 | | $^1$H-NMR (CDCl$_3$) δ: 0.89 (3H, t, J = 7.3 Hz), 0.93 (3H, t, J = 7.3 Hz), 1.61 (2H, qt, J = 7.3, 7.6 Hz), 1.75-1.91 (4H, m), 1.99-2.23 (2H, m), 2.59 (2H, t, J = 7.6 Hz), 3.59 (2H, t, J = 6.2 Hz), 3.78 (1H, s), 3.79 (2H, t, J = 5.9 Hz), 5.93-5.95 (2H, m), 6.05 (1H, s), 6.73 (1H, d, J = 8.4 Hz), 6.93 (1H, dd, J = 2.2, 8.4 Hz), 7.02 (1H, d, J = 2.2 Hz), 7.05-7.53 (8H, m), 7.77 (1H, s). |
| 180 | | $^1$H-NMR (CDCl$_3$) δ: 0.88 (3H, t, J = 7.0 Hz), 0.93 (3H, t, J = 7.3 Hz), 1.63 (2H, qt, J = 7.3, 7.6 Hz), 1.74-1.90 (4H, m), 1.98-2.24 (2H, m), 2.58 (2H, t, J = 7.6 Hz), 3.59 (2H, t, J = 6.5 Hz), 3.79 (2H, t, J = 5.9 Hz), 3.81 (1H, s), 4.22 (4H, s), 5.95 (1H, s), 6.83 (1H, d, J = 8.4 Hz), 6.94 (1H, dd, J = 2.4, 8.4 Hz), 7.02 (1H, d, J = 2.4 Hz), 7.05-7.38 (8H, m), 7.77 (1H, s). |

TABLE 1-53

| Example | Structural formula | Property values |
|---|---|---|
| 181 | | $^1$H-NMR (CDCl$_3$) δ: 0.85-0.95 (6H, m), 1.26-1.33 (16H, m), 1.53-1.64 (4H, m), 1.75-1.90 (7H, m), 2.53-2.58 (4H, m), 3.58 (1H, s), 3.61 (2H, t, J = 6.5 Hz), 3.74 (2H, t, J = 5.9 Hz), 4.53 (1H, q, J = 5.9 Hz), 5.75 (1H, s), 6.87 (2H, d, J = 8.6 Hz), 7.31 (2H, s), 7.36 (2H, d, J = 8.6 Hz). |

TABLE 1-53-continued

| Example | Structural formula | Property values |
| --- | --- | --- |
| 182 |  | $^1$H-NMR (CDCl$_3$) δ: 0.85-0.95 (6H, m), 1.22-1.36 (10H, m), 1.52-1.64 (4H, m), 1.75-1.89 (7H, m), 2.53-2.61 (4H, m), 3.49 (1H, s), 3.61 (2H, d, J = 6.5 Hz), 3.75 (2H, t, J = 5.4 Hz), 5.74 (1H, s), 5.97 (2H, s), 6.78 (1H, d, J = 7.8 Hz), 6.93 (1H, dd, J = 1.9, 7.8 Hz), 6.98 (1H, d, J = 1.9 Hz), 7.31 (2H, s). |
| 183 |  | $^1$H-NMR (CDCl$_3$) δ: 0.85-0.95 (9H, m), 1.22-1.36 (10H, m), 1.51-1.67 (4H, m), 1.72-1.90 (4H, m), 1.98-2.28 (2H, m), 2.53-2.58 (4H, m), 3.53 (1H, s), 3.60 (2H, t, J = 6.2 Hz), 3.74 (2H, t, J = 5.7 Hz), 5.92 (1H, s), 5.96-5.97 (2H, m), 6.78 (1H, d, J = 7.8 Hz), 6.95 (1H, dd, J = 1.9, 7.8 Hz), 7.04 (1H, d, J = 1.9 Hz), 7.31 (2H, s). |

TABLE 1-54

| Example | Structural formula | Property values |
| --- | --- | --- |
| 184 |  | $^1$H-NMR (CDCl$_3$) δ: 0.85-0.95 (9H, m), 1.21-1.35 (10H, m), 1.54-1.66 (4H, m), 1.74-1.89 (4H, m), 1.97-2.29 (2H, m), 2.53-2.58 (4H, m), 3.56-3.61 (3H, m), 3.74 (2H, t, J = 5.7 Hz), 4.24 (4H, s), 5.76 (1H, s), 6.85 (1H, d, J = 8.4 Hz), 6.95 (1H, dd, J = 2.2, 8.4 Hz), 7.02 (1H, d, J = 2.2 Hz), 7.31 (2H, s). |
| 185 |  | $^1$H-NMR (CDCl$_3$) δ: 0.90-0.97 (5H, m), 1.15-1.93 (26H, m), 2.53-2.62 (4H, m), 3.51 (1H, s), 3.61 (2H, t, J = 6.5 Hz), 3.75 (2H, t, 7.3 Hz), 4.53 (1H, q, J = 5.9 Hz), 5.68 (1H, s), 6.87 (2H, d, J = 8.6 Hz), 7.30-7.37 (4H, m). |

TABLE 1-54-continued

| Example | Structural formula | Property values |
|---|---|---|
| 186 | 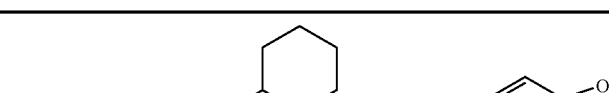 | $^1$H-NMR (CDCl$_3$) δ: 0.90-0.97 (5H, m), 1.11-1.89 (20H, m), 2.53-2.62 (4H, m), 3.58 (1H, s), 3.61 (2H, t, J = 6.5 Hz), 3.75 (2H, t, J = 5.7 Hz), 5.85 (1H, s), 5.96 (2H, s), 6.78 (1H, d, J = 8.1 Hz), 6.93 (1H, dd, J = 1.9, 8.1 Hz), 6.98 (1H, d, J = 1.9 Hz), 7.30 (2H, s). |

TABLE 1-55

| Example | Structural formula | Property values |
|---|---|---|
| 187 | 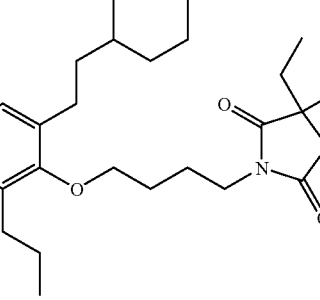 | $^1$H-NMR (CDCl$_3$) δ: 0.89-0.95 (8H, m), 1.11-1.84 (17H, m), 1.98-2.28 (2H, m), 2.52-2.62 (4H, m), 3.55 (1H, s), 5.60 (2H, t, J = 6.5 Hz), 3.75 (2H, t, J = 5.4 Hz), 5.96-5.97 (2H, m), 6.00 (1H, s), 6.79 (1H, d, J = 8.4 Hz), 6.95 (1H, dd, J = 1.9, 8.4 Hz), 7.04 (1H, d, J = 1.9 Hz), 7.30 (2H, s). |
| 188 | 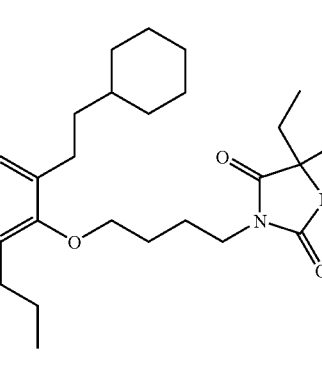 | $^1$H-NMR (CDCl$_3$) δ: 0.90-0.97 (8H, m), 1.10-1.85 (17H, m), 1.98-2.29 (2H, m), 2.53-2.62 (4H, m), 3.54 (1H, s), 3.59 (2H, t, J = 6.2 Hz), 3.74 (2H, t, J = 5.7 Hz), 4.24 (4H, s), 5.85 (1H, s), 6.85 (1H, d, J = 8.6 Hz), 6.96 (1H, dd, J = 2.4, 8.6 Hz), 7.03 (1H, d, J = 2.4 Hz), 7.30 (2H, s). |
| 189 | 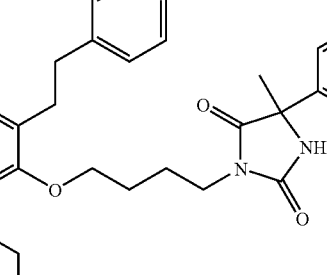 | $^1$H-NMR (CDCl$_3$) δ: 0.92 (3H, t, J = 7.3 Hz), 1.31 (6H, d, J = 5.9 Hz), 1.60 (2H, qt, J = 7.3, 7.6 Hz), 1.71-1.89 (7H, m), 2.56 (2H, t, J = 7.6 Hz), 2.76-2.84 (4H, m), 3.50 (1H, s), 3.60 (2H, t, J = 6.2 Hz), 3.71 (2H, t, J = 5.7 Hz), 4.51 (1H, q, J = 5.9 Hz), 5.76 (1H, s), 6.85 (2H, d, J = 8.9 Hz), 7.10-7.36 (9H, m). |

TABLE 1-56

| Example | Structural formula | Property values |
|---|---|---|
| 190 | | ¹H-NMR (CDCl₃) δ: 0.92 (3H, t, J = 7.3 Hz), 1.60 (2H, qt, J = 7.3, 7.6 Hz), 1.73-1.87 (7H, m), 2.56 (2H, t, J = 7.6 Hz), 2.86-2.93 (4H, m), 3.56 (1H, s), 3.60 (2H, d, J = 6.2 Hz), 3.71 (2H, t, J = 5.7 Hz), 5.91-5.96 (3H, m), 6.77 (1H, d, J = 8.1 Hz), 6.92 (1H, dd, J = 1.9, 8.1 Hz), 6.97 (1H, d, J = 1.9 Hz), 7.10-7.33 (7H, m). |
| 191 | | ¹H-NMR (CDCl₃) δ: 0.89 (3H, t, J = 7.6 Hz), 0.92 (3H, t, J = 7.3 Hz), 1.53-1.68 (2H, m), 1.73-1.88 (4H, m), 1.97-2.26 (2H, m), 2.56 (2H, t, J = 7.6 Hz), 2.86-2.90 (4H, m), 3.54 (1H, s), 3.59 (2H, t, J = 6.5 Hz), 3.71 (2H, t, J = 5.7 Hz), 5.93-5.95 (2H, m), 6.08 (1H, s), 6.77 (1H, d, J = 8.1 Hz), 6.94 (1H, dd, J = 1.9, 8.1 Hz), 7.03 (1H, d, J = 1.9 Hz), 7.09-7.32 (7H, m). |

TABLE 1-57

| Example | Structural formula | Property values |
|---|---|---|
| 192 | | ¹H-NMR (CDCl₃) δ: 0.89 (3H, t, J = 7.6 Hz), 0.92 (3H, t, J = 7.3 Hz), 1.60 (2H, tq, J = 7.0, 7.3 Hz), 1.75-1.88 (4H, m), 1.96-2.27 (2H, m), 2.52-2.58 (6H, m), 3.58 (2H, t, J = 6.2 Hz), 3.59 (1H, s), 3.70 (2H, t, J = 5.7 Hz), 4.22 (4H, s), 6.03 (1H, s), 6.84 (1H, d, J = 8.1 Hz), 6.95 (1H, dd, J = 2.2, 8.1 Hz), 7.03 (1H, d, J = 2.2 Hz), 7.09-7.32 (7H, m). |
| 193 | | ¹H-NMR (CDCl₃) δ: 0.93 (3H, t, J = 7.3 Hz), 1.25-1.43 (12H, m), 1.60 (2H, qt, J = 7.3, 7.8 Hz), 1.70-1.93 (11H, m), 2.55 (2H, t, J = 7.8 Hz), 2.78-2.90 (1H, m), 3.62 (2H, t, J = 6.5 Hz), 3.67 (1H, s), 3.73 (2H, t, J = 5.7 Hz), 4.53 (1H, q, J = 6.5 Hz), 5.87 (1H, s), 6.86 (2H, d, J = 8.9 Hz), 7.33-7.38 (4H, m). |

TABLE 1-57-continued

| Example | Structural formula | Property values |
|---|---|---|
| 194 | 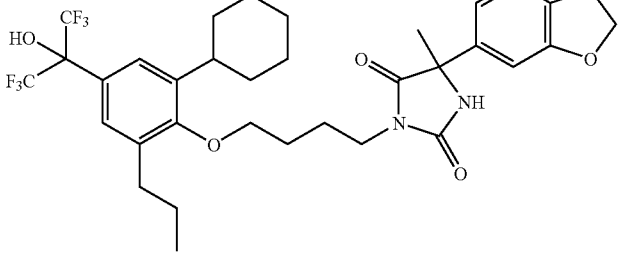 | $^1$H-NMR (CDCl$_3$) δ: 0.93 (3H, t, J = 7.3 Hz), 1.23-1.42 (6H, m), 1.53-1.67 (2H, m), 1.76-1.93 (11H, m), 2.60 (2H, t, J = 7.6 Hz), 2.78-2.90 (1H, m), 3.60 (1H, s), 3.62 (2H, t, J = 7.0 Hz), 3.73 (2H, t, J = 5.4 Hz), 5.81 (1H, s), 5.96 (2H, s), 6.78 (1H, d, J = 8.1 Hz), 6.94 (1H, dd, J = 1.9, 8.1 Hz), 6.98 (1H, d, J = 1.9 Hz), 7.30 (1H, s), 7.35 (1H, s). |

TABLE 1-58

| Example | Structural formula | Property values |
|---|---|---|
| 195 | 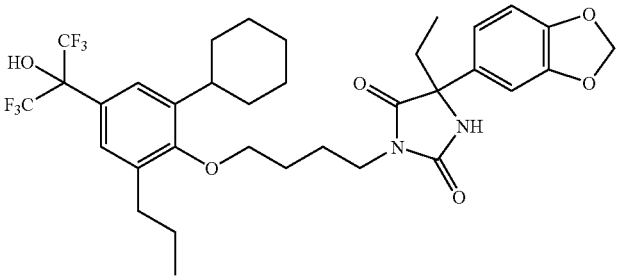 | $^1$H-NMR (CDCl$_3$) δ: 0.88-0.95 (6H, m), 1.23-1.43 (6H, m), 1.60 (2H, tq, J = 7.3, 7.6 Hz), 1.71-1.91 (8H, m), 2.01-2.26 (3H, m), 2.55 (2H, t, J = 7.6 Hz), 3.61 (2H, t, J = 6.8 Hz), 3.62 (1H, s), 3.73 (2H, t, J = 5.4 Hz), 5.95-5.97 (2H, m), 6.09 (1H, s), 6.78 (1H, d, J = 8.4 Hz), 6.96 (1H, dd, J = 1.9, 8.4 Hz), 7.04 (1H, d, J = 1.9 Hz), 7.29 (1H, s), 7.35 (1H, s). |
| 196 | 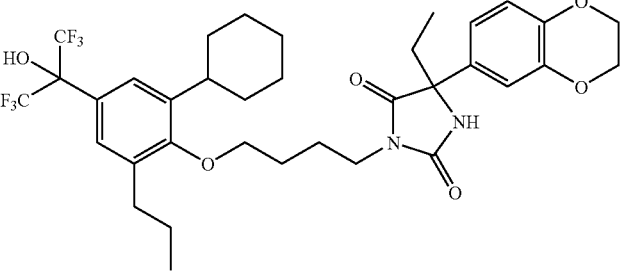 | $^1$H-NMR (CDCl$_3$) δ: 0.91 (3H, t, J = 7.3 Hz), 0.93 (3H, t, J = 7.3 Hz), 1.25-1.41 (6H, m), 1.60 (2H, qt, J = 7.3, 7.6 Hz), 1.72-1.90 (8H, m), 1.98-2.30 (3H, m), 2.56 (2H, t, J = 7.6 Hz), 3.54 (1H, s), 3.60 (2H, t, J = 6.5 Hz), 3.72 (2H, t, J = 5.1 Hz), 4.24 (4H, s), 5.82 (1H, s), 6.85 (1H, d, J = 8.4 Hz), 6.96 (1H, dd, J = 2.2, 8.4 Hz), 7.03 (1H, d, J = 2.2 Hz), 7.29 (1H, s), 7.34 (1H, s). |

TABLE 1-59

| Example | Structural formula | Property values |
|---|---|---|
| 197 | 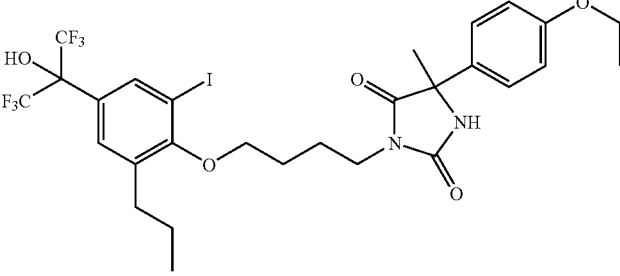 | $^1$H-NMR (CDCl$_3$) δ: 0.91 (3H, t, J = 7.3 Hz), 1.32 (6H, d, J = 5.9 Hz), 1.59 (2H, qt, J = 7.3, 7.6 Hz), 1.81 (3H, s), 1.84-1.91 (4H, m), 2.59 (2H, t, J = 7.6 Hz), 3.63 (2H, t, J = 6.2 Hz), 3.86 (2H, t, J = 5.7 Hz), 3.94 (1H, s), 4.53 (1H, q, J = 5.9 Hz), 5.86 (1H, s), 6.87 (2H, d, J = 8.9 Hz), 7.36 (2H, d, J = 8.9 Hz), 7.45 (1H, s), 7.93 (1H, d, J = 2.4 Hz). |

TABLE 1-59-continued

| Example | Structural formula | Property values |
|---|---|---|
| 198 | | $^1$H-NMR (CDCl$_3$) δ: 0.92 (3H, t, J = 7.3 Hz), 1.60 (2H, qt, J = 7.3, 7.6 Hz), 1.80 (3H, s), 1.83-1.92 (4H, m), 2.60 (2H, t, J = 7.6 Hz), 3.63 (2H, d, J = 6.2 Hz), 3.86 (2H, t, J = 5.4 Hz), 4.00 (1H, s), 5.97 (2H, s), 6.04 (1H, s), 6.79 (1H, d, J = 8.4 Hz), 6.94 (1H, dd, J = 1.9, 8.4 Hz), 6.98 (1H, d, J = 1.9 Hz), 7.45 (1H, s), 7.93 (1H, d, J = 1.9 Hz). |

TABLE 1-60

| Example | Structural formula | Property values |
|---|---|---|
| 199 | | $^1$H-NMR (CDCl$_3$) δ: 0.89-0.94 (6H, m), 1.59 (2H, qt, J = 7.3, 7.6 Hz), 1.79-1.91 (4H, m), 1.99-2.26 (2H, m), 2.59 (2H, t, J = 7.6 Hz), 3.62 (2H, t, J = 6.8 Hz), 3.86 (2H, t, J = 5.4 Hz), 3.92 (1H, s), 5.96-5.97 (2H, m), 6.15 (1H, s), 6.79 (1H, d, J = 8.4 Hz), 6.96 (1H, dd, J = 1.9, 8.4 Hz), 7.04 (1H, d, J = 1.9 Hz), 7.45 (1H, s), 7.93 (1H, d, J = 2.2 Hz). |
| 200 | | $^1$H-NMR (CDCl$_3$) δ: 0.89-0.94 (6H, m), 1.59 (2H, qt, J = 7.3, 7.6 Hz), 1.81-1.90 (4H, m), 1.98-2.29 (2H, m), 2.59 (2H, t, J = 7.6 Hz), 3.61 (2H, t, J = 6.2 Hz), 3.85 (2H, t, J = 5.4 Hz), 4.01 (1H, s), 4.24 (4H, s), 6.09 (1H, s), 6.84 (1H, d, J = 8.6 Hz), 6.96 (1H, dd, J = 2.4, 8.6 Hz), 7.03 (1H, d, J = 2.4 Hz), 7.45 (1H, s), 7.93 (1H, d, J = 2.2 Hz). |

TABLE 1-61

| Example | Structural formula | Property values |
|---|---|---|
| 201 | | $^1$H-NMR (CDCl$_3$) δ: 0.97 (3H, t, J = 7.3 Hz), 1.32 (6H, d, J = 6.3 Hz), 1.40-1.72 (6H, m), 1.78 (3H, s), 2.62 (2H, t, J = 7.6 Hz), 3.38 (2H, t, J = 6.9 Hz), 3.40 (2H, t, J = 5.6 Hz), 3.78 (1H, s), 4.53 (1H, q, J = 6.3 Hz), 5.73 (1H, s), 6.86 (2H, d, J = 8.9 Hz), 7.29-7.40 (5H, m), 7.47 (2H, s), 7.51 (2H, dd, J = 1.6, 8.2 Hz). |

TABLE 1-61-continued

| Example | Structural formula | Property values |
|---|---|---|
| 202 | | $^1$H-NMR (CDCl$_3$) δ: 0.88 (3H, t, J = 7.3 Hz), 0.97 (3H, t, J = 7.3 Hz), 1.51-1.69 (6H, m), 2.02 (1H, dd, J = 7.3, 14.2 Hz), 2.18 (1H, dd, J = 7.3, 14.2 Hz), 2.62 (2H, t, J = 7.6 Hz), 3.35-3.40 (4H, m), 3.85 (1H, s), 4.23 (4H, s), 5.87 (1H, s), 6.85 (1H, d, J = 8.2 Hz), 6.93 (1H, dd, J = 1.9, 8.2 Hz), 7.01 (1H, d, J = 1.9 Hz), 7.26-7.39 (3H, m), 7.46-7.53 (4H, m). |

TABLE 1-62

| Example | Structural formula | Property values |
|---|---|---|
| 203 | | $^1$H-NMR (CDCl$_3$) δ: 0.91 (3H, t, J = 7.6 Hz), 0.94 (3H, t, J = 7.3 Hz), 1.32 (6H, d, J = 5.9 Hz), 1.44-1.60 (4H, m), 1.74-1.86 (7H, m), 2.19 (2H, dt, J = 6.9, 7.3 Hz), 2.54 (2H, t, J = 7.6 Hz), 3.61 (2H, t, J = 6.6 Hz), 3.71 (2H, d, J = 5.6 Hz), 3.86 (1H, s), 4.52 (1H, q, J = 5.9 Hz), 5.92 (1H, s), 6.21 (1H, td, J = 6.9, 15.8 Hz), 6.56 (1H, d, J =15.8 Hz), 6.86 (2H, d, J = 8.6 Hz), 7.33 (1H, s), 7.35 (2H, d, J = 8.6 Hz), 7.59 (1H, s). |
| 204 | | $^1$H-NMR (CDCl$_3$) δ: 0.90-0.98 (9H, m), 1.45-1.64 (4H, m), 1.75-1.84 (4H, m), 2.04 (1H, qd, J = 7.3, 14.2 Hz), 2.17-2.23 (3H, m), 2.55 (2H, t, J = 7.6 Hz), 3.59 (2H, t, J = 6.6 Hz), 3.64 (1H, s), 3.74 (2H, t, J = 5.6 Hz), 4.24 (4H, s), 5.83 (1H, s), 6.23 (1H, td, J = 6.9, 16.2 Hz), 6.55 (1H, d, J = 16.2 Hz), 6.85 (1H, d, J = 8.6 Hz), 6.95 (1H, dd, J = 1.9, 8.6 Hz), 7.02 (1H, d, J = 1.9 Hz), 7.31 (1H, s), 7.59 (1H, s). |

TABLE 1-63

| Example | Structural formula | Property values |
|---|---|---|
| 205 | | $^1$H-NMR (CDCl$_3$) δ: 0.87 (3H, t, J = 7.3 Hz), 0.92 (3H, t, J = 7.3 Hz), 1.31 (6H, d, J = 6.3 Hz), 1.54-1.64 (4H, m), 1.75-1.84 (11H, m), 2.52-2.60 (4H, m), 3.61 (2H, t, J = 6.6 Hz), 3.74 (2H, d, J = 5.6 Hz), 3.76 (1H, s), 4.53 (1H, q, J = 6.3 Hz), 5.92 (1H, s), 6.87 (2H, d, J = 8.9 Hz), 7.31 (2H, s), 7.34 (2H, d, J = 8.9 Hz). |

TABLE 1-63-continued

| Example | Structural formula | Property values |
|---|---|---|
| 206 | 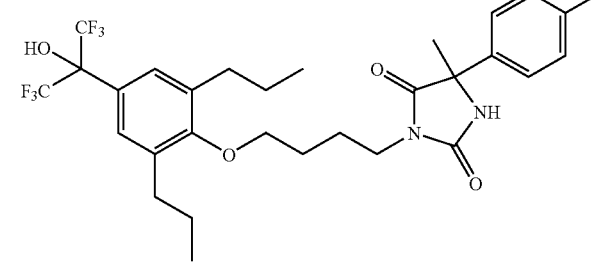 | $^1$H-NMR (CDCl$_3$) δ: 0.88-0.95 (9H, m), 1.25-1.36 (4H, m), 1.50-1.64 (4H, m), 1.76-1.86 (4H, m), 2.06 (1H, qd, J = 7.3, 14.2 Hz), 2.21 (1H, qd, 7.3, 14.2 Hz), 2.55-2.60 (4H, m), 3.56-3.60 (3H, m), 3.74 (2H, d, J = 5.6 Hz), 4.24 (4H, s), 5.94 (1H, s), 6.86 (1H, d, J = 8.6 Hz), 6.95 (1H, dd, J = 2.0, 8.6 Hz), 7.03 (1H, d, J = 2.0 Hz), 7.31 (2H, s). |
| 207 | | $^1$H-NMR (CDCl$_3$) δ: 0.89 (3H, t, J = 7.4 Hz), 1.55 (2H, qt, J = 7.4, 7.6 Hz), 1.70 (3H, s), 1.75-1.82 (4H, m), 2.56 (2H, t, J = 7.6 Hz), 3.59 (2H, t, J = 6.5 Hz), 3.39 (2H, t, J = 5.5 Hz), 4.10 (1H, s), 5.96 (2H, s), 6.72-6.78 (3H, m), 7.23-7.27 (2H, m), 7.42-7.45 (2H, m). |

TABLE 1-64

| Example | Structural formula | Property values |
|---|---|---|
| 208 | 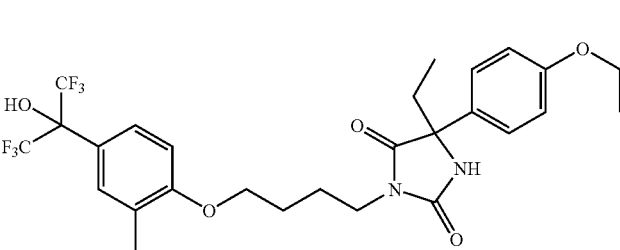 | $^1$H-NMR (CDCl$_3$) δ: 0.92 (6H, t, J = 7.3 Hz), 1.59 (4H, qt, J = 7.3, 7.8 Hz), 1.73-1.90 (7H, m), 2.55 (4H, t, J = 7.8 Hz), 3.62 (2H, t, J = 7.0 Hz), 3.73 (2H, t, J = 5.9 Hz), 3.95 (1H, s), 5.84 (1H, s), 5.89 (1H, s), 6.75 (2H, d, J = 8.6 Hz), 7.25 (2H, d, J = 8.6 Hz), 7.32 (2H, s). |
| 209 | | $^1$H-NMR (CDCl$_3$) δ: 0.87-0.93 (6H, m), 1.32 (6H, d, J = 6.0 Hz), 1.59 (2H, tq, J = 7.0, 7.4 Hz), 1.78-1.81 (4H, m), 1.98-2.27 (2H, m), 2.57 (2H, t, J = 7.0 Hz), 3.58 (2H, t, J = 6.5 Hz), 3.69 (1H, s), 3.96 (2H, d, J = 5.3 Hz), 4.53 (1H, septet, J = 6.0 Hz), 5.96 (1H, s), 6.80 (1H, d, J = 8.6 Hz), 6.87 (2H, d, J = 8.6 Hz), 7.38 (2H, d, J = 8.6 Hz), 7.41 (1H, s), 7.44 (1H, d, J = 8.6 Hz). |

TABLE 1-65

| Example | Structural formula | Property values |
|---|---|---|
| 210 | | $^1$H-NMR (CDCl$_3$) δ: 0.90-0.95 (9H, m), 1.32 (6H, d, J = 5.9 Hz), 1.53-1.67 (4H, m), 1.75-1.90 (4H, m), 1.98-2.33 (2H, m), 2.56 (4H, t, J = 7.6 Hz), 3.50 (1H, s), 3.60 (2H, t, J = 6.5 Hz), 3.74 (2H, t, J = 5.9 Hz), 4.53 (1H, septet, J = 5.9 Hz), 5.77 (1H, s), 6.87 (2H, d, J = 8.9 Hz), 7.31 (2H, s), 7.38 (2H, d, J = 8.9 Hz). |
| 211 | | $^1$H-NMR (CDCl$_3$) δ: 0.87-0.93 (6H, m), 1.02 (3H, t, J = 7.3 Hz), 1.59 (2H, tq, J = 7.0, 7.6 Hz), 1.73-1.86 (6H, m), 2.01-2.28 (2H, m), 2.57 (2H, t, J = 7.0 Hz), 3.58 (2H, t, J = 6.5 Hz), 3.63 (1H, s), 3.90 (2H, t, J = 6.8 Hz), 3.96 (2H, t, J = 5.1 Hz), 5.91 (1H, s), 6.80 (1H, d, J = 8.4 Hz), 6.89 (2H, d, J = 8.9 Hz), 7.38-7.48 (4H, m). |
| 212 | | $^1$H-NMR (CDCl$_3$) δ: 0.90-0.95 (9H, m), 1.02 (3H, t, J = 7.0 Hz), 1.53-1.85 (10H, m), 2.02-2.30 (2H, m), 2.56 (4H, t, J = 7.6 Hz), 3.46 (1H, s), 3.60 (2H, t, J = 6.5 Hz), 3.74 (2H, t, J = 6.2 Hz), 3.90 (2H, t, J = 6.5 Hz), 5.73 (1H, s), 6.89 (1H, d, J = 8.9 Hz), 7.31 (2H, s), 7.39 (2H, d, J = 8.9 Hz). |

TABLE 1-66

| Example | Structural formula | Property values |
|---|---|---|
| 213 | | $^1$H-NMR (CDCl$_3$) δ: 0.90 (3H, t, J = 7.3 Hz), 1.56 (2H, qt, J = 7.3, 7.4 Hz), 1.75-1.86 (7H, m), 2.01-2.12 (2H, m), 2.57 (2H, t, J = 7.4 Hz), 2.87-2.90 (4H, m), 3.59 (2H, t, J = 6.2 Hz), 3.67 (1H, s), 3.96 (2H, t, J = 5.1 Hz), 5.83 (1H, s), 6.81 (1H, d, J = 8.6 Hz), 7.33-7.47 (5H, m). |
| 214 | | $^1$H-NMR (CDCl$_3$) δ: 0.93 (6H, t, J = 7.3 Hz), 1.60 (4H, qt, J = 7.3, 7.6 Hz), 1.75-1.90 (7H, m), 2.02-2.13 (2H, m), 2.56 (4H, t, J = 7.6 Hz), 2.86-2.93 (4H, m), 3.49 (1H, s), 3.62 (2H, t, J = 6.8 Hz), 3.75 (2H, t, J = 5.7 Hz), 5.70 (1H, s), 7.22 (2H, s), 7.31-7.33 (3H, m). |

TABLE 1-66-continued

| Example | Structural formula | Property values |
| --- | --- | --- |
| 215 | | $^1$H-NMR (CDCl$_3$) δ: 0.90 (3H, t, J = 7.3 Hz), 1.36 (6H, d, J = 5.9 Hz), 1.56 (2H, qt, J = 7.3, 7.6 Hz), 1.77-1.88 (7H, m), 2.57 (2H, t, J = 7.6 Hz), 3.61 (2H, t, J = 6.5 Hz), 3.64 (1H, s), 3.83 (3H, s), 3.97 (2H, t, J = 5.4 Hz), 4.52 (1H, q, J = 5.9 Hz), 5.77 (1H, s), 6.77-6.99 (4H, m), 7.41-7.45 (2H, m). |

TABLE 1-67

| Example | Structural formula | Property values |
| --- | --- | --- |
| 216 | | $^1$H-NMR (CDCl$_3$) δ: 0.92 (6H, t, J = 7.3 Hz), 1.36 (6H, d, J = 5.9 Hz), 1.60 (4H, tq, J = 7.3, 7.0 Hz), 1.75-1.90 (7H, m), 2.54 (4H, t, J = 7.0 Hz), 3.63 (2H, t, J = 7.0 Hz), 3.65 (1H, s), 3.75 (2H, t, J = 5.7 Hz), 3.83 (3H, s), 4.52 (1H, q, J = 5.9 Hz), 5.79 (1H, s), 6.84-6.99 (3H, m), 7.30 (2H, s). |
| 217 | | $^1$H-NMR (CDCl$_3$) δ: 0.90 (3H, t, J = 7.3 Hz), 1.02 (3H, t, J = 7.3 Hz), 1.56 (2H, qt, J = 7.3, 7.6 Hz), 1.76-1.92 (9H, m), 2.57 (2H, t, J = 7.6 Hz), 3.60 (2H, t, J = 6.2 Hz), 3.75 (1H, s), 3.85 (3H, s), 3.93-3.98 (4H, m), 5.90 (1H, s), 6.77-6.99 (4H, m), 7.42-7.46 (2H, m). |
| 218 | | $^1$H-NMR (CDCl$_3$) δ: 0.92 (6H, t, J = 7.3 Hz), 1.03 (3H, t, 7.3 Hz), 1.60 (4H, qt, J = 7.3, 7.6 Hz), 1.76-1.90 (9H, m), 2.55 (4H, t, J = 7.6 Hz), 3.56 (1H, s), 3.63 (2H, t, J = 7.0 Hz), 3.75 (2H, t, J = 5.9 Hz), 3.85 (3H, s), 3.94-3.97 (2H, m), 5.74 (1H, s), 6.83-7.00 (2H, m), 7.31 (2H, s). |

TABLE 1-68

| Example | Structural formula | Property values |
|---|---|---|
| 219 | | $^1$H-NMR (CDCl$_3$) δ: 0.88 (3H, t, J = 7.3 Hz), 1.48-1.59 (2H, m), 1.76-1.88 (4H, m), 1.84 (3H, s), 2.55 (2H, t, J = 7.3 Hz), 3.62 (2H, t, J = 6.2 Hz), 3.95 (2H, t, J = 5.7 Hz), 6.79 (1H, d, J = 8.6 Hz), 7.16-7.23 (2H, m), 7.40-7.52 (4H, m), 7.88 (1H, bd, J = 8.6 Hz), 8.03 (1H, bd, J = 7.8 Hz), 8.30 (1H, bs). |
| 220 | | $^1$H-NMR (CDCl$_3$) δ: 0.91 (6H, t, J = 7.3 Hz), 1.55-1.63 (4H, m), 1.80-1.90 (4H, m), 1.86 (3H, s), 2.55 (4H, t, J = 7.6 Hz), 2.74 (2H, bs), 3.64 (2H, t, J = 6.2 Hz), 3.75 (2H, t, J = 5.7 Hz), 7.30 (2H, s), 7.47 (1H, bs), 7.49 (1H, dd, J = 7.8, 7.6 Hz), 7.91 (1H, d, J = 7.8 Hz), 8.03 (1H, d, J = 7.6 Hz), 8.33 (1H, s). |
| 221 | | $^1$H-NMR (CDCl$_3$) δ: 0.89 (3H, t, J = 7.3 Hz), 1.49-1.63 (2H, m), 1.76-1.90 (4H, m), 1.80 (3H, s), 2.57 (2H, t, J = 7.3 Hz), 3.59 (2H, t, J = 6.8 Hz), 3.64 (1H, bs), 3.95 (2H, t, J = 5.1 Hz), 5.05 (2H, s), 5.97 (1H, bs), 6.80 (1H, d, J = 8.6 Hz), 6.94 (1H, dd, J = 7.0, 2.2 Hz), 7.07 (1H, dd, J = 7.0, 2.2 Hz), 7.13 (1H, dd, J = 2.2, 2.2 Hz), 7.27-7.43 (8H, m). |

TABLE 1-69

| Example | Structural formula | Property values |
|---|---|---|
| 222 | 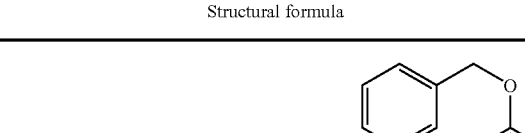 | $^1$H-NMR (CDCl$_3$) δ: 0.92 (6H, t, J = 7.3 Hz), 1.53-1.67 (4H, m), 1.76-1.90 (4H, m), 1.82 (3H, s), 2.56 (4H, t, J = 7.6 Hz), 3.49 (1H, bs), 3.61 (2H, t, J = 6.5 Hz), 3.74 (2H, t, J = 6.5 Hz), 5.06 (2H, s), 5.82 (1H, bs), 6.94 (1H, dd, J = 7.6, 1.9 Hz), 7.07 (1H, dd, J = 7.0, 1.9 Hz), 7.13 (1H, dd, J = 1.9, 1.9 Hz), 7.27-7.43 (8H, m). |

TABLE 1-69-continued

| Example | Structural formula | Property values |
|---|---|---|
| 223 | | $^1$H-NMR (CDCl$_3$) δ: 0.89 (3H, t, J = 7.6 Hz), 1.49-1.61 (2H, m), 1.78 (7H, bs), 2.57 (2H, t, J = 7.0 Hz), 3.58 (2H, t, J = 6.5 Hz), 3.68 (1H, bs), 3.95 (2H, t, J = 5.7 Hz), 5.68 (1H, bs), 5.94 (1H, bs), 6.77-6.82 (2H, m), 6.97 (1H, dd, J = 2.2, 2.2 Hz), 7.01 (1H, d, J = 7.6 Hz), 7.24 (1H, dd, J = 7.8, 7.8 Hz), 7.41-7.46 (2H, m). |
| 224 | | $^1$H-NMR (CDCl$_3$) δ: 0.90 (6H, t, J = 7.6 Hz), 1.49-1.64 (4H, m), 1.72 (3H, s), 1.77-1.84 (4H, m), 2.52 (4H, t, J = 7.6 Hz), 3.55-3.80 (5H, m), 6.24 (1H, bs), 6.77 (1H, s), 6.83 (1H, d, J = 7.0 Hz), 6.99-7.01 (2H, m), 7.22-7.32 (3H, m). |

TABLE 1-70

| Example | Structural formula | Property values |
|---|---|---|
| 225 | | $^1$H-NMR (CDCl$_3$) δ: 1.32 (6H, d, J = 5.8 Hz), 1.75-1.84 (4H, m), 1.79 (3H, s), 2.21 (3H, s), 3.59 (2H, d, J = 6.4 Hz), 3.72 (1H, s), 3.97 (2H, d, J = 5.6 Hz), 4.48-4.56 (1H, m), 5.90 (1H, bs), 6.79 (1H, d, J = 8.5 Hz), 6.87 (2H, d, J = 8.8 Hz), 7.35 (2H, d, J = 8.8 Hz), 7.44 (1H, s), 7.45 (1H, d, J = 8.5 Hz). |
| 226 | | $^1$H-NMR (CDCl$_3$) δ: 1.75-1.85 (4H, m), 1.78 (3H, s), 2.21 (3H, s), 3.59 (2H, t, J = 6.2 Hz), 3.72 (1H, s) , 3.97 (2H, t, J = 5.4 Hz), 5.96 (2H, s), 6.01 (1H, bs), 6.79 (1H, dd, J = 7.8, 1.6 Hz), 6.80 (1H, d, J = 8.1 Hz), 6.93 (1H, d, J = 7.8 Hz), 6.97 (1H, d, J = 1.6 Hz), 7.44 (1H, s), 7.46 (1H, d, J = 8.1 Hz). |
| 227 | | $^1$H-NMR (CDCl$_3$) δ: 0.89 (3H, d, J = 7.3 Hz), 1.79-1.81 (4H, m), 2.00-2.10 (1H, m), 2.14-2.24 (1H, m), 2.21 (3H, s), 3.58 (2H, t, J = 5.7 Hz), 3.72 (1H, bs), 3.97 (2H, t, J = 5.4 Hz), 5.96 (2H, s), 6.18 (1H, bs), 6.78 (2H, d, J = 8.1 Hz), 6.95 (1H, dd, J = 8.1, 1.6 Hz), 6.97 (1H, d, J = 1.6 Hz), 7.44 (1H, s), 7.45 (1H, d, J = 8.1 Hz). |

TABLE 1-71

| Example | Structural formula | Property values |
|---|---|---|
| 228 | | $^1$H-NMR (CDCl$_3$) δ: 0.89 (3H, d, J = 7.3 Hz), 1.81 (4H, bs), 1.99-2.10 (1H, m), 2.14-2.25 (1H, m), 2.21 (3H, s), 3.57 (2H, bs), 3.72 (1H, bs), 3.97 (2H, bs), 4.23 (4H, s), 6.03 (1H, bs), 6.79 (1H, d, J = 8.1 Hz), 6.85 (1H, d, J = 8.6 Hz), 6.95 (1H, dd, J = 8.1, 2.2 Hz), 7.02 (1H, d, J = 2.2 Hz), 7.44 (1H, s), 7.45 (1H, d, J = 8.6 Hz). |
| 229 | | $^1$H-NMR (CDCl$_3$) δ: 0.92 (3H, t, J = 7.3 Hz), 1.32 (6H, d, J = 5.9 Hz), 1.55-1.63 (2H, m), 1.75-1.84 (4H, m), 1.81 (3H, s), 2.26 (3H, s), 2.56 (2H, t, J = 7.3 Hz), 3.48 (1H, bs), 3.62 (2H, t, J = 5.9 Hz), 3.75 (2H, t, J = 6.2 Hz), 4.48-4.57 (1H, m), 5.63 (1H, bs), 6.87 (2H, d, J = 8.6 Hz), 7.30 (2H, bs), 7.35 (2H, d, J = 8.6 Hz). |

TABLE 1-72

| Example | Structural formula | Property values |
|---|---|---|
| 230 | | $^1$H-NMR (CDCl$_3$) δ: 0.92 (3H, t, J = 7.3 Hz), 1.52-1.63 (2H, m), 1.75-1.86 (4H, m), 1.79 (3H, s), 2.26 (3H, s), 2.56 (2H, t, J = 7.6 Hz), 3.58 (1H, bs), 3.61 (2H, t, J = 6.5 Hz), 3.75 (2H, t, J = 5.9 Hz), 5.85 (1H, bs), 5.96 (2H, s), 6.78 (1H, d, J = 8.4 Hz), 6.93 (1H, dd, J = 8.4, 2.2 Hz), 6.98 (1H, d, J = 2.2 Hz), 7.31 (2H, bs). |
| 231 | | $^1$H-NMR (CDCl$_3$) δ: 0.89 (3H, t, J = 7.3 Hz), 0.92 (3H, t, J = 7.3 Hz), 1.52-1.63 (2H, m), 1.75-1.86 (4H, m), 2.01-2.11 (1H, m), 2.15-2.26 (1H, m), 2.26 (3H, s), 2.55 (2H, t, J = 7.8 Hz), 3.57 (1H, bs), 3.60 (2H, t, J = 6.5 Hz), 3.75 (2H, t, J = 5.9 Hz), 5.96 (2H, s), 6.00 (1H, bs), 6.78 (1H, d, J = 8.4 Hz), 6.95 (1H, dd, J = 8.4, 1.9 Hz), 7.04 (1H, d, J = 1.9 Hz), 7.31 (2H, bs). |

TABLE 1-73

| Example | Structural formula | Property values |
|---|---|---|
| 232 | | $^1$H-NMR (CDCl$_3$) δ: 0.90 (3H, t, J = 7.3 Hz), 0.92 (3H, t, J = 7.3 Hz), 1.55-1.63 (2H, m), 1.75-1.85 (4H, m), 2.00-2.11 (1H, m), 2.18-2.26 (1H, m), 2.26 (3H, s), 2.56 (2H, t, J = 7.6 Hz), 3.50 (1H, bs), 3.59 (2H, t, J = 6.8 Hz), 3.75 (2H, t, J = 5.9 Hz), 4.24 (4H, s), 5.75 (1H, bs), 6.85 (1H, d, J = 8.6 Hz), 6.95 (1H, dd, J = 8.6, 2.4 Hz), 7.02 (1H, d, J = 2.4 Hz), 7.30 (2H, bs). |
| 233 | | $^1$H-NMR (CDCl$_3$) δ: 1.31 (6H, d, J = 6.0 Hz), 1.62-1.79 (7H, m), 1.88 (3H, d, J = 6.6 Hz), 3.54 (2H, t, J = 7.3 Hz), 3.65 (2H, t, J = 6.5 Hz), 3.97 (2H, s), 4.50 (1H, q, J = 6.0 Hz), 5.91 (1H, s), 6.22 (1H, dq, J = 6.6, 15.8 Hz), 6.57 (1H, d, J = 15.8 Hz), 6.85 (2H, d, J = 8.8 Hz), 7.10-7.30 (7H, m), 7.34 (2H, d, J = 8.8 Hz), 7.62 (1H, s). |

TABLE 1-74

| Example | Structural formula | Property values |
|---|---|---|
| 234 | | $^1$H-NMR (CDCl$_3$) δ: 0.89 (3H, t, J = 7.3 Hz), 1.55-1.80 (4H, m), 1.89 (3H, t, J = 6.6 Hz), 1.99-2.26 (2H, m), 3.53 (2H, t, J = 6.6 Hz), 3.63 (2H, t, J = 6.9 Hz), 3.97 (2H, s), 4.29 (4H, s), 5.54 (1H, s), 6.23 (1H, dq, J = 6.6, 16.0 Hz), 6.57 (1H, d, J = 16.0 Hz), 6.84 (1H, d, J = 8.6 Hz), 6.94 (1H, dd, J = 2.5, 8.6 Hz), 7.02 (1H, d, J = 2.5 Hz), 7.10-7.29 (7H, m), 7.61 (1H, s). |
| 235 | | $^1$H-NMR (CDCl$_3$) δ: 0.96 (3H, t, J = 7.3 Hz), 1.39 (2H, qt, J = 7.3, 7.6 Hz), 1.65-1.77 (6H, m), 1.79 (3H, s), 1.89 (3H, dd, J = 1.6, 6.6 Hz), 3.54 (2H, t, J = 6.6 Hz), 3.62 (2H, t, J = 5.6 Hz), 3.78 (1H, s), NH 3.92 (2H, t, J = 6.6 Hz), 3.96 (2H, s), 5.94 (1H, s), 6.23 (1H, qd, J = 6.6, 15.8 Hz), 6.55 (1H, dd, 1.6, 15.8 Hz), 6.87 (2H, d, J = 8.9 Hz), 7.08-7.24 (5H, m), 7.30 (1H, s), 7.35 (2H, d, J = 8.9 Hz), 7.62 (1H, s). |

TABLE 1-75

| Example | Structural formula | Property values |
|---|---|---|
| 236 | | $^1$H-NMR (CDCl$_3$) δ: 0.89 (3H, t, J = 7.3 Hz), 1.64-1.80 (4H, m), 1.87 (3H, dd, J = 1.3, 6.6 Hz), 2.07 (1H, qd, J = 7.3, 14.2 Hz), 2.25 (1H, qd, J = 7.3, 14.2 Hz), 2.53 (2H, t, J = 6.6 Hz), 3.61 (2H, t, J = 5.6 Hz), 3.77 (3H, s), 3.88 (1H, s), 3.95 (2H, s), 6.21 (1H, s), 6.22 (1H, qd, J = 6.6, 15.8 Hz), 6.55 (1H, dd, J = 1.6, 15.8 Hz), 6.88 (2H, d, J = 8.9 Hz), 7.08-7.23 (5H, m), 7.30 (1H, s), 7.41 (2H, d, J = 8.9 Hz), 7.62 (1H, s). |
| 237 | | $^1$H-NMR (CDCl$_3$) δ: 0.92 (3H, d, J = 7.3 Hz), 1.31 (6H, d, J = 6.1 Hz), 1.61 (2H, qt, J = 7.3, 7.8 Hz), 1.68-1.79 (7H, m), 2.57 (2H, t, J = 7.8 Hz), 3.46 (1H, s), 3.55 (2H, t, J = 6.7 Hz), 3.64 (2H, t, J = 5.9 Hz), 3.98 (2H, s), 4.50 (1H, q, J = 6.1 Hz), 6.08 (1H, s), 6.85 (2H, d, J = 9.0 Hz), 7.10-7.38 (9H, m). |

TABLE 1-76

| Example | Structural formula | Property values |
|---|---|---|
| 238 | | $^1$H-NMR (CDCl$_3$) δ: 0.88 (3H, t, J = 7.4 Hz), 0.92 (3H, t, J = 7.3 Hz), 1.52-1.60 (4H, m), 1.66-1.80 (4H, m), 2.57 (2H, t, J = 7.6 Hz), 3.52 (2H, t, J = 6.5 Hz), 3.64 (2H, t, J = 5.7 Hz), 3.98 (2H, s), 4.21 (4H, s), 6.35 (1H, s), 6.83 (1H, d, J = 8.6 Hz), 6.95 (1H, dd, J = 2.2, 8.6 Hz), 7.03 (1H, d, J = 2.2 Hz), 7.09-7.27 (6H, m), 7.37 (1H, s), 7.96 (1H, s). |
| 239 | | $^1$H-NMR (CDCl$_3$) δ: 0.93 (3H, t, J = 7.3 Hz), 0.96 (3H, t, J = 7.3 Hz), 1.47 (2H, qt, J = 7.3, 7.6 Hz), 1.56-1.78 (8H, m), 1.79 (3H, s), 2.57 (2H, t, J = 7.6 Hz), 3.55 (2H, t, J = 6.6 Hz), 3.64 (2H, d, J = 5.6 Hz), 3.66 (1H, s), 3.92 (2H, t, J = 6.3 Hz), 3.98 (2H, s), 5.85 (1H, s), 6.87 (2H, d, J = 8.9 Hz), 7.09-7.24 (5H, m), 7.27 (1H, s), 7.35 (2H, d, J = 8.9 Hz), 7.36 (1H, s). |

TABLE 1-77

| Example | Structural formula | Property values |
|---|---|---|
| 240 | 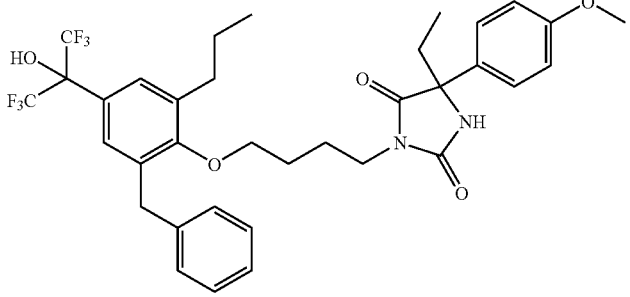 | $^1$H-NMR (CDCl$_3$) δ: 0.89 (3H, t, J = 7.3 Hz), 0.92 (3H, t, J = 7.3 Hz), 1.59 (2H, qt, J = 7.3, 7.6 Hz), 1.69-1.79 (4H, m), 2.05 (1H, qd, J = 7.3, 14.2 Hz), 2.23 (1H, qd, J = 7.3, 14.2 Hz), 2.56 (2H, t, J = 7.6 Hz), 3.54 (2H, t, J = 6.6 Hz), 3.63 (2H, t, J = 5.6 Hz), 3.68 (1H, s), 3.77 (3H, s), 3.98 (2H, s), 6.05 (1H, s), 6.88 (2H, d, J = 8.9 Hz), 7.09-7.24 (6H, m) 7.36 (1H, s), 7.41 (2H, d, J = 8.9 Hz). |
| 241 | 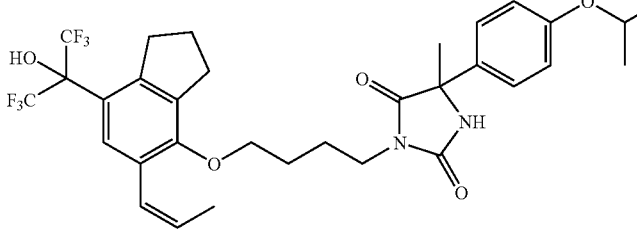 | $^1$H-NMR (CDCl$_3$) δ: 1.33 (6H, d, J = 6.1 Hz), 1.72-1.90 (7H, m), 1.98-2.02 (2H, m), 2.82-2.86 (2H, m), 3.19-3.22 (2H, m), 3.40 (1H, s), 3.54-3.59 (4H, m), 3.82-3.85 (2H, m), 4.51-4.55 (1H, m), 5.76 (1H, s), 5.79-5.83 (2H, m), 6.46-6.67 (1H, m), 6.85-6.89 (2H, m), 7.26-7.36 (3H, m). |

TABLE 1-78

| Example | Structural formula | Property values |
|---|---|---|
| 242 | 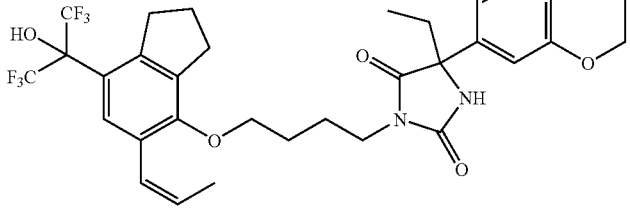 | $^1$H-NMR (CDCl$_3$) δ: 0.89 (3H, t, J = 7.3 Hz), 1.71-1.88 (4H, m), 1.77 (3H, d, J = 7.1 Hz), 1.99-2.06 (3H, m), 2.18-2.23 (1H, m), 2.77-2.88 (2H, m), 3.19-3.23 (2H, m), 3.52-3.57 (2H, m), 3.72 (1H, s), 3.83 (2H, t, J = 6.1 Hz), 4.24 (4H, s), 5.81 (1H, dq, J = 11.5, 7.1 Hz), 5.90 (1H, s), 6.47 (1H, d, J = 11.5 Hz), 6.85 (1H, d, J = 8.6 Hz), 6.95 (1H, dd, J = 8.6, 2.4 Hz), 7.02 (1H, d, J = 2.4 Hz), 7.26 (1H, s). |
| 243 | 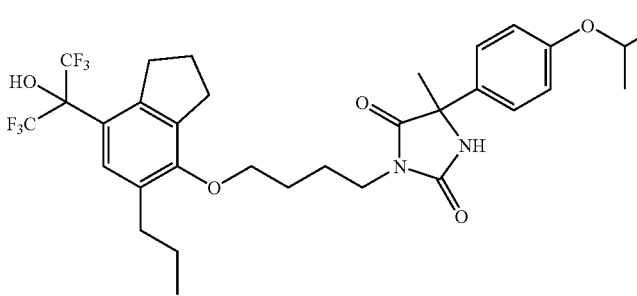 | $^1$H-NMR (CDCl$_3$) δ: 0.90 (3H, t, J = 7.6 Hz), 1.32 (6H, d, J = 5.9 Hz), 1.48-1.62 (2H, m), 1.75-1.84 (4H, m), 1.80 (3H, s), 1.96-2.04 (2H, m), 2.53 (2H, t, J = 7.3 Hz), 2.78-2.88 (2H, m), 3.11-3.21 (2H, m), 3.59 (2H, t, J = 7.0 Hz), 3.84 (2H, t, J = 6.2 Hz), 4.48-4.57 (1H, m), 5.97 (1H, bs), 6.86 (2H, d, J = 8.6 Hz), 7.15 (1H, s), 7.35 (2H, d, J = 8.6 Hz). |

TABLE 1-79

| Example | Structural formula | Property values |
|---|---|---|
| 244 | | $^1$H-NMR (CDCl$_3$) δ: 0.88-0.93 (6H, m), 1.50-1.59 (2H, m), 1.74-1.82 (4H, m), 1.96-2.08 (3H, m), 2.17-2.25 (1H, m), 2.52 (2H, t, J = 7.6 Hz), 2.75-2.88 (2H, m), 3.14-3.24 (2H, m), 3.57 (2H, t, J = 6.8 Hz), 3.72 (1H, s), 3.83 (2H, t, J = 5.9 Hz), 4.23 (4H, s), 6.23 (1H, bs), 6.84 (1H, d, J = 8.6 Hz), 6.96 (1H, dd, J = 8.6, 2.2 Hz), 7.03 (1H, d, J = 2.2 Hz), 7.15 (1H, bs). |
| 245 | | $^1$H-NMR (CDCl$_3$) δ: 1.29 (3H, d, J = 6.5 Hz), 1.29 (3H, d, J = 5.9 Hz), 1.75 (3H, s), 1.81-1.90 (4H, m), 3.59 (2H, t, J = 6.2 Hz), 3.84 (1H, bs), 3.86 (2H, t, J = 5.9 Hz), 4.43-4.52 (1H, m), 5.62 (1H, bs), 6.81 (2H, d, J = 8.9 Hz), 7.08-7.40 (12H, m), 7.54 (4H, d, J = 7.3 Hz), 7.84 (2H, bs). |
| 246 | | $^1$H-NMR (CDCl$_3$) δ: 1.73 (3H, s), 1.80-1.90 (4H, m), 3.59 (2H, t, J = 6.8 Hz), 3.79 (1H, bs), 3.86 (2H, t, J = 5.9 Hz), 5.69 (1H, bs), 5.91 (2H, s), 6.72 (2H, d, J = 8.4 Hz), 6.88 (1H, dd, J = 8.4, 2.2 Hz), 6.94 (1H, d, J = 2.2 Hz), 7.09-7.41 (10H, m), 7.54 (4H, d, J = 6.8 Hz), 7.84 (2H, bs). |

TABLE 1-80
| Example | Structural formula | Property values |
|---|---|---|
| 247 | 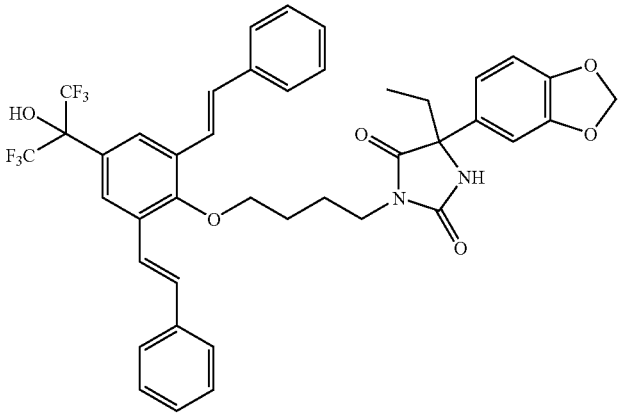 | $^1$H-NMR (CDCl$_3$) δ: 0.85 (3H, t, J = 7.6 Hz), 1.80-1.90 (4H, m), 1.96-2.05 (1H, m), 2.08-2.19 (1H, m), 3.58 (2H, t, J = 6.5 Hz), 3.85 (2H, t, J = 5.4 Hz), 3.86 (1H, bs), 5.91-5.92 (3H, m), 6.72 (2H, d, J = 8.1 Hz), 6.90 (1H, dd, J = 8.1, 2.2 Hz), 7.00 (1H, d, J = 2.2 Hz), 7.08-7.40 (10H, m), 7.53 (4H, d, J = 6.8 Hz), 7.84 (2H, bs). |
| 248 | 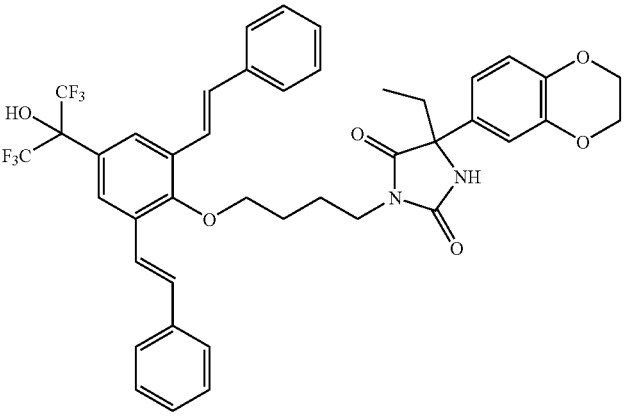 | $^1$H-NMR (CDCl$_3$) δ: 0.85 (3H, t, J = 7.3 Hz), 1.80-1.90 (4H, m), 1.95-2.05 (1H, m), 2.10-2.20 (1H, m), 3.57 (2H, t, J = 6.8 Hz), 3.85 (2H, t, J = 5.9 Hz), 3.91 (1H, bs), 4.19 (4H, s), 5.84 (1H, bs), 6.80 (1H, d, J = 8.6 Hz), 6.91 (1H, dd, J = 8.6, 2.4 Hz), 7.00 (1H, d, J = 2.4 Hz), 7.08-7.40 (10H, m), 7.53 (4H, d, J = 7.3 Hz), 7.84 (2H, bs). |
| 249 | 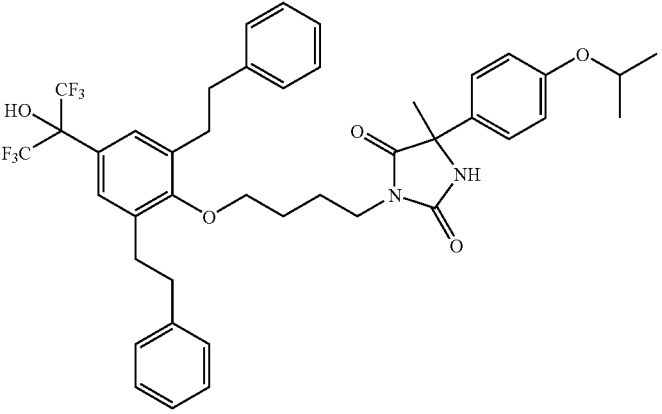 | $^1$H-NMR (CDCl$_3$) δ: 1.30 (6H, d, J = 5.9 Hz), 1.78 (3H, s), 1.78-1.85 (4H, m), 2.89 (8H, bs), 3.59 (2H, t, J = 6.8 Hz), 3.68 (2H, t, J = 5.9 Hz), 3.91 (1H, s), 4.45-4.54 (1H, m), 5.62 (1H, bs), 6.84 (2H, d, J =8.9 Hz), 7.09-7.35 (14H, m). |

TABLE 1-81
| Example | Structural formula | Property values |
|---|---|---|
| 250 | 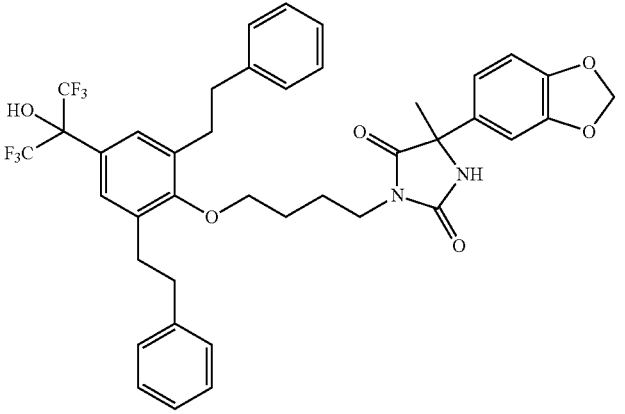 | ¹H-NMR (CDCl₃) δ: 1.76 (3H, s), 1.76-1.85 (4H, m), 2.89 (8H, bs), 3.59 (2H, t, J = 6.8 Hz), 3.68 (2H, t, J = 6.2 Hz), 5.71 (1H, bs), 5.93 (2H, s), 6.75 (1H, d, J = 8.4 Hz), 6.91 (1H, dd, J = 8.4, 1.9 Hz), 6.96 (1H, d, J = 1.9 Hz), 7.08-7.27 (12H, m). |
| 251 | 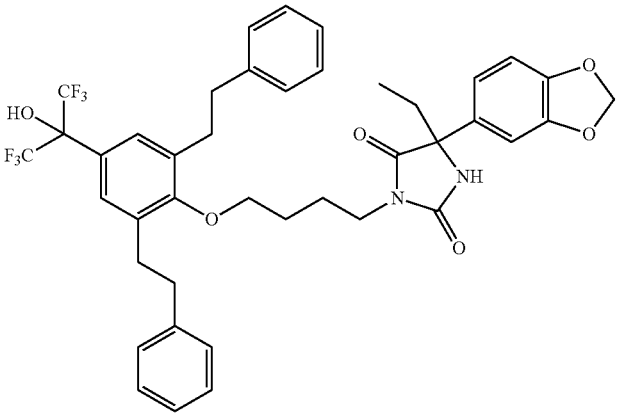 | ¹H-NMR (CDCl₃) δ: 0.87 (3H, t, J = 7.3 Hz), 1.79 (4H, bs), 1.98-2.06 (1H, m), 2.11-2.22 (1H, m), 2.88 (8H, bs), 3.57 (2H, t, J = 6.8 Hz), 3.67 (2H, t, J = 5.7 Hz), 5.84 (1H, bs), 5.92-5.94 (2H, m), 6.76 (1H, d, J = 8.4 Hz), 6.92 (1H, dd, J = 8.4, 1.9 Hz), 7.02 (1H, d, J = 1.9 Hz), 7.08-7.26 (12H, m). |
| 252 | 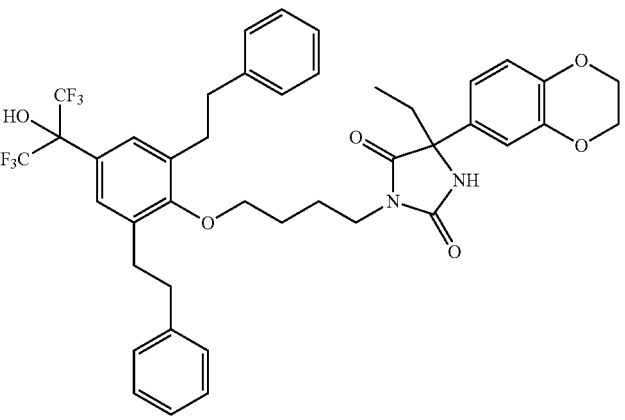 | ¹H-NMR (CDCl₃) δ: 0.87 (3H, t, J = 7.6 Hz), 1.79 (4H, bs), 1.98-2.06 (1H, m), 2.12-2.23 (1H, m), 2.88 (8H, bs), 3.35 (1H, bs), 3.56 (2H, t, J = 6.5 Hz), 3.67 (2H, t, J = 5.7 Hz), 4.21 (4H, s), 5.81 (1H, bs), 6.83 (1H, d, J = 8.4 Hz), 6.93 (1H, dd, J = 8.4, 2.4 Hz), 7.02 (1H, d, J = 2.4 Hz), 7.08-7.26 (12H, m). |

TABLE 1-82

| Example | Structural formula | Property values |
| --- | --- | --- |
| 253 | | $^1$H-NMR (CDCl$_3$) δ: 0.85 (6H, d, J = 6.8 Hz), 0.92 (3H, t, J = 7.3 Hz), 1.32 (6H, d, J = 5.9 Hz), 1.54-1.67 (2H, m), 1.81 (3H, s), 1.81-1.93 (5H, m), 2.45 (2H, d, J = 7.0 Hz), 2.56 (2H, t, J = 7.6 Hz), 3.56 (1H, bs), 3.61 (2H, t, J = 7.0 Hz), 3.74 (2H, t, J = 5.9 Hz), 4.48-4.57 (1H, m), 5.75 (1H, bs), 6.86 (2H, d, J = 8.9 Hz), 7.26 (1H, d, J = 1.9 Hz), 7.32 (1H, d, J = 1.9 Hz), 7.35 (2H, d, J = 8.9 Hz). |
| 254 | | $^1$H-NMR (CDCl$_3$) δ: 0.86 (6H, d, J = 6.8 Hz), 0.92 (3H, t, J = 7.3 Hz), 1.54-1.68 (2H, m), 1.79 (3H, s), 1.82-1.93 (5H, m), 2.45 (2H, d, J = 7.3 Hz), 2.56 (2H, t, =7.6 Hz), 3.59 (1H, bs), 3.61 (2H, t, J = 7.0 Hz), 3.74 (2H, t, J = 5.7 Hz), 5.87 (1H, bs), 5.96 (2H, s), 6.78 (1H, d, J = 8.1 Hz), 6.93 (1H, dd, J = 8.1, 1.9 Hz), 6.98 (1H, d, J = 1.9 Hz), 7.26 (1H, s), 7.32 (1H, s). |

TABLE 1-83

| Example | Structural formula | Property values |
| --- | --- | --- |
| 255 | | $^1$H-NMR (CDCl$_3$) δ: 0.85 (6H, d, J = 6.5 Hz), 0.89 (3H, t, J = 7.3 Hz), 0.92 (3H, t, J = 7.3 Hz), 1.53-1.67 (2H, m), 1.75-1.93 (5H, m), 2.01-2.11 (1H, m), 2.15-2.25 (1H, m), 2.44 (2H, d, J = 7.3 Hz), 2.56 (2H, t, J = 7.0 Hz), 3.59 (2H, t, J = 6.5 Hz), 3.61 (1H, bs), 3.74 (2H, t, J = 5.9 Hz), 5.96 (2H, s), 6.06 (1H, bs), 6.78 (1H, d, J = 8.4 Hz), 6.95 (1H, dd, J = 8.4, 1.9 Hz), 7.04 (1H, d, J = 1.9 Hz), 7.26 (1H, s), 7.32 (1H, s). |
| 256 | | $^1$H-NMR (CDCl$_3$) δ: 0.85 (6H, d, J = 6.5 Hz), 0.90 (3H, t, J = 7.3 Hz), 0.92 (3H, t, J = 7.3 Hz), 1.53-1.67 (2H, m), 1.75-1.93 (5H, m), 2.00-2.11 (1H, m), 2.16-2.26 (1H, m), 2.44 (2H, d, J = 7.3 Hz), 2.56 (2H, t, J = 7.6 Hz), 3.58 (1H, bs), 3.59 (2H, t, J = 6.8 Hz), 3.74 (2H, t, J = 5.9 Hz), 4.24 (4H, s), 5.89 (1H, bs), 6.84 (1H, d, J = 8.4 Hz), 6.95 (1H, dd, J = 8.4, 2.2 Hz), 7.02 (1H, d, J = 2.2 Hz), 7.26 (1H, s), 7.32 (1H, s). |

TABLE 1-84

| Example | Structural formula | Property values |
|---|---|---|
| 257 | 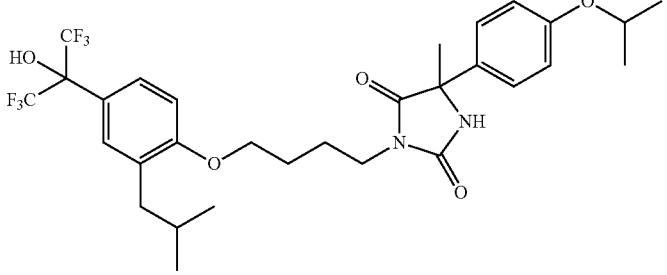 | $^1$H-NMR (CDCl$_3$) δ: 0.85 (6H, d, J = 6.8 Hz), 1.32 (6H, d, J = 6.2 Hz), 1.80-1.89 (5H, m), 1.80 (3H, s), 2.47 (2H, d, J = 6.8 Hz), 3.59 (2H, t, J = 6.8 Hz), 3.59 (1H, bs), 3.96 (2H, t, J = 5.9 Hz), 4.48-4.57 (1H, m), 5.76 (1H, bs), 6.81 (1H, d, J = 8.4 Hz), 6.86 (2H, d, J = 8.9 Hz), 7.34 (2H, d, J = 8.9 Hz), 7.36 (1H, s), 7.45 (1H, d, J = 8.4 Hz). |
| 258 | 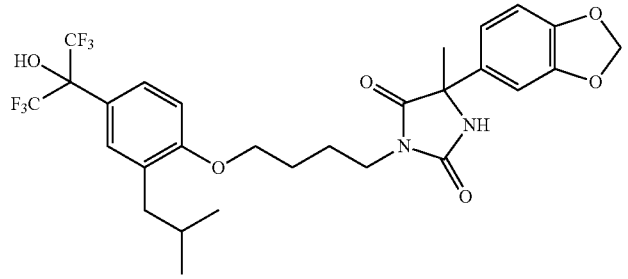 | $^1$H-NMR (CDCl$_3$) δ: 0.85 (6H, d, J = 6.5 Hz), 1.78 (8H, bs), 2.47 (2H, d, J = 7.0 Hz), 3.57 (1H, bs), 3.59 (2H, bs), 3.96 (2H, bs), 5.84 (1H, bs), 5.96 (2H, s), 6.77-6.83 (2H, m), 6.92 (1H, dd, J = 8.1, 1.9 Hz), 6.97 (1H, d, J = 1.9 Hz), 7.37 (1H, s), 7.46 (1H, d, J = 8.9 Hz). |
| 259 | 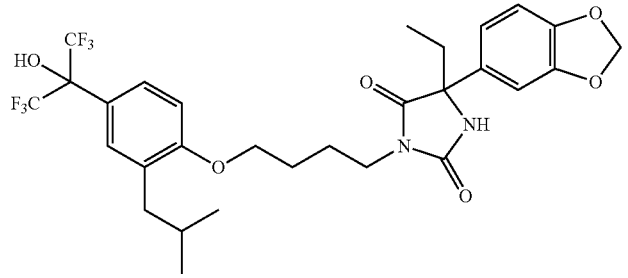 | $^1$H-NMR (CDCl$_3$) δ: 0.84-0.92 (9H, m) 1.81 (5H, bs), 2.00-2.24 (2H, m), 2.47 (2H, d, J = 6.8 Hz), 3.58 (1H, bs), 3.61 (2H, bs), 3.98 (2H, bs), 5.96-5.98 (2H, m), 6.05 (1H, bs), 6.77-7.06 (4H, m), 7.28-7.47 (2H, m). |

TABLE 1-85

| Example | Structural formula | Property values |
|---|---|---|
| 260 | 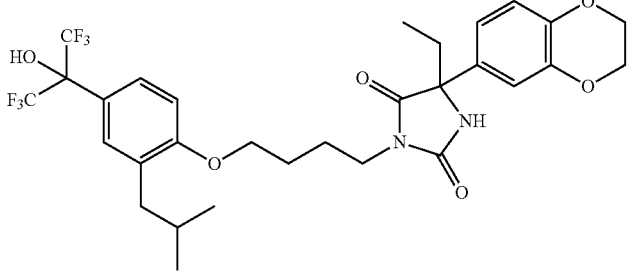 | $^1$H-NMR (CDCl$_3$) δ: 0.84-0.92 (9H, m) 1.81 (5H, bs), 2.00-2.26 (2H, m), 2.48 (2H, bs), 3.58 (2H, bs), 3.79 (1H, bs), 3.97 (2H, bs), 4.23-4.26 (4H, m), 6.13 (1H, bs), 6.79-7.47 (6H, m). |

TABLE 1-85-continued

| Example | Structural formula | Property values |
|---|---|---|
| 261 | | ¹H-NMR (CDCl₃) δ: 1.31 (6H, d, J = 5.4 Hz), 1.77 (3H, s), 1.82 (4H, bs), 2.82-2.92 (4H, m), 3.58 (1H, bs), 3.61 (2H, bs), 3.98 (2H, t, J = 5.1 Hz), 4.45-4.54 (1H, m), 5.79 (1H, bs), 6.82 (1H, d, J = 8.4 Hz), 6.84 (2H, d, J = 8.4 Hz), 7.10-7.35 (8H, m), 7.47 (1H, d, J = 8.4 Hz). |
| 262 | | ¹H-NMR (CDCl₃) δ: 1.76-1.86 (7H, m), 2.80-2.93 (4H, m), 3.55 (1H, s), 3.60 (2H, t, J = 6.5 Hz), 3.98 (2H, t, J = 5.1 Hz), 5.87 (1H, s), 5.93 (2H, s), 6.75 (1H, d, J = 7.8 Hz), 6.83 (1H, d, J = 8.9 Hz), 6.90 (1H, dd, J = 1.9, 7.8 Hz), 6.96 (1H, d, J = 1.9 Hz), 7.10-7.31 (6H, m), 7.47 (1H, d, J = 6.8 Hz). |

TABLE 1-86

| Example | Structural formula | Property values |
|---|---|---|
| 263 | | ¹H-NMR (CDCl₃) δ: 0.86 (3H, t, J = 7.3 Hz), 1.80-1.83 (4H, m), 1.98-2.21 (2H, m), 2.81-2.92 (4H, m), 3.59 (2H, t, J = 6.8 Hz), 3.62 (1H, bs), 3.97 (2H, t, J = 5.4 Hz), 5.92-5.94 (2H, m), 6.14 (1H, bs), 6.75 (1H, d, J = 8.4 Hz), 6.82 (1H, d, J = 8.4 Hz), 6.93 (1H, dd, J = 8.4, 2.2 Hz), 7.02 (1H, d, J = 2.2 Hz), 7.09-7.30 (6H, m), 7.46 (1H, d, J = 8.4 Hz). |
| 264 | | ¹H-NMR (CDCl₃) δ: 0.86 (3H, t, J = 7.3 Hz), 1.80-1.83 (4H, m), 1.97-2.22 (2H, m), 2.81-2.92 (4H, m), 3.58 (2H, t, J = 6.5 Hz), 3.64 (1H, bs), 3.97 (2H, t, J = 5.7 Hz), 4.21 (4H, s), 6.03 (1H, bs), 6.80-6.84 (2H, m), 6.94 (1H, dd, J = 8.6, 1.9 Hz), 7.01 (1H, d, J = 1.9 Hz), 7.09-7.30 (6H, m), 7.46 (1H, d, J = 8.9 Hz). |

TABLE 1-86-continued

| Example | Structural formula | Property values |
|---|---|---|
| 265 | | $^1$H-NMR (CDCl$_3$) δ: 1.31 (6H, d, J = 5.9 Hz), 1.77 (3H, s), 1.77-1.85 (4H, m), 2.75-2.89 (4H, m), 3.55 (1H, bs), 3.60 (2H, t, J = 6.2 Hz), 3.77 (3H, s), 3.98 (2H, t, J = 5.7 Hz), 4.46-4.54 (1H, m), 5.72 (1H, bs), 6.78-6.86 (5H, m), 7.04 (2H, d, J = 1.9 Hz), 7.30-7.35 (3H, m), 7.46 (1H, d, J = 8.4 Hz). |

TABLE 1-87

| Example | Structural formula | Property values |
|---|---|---|
| 266 | | $^1$H-NMR (CDCl$_3$) δ: 1.76 (3H, s), 1.82 (4H, bs), 2.77-2.87 (4H, m), 3.58 (1H, bs), 3.60 (2H, t, J = 6.5 Hz), 3.77 (3H, s), 3.98 (2H, t, J = 5.7 Hz), 5.85 (1H, bs), 5.93 (2H, s), 6.74-6.92 (5H, m), 6.95 (1H, d, J = 1.9 Hz), 7.02 (1H, d, J = 8.6 Hz), 7.16-7.31 (2H, m), 7.46 (1H, d, J = 8.1 Hz). |
| 267 | | $^1$H-NMR (CDCl$_3$) δ: 0.87 (3H, t, J = 7.3 Hz), 1.80-1.83 (4H, m), 1.98-2.22 (2H, m), 2.77-2.87 (4H, m), 3.59 (3H, bs), 3.77 (3H, s), 3.98 (2H, t, J = 5.4 Hz), 5.92-5.94 (2H, m), 6.00 (1H, bs), 6.74-6.84 (4H, m), 6.93 (1H, dd, J = 7.8, 2.2 Hz), 7.01-7.04 (3H, m), 7.30 (1H, bs), 7.46 (1H, d, J = 8.9 Hz). |

TABLE 1-87-continued
| Example | Structural formula | Property values |
| --- | --- | --- |
| 268 | 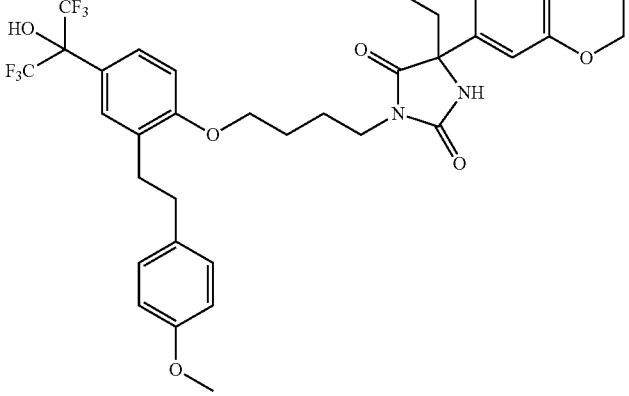 | $^1$H-NMR (CDCl$_3$) δ: 0.87 (3H, t, J = 7.3 Hz), 1.80-1.83 (4H, m), 1.97-2.23 (2H, m), 2.75-2.89 (4H, m), 3.58 (2H, t, 7.0 Hz), 3.58 (1H, bs), 3.77 (3H, s), 3.98 (2H, t, J = 5.7 Hz), 4.21 (4H, s), 5.89 (1H, bs), 6.78-6.84 (4H, m), 6.93 (1H, dd, J = 8.6, 2.4 Hz), 7.01-7.04 (3H, m), 7.30 (1H, bs), 7.46 (1H, d, J = 8.6 Hz). |
TABLE 1-88
| Example | Structural formula | Property values |
| --- | --- | --- |
| 269 | 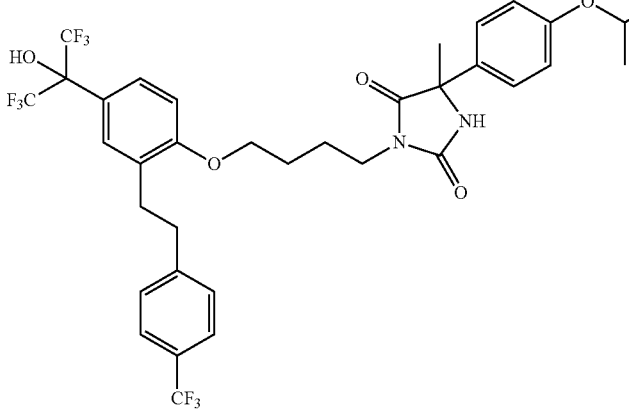 | $^1$H-NMR (CDCl$_3$) δ: 1.30 (6H, d, J = 7.3 Hz), 1.78 (3H, s), 1.82 (4H, m), 2.90 (4H, bs), 3.54 (1H, bs), 3.61 (2H, t, J = 5.7 Hz), 3.98 (2H, t, J = 5.7 Hz), 4.45-4.54 (1H, m), 5.70 (1H, bs), 6.83 (3H, bd, J = 8.9 H), 7.16-7.34 (5H, m), 7.46-7.49 (3H, m). |
| 270 | 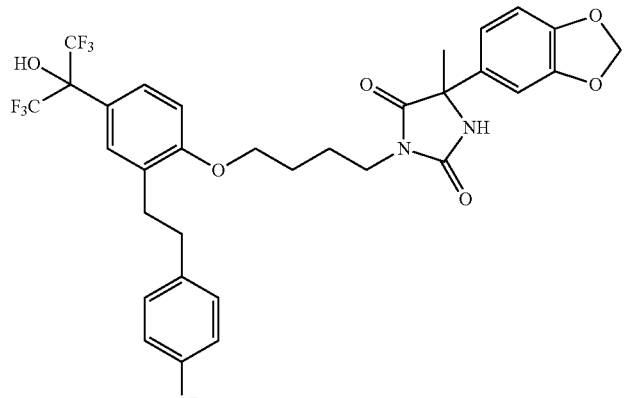 | $^1$H-NMR (CDCl$_3$) δ: 1.76 (3H, s), 1.82 (4H, bs), 2.90 (4H, bs), 3.50 (1H, bs), 3.61 (2H, t, J = 6.8 Hz), 3.98 (2H, bs), 5.76 (1H, bs), 5.92 (2H, s), 6.75 (1H, d, J = 8.4 Hz), 6.84 (1H, d, J = 8.9 Hz), 6.90 (1H, dd, J = 8.4, 1.6 Hz), 6.94 (1H, d, J = 1.6 Hz), 7.15-7.26 (3H, m), 7.46-7.49 (3H, m). |

TABLE 1-88-continued

| Example | Structural formula | Property values |
|---|---|---|
| 271 | | ¹H-NMR (CDCl₃) δ: 0.86 (3H, t, J = 7.3 Hz), 1.81-1.83 (4H, m), 1.98-2.22 (2H, m), 2.90 (4H, bs), 3.50 (1H, bs), 3.59 (2H, t, J = 7.6 Hz), 3.98 (2H, bs), 5.86 (1H, bs), 5.92-5.94 (2H, m), 6.75 (1H, d, J = 8.4 Hz), 6.83 (1H, d, J = 8.9 Hz), 6.92 (1H, dd, J = 8.4, 1.9 Hz), 7.01 (1H, d, J = 1.9 Hz), 7.16-7.26 (3H, m), 7.46-7.49 (3H, m). |

TABLE 1-89

| Example | Structural formula | Property values |
|---|---|---|
| 272 | | ¹H-NMR (CDCl₃) δ: 0.86 (3H, t, J = 7.3 Hz), 1.81-1.83 (4H, m), 1.98-2.23 (2H, m), 2.90 (4H, bs), 3.53 (1H, bs), 3.59 (2H, t, J = 6.2 Hz), 3.98 (2H, bs), 4.21 (4H, s), 5.78 (1H, bs), 6.82 (1H, d, J = 8.4 Hz), 6.83 (1H, d, J = 8.6 Hz), 6.93 (1H, dd, J = 8.4, 2.4 Hz), 7.01 (1H, d, J = 2.4 Hz), 7.16-7.26 (3H, m), 7.47-7.50 (3H, m). |
| 273 | | ¹H-NMR (CDCl₃) δ: 0.93 (3H, t, J =7.3 Hz), 1.32 (6H, d, J = 5.4 Hz), 1.53-1.64 (2H, m), 1.79 (3H, s), 2.10-2.19 (2H, m), 2.60 (2H, t, J = 7.3 Hz), 3.71-3.77 (2H, m), 3.95 (2H, t, J = Hz), 4.50-4.57 (1H, m), 5.84 (1H, bs), 6.74 (1H, d, J = 8.4 Hz), 6.84 (2H, d, J = 8.4 Hz), 7.33 (2H, d, J = 8.4 Hz), 7.41 (1H, s), 7.43 (1H, d, J = 8.4 Hz). |

TABLE 1-90

| Example | Structural formula | Property values |
|---|---|---|
| 274 | 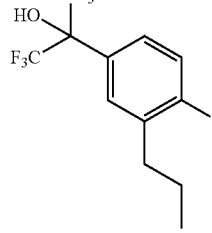 | $^1$H-NMR (CDCl$_3$) δ: 0.93 (3H, t, J = 7.3 Hz), 1.53-1.63 (2H, m), 1.77 (3H, s), 2.09-2.18 (2H, m), 2.61 (2H, t, J = 7.0 Hz), 3.63 (1H, bs), 3.73 (2H, t, J = 6.8 Hz), 3.95 (2H, t, J = 6.5 Hz), 5.96 (3H, s), 6.76 (1H, d, J = 8.1 Hz), 6.76 (1H, d, J = 8.4 Hz), 6.92 (1H, dd, J = 8.1, 1.9 Hz), 6.97 (1H, d, J = 1.9 Hz), 7.42 (1H, s), 7.44 (1H, d, J = 8.4 Hz). |
| 275 | | $^1$H-NMR (CDCl$_3$) δ: 0.90 (3H, t, J = 7.3 Hz), 0.93 (3H, t, J = 7.3 Hz), 1.53-1.64 (2H, m), 2.03-2.22 (4H, m), 2.61 (2H, t, J = 7.3 Hz), 3.65 (1H, bs), 3.72 (2H, t, J = 7.0 Hz), 3.94 (2H, t, J = 5.9 Hz), 5.96 (2H, s), 6.17 (1H, bs), 6.75 (1H, d, J = 8.4 Hz), 6.76 (1H, d, J = 8.4 Hz), 6.94 (1H, dd, J = 8.4, 1.9 Hz), 7.03 (1H, d, J = 1.9 Hz), 7.42 (1H, s), 7.44 (1H, d, J = 8.4 Hz). |

TABLE 1-91

| Example | Structural formula | Property values |
|---|---|---|
| 276 | 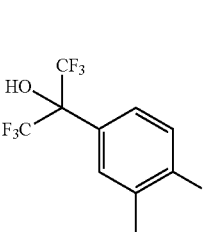 | $^1$H-NMR (CDCl$_3$) δ: 0.88 (3H, t, J = 7.3 Hz), 0.92 (3H, t, J = 7.3 Hz), 1.55-1.62 (2H, m), 1.99-2.23 (4H, m), 2.60 (2H, t, J = 7.3 Hz), 3.65 (1H, bs), 3.71 (2H, t, J = 6.8 Hz), 3.94 (2H, t, J = 5.9 Hz), 4.23 (4H, s), 6.06 (1H, bs), 6.74 (1H, d, J = 8.6 Hz), 6.82 (1H, d, J = 8.6 Hz), 6.94 (1H, d, J = 8.6 Hz), 7.01 (1H, s), 7.41 (1H, s), 7.43 (1H, d, J = 8.6 Hz). |
| 277 | | $^1$H-NMR (CDCl$_3$) δ: 1.47 (3H, s), 1.54-1.68 (2H, m), 2.61 (2H, t, J = 7.3 Hz), 2.77 (1H, d, J = 13.8 Hz), 3.03 (1H, d, J = 13.8 Hz), 3.54 (2H, t, J = 6.8 Hz), 3.64 (3H, s), 3.74 (1H, bs), 5.64 (1H, bs), 6.72 (2H, d, J = 8.6 Hz), 6.77 (2H, d, J = 8.6 Hz), 7.06 (2H, d, J = 8.6 Hz), 7.45 (2H, d, J = 8.6 Hz). |
| 278 | 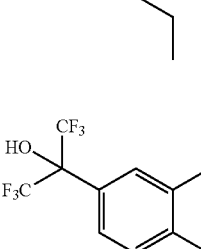 | $^1$H-NMR (CDCl$_3$) δ: 0.93 (6H, t, J = 7.3 Hz), 1.32 (6H, d, J = 5.9 Hz), 1.54-1.62 (4H, m), 1.81 (3H, s), 2.14 (2H, bs), 2.53 (4H, t, J = 7.3 Hz), 3.71-3.78 (2H, m), 4.49-4.53 (1H, m), 6.82 (2H, d, J = 6.8 Hz), 7.30-7.34 (4H, m). |

TABLE 1-92

| Example | Structural formula | Property values |
|---|---|---|
| 279 | | $^1$H-NMR (CDCl$_3$) δ: 0.93 (6H, t, J = 7.3 Hz), 1.52-1.63 (4H, m), 1.78 (3H, s), 2.09-2.19 (2H, m), 2.54 (4H, t, J = 7.8 Hz), 3.61 (1H, bs), 3.77 (2H, t, J = 6.8 Hz), 3.79 (2H, t, J = 5.9 Hz), 5.90 (1H, bs), 5.94 (2H, s), 6.73 (1H, d, J = 7.8 Hz), 6.91 (1H, dd, J = 7.8, 2.2 Hz), 6.97 (1H, d, J = 2.2 Hz), 7.31 (2H, s). |
| 280 | | $^1$H-NMR (CDCl$_3$) δ: 0.87-0.95 (9H, m), 1.52-1.65 (4H, m), 2.04-2.21 (4H, m), 2.53 (2H, t, J = 7.6 Hz), 3.65 (1H, bs), 3.75 (2H, t, J = 7.0 Hz), 3.77 (2H, t, J = 5.9 Hz), 5.95 (2H, s), 6.13 (1H, bs), 6.73 (1H, d, J = 8.1 Hz), 6.75 (1H, dd, J = 8.1, 1.6 Hz), 7.03 (1H, d, J = 1.6 Hz), 7.30 (2H, s). |
| 281 | | $^1$H-NMR (CDCl$_3$) δ: 0.87-0.95 (9H, m), 1.52-1.63 (4H, m), 2.01-2.25 (4H, m), 2.54 (4H, t, J = 7.3 Hz), 3.65 (1H, bs), 3.74 (2H, t, J = 7.8 Hz), 3.77 (2H, J = 6.5 Hz), 4.23 (4H, s), 6.00 (1H, bs), 6.81 (1H, d, J = 8.6 Hz), 6.94 (1H, dd, J = 8.6, 1.9 Hz), 7.02 (1H, d, J = 1.9 Hz), 7.30 (2H, s). |

TABLE 1-93

| Example | Structural formula | Property values |
|---|---|---|
| 282 | | $^1$H-NMR (CDCl$_3$) δ: 0.95 (6H, t, J = 7.3 Hz), 1.46 (3H, s), 1.55-1.68 (4H, m), 1.84-1.89 (2H, m), 2.57 (4H, t, J = 7.6 Hz), 2.83 (1H, d, J = 13.8 Hz), 3.01 (1H, d, J = 13.8 Hz), 3.60 (2H, t, J = 7.6 Hz), 3.61 (1H, bs), 3.65 (2H, t, J = 6.2 Hz), 5.36 (1H, bs), 6.79 (2H, d, J = 8.4 Hz), 7.07 (2H, d, J = 8.4 Hz), 7.32 (2H, s). |
| 283 | | $^1$H-NMR (CDCl$_3$) δ: 0.91 (3H, t, J = 7.6 Hz), 1.32 (6H, d, J = 5.9 Hz), 1.59 (2H, qt, J = 7.3, 7.6 Hz), 1.79 (3H, s), 2.59 (2H, t, J = 7.6 Hz), 3.91 (1H, s), 4.14 (2H, s), 4.51-4.56 (3H, m), 5.85 (2H, s), 5.94 (1H, s), 6.78 (1H, d, J = 8.9 Hz), 6.87 (2H, d, J = 8.3 Hz), 7.34 (2H, d, J = 8.3 Hz), 7.42-7.45 (2H, m). |

TABLE 1-93-continued

| Example | Structural formula | Property values |
|---|---|---|
| 284 | | ¹H-NMR (CDCl₃) δ: 0.91 (3H, t, J = 7.3 Hz), 1.54-1.66 (2H, m), 1.78 (3H, s), 2.60 (2H, t, J = 7.3 Hz), 3.71 (1H, s), 4.15 (2H, d, J = 3.6 Hz), 4.52 (2H, s), 5.86 (2H, d, J = 3.6 Hz), 5.9-5.97 (3H, m), 6.77-6.81 (2H, m), 6.91-6.95 (2H, m), 7.42-7.46 (2H, m). |

TABLE 1-94

| Example | Structural formula | Property values |
|---|---|---|
| 285 | | ¹H-NMR (CDCl₃) δ: 0.87 (3H, t, J = 7.3, 7.3 Hz), 0.91 (3H, t, J = 7.3 Hz), 1.58 (2H, qt, J = 7.3, 7.3 Hz), 2.04 (1H, dd, J = 7.3, 14.5 Hz), 2.20 (1H, dd, J = 7.3, 14.5 Hz), 2.59 (2H, t, J = 7.3 Hz), 3.80 (1H, s), 4.16 (2H, d, J = 4.9 Hz), 4.24 (4H, s), 4.47 (2H, d, J = 3.3 Hz), 5.77-5.94 (2H, m), 6.09 (1H, s), 6.78 (1H, d, J = 8.2 Hz), 6.85 (1H, d, J = 8.6 Hz), 6.95 (1H, dd, J = 2.0, 8.6 Hz), 7.02 (1H, d, J = 2.0 Hz), 7.42-7.46 (2H, m). |
| 286 | | ¹H-NMR (CDCl₃) δ: 0.92 (6H, t, J = 7.3 Hz), 1.32 (6H, d, J = 6.3 Hz), 1.59 (4H, qt, J = 7.3, 7.6 Hz), 1.82 (3H, s), 2.55 (4H, t, J = 7.6 Hz), 3.67 (1H, s), 4.17 (2H, d, J = 4.0 Hz), 4.27 (2H, d, J = 3.3 Hz), 4.53 (1H, q, J = 6.3 Hz), 5.84 (1H, s), 5.87-5.91 (2H, m), 6.88 (2H, d, J = 8.9 Hz), 7.31 (2H, s), 7.37 (2H, d, J = 8.9 Hz). |

TABLE 1-95

| Example | Structural formula | Property values |
|---|---|---|
| 287 | | ¹H-NMR (CDCl₃) δ: 0.88-0.99 (9H, m), 1.52-1.68 (4H, m), 2.02-2.28 (2H, m), 2.52-2.61 (4H, m), 3.42 (1H, s), 4.16 (2H, d, J = 4.9 Hz), 4.26 (2H, d, J = 3.5 Hz), 4.34 (1H, s), 5.88-6.02 (4H, m), 6.80 (1H, d, J = 7.8 Hz), 6.96 (1H, dd, J = 1.9, 7.8 Hz), 7.04 (1H, d, J = 1.9 Hz), 7.31-7.34 (2H, m). |

TABLE 1-95-continued

| Example | Structural formula | Property values |
|---|---|---|
| 288 | | ¹H-NMR (CDCl₃) δ: 0.90 (3H, t, J = 7.3 Hz), 0.92 (6H, d, J = 7.3 Hz), 1.59 (4H, qt, J = 7.3, 7.6 Hz), 2.07 (1H, qd, J = 7.3, 14.2 Hz), 2.21 (1H, qd, 7.3, 14.2 Hz), 2.55 (4H, t, J = 7.6 Hz), 3.55 (1H, s), 4.15 (2H, d, J = 4.6 Hz), 4.24-4.27 (6H, m), 5.80 (1H, s), 5.85-5.92 (2H, m), 6.86 (1H, d, J = 8.6 Hz), 6.96 (1H, dd, J = 2.3, 8.6 Hz), 7.03 (1H, d, J = 2.3 Hz), 7.31 (2H, s). |

TABLE 1-96

| Example | Structural formula | Property values |
|---|---|---|
| 289 | | ¹H-NMR (CDCl₃) δ: 0.92 (3H, t, J = 7.3 Hz), 1.32 (6H, d, J = 6.3 Hz), 1.60 (2H, qt, J = 7.3, 7.6 Hz), 1.80 (3H, s), 2.60 (2H, t, J = 7.6 Hz), 3.84 (1H, s), 4.20 (2H, d, J = 7.3 Hz), 4.53 (1H, q, J = 6.3 Hz), 4.77 (2H, d, J = 5.9 Hz), 5.65 (1H, dd, J = 7.3, 10.9 Hz), 5.87 (1H, dd, J = 5.9, 10.9 Hz), 5.98 (1H, s), 6.85-6.90 (3H, m), 7.35 (2H, d, J = 8.9 Hz), 7.42-7.46 (2H, m). |
| 290 | | ¹H-NMR (CDCl₃) δ: 0.92 (3H, t, J = 7.3 Hz), 1.66 (2H, qt, J = 7.3, 7.6 Hz), 1.79 (3H, s), 2.60 (2H, t, J = 7.6 Hz), 3.69 (1H, s), 4.20 (2H, d, J = 7.3 Hz), 4.78 (2H, d, J = 5.9 Hz), 5.65 (1H, dd, J = 7.3, 10.9 Hz), 5.90 (1H, dd, J = 5.9, 10.9 Hz), 5.96 (2H, s), 6.80 (1H, d, J = 8.3 Hz), 6.88 (1H, d, J = 8.6 Hz), 6.96 (1H, dd, J = 1.7, 8.3 Hz), 6.97 (1H, d, J = 1.7 Hz), 7.43-7.47 (2H, m). |

TABLE 1-97

| Example | Structural formula | Property values |
|---|---|---|
| 291 | | ¹H-NMR (CDCl₃) δ: 0.89 (3H, t, J = 7.3 Hz), 0.91 (3H, t, J = 7.3 Hz), 1.60 (2H, qt, J = 7.3, 7.6 Hz), 2.05 (1H, qd, J = 7.3, 14.2 Hz), 2.20 (1H, qd, J = 7.3, 14.2 Hz), 2.60 (2H, t, J = 7.6 Hz), 3.67 (1H, s), 4.19 (2H, d, J = 7.3 Hz), 4.77 (2H, d, J = 5.9 Hz), 5.63 (1H, dd, J = 7.3, 10.9 Hz), 5.86 (1H, dd, J = 5.9, 10.9 Hz), 5.92-5.97 (2H, m), 6.14 (1H, s), 6.79 (1H, d, J = 8.2 Hz), 6.88 (1H, d, J = 8.2 Hz), 6.95 (1H, dd, J = 1.7, 8.2 Hz), 7.03 (1H, d, J = 1.7 Hz), 7.42-7.47 (2H, m). |

TABLE 1-97-continued

| Example | Structural formula | Property values |
|---|---|---|
| 292 | 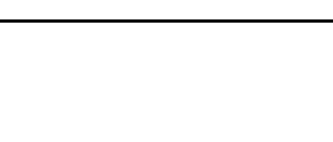 | $^1$H-NMR (CDCl$_3$) δ: 0.88 (3H, t, J = 7.3 Hz), 0.92 (3H, t, J = 7.3 Hz), 1.59 (2H, qt, J = 7.3, 7.6 Hz), 2.05 (1H, qd, J = 7.3, 14.2 Hz), 2.16 (1H, qd, J = 7.3, 14.2 Hz), 2.60 (2H, t, J = 7.6 Hz), 3.77 (1H, s), 4.18 (2H, d, J = 6.9 Hz), 4.23 (4H, s), 4.77 (2H, d, J = 5.9 Hz), 5.62 (1H, dd, J = 6.9, 10.9 Hz), 5.87 (1H, dd, J = 5.9, 10.9 Hz), 6.21 (1H, s), 6.84-6.88 (2H, m), 6.79 (1H, dd, J = 2.3, 8.6 Hz), 7.03 (1H, d, J = 2.3 Hz), 7.42-7.46 (2H, m). |

TABLE 1-98

| Example | Structural formula | Property values |
|---|---|---|
| 293 | | $^1$H-NMR (CDCl$_3$) δ: 0.94 (6H, t, J = 7.3 Hz), 1.32 (6H, d, J = 6.3 Hz), 1.63 (4H, qt, J = 7.3, 7.6 Hz), 1.78 (3H, s), 2.62 (4H, t, J = 7.6 Hz), 3.81 (1H, s), 4.12 (2H, d, J = 6.9 Hz), 4.48-4.58 (3H, m), 5.62 (1H, dd, J = 6.9, 11.0 Hz), 5.90 (1H, s), 5.97 (1H, dd, J = 6.3, 11.0 Hz), 6.86 (2H, d, J = 8.9 Hz), 7.33 (2H, d, J = 8.9 Hz), 7.34 (2H, s). |
| 294 | | $^1$H-NMR (CDCl$_3$) δ: 0.94 (6H, t, J = 7.3 Hz), 1.63 (4H, qt, J = 7.3, 7.6 Hz), 1.76 (3H, s), 2.62 (4H, t, J = 7.6 Hz), 3.84 (1H, s), 4.12 (2H, d, J = 7.3 Hz), 4.53 (2H, d, J = 6.3 Hz), 5.61 (1H, dd, J = 7.3, 11.2 Hz), 5.93-6.00 (3H, m), 6.78 (1H, d, J = 8.2 Hz), 6.91 (1H, dd, J = 2.0, 8.2 Hz), 6.95 (1H, d, J = 2.0 Hz), 7.34 (2H, s). |

TABLE 1-99

| Example | Structural formula | Property values |
|---|---|---|
| 295 | 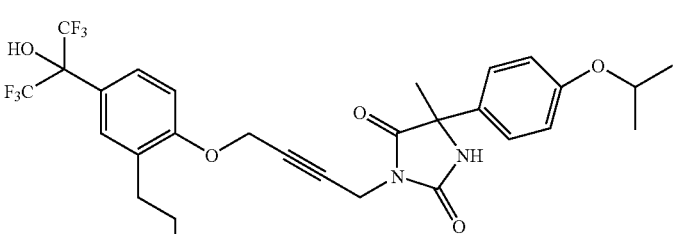 | $^1$H-NMR (CDCl$_3$) δ: 0.87 (3H, t, J = 7.3 Hz), 0.94 (6H, t, J = 7.3 Hz), 1.63 (4H, qt, J = 7.3, 7.6 Hz), 2.03 (1H, qd, J = 7.3, 14.2 Hz), 2.17 (1H, qd, J = 7.3, 14.2 Hz), 2.59 (4H, t, J = 7.6 Hz), 3.70 (1H, s), 4.11 (2H, d, J = 7.3 Hz), 4.53 (2H, d, J = 6.3 Hz), 5.60 (1H, dd, J = 7.3, 10.9 Hz), 5.91-6.01 (3H, m), 6.14 (1H, s), 6.78 (1H, d, J = 8.2 Hz), 6.92 (1H, dd, J = 2.0, 8.2 Hz), 7.01 (1H, d, J = 2.0 Hz), 7.34 (2H, s). |
| 296 | | $^1$H-NMR (CDCl$_3$) δ: 0.87 (3H, t, J = 7.3 Hz), 0.94 (3H, t, J = 7.3 Hz), 1.63 (2H, qt, J = 7.3, 7.6 Hz), 2.02 (1H, qd, J = 7.3, 14.2 Hz), 2.18 (1H, qd, J = 7.3, 14.2 Hz), 2.62 (2H, t, J = 7.6 Hz), 3.79 (1H, s), 4.10 (2H, d, J = 6.9 Hz), 4.24 (4H, s), 4.53 (2H, d, J = 6.3 Hz), 5.60 (1H, dd, J = 6.9, 11.2 Hz), 5.94 (1H, dd, J = 6.3, 11.2 Hz), 6.08 (1H, s), 6.84 (1H, d, J = 8.6 Hz), 6.93 (1H, dd, J = 2.3, 8.6 Hz), 7.00 (1H, d, J = 2.3 Hz), 7.34 (2H, s). |

TABLE 1-100

| Example | Structural formula | Property values |
|---|---|---|
| 298 | 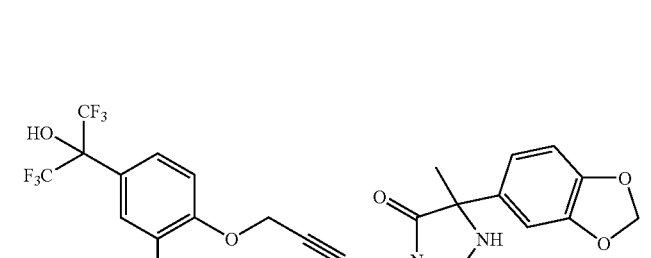 | $^1$H-NMR (CDCl$_3$) δ: 0.92 (3H, t, J = 7.3 Hz), 1.54-1.64 (2H, m), 1.74 (3H, s), 2.59 (2H, t, J = 7.6 Hz), 3.70 (1H, s), 4.30 (2H, brs), 4.30 (2H, brs), 5.89 (1H, s), 5.97 (2H, s), 6.78 (1H, d, J = 8.1 Hz), 6.89-6.96 (3H, m), 7.42-7.47 (2H, m). |
| 298 | | $^1$H-NMR (CDCl$_3$) δ: 0.92 (3H, t, J = 7.3 Hz), 1.54-1.64 (2H, m), 1.74 (3H, s), 2.59 (2H, t, J = 7.6 Hz), 3.70 (1H, s), 4.30 (2H, brs), 4.30 (2H, brs), 5.89 (1H, s), 5.97 (2H, s), 6.78 (1H, d, J = 8.1 Hz), 6.89-6.96 (3H, m), 7.42-7.47 (2H, m). |

TABLE 1-100-continued

| Example | Structural formula | Property values |
|---|---|---|
| 299 | 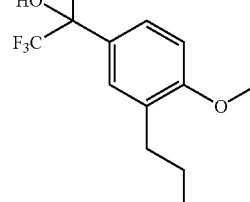 | $^1$H-NMR (CDCl$_3$) δ: 0.82 (3H, t, J = 7.3 Hz), 0.92 (3H, t, J = 7.3 Hz), 1.54-1.63 (2H, m), 1.95-2.25 (2H, m), 2.58 (2H, t, J = 7.3 Hz), 3.70 (1H, s), 4.29 (2H, brs), 4.69 (2H, brs), 5.96 (2H, s), 5.98 (1H, s), 6.78 (1H, d, J = 8.4 Hz), 6.90-7.00 (3H, m), 7.42-7.47 (2H, m). |

TABLE 1-101

| Example | Structural formula | Property values |
|---|---|---|
| 300 | 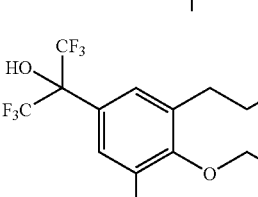 | $^1$H-NMR (CDCl$_3$) δ: 0.82 (3H, t, 7.3 Hz), 0.92 (3H, t, J = 7.3 Hz), 1.54-1.65 (2H, m), 1.99-2.22 (2H, m), 2.33 (3H, s), 2.58 (2H, t, J = 7.3 Hz), 3.72 (1H, s), 4.20-4.22 (4H, m), 4.28 (2H, brs), 4.69 (2H, br), 5.86 (1H, s), 6.85 (1H, d, J = 8.4 Hz), 6.92-6.95 (2H, m), 7.00 (1H, d, J = 2.2 Hz), 7.42-7.47 (2H, m). |
| 301 | | $^1$H-NMR (CDCl$_3$) δ: 0.92 (3H, t, J = 7.3 Hz), 1.54-1.64 (2H, m), 1.74 (3H, s), 2.59 (2H, t, J = 7.6 Hz), 3.70 (1H, s), 4.30 (2H, brs), 4.30 (2H, brs), 5.89 (1H, s), 5.97 (2H, s), 6.78 (1H, d, J = 8.1 Hz), 6.89-6.96 (3H, m), 7.42-7.47 (2H, m). |
| 302 | | $^1$H-NMR (CDCl$_3$) δ: 0.93 (6H, t, J = 7.3 Hz), 1.56-1.64 (4H, m), 1.79 (3H, s), 2.60 (2H, t, J = 7.8 Hz), 3.96 (1H, s), 4.28 (2H, brs), 4.51 (2H, brs), 5.89 (1H, s), 5.97 (2H, s), 6.80 (1H, d, J = 8.1 Hz), 6.89-6.95 (2H, m), 7.31 (2H, s). |

TABLE 1-102

| Example | Structural formula | Property values |
|---|---|---|
| 303 | 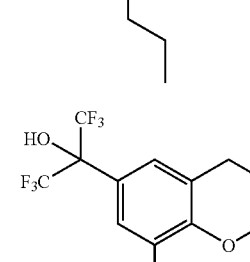 | $^1$H-NMR (CDCl$_3$) δ: 0.88 (3H, t, J = 7.3 Hz), 0.93 (6H, t, J = 7.3 Hz), 1.55-1.64 (4H, m), 2.01-2.25 (2H, m), 2.60 (4H, t, J = 7.6 Hz), 3.93 (1H, s), 4.26 (2H, brs), 4.88 (2H, brs), 5.90 (1H, s), 5.97 (2H, s), 6.80 (1H, d, J = 8.4 Hz), 6.94 (1H, dd, J = 8.1, 1.9 Hz), 7.01 (1H, d, J = 1.9 Hz), 7.31 (2H, s). |

TABLE 1-102-continued

| Example | Structural formula | Property values |
|---|---|---|
| 304 | 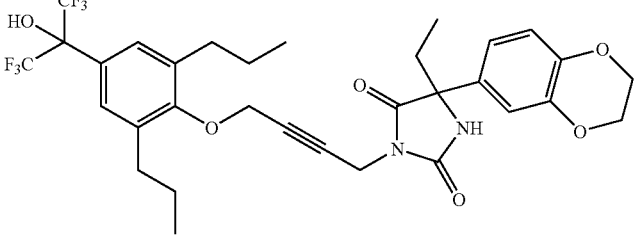 | $^1$H-NMR (CDCl$_3$) δ: 0.87 (3H, t, J = 7.6 Hz), 0.93 (6H, t, J = 7.3 Hz), 1.53-1.63 (4H, m), 2.01-2.22 (2H, m), 2.59 (4H, t, J = 7.8 Hz), 3.98 (1H, s), 4.22-4.25 (6H, m), 4.49 (2H, brs), 5.84 (1H, s), 6.86 (1H, d, J = 8.1 Hz), 6.95 (1H, dd, J = 8.1, 1.9 Hz), 7.00 (1H, d, J = 1.9 Hz), 7.31 (2H, s). |
| 305 | 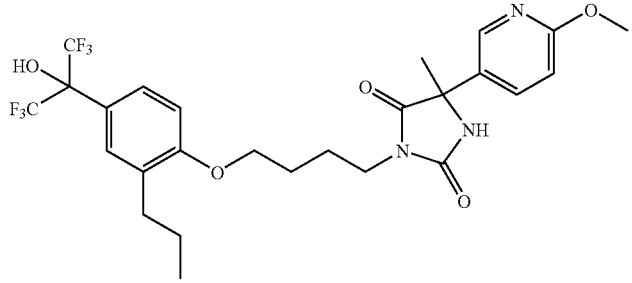 | $^1$H-NMR (CDCl$_3$) δ: 0.90 (3H, t, J = 7.3 Hz), 1.53-1.61 (2H, m), 1.72-2.04 (7H, m), 2.57 (2H, t, J = 7.6 Hz), 3.55-3.70 (2H, m), 3.56-3.64 (2H, m), 3.94-4.04 (2H, m), 4.12 (3H, s), 6.80 (1H, d, J = 8.6 Hz), 7.14-7.20 (1H, m), 7.41-7.52 (2H, m), 8.00-8.10 (1H, m), 8.40-8.50 (1H, m). |

TABLE 1-103

| Example | Structural formula | Property values |
|---|---|---|
| 306 | 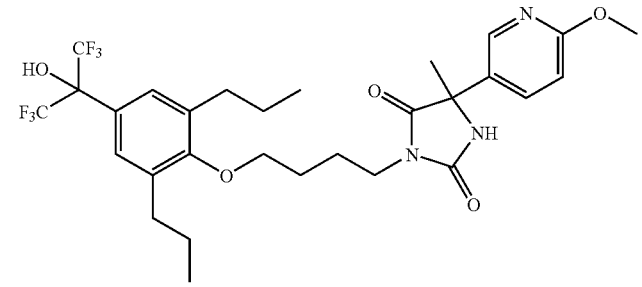 | $^1$H-NMR (CDCl$_3$) δ: 0.93 (3H, t, J = 7.3 Hz), 1.50-1.72 (2H, m), 1.72-1.95 (7H, m), 2.57 (2H, t, J = 7.7 Hz), 3.55-3.70 (2H, m), 3.70-3.82 (2H, m), 3.95 (3H, s), 5.77 (1H, s), 6.72-6.81 (1H, m), 7.31 (2H, s), 7.70-7.76 (1H, s), 8.21-8.31 (1H, m). |
| 307 | 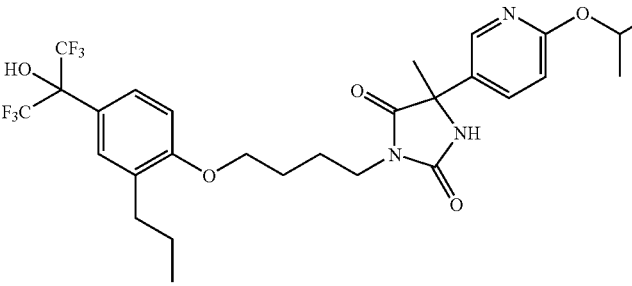 | $^1$H-NMR (CDCl$_3$) δ: 0.89 (3H, t, J = 7.3 Hz), 1.45-1.60 (8H, m), 1.75-1.84 (7H, m), 2.56 (2H, t, J = 7.6 Hz), 3.58 (2H, t, J = 6.6 Hz), 3.98 (2H, t, J = 5.6 Hz), 5.32-5.42 (1H, m), 6.81 (1H, d, J = 8.6 Hz), 6.95-7.02 (1H, m), 7.40 (1H, s), 7.46 (1H, d, J = 8.6 Hz), 7.99-8.09 (1H, m), 8.29-8.35 (1H, m), 8.55-8.64 (1H, m). |
| 308 | 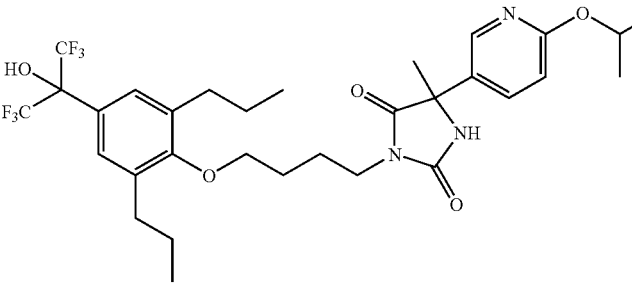 | $^1$H-NMR (CDCl$_3$) δ: 0.92 (6H, t, J = 7.3 Hz), 1.46-1.52 (6H, m), 1.60 (4H, qt, J = 7.3, 7.6 Hz), 2.55 (4H, t, J = 7.6 Hz), 3.62 (2H, t, J = 6.6 Hz), 3.75 (2H, t, J = 5.6 Hz), 5.32-5.44 (1H, m), 6.97-7.02 (1H, m), 7.31 (2H, s), 7.95-8.03 (1H, m), 8.29-8.35 (1H, s) , 8.57-8.62 (1H, m). |

TABLE 1-104

| Example | Structural formula | Property values |
|---|---|---|
| 309 | | $^1$H-NMR (CDCl$_3$) δ: 0.90 (3H, t, J = 7.3 Hz), 1.35 (6H, d, J = 5.9 Hz), 1.58 (2H, qt, J = 7.3, 7.6 Hz), 1.76-1.84 (7H, m), 2.57 (2H, t, J = 7.6 Hz), 3.60 (2H, t, J = 6.6 Hz), 3.69 (1H, s), 3.97 (2H, t, J = 5.9 Hz), 4.53 (1H, q, J = 5.9 Hz), 5.99 (1H, s), 6.81 (1H, d, J = 8.6 Hz), 6.95 (1H, dd, J = 8.6, 8.6 Hz), 7.15 (1H, dd, 2.6, 8.6 Hz), 7.19 (1H, d, J = 2.6 Hz), 7.41-7.47 (2H, m). |
| 310 | | $^1$H-NMR (CDCl$_3$) δ: 0.92 (6H, t, J = 7.3 Hz), 1.35 (6H, d, J = 5.9 Hz), 1.56-1.65 (4H, m), 1.77-1.83 (7H, m), 2.56 (4H, t, J = 7.6 Hz), 3.58 (1H, s), 3.61 (2H, t, J = 6.6 Hz), 3.76 (2H, t, J = 5.6 Hz), 4.53 (1H, q, J = 5.9 Hz), 5.81 (1H, s), 6.95 (1H, dd, J = 8.6, 8.6 Hz), 7.15 (1H, d, J = 8.6 Hz), 7.20 (1H, s), 7.31 (2H, s). |

TABLE 1-105

| Example | Structural formula | Property values |
|---|---|---|
| 311 | | $^1$H-NMR (CDCl$_3$) δ: 0.90 (6H, t, J = 7.3 Hz), 1.35 (6H, d, J = 6.3 Hz), 1.57 (2H, qt, J = 7.3, 7.6 Hz), 2.04 (1H, qd, J = 7.3, 14.2 Hz), 2.21 (1H, qd, J = 7.3, 14.2 Hz), 2.57 (2H, t, J = 7.6 Hz), 3.58 (2H, t, J = 6.3 Hz), 3.61 (1H, s), 3.97 (2H, t, J = 5.6 Hz), 4.53 (1H, q, J = 6.3 Hz), 6.14 (1H, s), 6.80 (1H, d, J = 8.6 Hz), 6.95 (1H, dd, J = 8.6, 8.6 Hz), 7.17 (1H, dd, 2.6, 8.6 Hz), 7.26 (1H, d, J = 2.6, 12.5 Hz), 7.42 (1H, s), 7.44 (1H, d, J = 8.6 Hz). |
| 312 | | $^1$H-NMR (CDCl$_3$) δ: 0.91 (3H, t, J = 7.3 Hz), 0.92 (3H, t, J = 7.3 Hz), 1.35 (6H, d, J = 5.9 Hz), 1.59 (4H, qt, J = 7.3, 7.6 Hz), 1.75-1.85 (4H, m), 1.99-2.28 (2H, m), 2.56 (4H, t, J = 7.6 Hz), 3.45 (1H, s), 3.60 (2H, t, J = 6.6 Hz), 3.75 (2H, t, J = 5.6 Hz), 4.53 (1H, q, J = 5.9 Hz), 5.89 (1H, s), 6.95 (1H, dd, J = 8.6, 8.6 Hz), 7.17 (1H, dd, J = 2.3, 8.6 Hz), 7.26 (1H, dd, J = 2.3, 12.5 Hz), 7.31 (2H, s). |

TABLE 1-106

| Example | Structural formula | Property values |
|---|---|---|
| 313 | | $^1$H-NMR (CDCl$_3$) δ: 0.85 (3H, t, J = 7.3 Hz), 1.50 (2H, qt, J = 7.3, 7.6 Hz), 1.76-1.84 (4H, m), 1.96 (3H, s), 2.52 (2H, t, J = 7.6 Hz), 3.64 (2H, t, J = 6.6 Hz), 4.00 (2H, t, J = 5.9 Hz), 6.09 (1H, s), 6.78 (1H, d, J = 8.6 Hz), 7.41-7.48 (2H, m), 7.88 (1H, d, J = 8.9 Hz), 7.88 (1H, d, 8.9 Hz), 8.87-8.89 (2H, m). |
| 314 | | $^1$H-NMR (CDCl$_3$) δ: 0.88 (6H, t, J = 7.3 Hz), 1.54 (4H, qt, J = 7.3, 7.6 Hz), 1.78--1.82 (4H, m), 2.51 (4H, t, J = 7.6 Hz), 3.66 (2H, t, J = 6.6 Hz), 3.73 (2H, t, J = 6.3 Hz), 6.20 (1H, s), 7.18 (1H, d, J = 8.9 Hz), 7.31 (1H, s), 7.94 (1H, d, J = 8.9 Hz), 8.06 (1H, d, J = 8.9 Hz), 8.27 (1H, s) , 8.88 (2H, s). |
| 315 | | $^1$H-NMR (CDCl$_3$) δ: 0.88-0.95 (3H, m), 1.30-1.33 (6H, m), 1.52-1.90 (9H, m), 2.16-2.54 (9H, m), 3.78 (1H, s), 3.90-3.96 (2H, m), 4.15-4.21 (1H, m), 4.52 (1H, q, J = 5.9 Hz), 5.81 (1H, s), 6.76-6.88 (3H, m), 7.16-7.46 (4H, m). |

TABLE 1-107

| Example | Structural formula | Property values |
|---|---|---|
| 316 | | $^1$H-NMR (CDCl$_3$) δ: 0.88-0.95 (3H, m), 1.40-1.45 (3H, m), 1.55-2.27 (9H, m), 2.54-2.62 (2H, m), 3.59 (1H, s), 3.90-3.97 (2H, m), 4.15-4.24 (1H, m), 5.77 (1H, s), 5.95-5.96 (2H, m), 6.76-6.97 (4H, m), 7.42-7.47 (2H, m). |
| 317 | | $^1$H-NMR (CDCl$_3$) δ: 0.88-0.95 (3H, m), 1.40-1.45 (3H, m), 1.55-2.27 (9H, m), 2.54-2.62 (2H, m), 3.59 (1H, s), 3.90-3.97 (2H, m), 4.15-4.24 (1H, m), 5.77 (1H, s), 5.95-5.96 (2H, m), 6.76-6.97 (4H, m), 7.42-7.47 (2H, m). |

TABLE 1-107-continued

| Example | Structural formula | Property values |
|---|---|---|
| 318 | | ¹H-NMR (CDCl₃) δ: 0.88-0.95 (6H, m), 1.39-1.43 (3H, m), 1.52-2.26 (8H, m), 2.53-2.61 (2H, m), 3.61 (1H, s), 3.89-3.95 (2H, m), 4.14-4.25 (5H, m), 5.83 (1H, s), 6.76-7.01 (4H, m), 7.41-7.46 (2H, m). |
| 319 | | ¹H-NMR (CDCl₃) δ: 0.90-0.96 (6H, m), 1.31-1.33 (6H, m), 1.42-1.47 (3H, m), 1.53-2.26 (11H, m), 2.52-2.59 (4H, m), 3.59 (1H, s), 3.71-3.75 (2H, m), 4.17-4.26 (1H, m), 4.48-4.58 (1H, m), 5.69 (1H, s), 6.85-6.88 (2H, m), 7.31 (2H, s), 7.33-7.36 (2H, m). |

TABLE 1-108

| Example | Structural formula | Property values |
|---|---|---|
| 320 | | ¹H-NMR (CDCl₃) δ: 0.90-0.97 (6H, m), 1.43-1.48 (3H, m), 1.53-2.26 (11H, m), 2.53-2.59 (4H, m), 3.48 (1H, s), 3.67-3.76 (2H, m), 4.16-4.27 (1H, m), 5.68 (1H, s), 5.96-5.97 (2H, m), 6.77-6.97 (3H, m), 7.31 (2H, s). |
| 321 | | ¹H-NMR (CDCl₃) δ: 0.89-0.96 (9H, m), 1.41-1.46 (3H, m), 1.53-2.25 (10H, m), 2.52-2.58 (2H, m), 3.54 (1H, s), 3.70-3.74 (2H, m), 4.17-4.26 (1H, m), 5.90 (1H, s), 5.96-5.97 (2H, m), 6.76-7.03 (3H, m), 7.31 (2H, s). |
| 322 | | ¹H-NMR (CDCl₃) δ: 0.89-0.96 (9H, m), 1.41-1.45 (3H, m), 1.52-2.26 (10H, m), 2.52-2.58 (4H, m), 3.64 (1H, s), 3.70-3.74 (2H, m), 5.92 (1H, s), 6.82-7.02 (3H, m), 7.31 (2H, s). |

TABLE 1-109

| Example | Structural formula | Property values |
|---|---|---|
| 323 | | $^1$H-NMR (CDCl$_3$) δ: 0.88 (3H, t, J = 7.3 Hz), 1.46-1.66 (9H, m), 1.97-2.03 (2H, m), 2.52 (2H, t, J = 7.6 Hz), 3.59-3.64 (1H, m), 3.77-3.82 (2H, m), 3.95-4.02 (1H, m), 4.85 (1H, s), 5.95 (2H, s), 6.68-6.89 (4H, m), 6.98 (1H, s), 7.41-7.48 (2H, m). |
| 324 | | $^1$H-NMR (CDCl$_3$) δ: 0.92 (6H, t, J = 7.3 Hz), 1.32 (6H, d, J = 5.9 Hz), 1.43 (3H, s), 1.60 (4H, qt, J = 7.3, 7.6 Hz), 1.75-1.87 (4H, m), 2.56 (4H. t, J = 7.6 Hz), 3.61 (2H, t, J = 6.6 Hz), 3.68-3.77 (3H, m), 4.52 (1H, q, J = 5.9 Hz), 5.02 (1H, s), 5.85 (1H, s), 6.86 (2H, d, J = 8.9 Hz), 6.98 (1H, s), 7.31 (2H, s), 7.35 (2H, d, J = 8.9Hz). |
| 325 | | $^1$H-NMR (CDCl$_3$) δ: 0.90 (3H, d, J = 7.3 Hz), 1.57 (2H, qt, J = 7.3, 7.6 Hz), 1.64 (3H, s), 1.65-1.85 (4H, m), 2.58 (2H, t, J = 7.8 Hz), 3.25 (1H, td, J = 6.9, 13.5 Hz), 3.32-3.39 (2H, m), 3.43 (1H, d, J = 8.6 Hz), 4.00 (2H, t, J = 5.6 Hz), 4.54 (1H, s), 5.96 (2H, s), 6.79-6.90 (4H, m), 7.32 (1H, s), 7.37 (1H, d, J = 9.6 Hz). |

TABLE 1-110

| Example | Structural formula | Property values |
|---|---|---|
| 326 | | $^1$H-NMR (CDCl$_3$) δ: 0.76 (3H, t, J = 7.2 Hz), 1.43-1.53 (2H, m), 1.63-1.73 (2H, m), 1.87 (2H, tt, J = 6.9, 7.9 Hz), 2.56 (1H, s), 3.11 (1H, td, J = 7.2, 13.9 Hz), 3.21 (1H, td, J = 7.2, 13.9 Hz), 3.29 (1H, d, J = 8.5 Hz), 3.37 (1H, d, J = 8.5 Hz), 3.89-3.99 (4H, m), 4.90 (1H, s), 5.95 (2H, s), 6.74 (1H, dd, J = 2.0, 8.1 Hz), 6.75-6.80 (2H, m), 6.82 (1H, d, J = 8.6 Hz), 7.09-7.23 (5H, m), 7.48 (1H, s), 7.53 (1H, d, J = 8.6Hz). |
| 327 | | $^1$H-NMR (CDCl$_3$) δ: 0.91 (3H, t, J = 7.3 Hz), 0.94 (3H, t, J = 7.3 Hz), 1.64 (2H, qt, J = 7.3, 7.6 Hz), 1.76-1.86 (4H, m), 2.01-2.26 (2H, m), 2.66 (2H, t, J = 7.6 Hz), 3.59 (2H, t, J = 6.2 Hz), 3.98 (2H, t, J = 5.7 Hz), 4.10 (1H, s), 5.97 (2H, s), 5.99 (1H, s), 6.80 (1H, d, J = 7.8 Hz), 6.95 (1H, dd, J = 1.6, 7.8 Hz), 7.04 (1H, d, J = 1.6 Hz), 7.71 (1H, s) , 8.02 (1H, s). |

TABLE 1-110-continued

| Example | Structural formula | Property values |
|---|---|---|
| 328 | 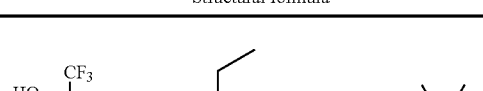 | $^1$H-NMR (CDCl$_3$) δ: 0.95 (3H, t, J = 7.3 Hz), 1.37 (6H, s), 1.58-2.10 (6H, m), 2.59 (2H, t, J = 7.6 Hz), 2.80-2.90 (4H, m), 2.91 (3H, s), 3.59 (2H, t, J = 6.5 Hz), 3.75 (2H, t, J = 6.2 Hz), 7.11-7.76 (7H, m). |

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GAL4-response element located adjacent to the promoter as well as a luciferase reporter gene.

<Assay>

An LXRα/GAL4 or LXRβ/GAL4 hybrid and GAL4-responsive reporter vector pG5luc-stable-expression CHOK-1 cells were seeded under 5% CO$_2$ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα- or LXRβ-LBD was measured. T0901317 (the compound of Example 12 of WO2000/54759) was assessed at the same time as a comparative compound. The luciferase activity results are shown in Tables 2-1 to 2-4 as activity values (% eff) at the respective concentration of the test compound, relative to the T0901317 luminescence intensity of 100 at 10 μM.

<Results>

As shown in Tables 2-1 to 2-4, it was confirmed experimentally that the carbinol derivative of the present invention is an LXR agonist having a higher selectivity to LXRβ than T0901317 which is a control agent.

Table 2-1
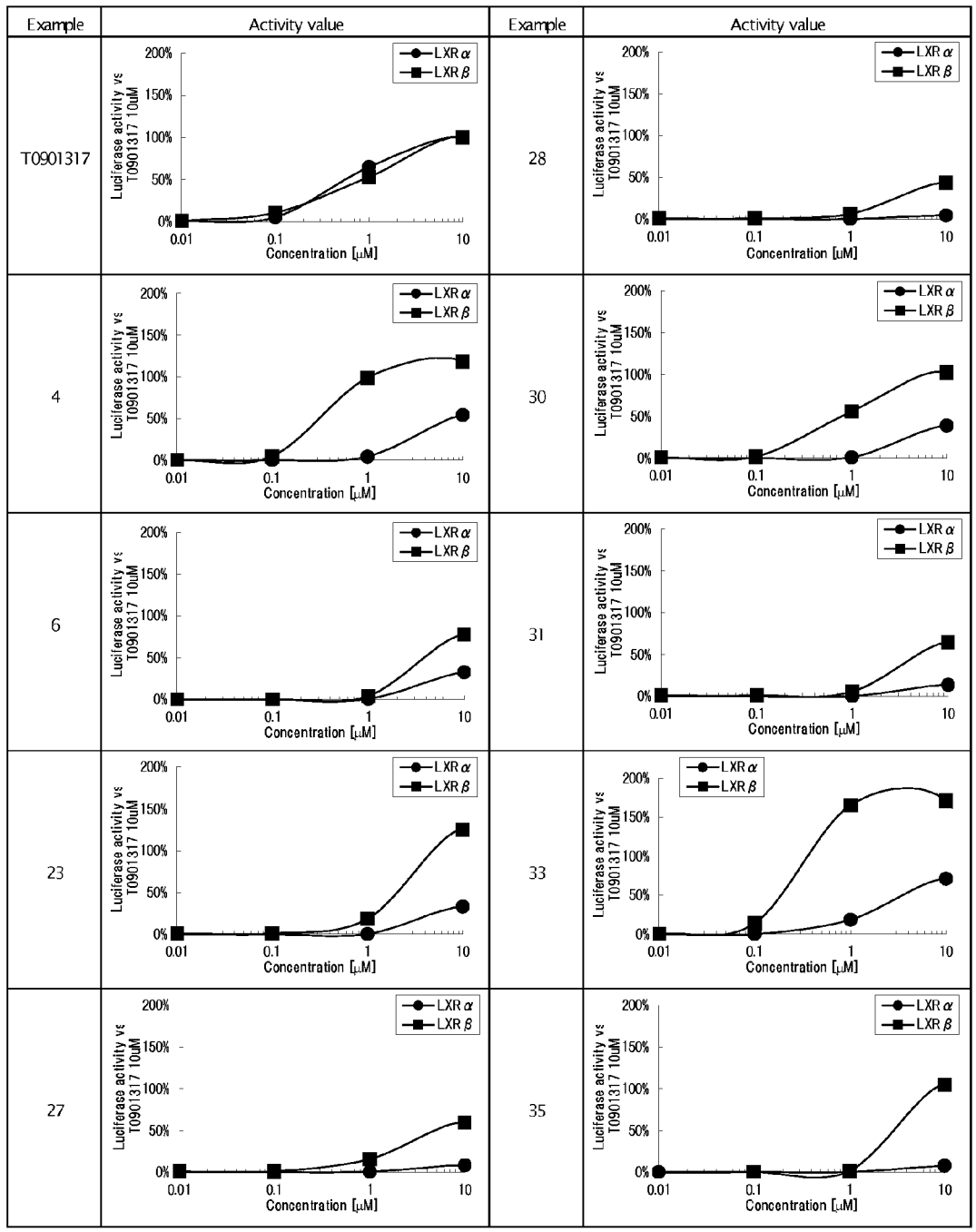

Table 2-2
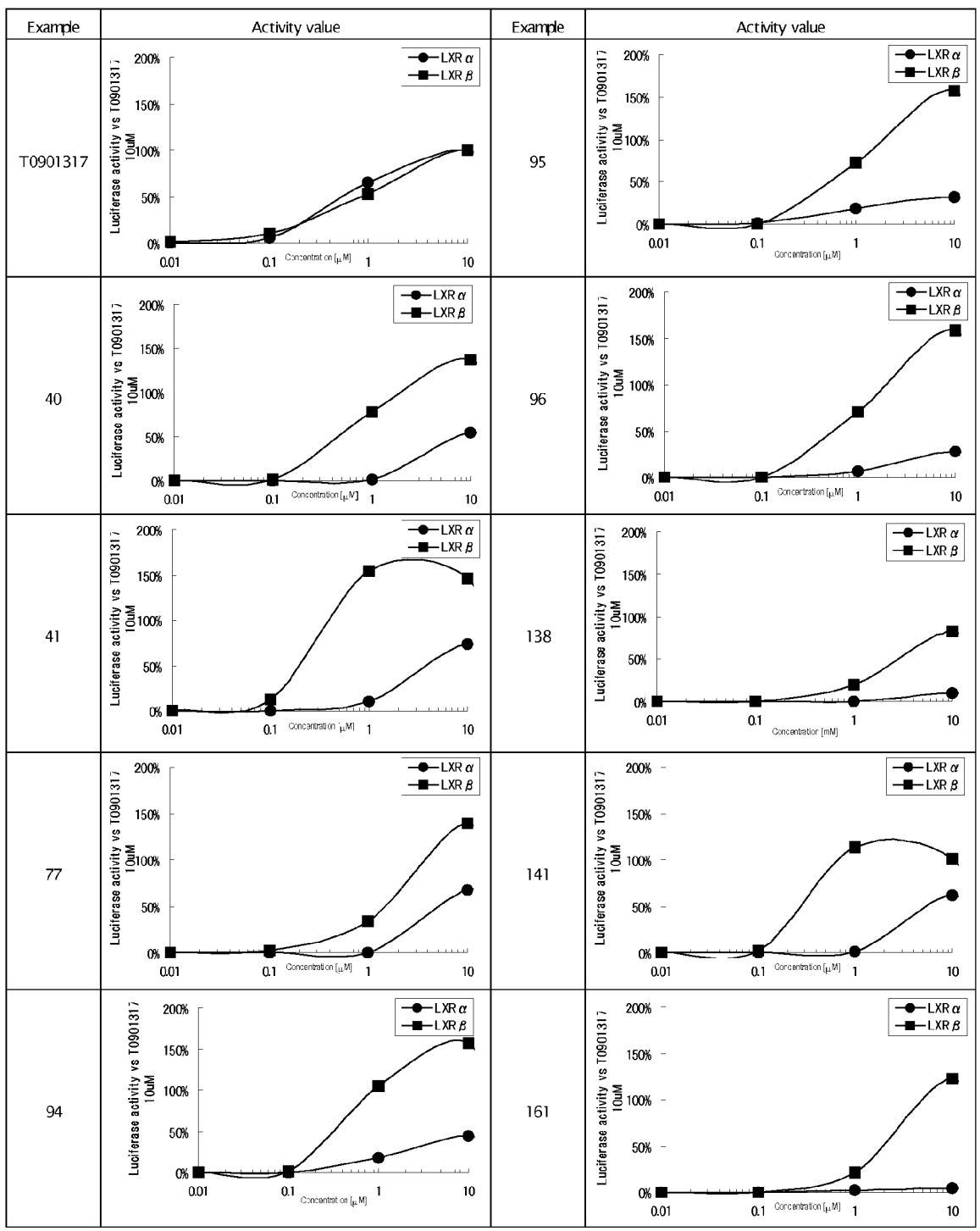

Table 2-3
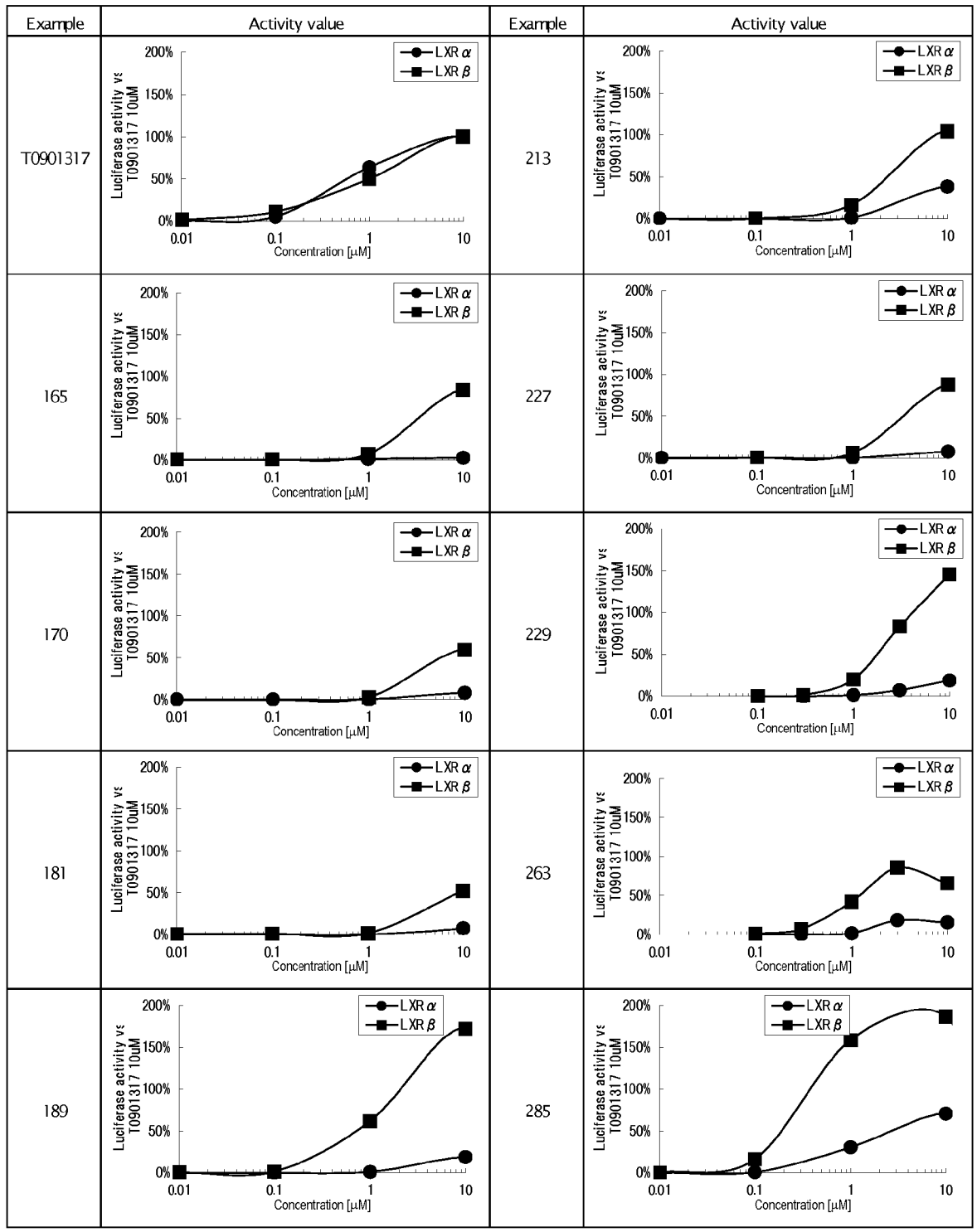

Table 2-4
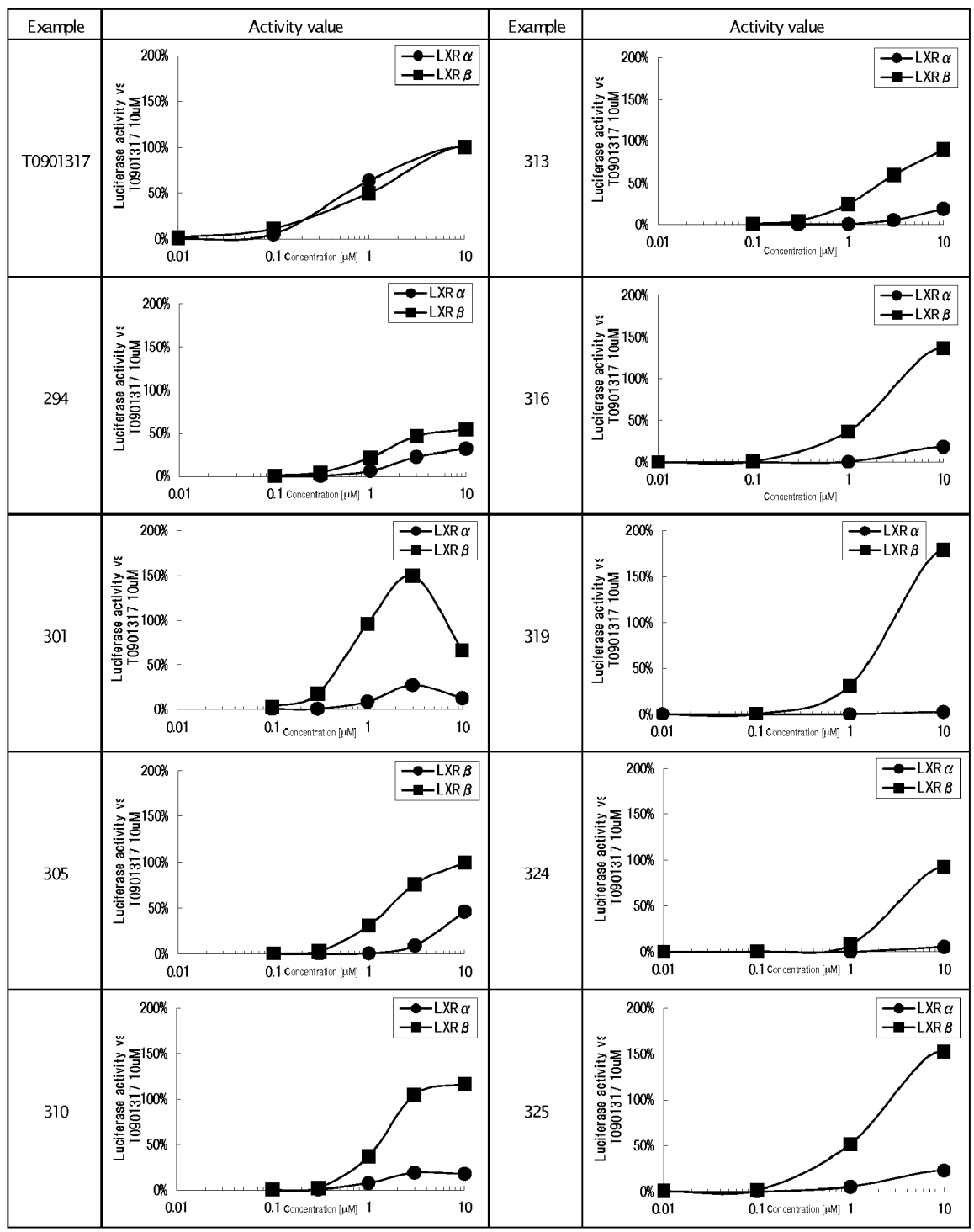

The invention claimed is:

1. A carbinol compound represented by the following general formula (1) or salt thereof:

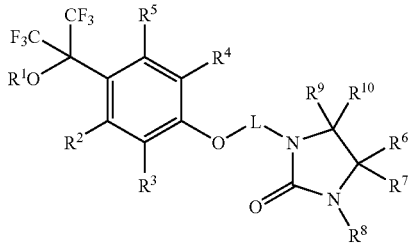
(1)

wherein $R^1$ represents a hydrogen atom, $C_{1-8}$ alkyl group, $C_{1-6}$ alkoxy-$C_{1-8}$ alkyl group or $C_{1-8}$ acyl group, wherein $R^2$, $R^3$, $R^4$ and $R^5$ each independently represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl-$C_{1-8}$ alkyl group, $C_{1-6}$ alkoxy group, $C_{6-10}$ aryl group, $C_{6-10}$ aryl-$C_{1-8}$ alkyl group, $C_{6-10}$ aryl-$C_{2-6}$ alkenyl group, $C_{1-6}$ alkylthio group, $C_{1-6}$ alkylsulfinyl group, $C_{1-6}$ alkylsulfonyl group, $C_{6-10}$ arylsulfonyl group, nitro group, amino group, mono-$C_{1-6}$ alkylamino group, di-$C_{1-6}$ alkylamino group, $C_{3-8}$ cycloalkyl-$C_{1-8}$ alkyl group, $C_{3-8}$ cycloalkyl-$C_{2-8}$ alkenyl group, $C_{3-8}$ cycloalkyl-$C_{2-8}$ alkynyl group or halo-$C_{1-6}$ alkyl group, where the $C_{6-10}$ aryl may be substituted with the same or different 1 to 3 substituents selected from the following group A, wherein $R^6$ and $R^7$ each independently represents a hydrogen atom, $C_{1-8}$ alkyl group, $C_{3-8}$ cycloalkyl group, $C_{6-10}$ aryl group or 5- to 11-membered heterocyclic group, where the $C_{6-10}$ aryl or the 5- to 11-membered heterocycle may be substituted with the same or different 1 to 3 substituents selected from the following group A, or $R^6$ and $R^7$ may together form a 5- to 7-membered carbocycle, wherein $R^8$ represents a hydrogen atom, $C_{1-8}$ alkyl group, halo-$C_{1-6}$ alkyl group or $C_{3-8}$ cycloalkyl group, wherein $R^9$ and $R^{10}$ each independently represents a hydrogen atom, hydroxy group or $C_{1-6}$ alkoxy group, or $R^9$ and $R^{10}$ may together form a carbonyl group, and L represents a $C_{3-15}$ alkyl chain, $C_{3-15}$ alkenyl chain or $C_{3-15}$ alkynyl chain, and wherein Group A consists of a halogen atom, $C_{1-8}$ alkyl group, halo-$C_{1-6}$ alkyl group, cyano group, nitro group, hydroxy group, amino group, mono-$C_{1-6}$ alkylamino group, di-$C_{1-6}$ alkylamino group, $C_{1-6}$ alkoxy group, halo-$C_{1-6}$ alkoxy group, carboxyl group, $C_{2-8}$ acyloxy group, $C_{1-6}$ alkoxycarbonyl group, $C_{6-10}$ aryl group, $C_{6-10}$ aryl-$C_{1-6}$ alkoxy group which may be substituted with the same or different 1 to 3 substituents selected from a $C_{1-8}$ alkyl group, halogen atom or $C_{1-6}$ alkoxy group, $C_{1-6}$ alkylthio group, $C_{1-6}$ alkylsulfinyl group, $C_{1-6}$ alkylsulfonyl group and $C_{6-10}$ arylsulfonyl group.

2. A medicine comprising the carbinol compound or salt thereof according to claim 1 as an active ingredient.

3. A liver X receptor regulator comprising the carbinol compound or salt thereof according to claim 1 as an active ingredient.

4. A pharmaceutical composition consisting of the carbinol compound or salt thereof according to claim 1 and a pharmaceutically acceptable carrier.

5. The medicine according to claim 2, wherein the medicine is administered in the form of an oral preparation, injection, suppository, ointment, inhalation, eye-drops, nasal preparation, or adhesive patch.

6. The liver X receptor regulator according to claim 3, wherein said liver X receptor regulator has a higher selectivity for activating LXRβ expression than LXRα expression.

* * * * *

UNITED STATES PATENT AND TRADEMARK OFFICE
CERTIFICATE OF CORRECTION

| | | |
|---|---|---|
| PATENT NO. | : 8,168,666 B2 | Page 1 of 1 |
| APPLICATION NO. | : 12/516944 | |
| DATED | : May 1, 2012 | |
| INVENTOR(S) | : Takayuki Matsuda et al. | |

It is certified that error appears in the above-identified patent and that said Letters Patent is hereby corrected as shown below:

Title Page, Item (75) Inventors:

The sixth inventor's name should be amended as follows, due to a transliteration error which was typographical/clerical in nature:

[[Yuuichirou Watanabe, Higashimurayama (JP)]]

--Yuichiro Watanabe, Higashimurayama (JP)--

Signed and Sealed this
Twenty-fourth Day of July, 2012

David J. Kappos
*Director of the United States Patent and Trademark Office*